(12) United States Patent
Crowe, Jr.

(10) Patent No.: US 12,233,127 B2
(45) Date of Patent: Feb. 25, 2025

(54) HUMAN MONOCLONAL ANTIBODIES TO A NEW UNIVERSAL INFLUENZA A HEMAGGLUTININ HEAD DOMAIN EPITOPE

(71) Applicant: Vanderbilt University, Nashville, TN (US)

(72) Inventor: James E. Crowe, Jr., Nashville, TN (US)

(73) Assignee: Vanderbilt University, Nashville, TN (US)

( * ) Notice: Subject to any disclaimer, the term of this patent is extended or adjusted under 35 U.S.C. 154(b) by 949 days.

(21) Appl. No.: 17/270,115

(22) PCT Filed: Aug. 22, 2019

(86) PCT No.: PCT/US2019/047606
§ 371 (c)(1),
(2) Date: Feb. 22, 2021

(87) PCT Pub. No.: WO2020/041540
PCT Pub. Date: Feb. 27, 2020

(65) Prior Publication Data
US 2021/0252150 A1 Aug. 19, 2021

Related U.S. Application Data

(60) Provisional application No. 62/848,301, filed on May 15, 2019, provisional application No. 62/721,675, filed on Aug. 23, 2018.

(51) Int. Cl.
| | |
|---|---|
| *A61K 39/42* | (2006.01) |
| *A61P 31/16* | (2006.01) |
| *C07K 16/10* | (2006.01) |
| *G01N 33/569* | (2006.01) |
| *A61K 39/00* | (2006.01) |

(52) U.S. Cl.
CPC ............ *A61K 39/42* (2013.01); *A61P 31/16* (2018.01); *C07K 16/1018* (2013.01); *G01N 33/56983* (2013.01); *A61K 2039/505* (2013.01); *G01N 2333/11* (2013.01)

(58) Field of Classification Search
None
See application file for complete search history.

(56) References Cited

U.S. PATENT DOCUMENTS

| | | |
|---|---|---|
| 2005/0058649 A1 | 3/2005 | Landes et al. |
| 2009/0028872 A1 | 1/2009 | Terret |
| 2013/0289246 A1* | 10/2013 | Crowe ............ C07K 16/1018 530/387.3 |

FOREIGN PATENT DOCUMENTS

| | | | | |
|---|---|---|---|---|
| CN | 104587465 A | * | 5/2015 | |
| WO | WO-2020232426 A1 | * | 11/2020 | ......... A61K 31/7105 |

OTHER PUBLICATIONS https://www.merriam-webster.com/dictionary/deliver, printed Mar. 2024.*
Bangaru et al (Cell, May 16, 2019, 177:1136-1152).*
Bangaru (Dissertation "Human antibody response to zoonotic influenza A viruses" Apr. 2, 2018; Vanderbilt University).*
English translation of CN104587465, (2015).*
Zhang et al (Vaccine, 2011; 29:1558-1564).*
Mertz et al (Vaccine, 2017, 35:521-528).*
Chaisri et al (BioMed Research International, vol. 2018, Article ID 9747549, p. 1-23; published May 28, 2018).*
Altman, Meghan O et al. "Lamprey VLRB response to influenza virus supports universal rules of immunogenicity and antigenicity." *eLife* vol. 4 e07467. Aug. 7, 2015.
Angeletti, Davide et al. "Defining B cell immunodominance to viruses." *Nature immunology* vol. 18,4 (2017): 456-463.
Caton, A J et al. "The antigenic structure of the influenza virus A/PR/8/34 hemagglutinin (H1 subtype)." *Cell* vol. 31,2 Pt 1 (1982): 417-27.
Das, Suman R., et al. "Defining influenza A virus hemagglutinin antigenic drift by sequential monoclonal antibody selection." *Cell host & microbe* 13.3 (2013): 314-323.
Ekiert, Damian C., et al. "Cross-neutralization of influenza A viruses mediated by a single antibody loop." *Nature* 489.7417 (2012): 526-532.
Gerhard, Walter, et al. "Antigenic structure of influenza virus baemagglutinin defined by hybridoma antibodies." *Nature* 290.5808 (1981): 713-717.
Hong, Minsun, et al. "Antibody recognition of the pandemic H1N1 Influenza virus hemagglutinin receptor binding site." *Journal of virology* 87.22 (2013): 12471-12480.
Joyce, M. Gordon, et al. "Vaccine-induced antibodies that neutralize group 1 and group 2 influenza A viruses." *Cell* 166.3 (2016): 609-623.
Julien, Jean-Philippe, Peter S. Lee, and Ian A. Wilson. "Structural insights into key sites of vulnerability on HIV-1 Env and influenza HA." *Imm. reviews* 250.1 (2012): 180-198.
Laursen, Nick S., and Ian A. Wilson. "Broadly neutralizing antibodies against influenza viruses." *Antiviral research* 98.3 (2013): 476-483.
Lee, Peter S., et al. "Heterosubtypic antibody recognition of the influenza virus hemagglutinin receptor binding site enhanced by avidity." *Proceedings of the National Academy of Sciences* 109.42 (2012): 17040-17045.
Lee, Peter S., et al. "Receptor mimicry by antibody F045-092 facilitates universal binding to the H3 subtype of influenza virus." *Nature communications* 5.1 (2014): 1-9.
PCT International Search Report and Written Opinion issued in International Application No. PCT/US2019/047606, mailed Jan. 6, 2020.

(Continued)

*Primary Examiner* — Laura B Goddard
(74) *Attorney, Agent, or Firm* — Parker Highlander PLLC

(57) ABSTRACT

The present disclosure is directed to antibodies binding previously undefined epitopes on influenza A virus hemagglutinin and methods for use thereof.

16 Claims, 52 Drawing Sheets
Specification includes a Sequence Listing.

(56) References Cited

OTHER PUBLICATIONS

Schmidt, Aaron G., et al. "Viral receptor-binding site antibodies with diverse germline origins." *Cell* 161.5 (2015): 1026-1034.
Thornburg, Natalie J., et al. "H7N9 influenza virus neutralizing antibodies that possess few somatic mutations." *The Journal of clinical investigation* 126.4 (2016): 1482-1494.
Whittle, James RR, et al. "Broadly neutralizing human antibody that recognizes the receptor-binding pocket of influenza virus hemagglutinin." *Proceedings of the National Academy of Sciences* 108.34 (2011): 14216-14221.
Wu, Nicholas C., and Ian A. Wilson. "A perspective on the structural and functional constraints for immune evasion: insights from influenza virus." *Journal of molecular biology* 429.17 (2017): 2694-2709.
Xu, Rui, et al. "A recurring motif for antibody recognition of the receptor-binding site of influenza hemagglutinin." *Nature structural & molecular biology* 20.3 (2013): 363-370.
Yoshida, Reiko, et al. "Cross-protective potential of a novel monoclonal antibody directed against antigenic site B of the hemagglutinin of influenza A viruses." *PLoS pathogens* 5.3 (2009): e1000350.
Zhu, Xueyong, et al. "A unique and conserved neutralization epitope in H5N1 influenza viruses identified by an antibody against the A/Goose/Guangdong/1/96 bemagglutinin." *Journal of virology* 87.23 (2013): 12619-12635.

\* cited by examiner

FIGS. 1A-B

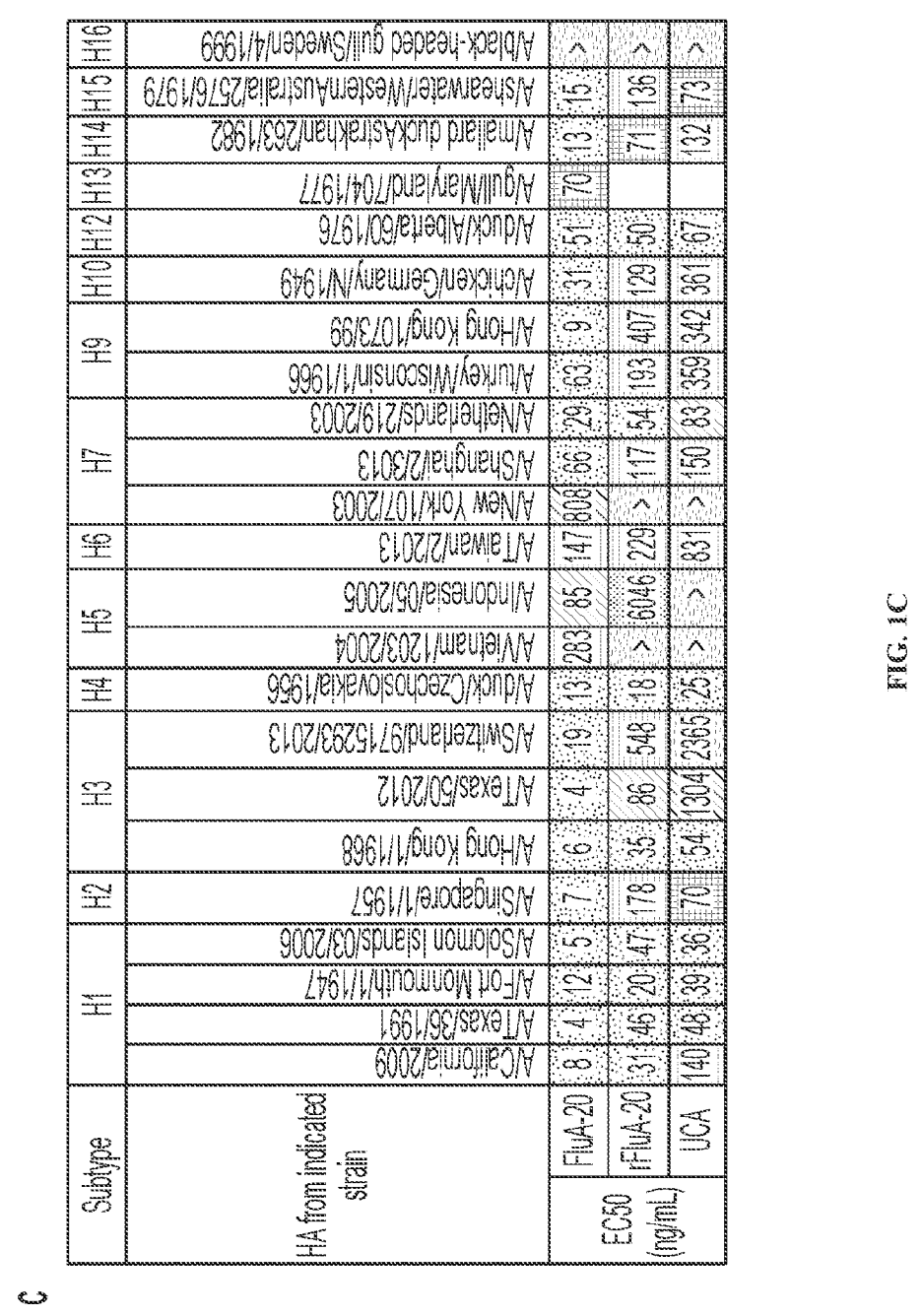

| Subtype | H1 | | | | H2 | | H3 | | H4 | H5 | | H6 | H7 | | | H9 | | H10 | H12 | H13 | H14 | H15 | H16 |
|---|---|---|---|---|---|---|---|---|---|---|---|---|---|---|---|---|---|---|---|---|---|---|---|
| HA from indicated strain | A/California/2009 | A/Texas/36/1991 | A/Fort Monmouth/1/1947 | A/Solomon Islands/03/2006 | A/Singapore/1/1957 | A/Hong Kong/1/1968 | A/Texas/50/2012 | A/Switzerland/9715293/2013 | A/duck/Czechoslovakia/1956 | A/Vietnam/1203/2004 | A/Indonesia/05/2005 | A/Taiwan/2/2013 | A/New York/107/2003 | A/Shanghai/2/2013 | A/Netherlands/219/2003 | A/turkey/Wisconsin/1/1966 | A/Hong Kong/1073/99 | A/chicken/Germany/N/1949 | A/duck/Alberta/60/1976 | A/gull/Maryland/704/1977 | A/mallard duck/Astrakhan/263/1982 | A/shearwater/WesternAustralia/2576/1979 | A/black-headed gull/Sweden/4/1999 |
| EC50 (ng/mL) FluA-20 | 8 | 4 | 12 | 5 | 7 | 6 | 4 | 19 | 13 | 283 | 85 | 147 | 808 | 66 | 29 | 63 | 9 | 31 | 51 | 70 | 13 | 15 | > |
| rFluA-20 | 31 | 45 | 20 | 47 | 178 | 35 | 86 | 548 | 18 | > | 6046 | 229 | > | 117 | 54 | 193 | 407 | 129 | 50 | | 71 | 136 | > |
| UCA | 140 | 48 | 39 | 36 | 70 | 54 | 304 | 2365 | 25 | > | > | 831 | > | 150 | 83 | 359 | 342 | 361 | 67 | | 132 | 73 | > |

FIG. 1C

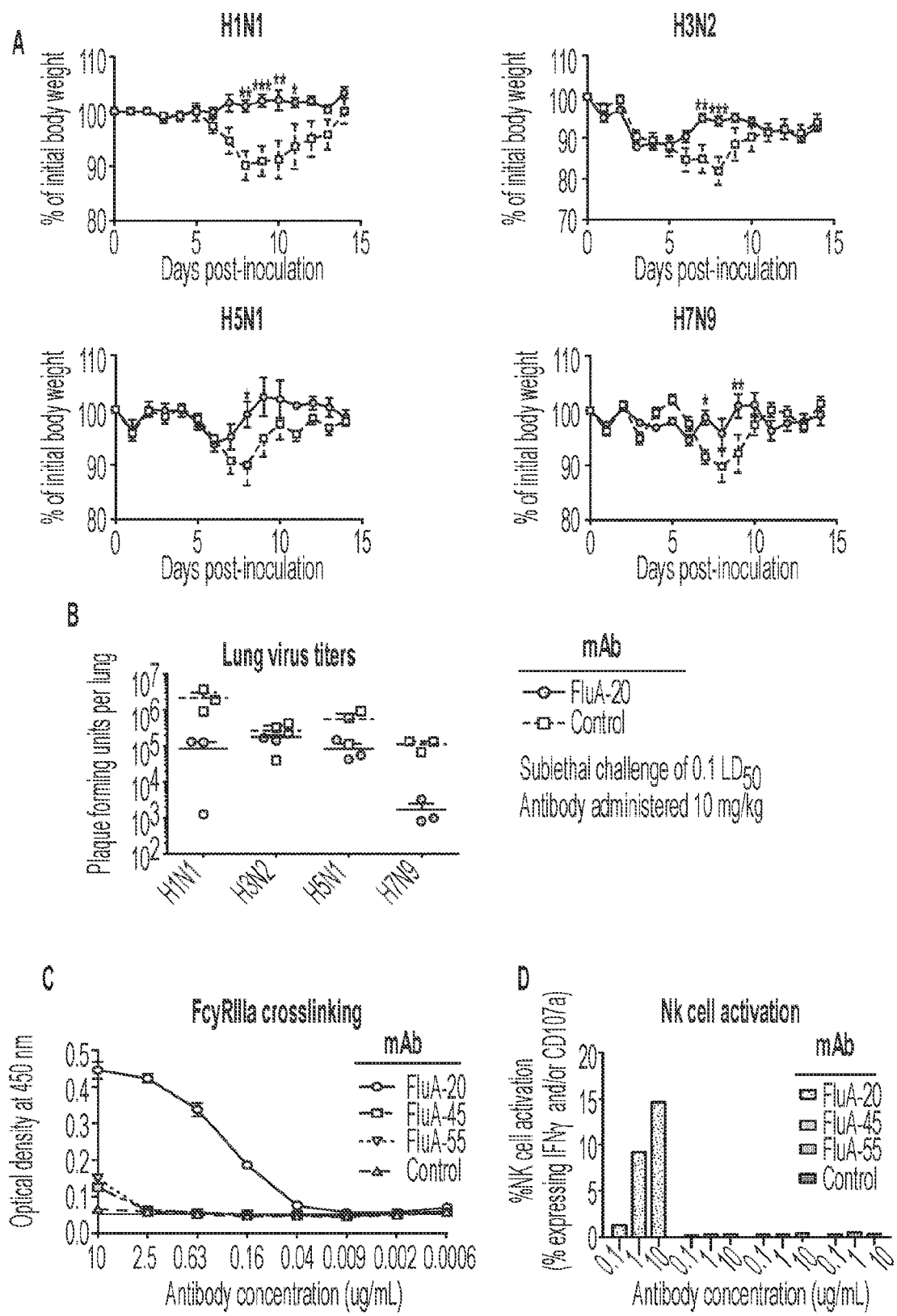
FIGS. 2A-D

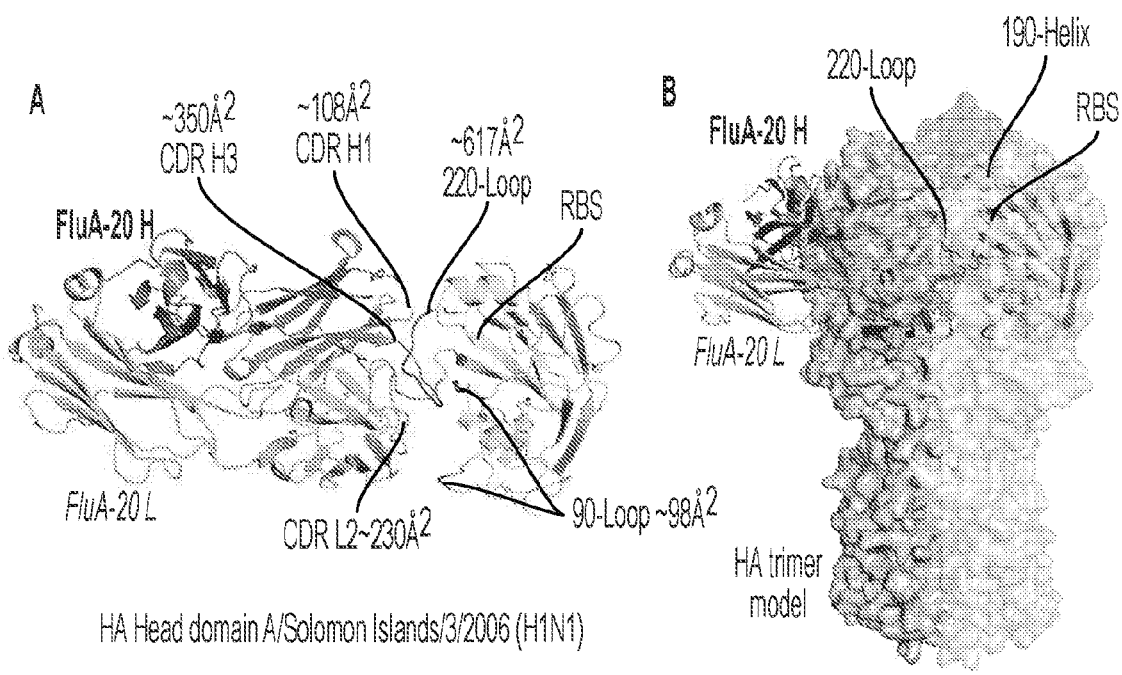
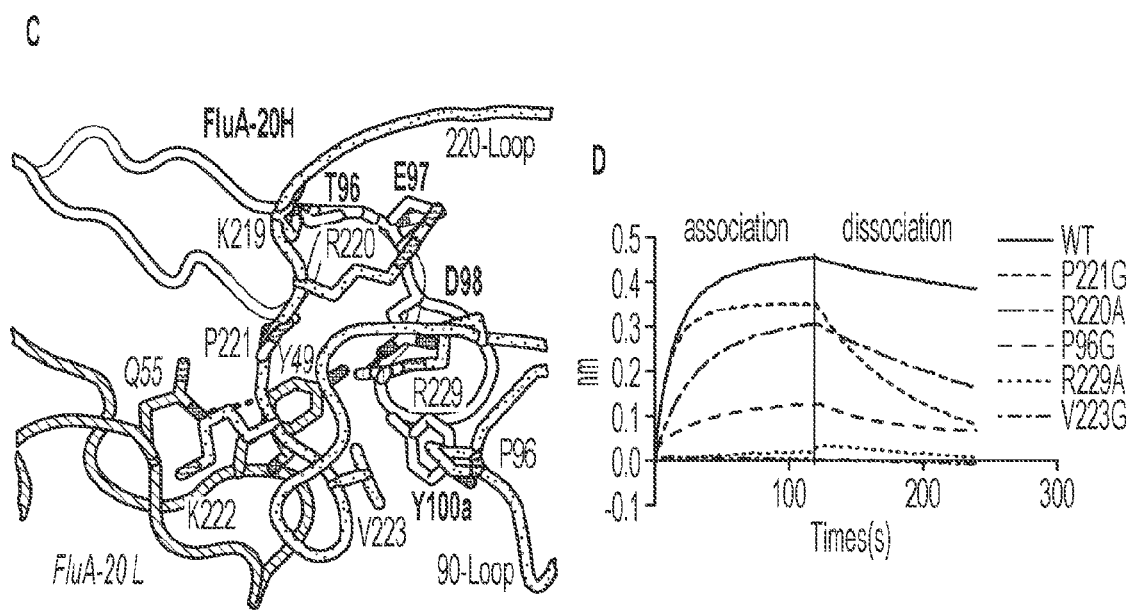
FIGS. 3A-D

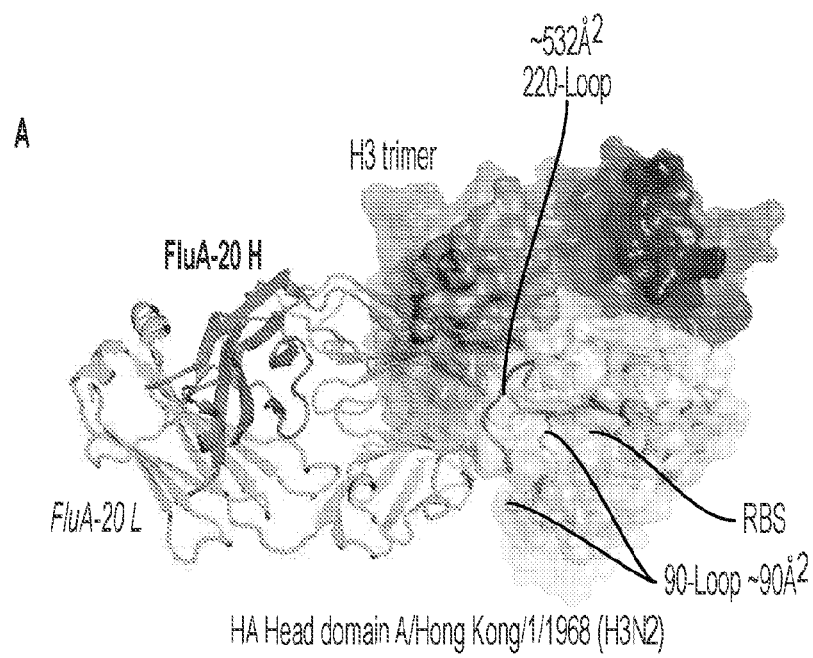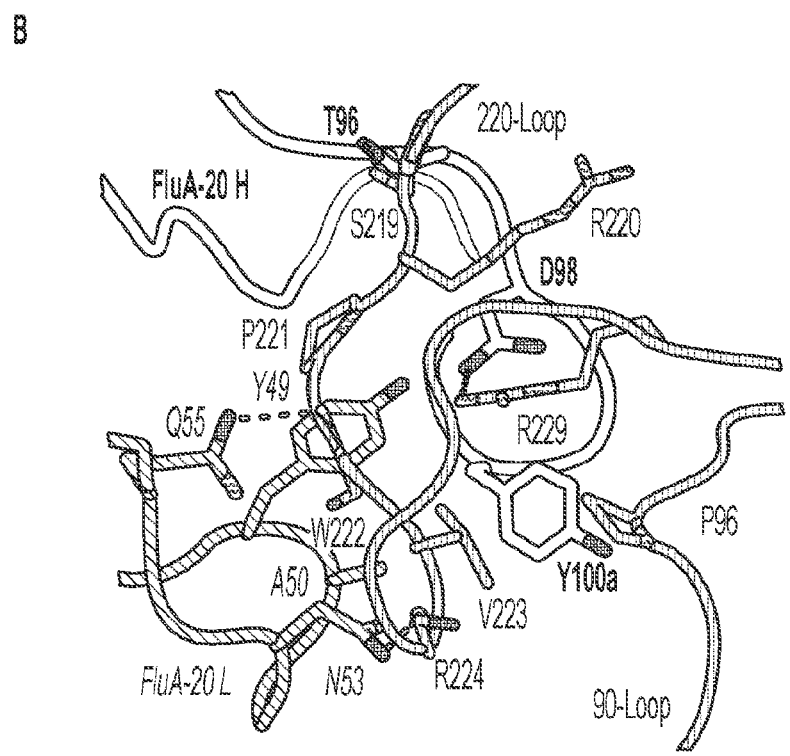
FIGS. 4A-B

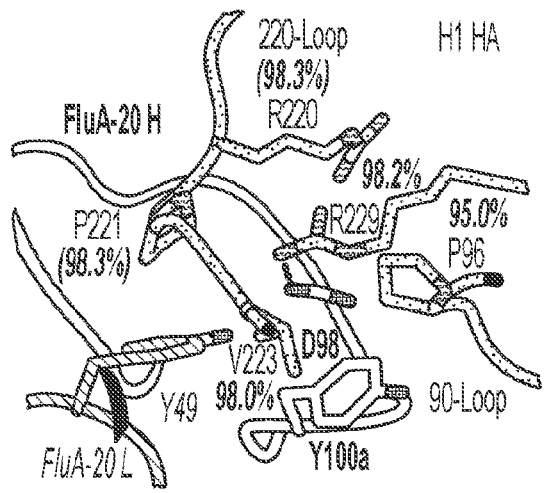
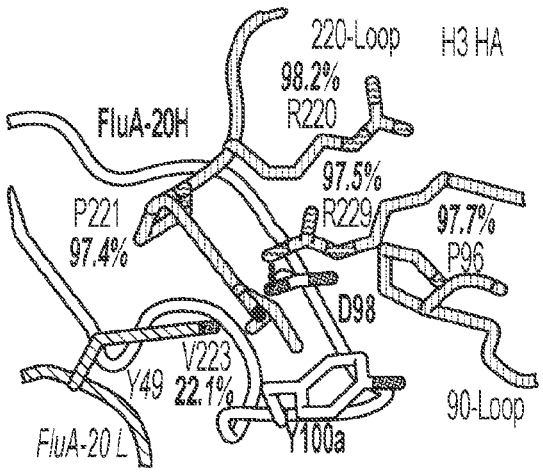

| Subtype | HA Stain | Affinity EC$_{50}$(ng/ml) | 90-Loop 88 | 96 | 98 | 216 | 219 | 220-Loop 220 | 221 | 222 | 223 | 224 | 229 |
|---|---|---|---|---|---|---|---|---|---|---|---|---|---|
| H1 | A/Solomon Islands/03/2006 | 5 | N | P | H | E | K | R | P | K | V | R | R |
| H1 | A/California/4/2009 | 8 | S | P | D | E | I | R | P | K | V | R | R |
| H1 | A/Texas/36/1991 | 4 | N | P | Y | E | K | R | P | K | V | R | R |
| H2 | A/Singapore/1/1957 | 7 | N | P | S | D | T | R | P | K | V | N | R |
| H3 | A/Hong Kong/1/1968 | 6 | S | P | D | N | S | R | P | W | V | R | R |
| H3 | A/Texas/50/2012 | 4 | S | P | D | N | S | R | P | R | I | R | R |
| H3 | A/Switzerland/9715293/2013 | 19 | S | P | D | N | S | R | P | R | I | R | R |
| H3 | A/Minnesota/11/10 | > | S | P | D | N | S | R | P | W | V | R | I |
| H5 | A/Vietnam/1203/2004 | 40 | N | P | D | R | T | R | S | K | V | N | R |
| H5 | A/Egypt/3300-NAMRU3/2008 | 85 | N | P | N | K | T | R | S | K | V | N | R |
| H7 | A/New York/107/2003a | 208 | R | P | R | N | A | R | - |  | - | R |
| H7 | A/Shanghai/2/3013 | 66 | R | P | K | S | A | R | P | Q | V | N | R |
| H9 | A/Hong Kong/1073/99 | 9 | S | P | N | V | P | R | P | L | V | N | R |
| H13 | A/gull/Maryland/704/1977 | 70 | A | P | E | E | V | R | P | G | Y | N | W |
| H14 | A/mallard duck/Astrakhan/263/1982 | 78 | P | P | D | N | S | R | P | R | V | R | R |
| H16 | A/gull/Sweden/4/1999 | > | N | P | E | E | T | R | I | G | Y | D | W |

FIGS. 5A-C

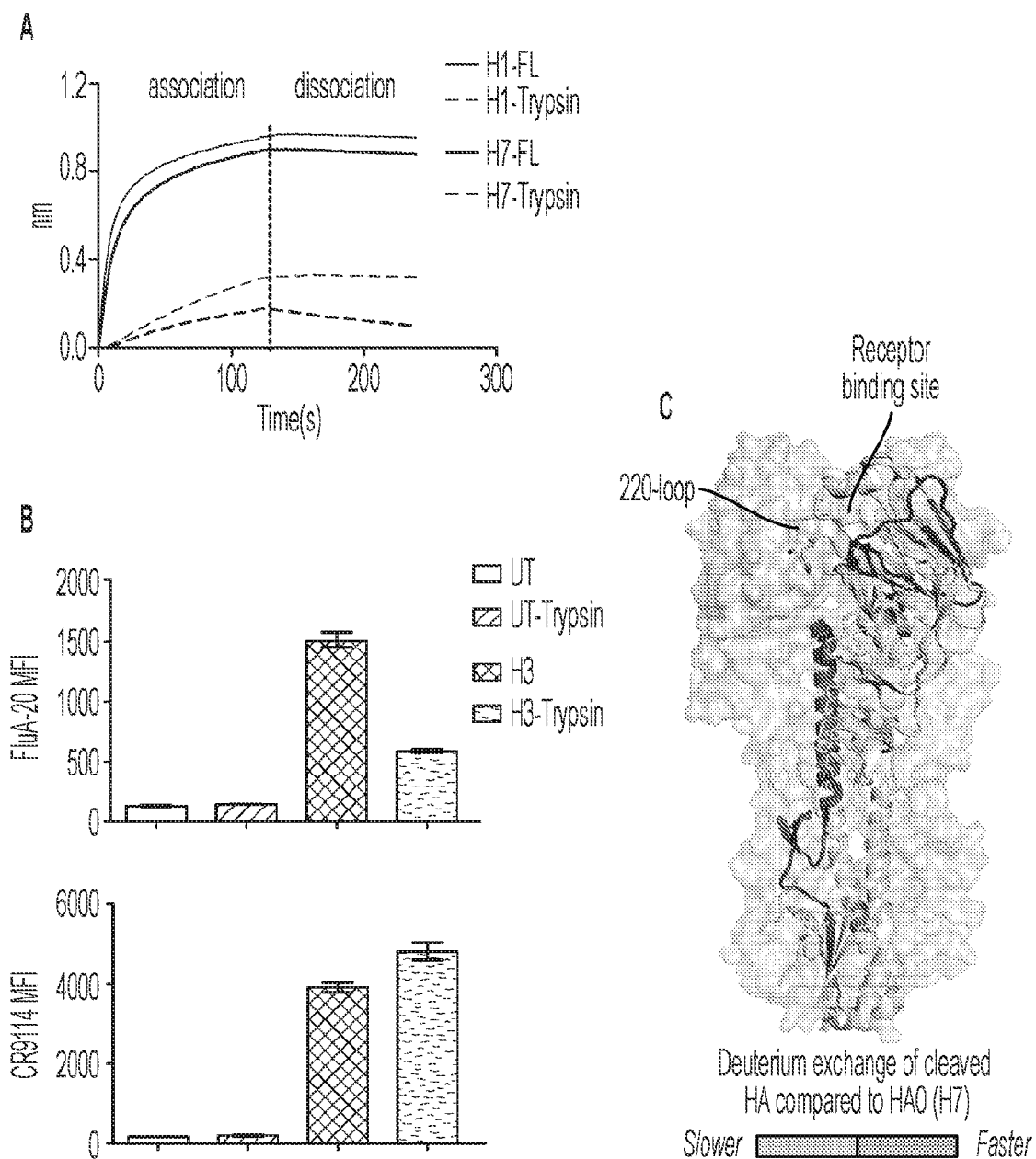
FIGS. 6A-C

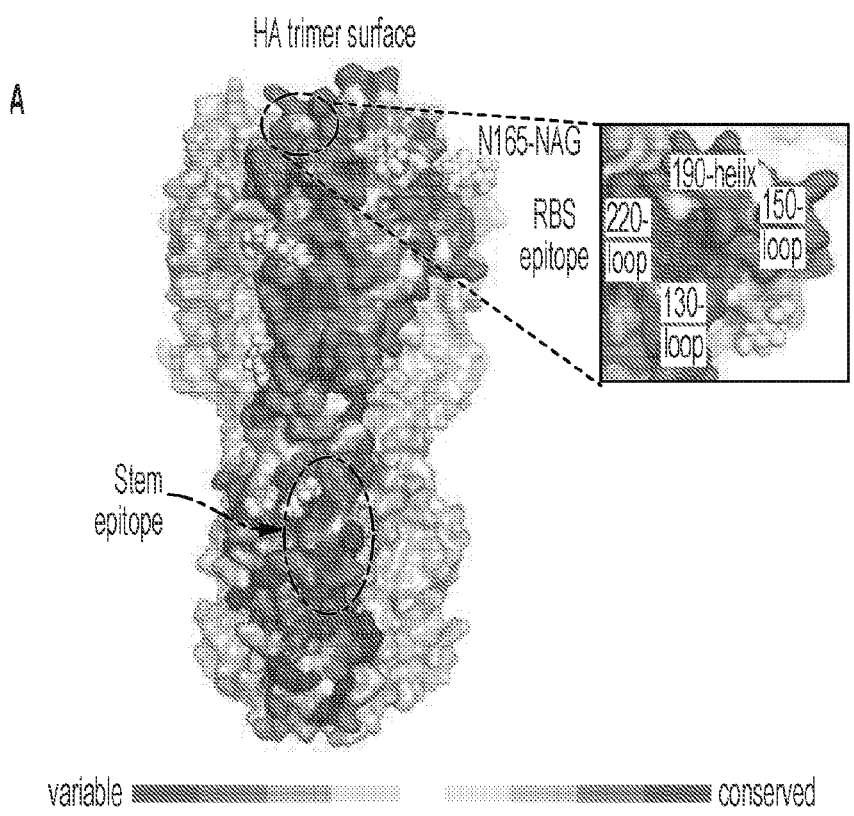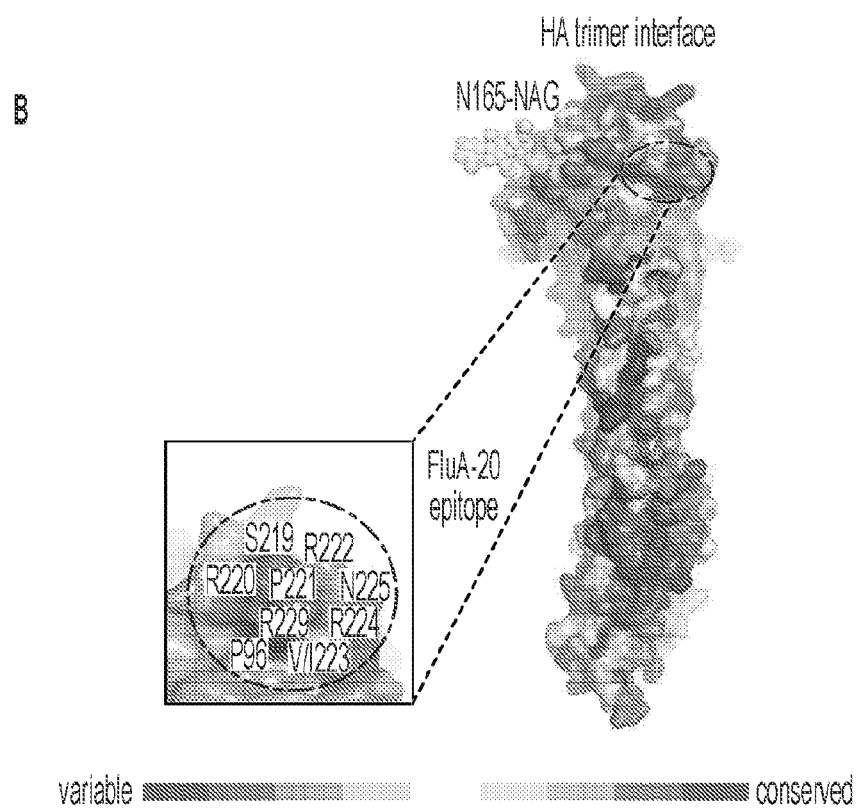
FIGS. 7A-B

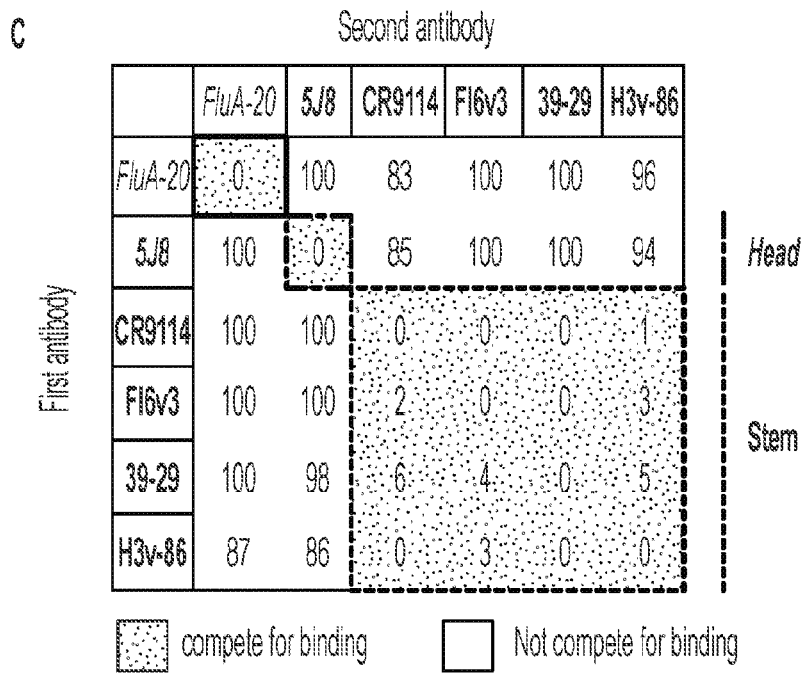
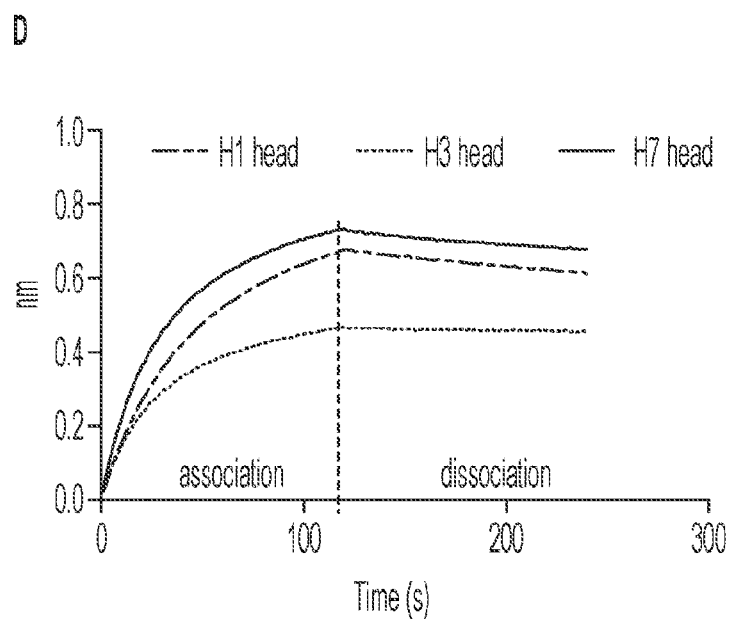
FIGS. 8C-D

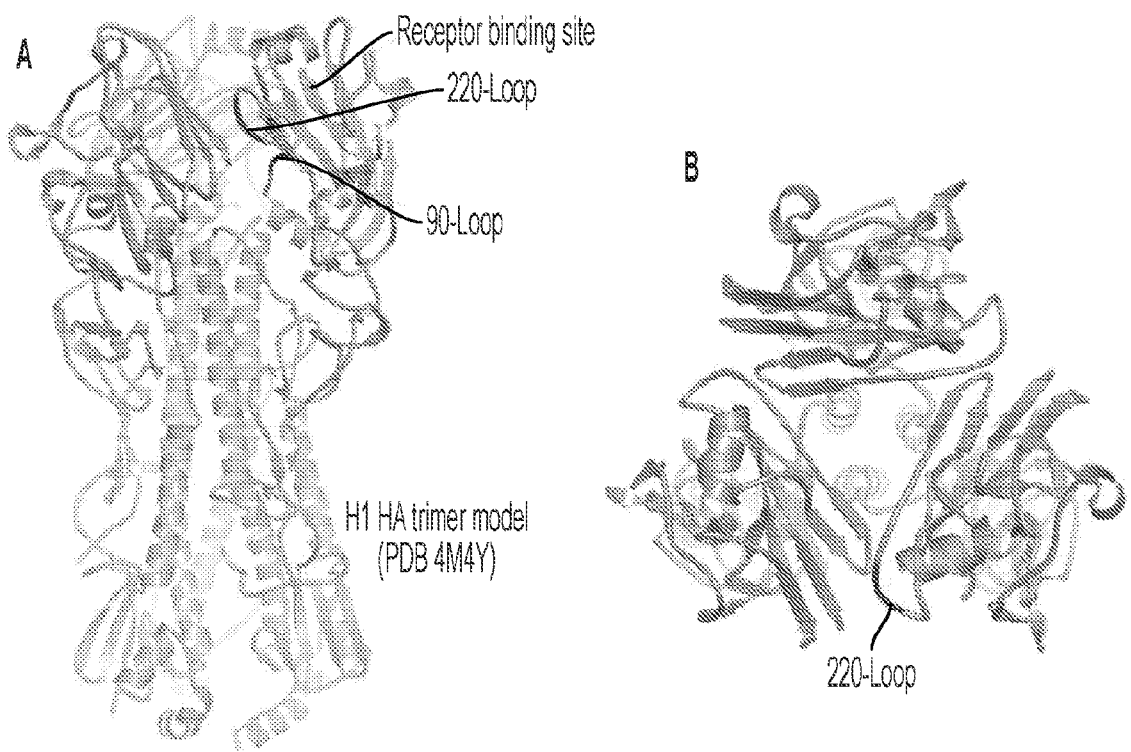
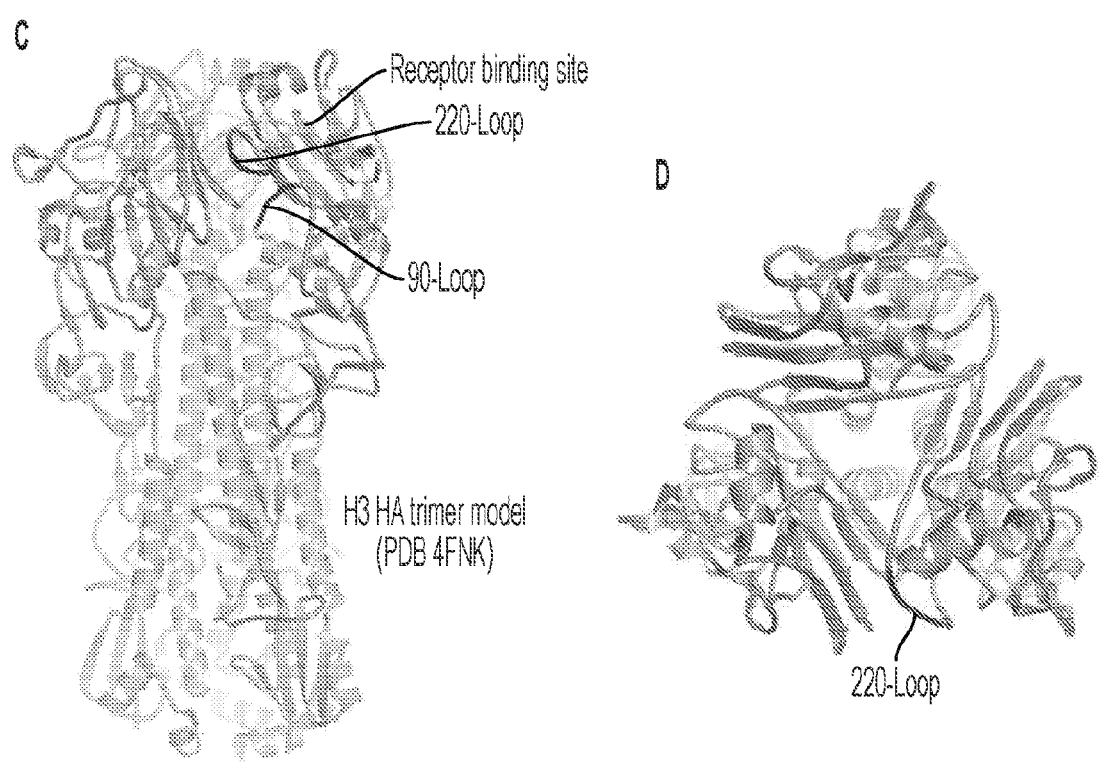
FIGS. 9A-D

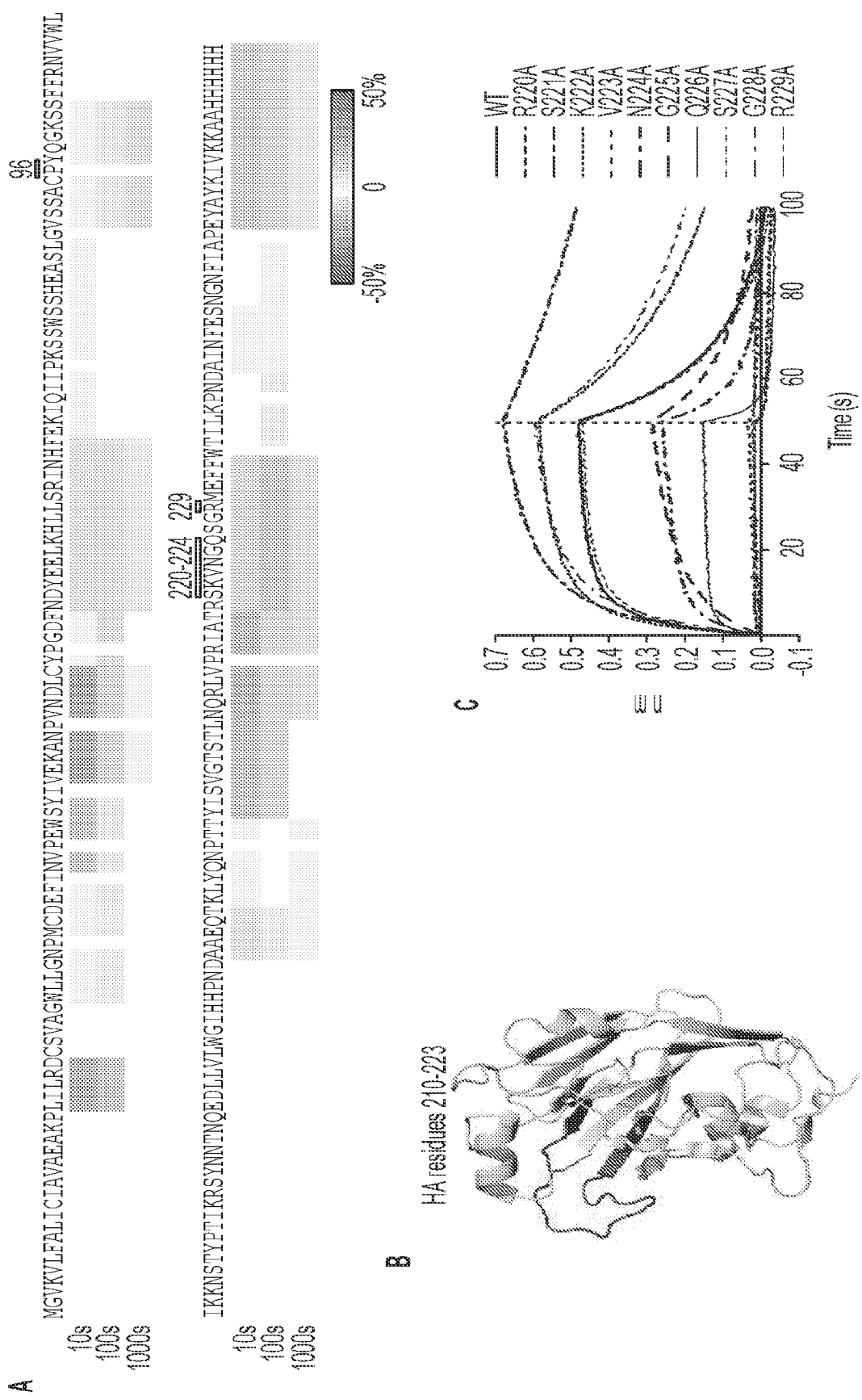
FIGS. 10A-C

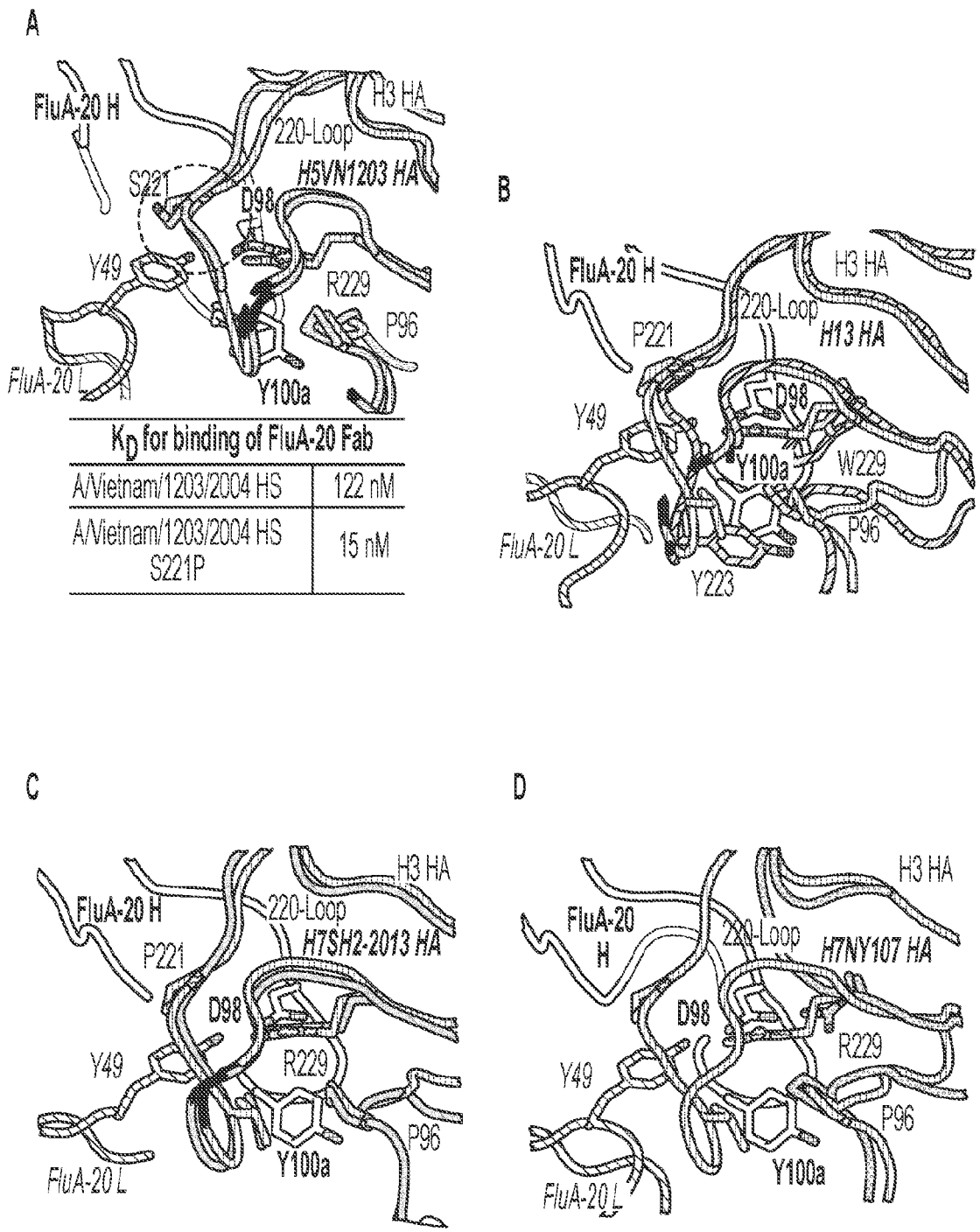
FIGS. 11A-D

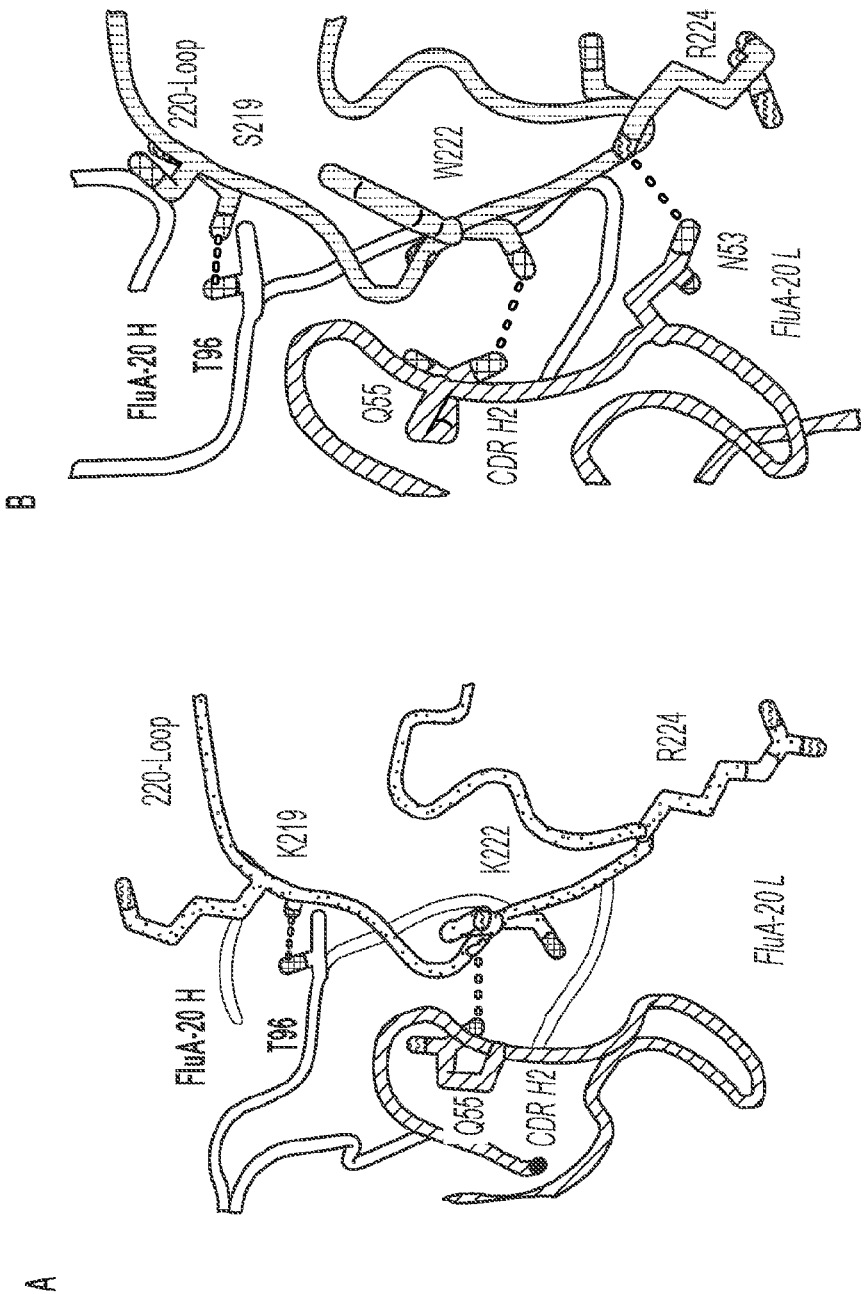
FIGS. 12A-B

A

FluA20_H aligned with UCA_H: 17 muta8ons
  FluA-20: QVQLEESGPGLVKPSETLSLTCSVSGVSVTSDIYYWTWIRQPPGKGLEWIGYIFYNGDTNYN
  UCA:     QVQLQESGPGLVKPSETLSLTCTVSGGSVSSGSYYWSWIRQPPGKGLEWIGYIYYSGSTNYN FluA-20: PSLKSRVTMSIDTSKNEFSLRLTSVTAADTAVYFCARGTEDLGYCSSGSCPNHWGQGTLVTV
  UCA:     PSLKSRVTISVDTSKNQFSLKLSSVTAADTAVYYCARGTEDLGYCSGGSCPNHWGQGTLVTV FluA20_L aligned with UCA_L: 12 muta8ons
  FluA-20: DIVMTQSPSSLSASIGDRVTITCRPSQNIRSFLNWFQHKPGKAPKLLIAASNLQSGVPS
  UCA:     DIQMTQSPSSLSASVGDRVTITCRASQSISSYLNWYQQKPGKAPKLLIVAASSLQSGVPS FluA-20: RFSGSGSGTEFTLTIRSLQPEDFATYYCQQSYNTPPTFGQGTKVEIK
  UCA:     RFSGSGSGTDFTLTISSLQPEDFATYYCQQSYSTPPTFGQGTKVEIK

FIG. 13A

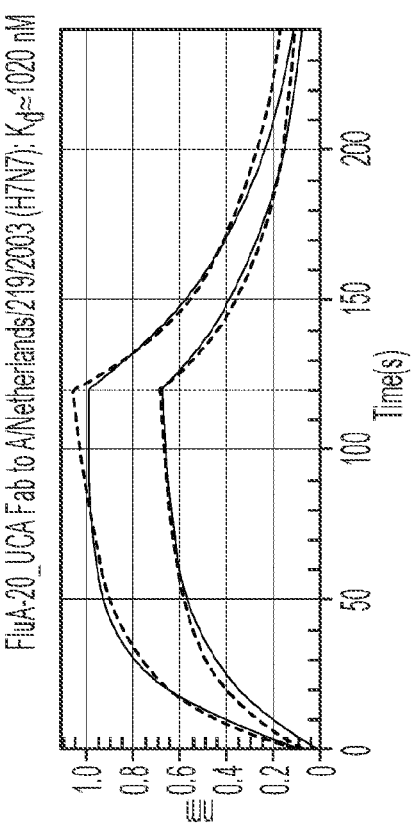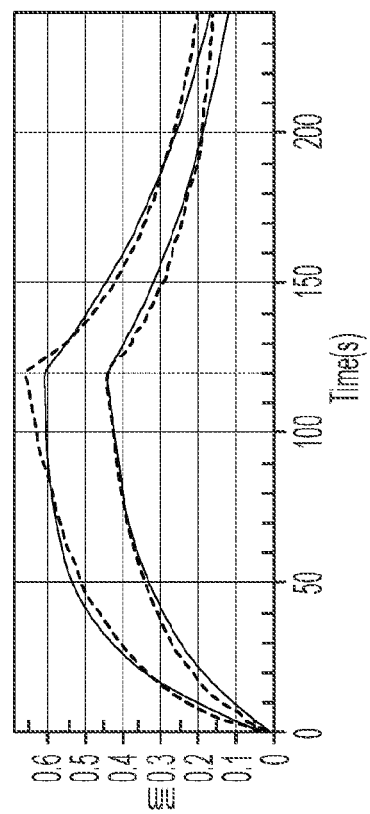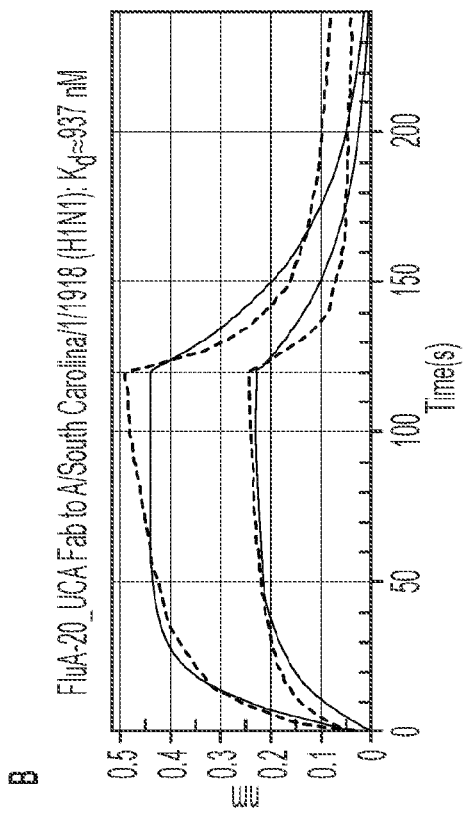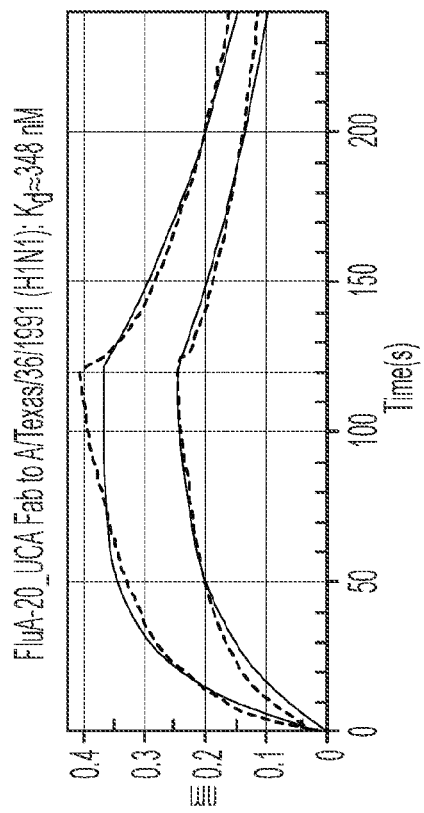
FIG. 13B
CONTINUED

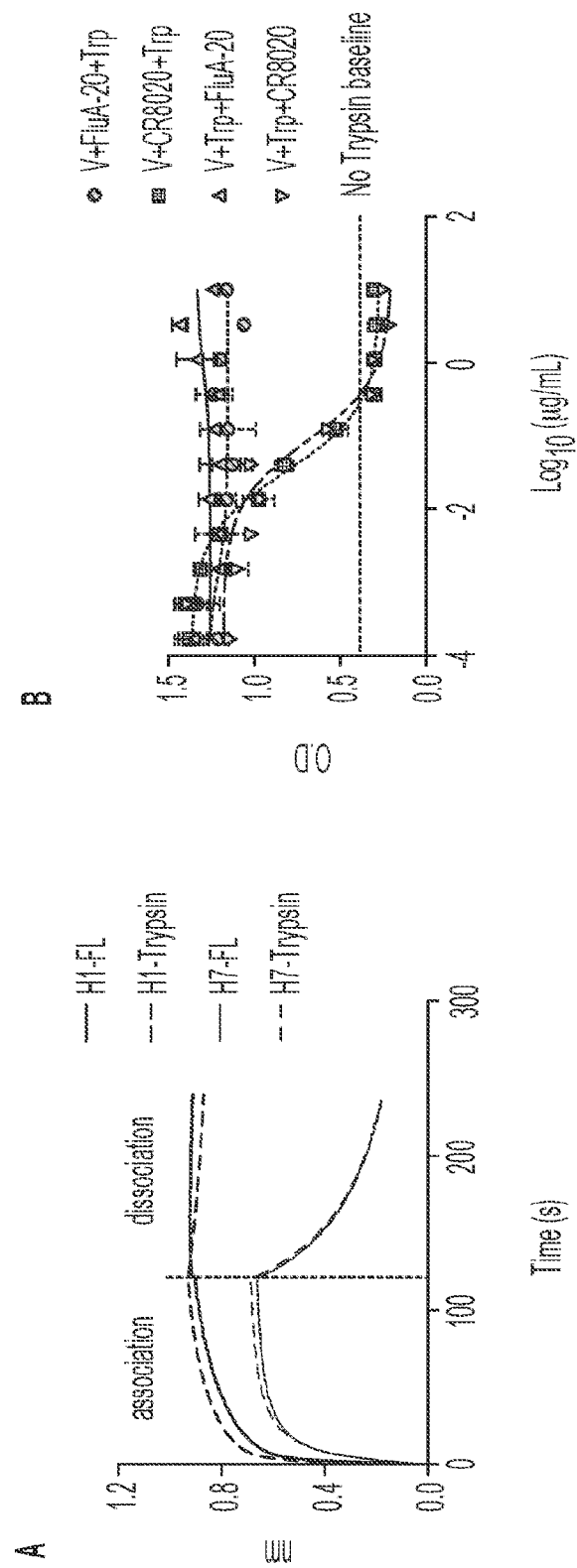
FIGS. 14A-B

| Influenza A virus | Crowe lab KD (nM) tested using HA on Octet | | ELISA EC50 (ng/mL); highest dilution tested 1/50,000 | |
|---|---|---|---|---|
| | H5.28 | H5.31 | H5.28 | H5.31 |
| A/California/04/2009 H1N1 | | | 74 | 45 |
| A/Fort Monthouth/1947 (H1N1) | | | 44 | 12 |
| A/South Carolina/1/1918 (H1N1) | 0.11 | 0.17 | 81 | 31 |
| A/Japan/305/1957 (H2N2) | 0.19 | 0.13 | | |
| A/Hong Kong/1/1968 (H3N2) | 75 | 5.4 | 16000 | 24 |
| A/Indonesia/5/2005 (H5N1) | | | 21000 | 27000 |
| A/Vietnam/03/2204 (H5N1) | | 3.8 | 366 | 6 |
| A/Netherlands/219/2003 (H7N9) | ND | 83 | | |
| A/turkey/Wisconsin/1/1966 (H9N2) | 65 | 17 | | |
| A/chicken/Germany/N/1948 (H10N7) | 85 | 14 | | |
| A/duck/Alberta/60/1976 (H12N5) | 71 | 13 | | |
| A/mallard duck/Astrakhan/263/1982 (H14N5) | ND | 2500 | | |

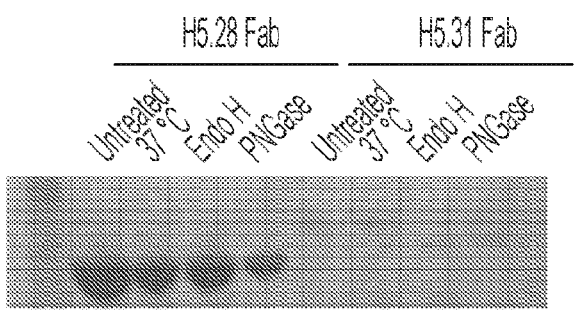
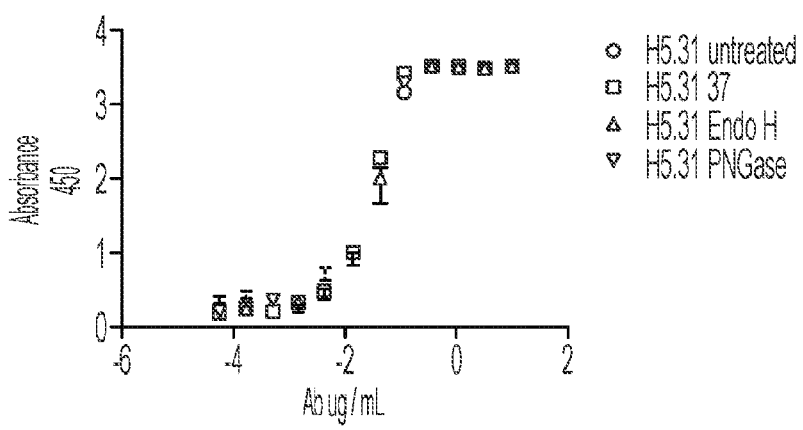
FIG. 19

FIG. 20

A
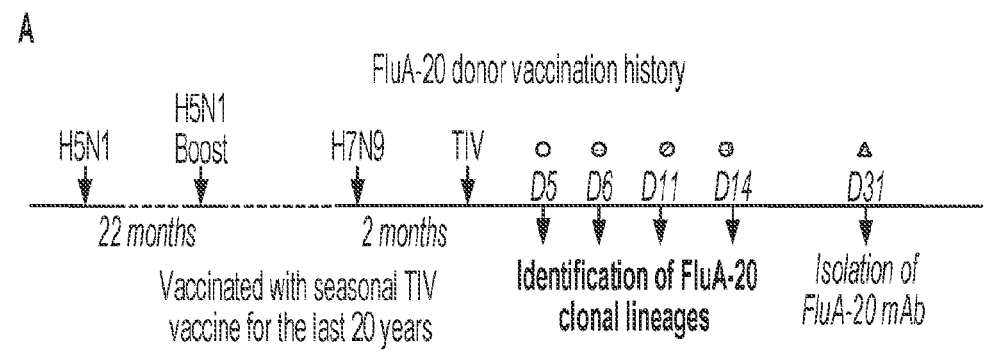
B
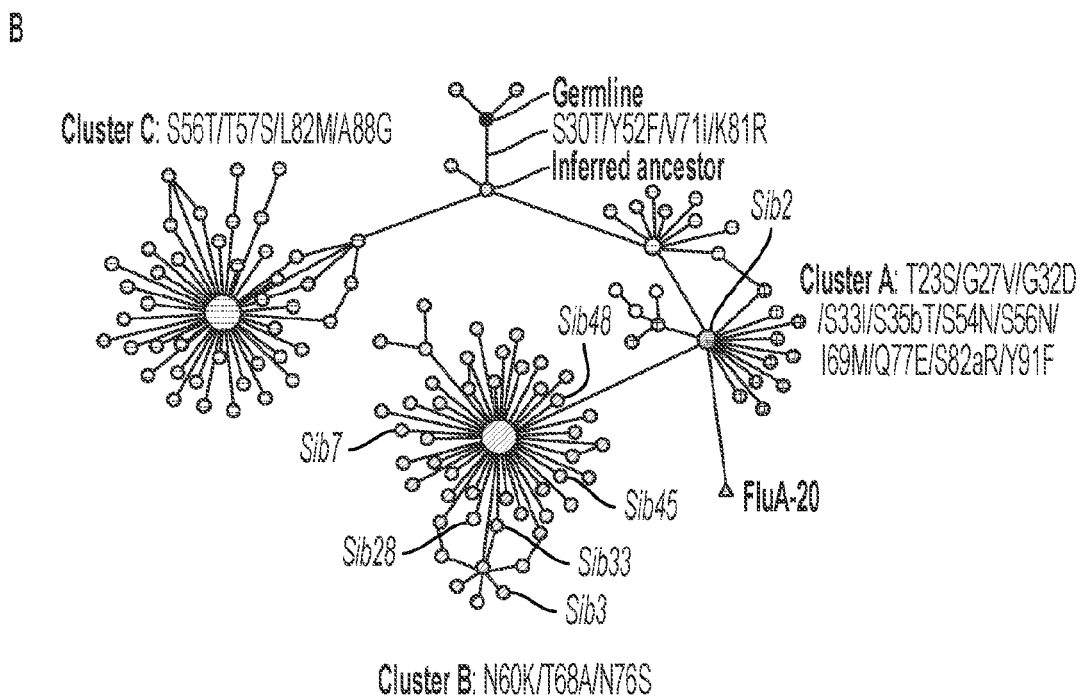
FIGS. 21A-B

FIG. 21C

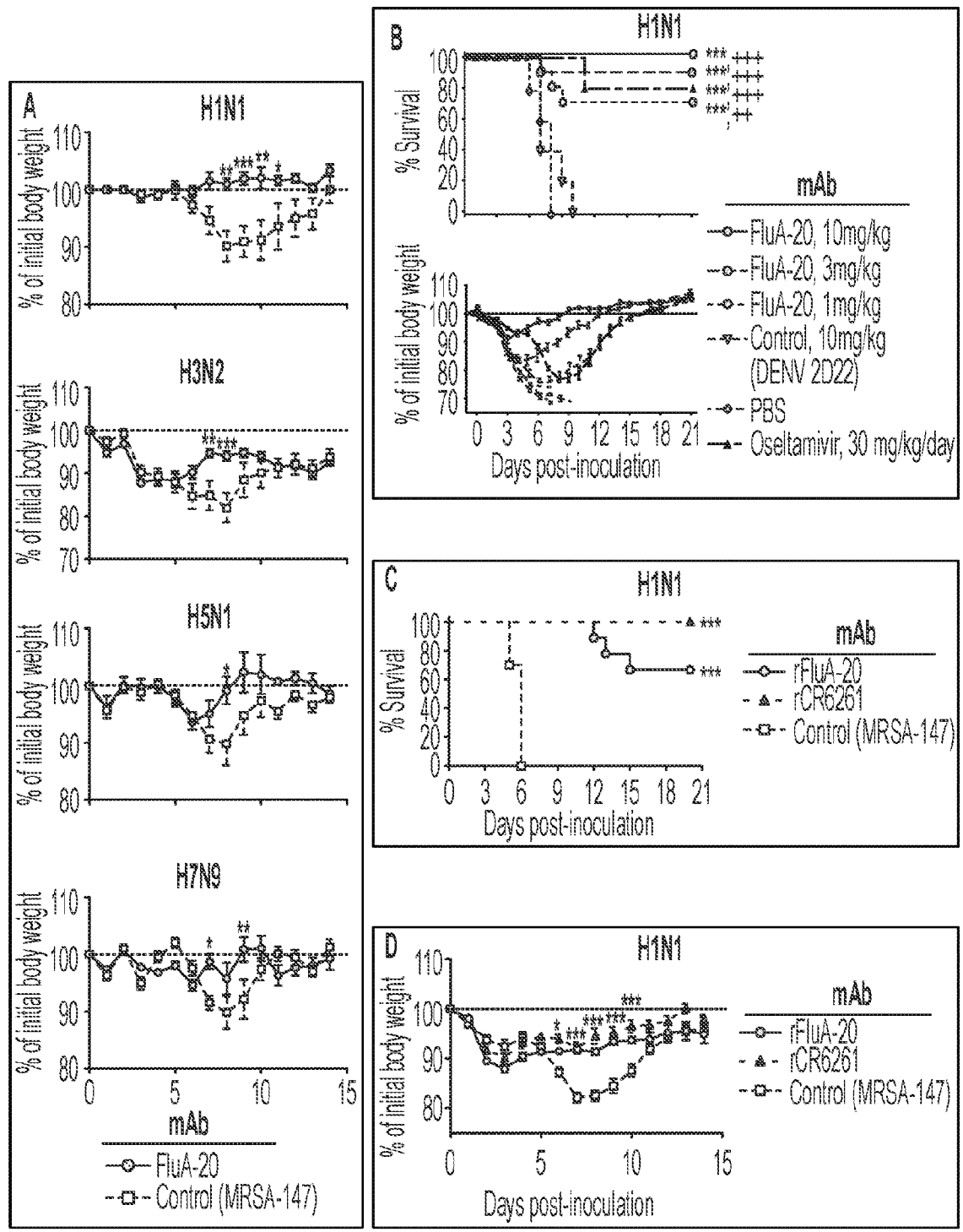
FIGS. 22A-D

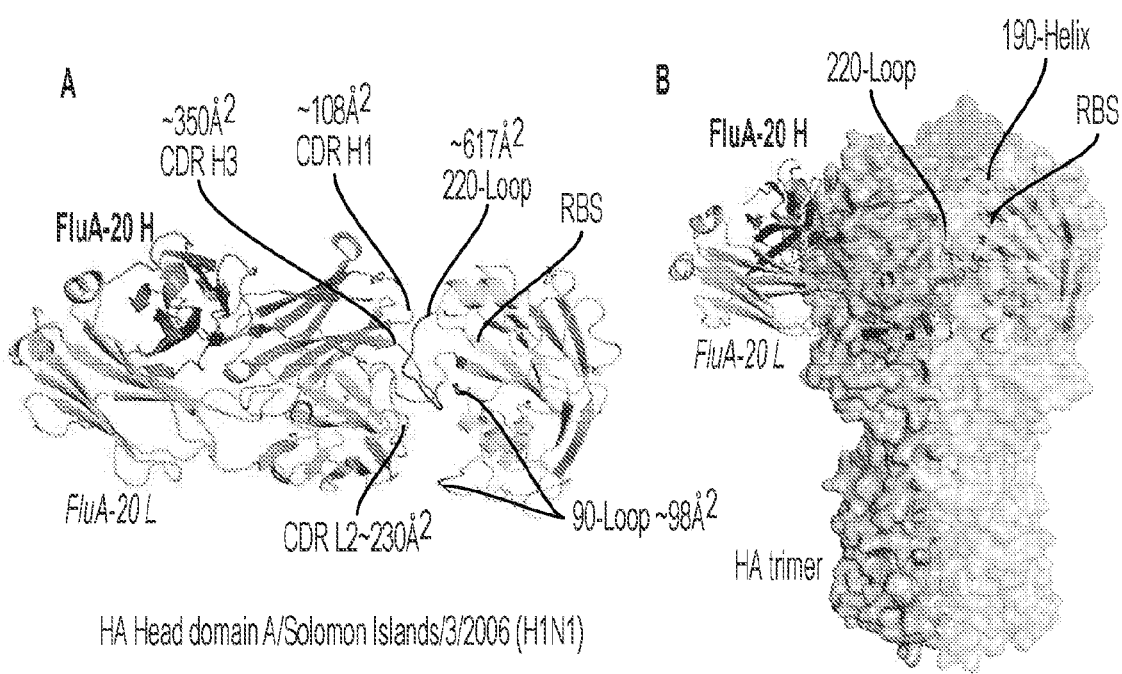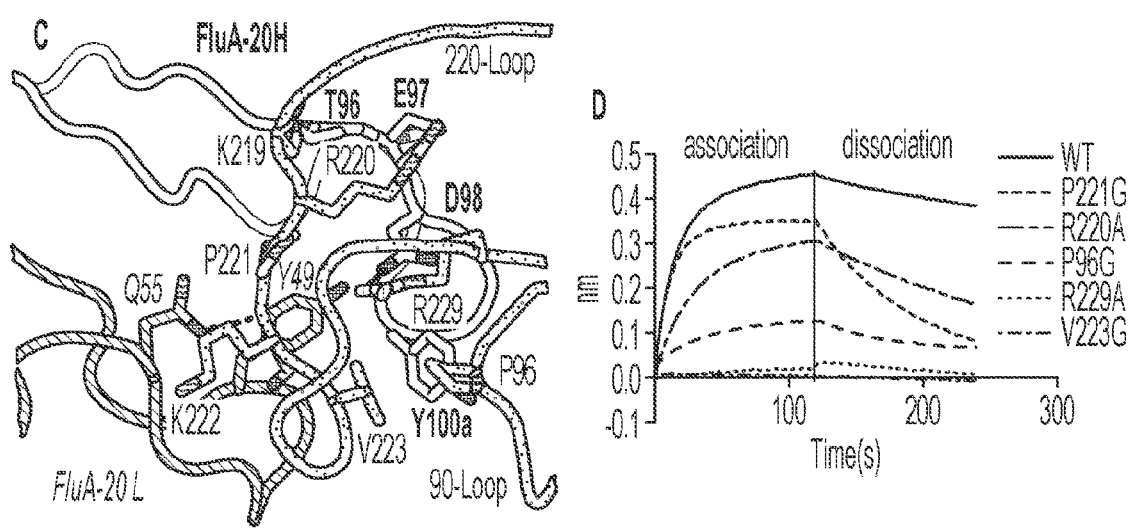
FIGS. 23A-D

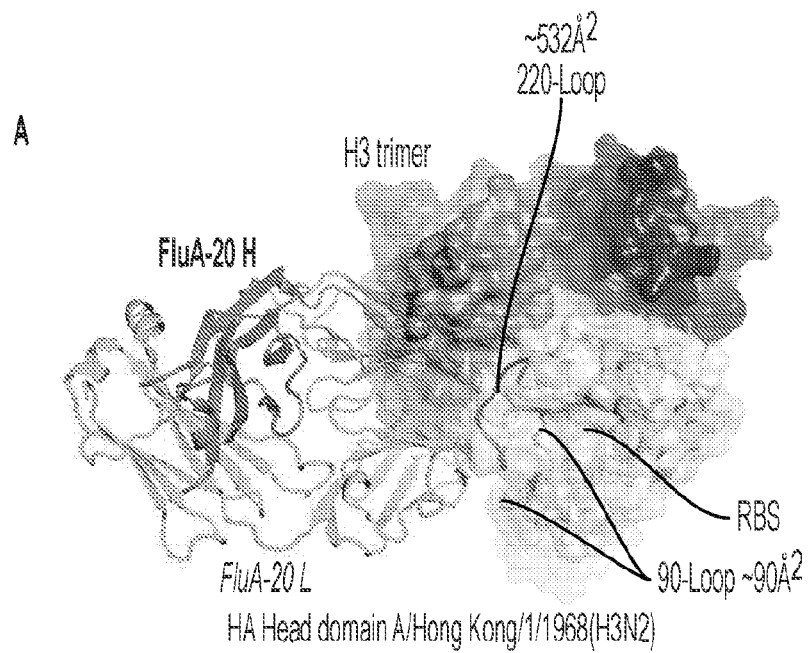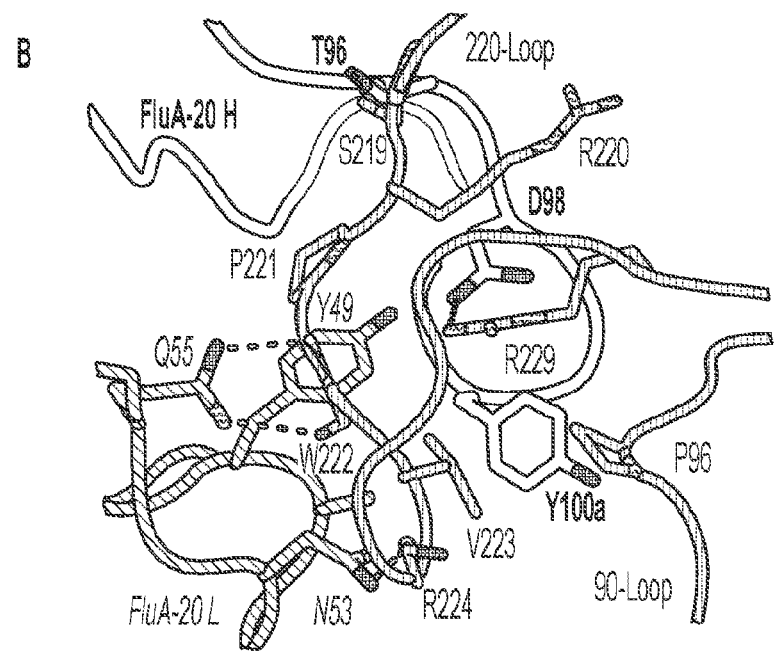
FIGS. 24A-B

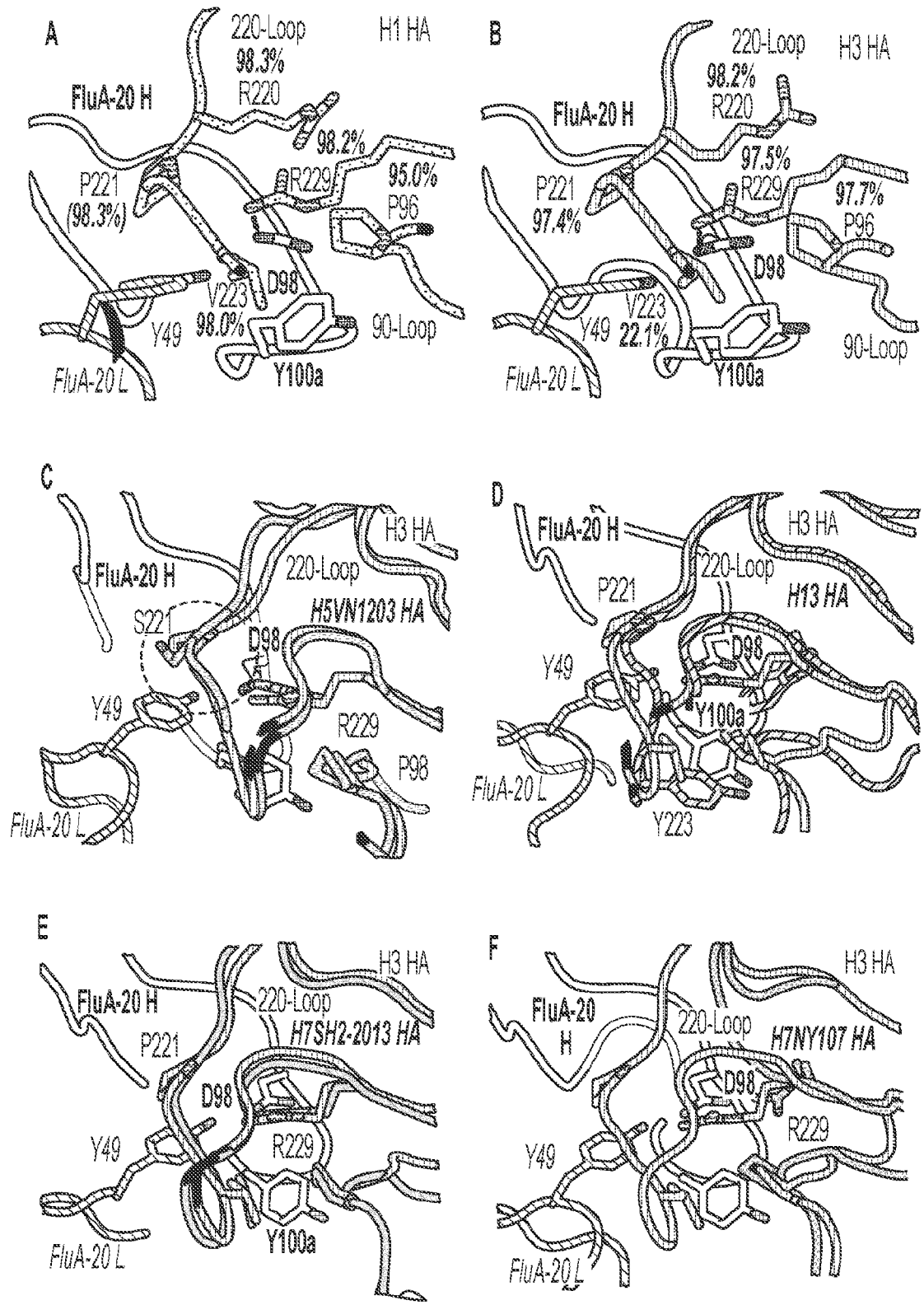
FIGS. 25A-F

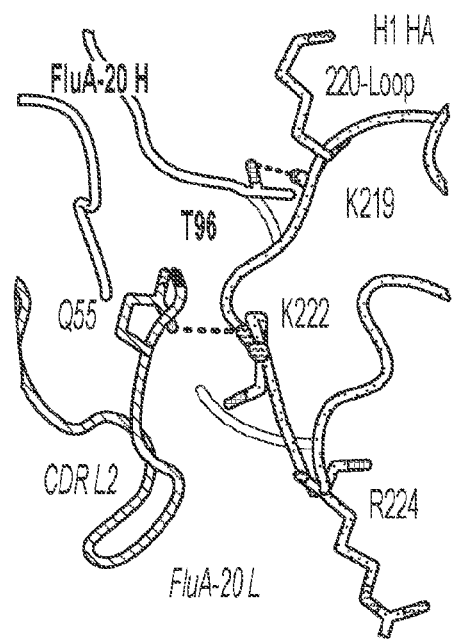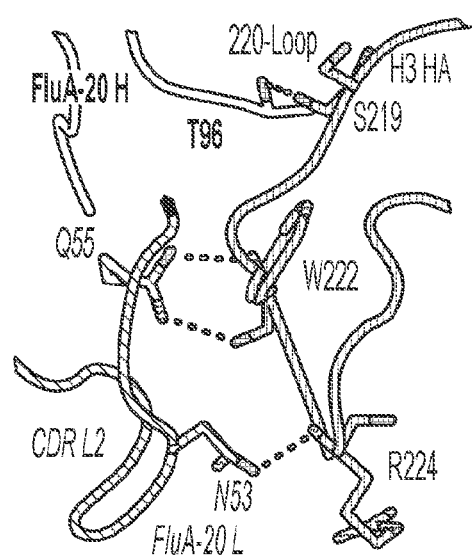
FIGS. 25G-H

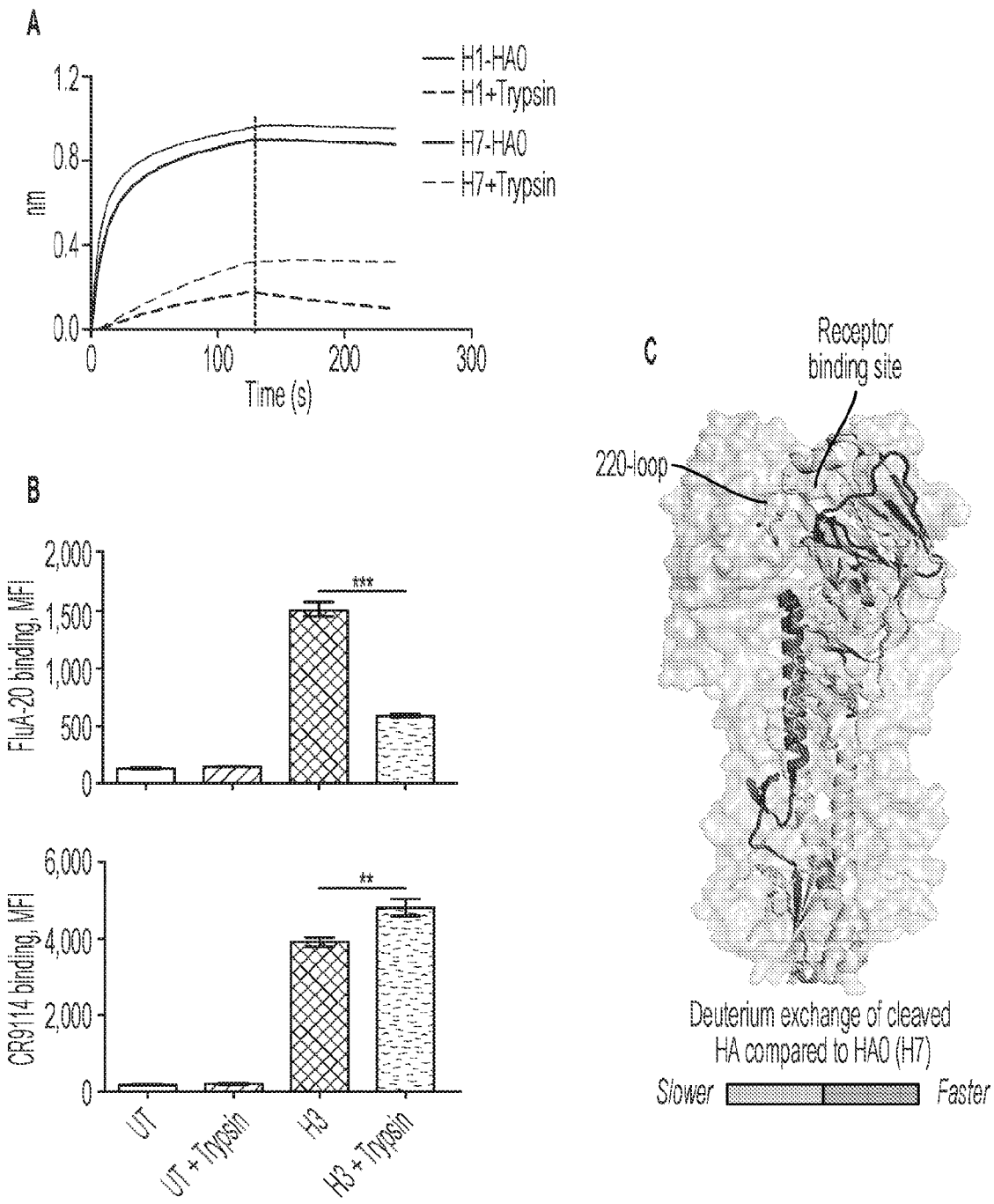
FIGS. 26A-C

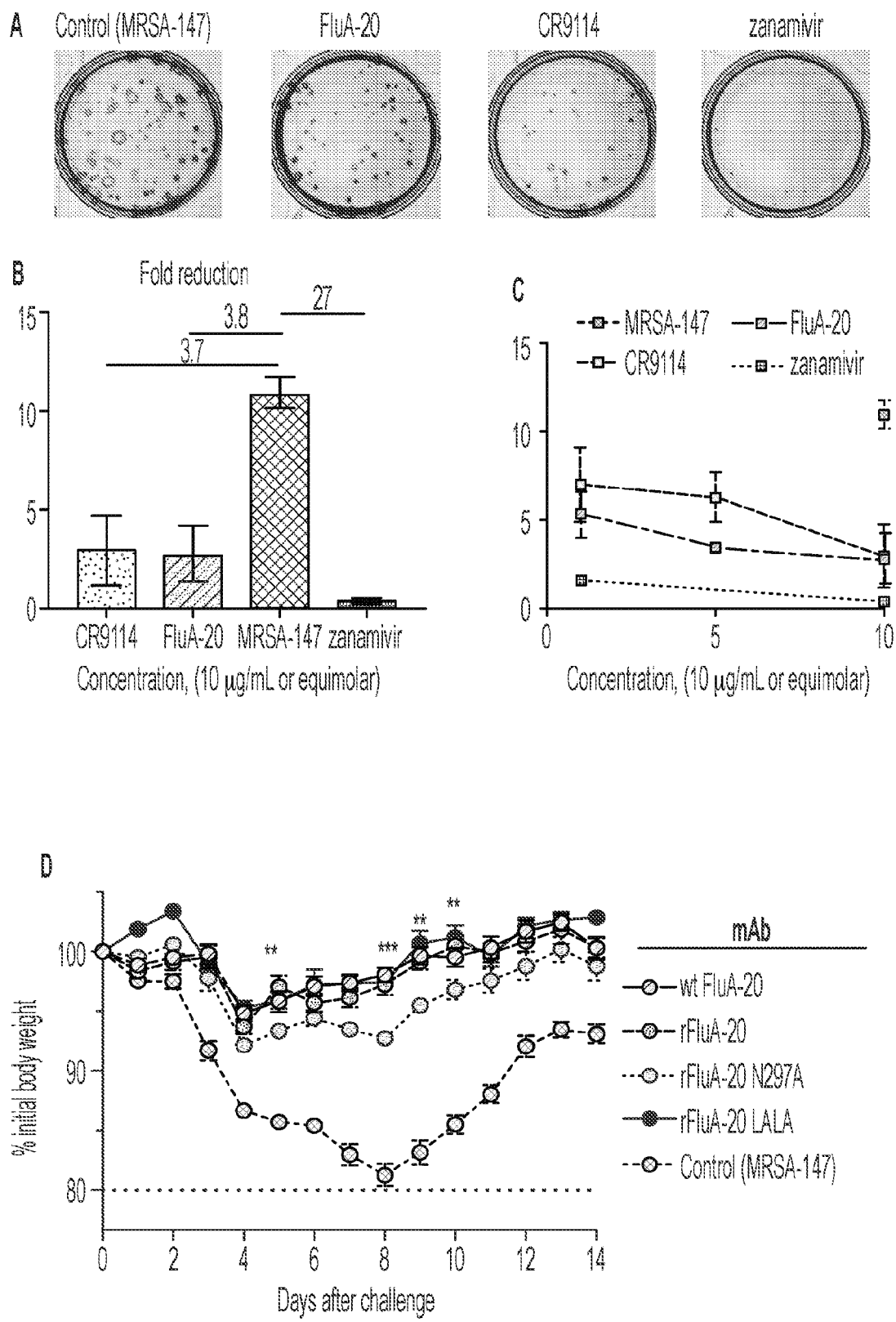
FIGS. 27A-D

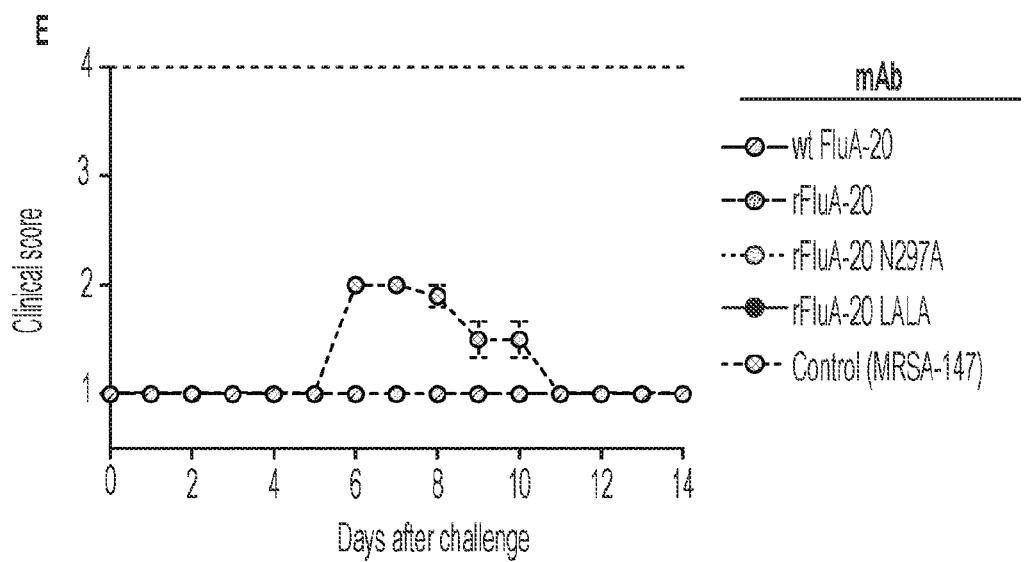
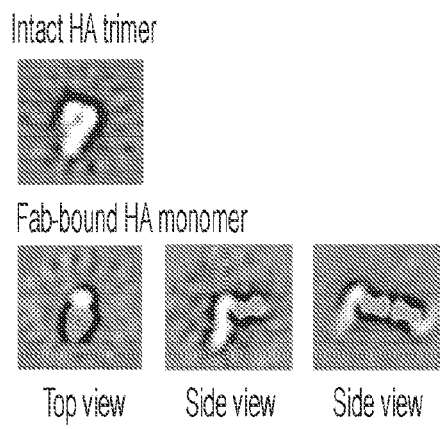
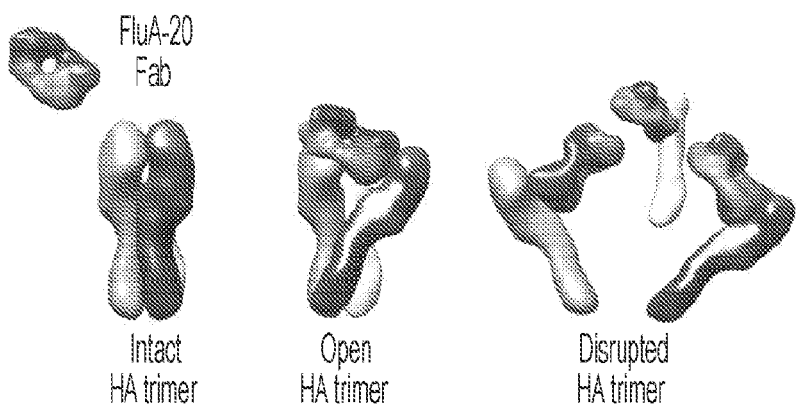
FIGS. 27E-G

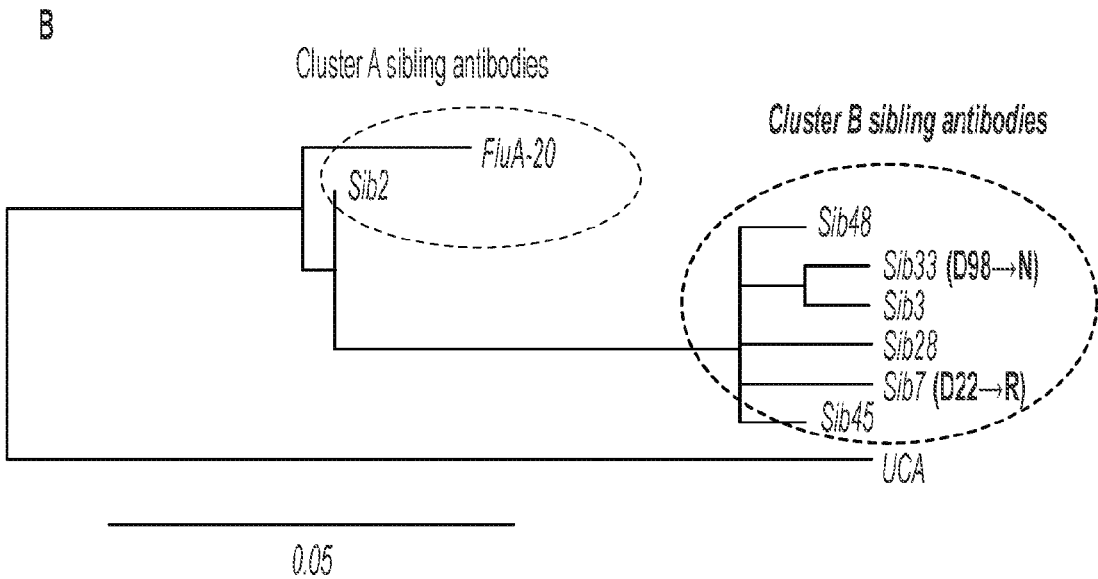

B

Cluster A sibling antibodies / Cluster B sibling antibodies

C

FluA-20_H aligned with UCA_H: 16 mutations
FluA-20: QVQLQESGPGLVKPSETLSLTCSVSGVSVTSDIYYWTWIRQPPGKGLEWIGYIFYNGDTNYN
UCA:    QVQLQESGPGLVKPSETLSLTCTVSGGSVSSGSYYWSWIRQPPGKGLEWIGYIYYSGSTNYN FluA-20: PSLKSRVTMSIDTSKNEFSLRLTSVTAADTAVYFCARGTELLGYCSSGSCPNHWGQGTLVTV
UCA:    PSLKSRVTISVDTSKNQFSLKLSSVTAADTAVYYCARGTELIGYCSGGSCPNHWGQGTLVTV

FluA-20_L aligned with UCA_L: 11 mutations
FluA-20: DIQMTQSPSSLSASIGDRVTITCRPSQNIRSFLNWFQHKPGKAPKLLIYAASNLQSGVPS
UCA:    DIQMTQSPSSLSASVGDRVTITCRASQSISSYLNWYQQKPGKAPKLLIYAASSLQSGVPS FluA-20: RFSGSGSGTEFTLTIRSLQPEDFATYYCQQSYNTPPTFGQGTKVEIK
UCA:    RFSGSGSGTDFTLTISSLQPEDFATYYCQQSYSTPPTFGQGTKVEIK

▭ CDR1  ▨ CDR2  ▨ CDR3

FIGS. 28B-C

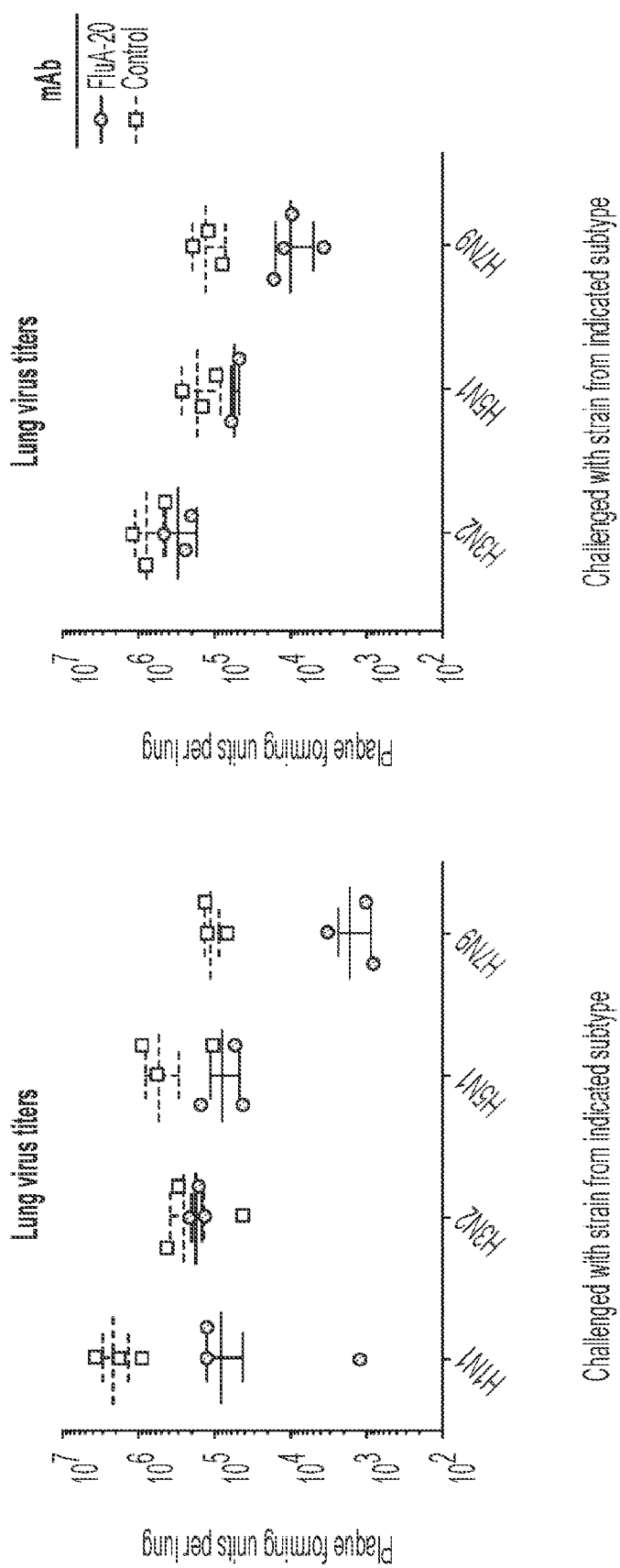
FIGS. 29A-B

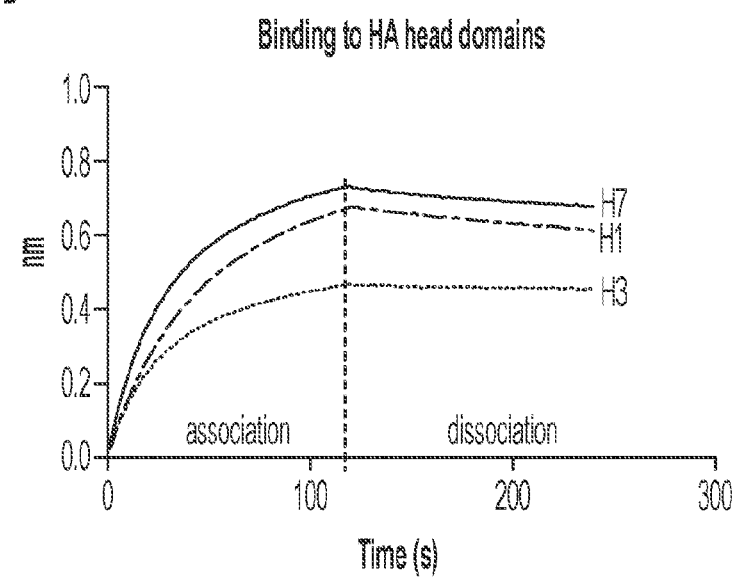
FIGS. 30A-B

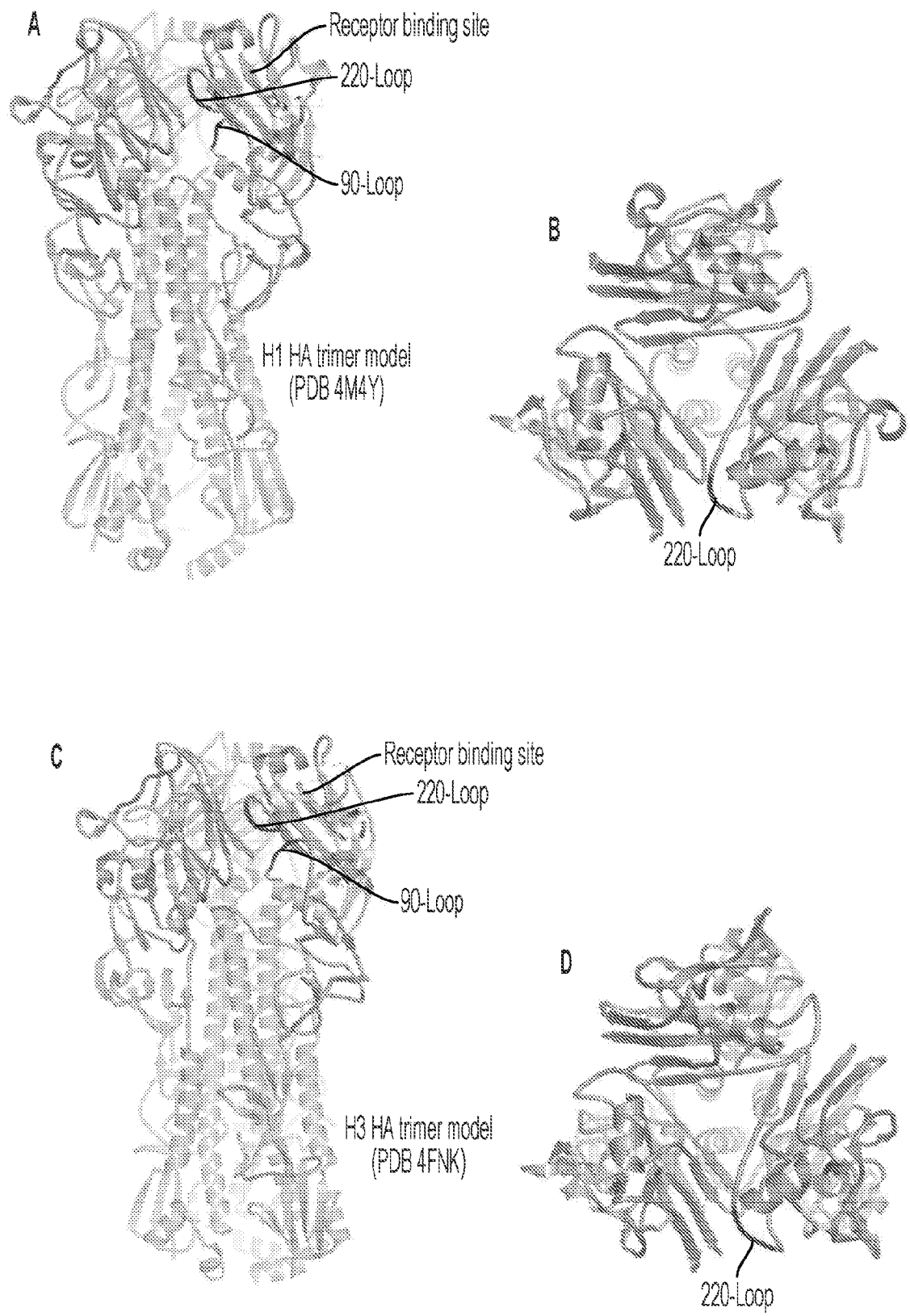
FIGS. 31A-D

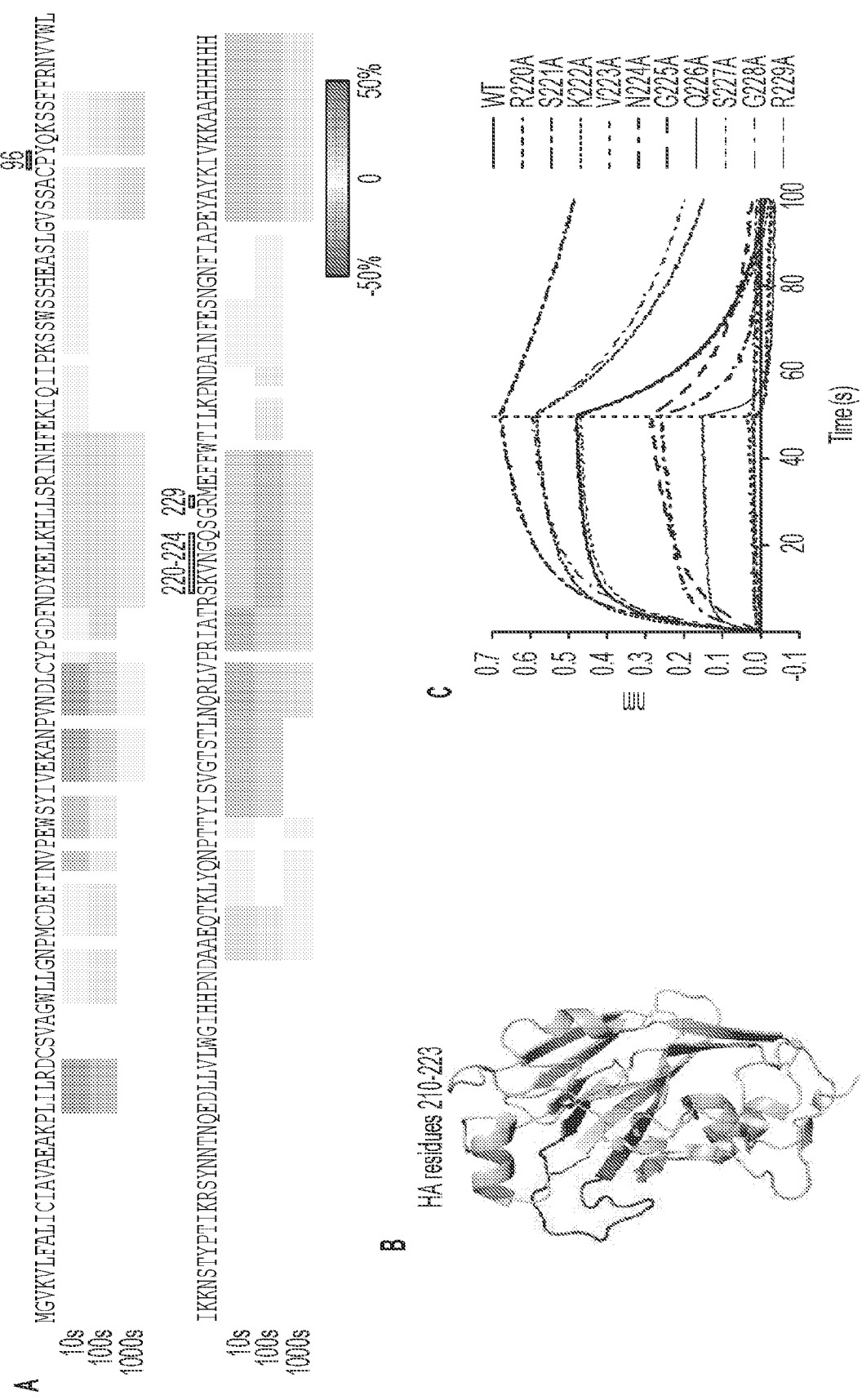
FIGS. 32A-C

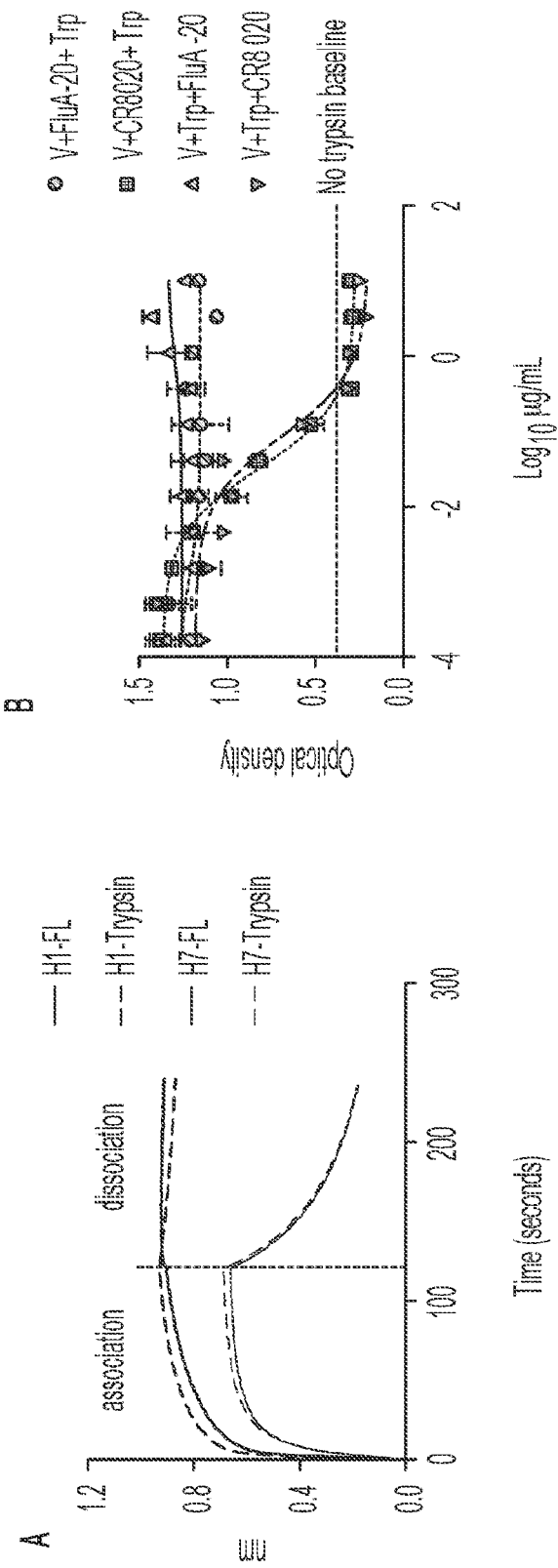
FIGS. 33A-B

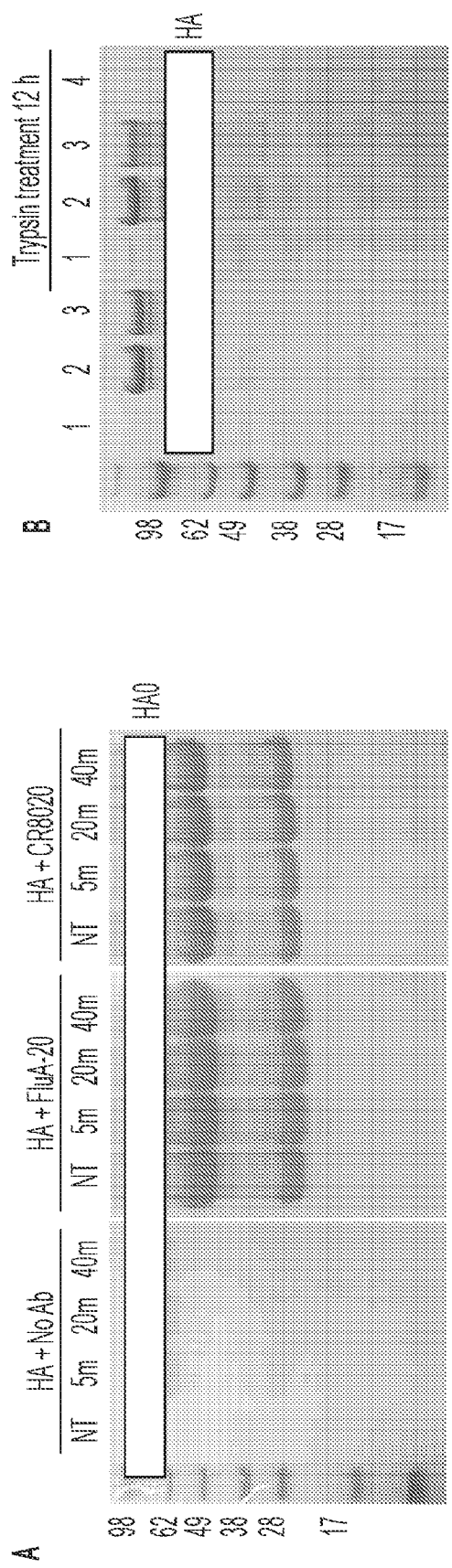
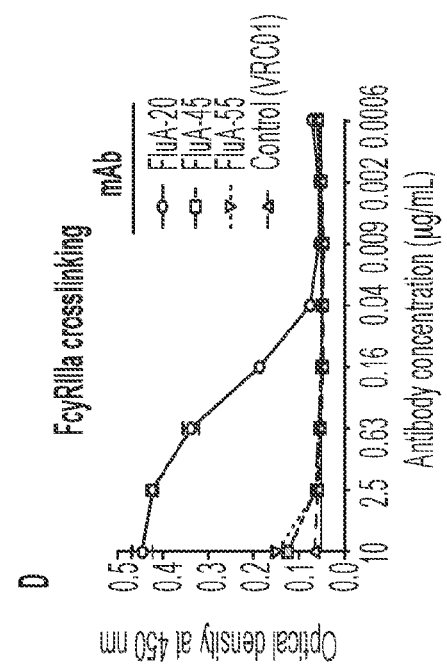
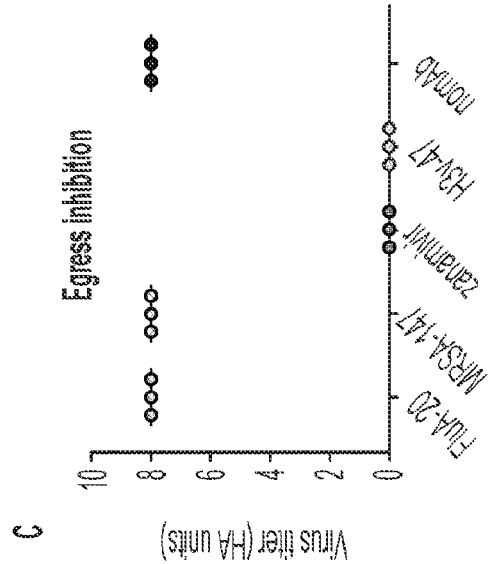
FIGS. 34A-D

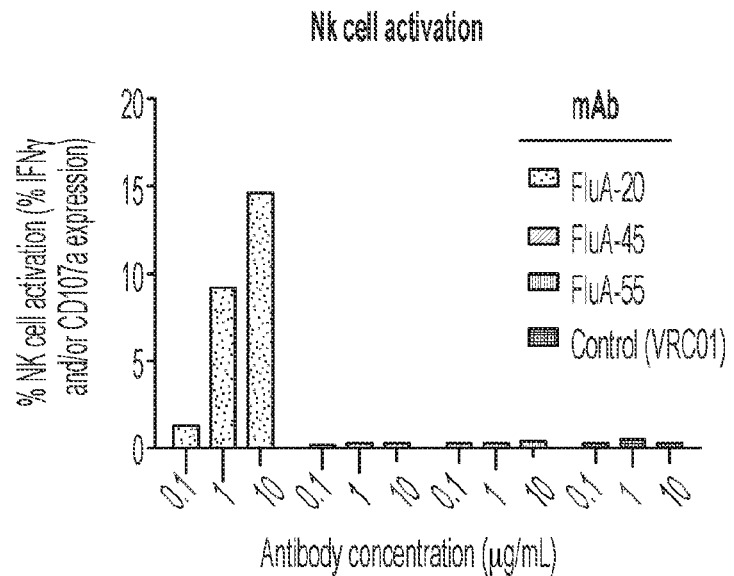
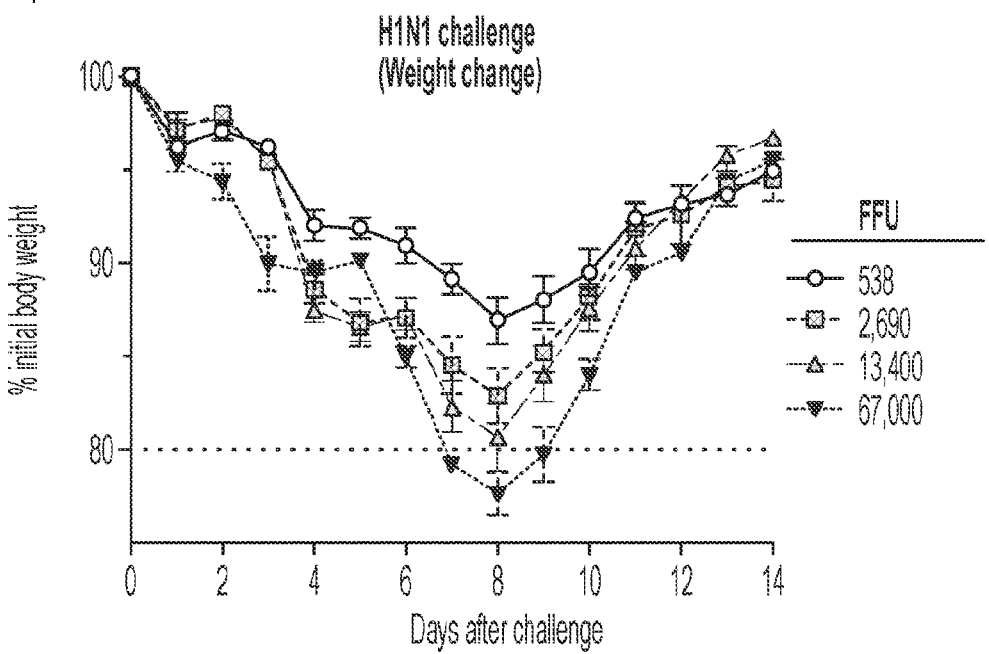
FIGS. 34E-F ered by IAV vaccine or

SEQUENCE LISTING

<160> NUMBER OF SEQ ID NOS: 48

<210> SEQ ID NO 1
<211> LENGTH: 378
<212> TYPE: DNA
<213> ORGANISM: Artificial sequence

```
<220> FEATURE:
<223> OTHER INFORMATION: Synthetic oligonucleotide

<400> SEQUENCE: 1
caggtgcagc tgcaggagtc gggcccagga ctggtgaagc cttcggagac cctgtccctc      60
acctgctctg tctctggtgt ctccgtcacc agtgatattt actactggac ctggatccgg     120
cagcccccag ggaagggact ggagtggatt gggtatatct tttataatgg ggacaccaac     180
tacaacccct ccctcaagag tcgagtcacc atgtcaatcg acacgtccaa gaacgagttc     240
tccctgaggc tgacgtctgt gaccgctgcg gacacggccg tgtatttctg tgccagaggg     300
acagaagatc taggatattg tagtagtggt agctgcccga atcactgggg ccagggaacc     360
ctggtcaccg tctcctca                                                    378

<210> SEQ ID NO 2
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 2
gacatccaga tgacccagtc tccatcctcc ctgtctgcat ctataggaga cagagtcacc      60
atcacttgcc ggccaagtca gaacattcgg agttttttga attggtttca gcacaaacca     120
gggaaagccc caaaactcct gatctatgct gcatccaatt tgcagagtgg ggtcccatca     180
aggttcagtg gcagtggatc tgggacagaa ttcactctca ccatcaggag tctgcaacct     240
gaagattttg caacttacta ctgtcaacag agttacaata cccctccgac gttcggccaa     300
gggaccaagg tggaaatcaa a                                                321

<210> SEQ ID NO 3
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 3
gaggtgcagc tggtggagtc tggggggaggc ttggtccagc ctgggggggtc cctgagactc     60 tcctgtgcag cctctggatt caccttcagt acctattgga tgacctgggt ccgccaggct     120
ccagggaagg ggctggagtg ggtggccaac ataaaccaag atggaggtga gaaatacttt     180
gtggactctg tgaagggccg attcaccatc tccagagaca cgccaaaaa ttcactgttt       240 ctgcaaatga acaccctgag agccgaggac acggctgtgt attactgtgc gagaggattt     300
ttggagaggt tattattggg ccgacaaggg gcctactact acgggatgga cgtctggggc     360
caagggacca cggtcaccgt ctcctca                                          387

<210> SEQ ID NO 4
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 4
gacatccaga tgacccagtc tccatcctcc ctgtctgcat ctgtcggaga cagagtcagc      60
atgacttgcc gggcaagtca gatcattagt agttccttaa attggtatca gcagaaacca     120
```

```
gggaaagccc ctaaactcct gatctatgct gcatccaatt tacaaagtgg ggtcccatca    180
aggttcagtg gcagtggatc tgggacagat ttcactctca ccatcagcag tctgcaacct    240
gaagattttg caacttacta ctgtcaacag agttacagta cccctccgga gctcactttc    300
ggcggaggga ccaaggtgga aatcaaa                                        327
```

<210> SEQ ID NO 5  
<211> LENGTH: 387  
<212> TYPE: DNA  
<213> ORGANISM: Artificial sequence  
<220> FEATURE:  
<223> OTHER INFORMATION: Synthetic oligonucleotide

<400> SEQUENCE: 5

```
gaggtgcagc tggtgcagtc tgggggaggc ttggtccaac ctggggggtc cctgagactc     60
tcctgtgaag cctctagatt cacctccagt tcctattgga taacctgggt ccgccaggct    120
ccagggaagg ggctggagtg ggtggccaat ataaagcaag atggaagtga aaatactttt    180
gtggactctg tgaagggccg attcaccatc tccagagaca cgccagtaa ttcactgtat     240 ctgcaaatga gcagcctgag agccgaggac acggctgtgt attactgtgc gagaggattt    300
ttggagaggt tattattggg ccgacaaggg gcctactact acgggatgga cgtctggggc    360
caagggacca cggtcaccgt ctcctca                                        387
```

<210> SEQ ID NO 6  
<211> LENGTH: 327  
<212> TYPE: DNA  
<213> ORGANISM: Artificial sequence  
<220> FEATURE:  
<223> OTHER INFORMATION: Synthetic oligonucleotide

<400> SEQUENCE: 6

```
gacatccaga tgacccagtc tccatcctcc ctgtctgcat ctgtcggaga cagagtcacc     60
atgacttgcc gggcaagtca gagcattagt agttccttaa attggtatca acagaaacca    120
gggaaagccc ctaaactcct gatctatgct gcatccaatt tacaaagtgg ggtcccatca    180
aggttcagtg gcagtggatc tgggacagat ttcactctca ccatcagcag tctgcaacct    240
gaagattttg caacttacta ctgtcaacag agttacacta tgcctccgga gctcactttc    300
ggcggaggga ccaaggtaca gatcaaa                                        327
```

<210> SEQ ID NO 7  
<211> LENGTH: 372  
<212> TYPE: DNA  
<213> ORGANISM: Artificial sequence  
<220> FEATURE:  
<223> OTHER INFORMATION: Synthetic oligonucleotide

<400> SEQUENCE: 7

```
caggtgcagc tggtggagtc gggcccagga ctggtgaagc cttcacagac cctgtccctc     60
acctgcactg tctctggtgg ctccatcaac agtagtcatt ccttctggag ttggatccgc    120
cagcccgccg ggaagggact ggagtggatt gggcgtatct attccactgg gaactccaac    180
tacaacccct ccctcaagag tcgagtcacc atatcattag acacgtccaa gaaccaattc    240
tccctgaagt tgagctctgt gaccgccgca gacacggccg tgtattactg tgcgagagaa    300
tccctatgga atccggatta ctactactac atggacgtct ggggcaaagg gaccctggtc    360
accgtctcct ca                                                        372
```

-continued

```
<210> SEQ ID NO 8
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 8
gacattgtga tgacccagtc tccatcctcc ctgtctgcat ctgtaggaga cagagtcacc      60
atcacttgcc gggcaagtca gagctttagc agccatttga attggtatca gcagaaacca     120
ggcagagccc ctgacctcct gatctatgct gcatccagtt tgcacagtgg ggtcccatca     180
aggttcagtg gcagtggatc tgggacagat ttcactctca ccatcagcag tcttcaacct     240
gaagactttg cagtttacta ctgtcaacag agttacagtg tcccgtacac ttttggccag     300
gggaccaagc tgcagatcaa a                                               321

<210> SEQ ID NO 9
<211> LENGTH: 126
<212> TYPE: PRT
<213> ORGANISM: Artificial sequence
<220> FEATURE:
<223> OTHER INFORMATION: Synthetic amino acid

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Ser Val Ser Gly Val Ser Val Thr Ser Asp
                20                  25                  30

Ile Tyr Tyr Trp Thr Trp Ile Arg Gln Pro Pro Gly Lys Gly Leu Glu
            35                  40                  45

Trp Ile Gly Tyr Ile Phe Tyr Asn Gly Asp Thr Asn Tyr Asn Pro Ser
        50                  55                  60

Leu Lys Ser Arg Val Thr Met Ser Ile Asp Thr Ser Lys Asn Glu Phe
65                  70                  75                  80

Ser Leu Arg Leu Thr Ser Val Thr Ala Ala Asp Thr Ala Val Tyr Phe
                85                  90                  95

Cys Ala Arg Gly Thr Glu Asp Leu Gly Tyr Cys Ser Ser Gly Ser Cys
            100                 105                 110

Pro Asn His Trp Gly Gln Gly Thr Leu Val Thr Val Ser Ser
        115                 120                 125

<210> SEQ ID NO 10
<211> LENGTH: 107
<212> TYPE: PRT
<213> ORGANISM: Artificial sequence
<220> FEATURE:
<223> OTHER INFORMATION: Synthetic amino acid

<400> SEQUENCE: 10

Asp Ile Gln Met Thr Gln Ser Pro Ser Ser Leu Ser Ala Ser Ile Gly
1               5                   10                  15

Asp Arg Val Thr Ile Thr Cys Arg Pro Ser Gln Asn Ile Arg Ser Phe
                20                  25                  30

Leu Asn Trp Phe Gln His Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Glu Phe Thr Leu Thr Ile Arg Ser Leu Gln Pro
65                  70                  75                  80
```

Glu Asp Phe Ala Thr Tyr Tyr Cys Gln Gln Ser Tyr Asn Thr Pro Pro
                85                  90                  95

Thr Phe Gly Gln Gly Thr Lys Val Glu Ile Lys
            100                 105

<210> SEQ ID NO 11
<211> LENGTH: 129
<212> TYPE: PRT
<213> ORGANISM: Artificial sequence
<220> FEATURE:
<223> OTHER INFORMATION: Synthetic amino acid

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Gly Glu Lys Tyr Phe Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Thr Leu Arg Ala Glu Asp Thr Ala Val Tyr Tyr Cys
                85                  90                  95

Ala Arg Gly Phe Leu Glu Arg Leu Leu Leu Gly Arg Gln Gly Ala Tyr
            100                 105                 110

Tyr Tyr Gly Met Asp Val Trp Gly Gln Gly Thr Thr Val Thr Val Ser
        115                 120                 125

Ser

<210> SEQ ID NO 12
<211> LENGTH: 109
<212> TYPE: PRT
<213> ORGANISM: Artificial sequence
<220> FEATURE:
<223> OTHER INFORMATION: Synthetic amino acid

<400> SEQUENCE: 12

Asp Ile Gln Met Thr Gln Ser Pro Ser Ser Leu Ser Ala Ser Val Gly
1               5                   10                  15

Asp Arg Val Ser Met Thr Cys Arg Ala Ser Gln Ile Ile Ser Ser Ser
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Glu Leu Thr Phe Gly Gly Gly Thr Lys Val Glu Ile Lys
            100                 105

<210> SEQ ID NO 13
<211> LENGTH: 129
<212> TYPE: PRT
<213> ORGANISM: Artificial sequence

```
<220> FEATURE:
<223> OTHER INFORMATION: Synthetic amino acid

<400> SEQUENCE: 13

Glu Val Gln Leu Val Gln Ser Gly Gly Gly Leu Val Gln Pro Gly Gly
1               5                   10                  15

Ser Leu Arg Leu Ser Cys Glu Ala Ser Arg Phe Thr Ser Ser Ser Tyr
            20                  25                  30

Trp Ile Thr Trp Val Arg Gln Ala Pro Gly Lys Gly Leu Glu Trp Val
        35                  40                  45

Ala Asn Ile Lys Gln Asp Gly Ser Glu Lys Tyr Phe Val Asp Ser Val
    50                  55                  60

Lys Gly Arg Phe Thr Ile Ser Arg Asp Asn Ala Ser Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Phe Leu Glu Arg Leu Leu Leu Gly Arg Gln Gly Ala Tyr
            100                 105                 110

Tyr Tyr Gly Met Asp Val Trp Gly Gln Gly Thr Thr Val Thr Val Ser
        115                 120                 125

Ser

<210> SEQ ID NO 14
<211> LENGTH: 109
<212> TYPE: PRT
<213> ORGANISM: Artificial sequence
<220> FEATURE:
<223> OTHER INFORMATION: Synthetic amino acid

<400> SEQUENCE: 14

Asp Ile Gln Met Thr Gln Ser Pro Ser Ser Leu Ser Ala Ser Val Gly
1               5                   10                  15

Asp Arg Val Thr Met Thr Cys Arg Ala Ser Gln Ser Ile Ser Ser Ser
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Met Pro Pro
                85                  90                  95

Glu Leu Thr Phe Gly Gly Gly Thr Lys Val Gln Ile Lys
            100                 105

<210> SEQ ID NO 15
<211> LENGTH: 124
<212> TYPE: PRT
<213> ORGANISM: Artificial sequence
<220> FEATURE:
<223> OTHER INFORMATION: Synthetic amino acid

<400> SEQUENCE: 15

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Asn Ser Ser
            20                  25                  30

His Ser Phe Trp Ser Trp Ile Arg Gln Pro Ala Gly Lys Gly Leu Glu
```

```
                35                  40                  45
Trp Ile Gly Arg Ile Tyr Ser Thr Gly Asn Ser Asn Tyr Asn Pro Ser
         50                  55                  60

Leu Lys Ser Arg Val Thr Ile Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Leu Trp Asn Pro Asp Tyr Tyr Tyr Met Asp
            100                 105                 110

Val Trp Gly Lys Gly Thr Leu Val Thr Val Ser Ser
        115                 120

<210> SEQ ID NO 16
<211> LENGTH: 107
<212> TYPE: PRT
<213> ORGANISM: Artificial sequence
<220> FEATURE:
<223> OTHER INFORMATION: Synthetic amino acid

<400> SEQUENCE: 16

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Phe Ser Ser His
            20                  25                  30

Leu Asn Trp Tyr Gln Gln Lys Pro Gly Arg Ala Pro Asp Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser Tyr Ser Val Pro Tyr
                85                  90                  95

Thr Phe Gly Gln Gly Thr Lys Leu Gln Ile Lys
            100                 105

<210> SEQ ID NO 17
<211> LENGTH: 10
<212> TYPE: PRT
<213> ORGANISM: Artificial sequence
<220> FEATURE:
<223> OTHER INFORMATION: Synthetic amino acid

<400> SEQUENCE: 17

Gly Val Ser Val Thr Ser Asp Ile Tyr Tyr
1               5                   10

<210> SEQ ID NO 18
<211> LENGTH: 7
<212> TYPE: PRT
<213> ORGANISM: Artificial sequence
<220> FEATURE:
<223> OTHER INFORMATION: Synthetic amino acid

<400> SEQUENCE: 18

Ile Phe Tyr Asn Gly Asp Thr
1               5

<210> SEQ ID NO 19
<211> LENGTH: 18
<212> TYPE: PRT
<213> ORGANISM: Artificial sequence
```

```
<220> FEATURE:
<223> OTHER INFORMATION: Synthetic amino acid

<400> SEQUENCE: 19

Ala Arg Gly Thr Glu Asp Leu Gly Tyr Cys Ser Ser Gly Ser Cys Pro
1               5                   10                  15

Asn His

<210> SEQ ID NO 20
<211> LENGTH: 8
<212> TYPE: PRT
<213> ORGANISM: Artificial sequence
<220> FEATURE:
<223> OTHER INFORMATION: Synthetic amino acid

<400> SEQUENCE: 20

Gly Phe Thr Phe Ser Thr Tyr Trp
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic amino acid

<400> SEQUENCE: 21

Ile Asn Gln Asp Gly Gly Glu Lys
1               5

<210> SEQ ID NO 22
<211> LENGTH: 22
<212> TYPE: PRT
<213> ORGANISM: Artificial sequence
<220> FEATURE:
<223> OTHER INFORMATION: Synthetic amino acid

<400> SEQUENCE: 22

Ala Arg Gly Phe Leu Glu Arg Leu Leu Leu Gly Arg Gln Gly Ala Tyr
1               5                   10                  15

Tyr Tyr Gly Met Asp Val
            20

<210> SEQ ID NO 23
<211> LENGTH: 8
<212> TYPE: PRT
<213> ORGANISM: Artificial sequence
<220> FEATURE:
<223> OTHER INFORMATION: Synthetic amino acid

<400> SEQUENCE: 23

Arg Phe Thr Ser Ser Ser Tyr Trp
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic amino acid

<400> SEQUENCE: 24

Ile Lys Gln Asp Gly Ser Glu Lys
1               5
```

```
<210> SEQ ID NO 25
<211> LENGTH: 22
<212> TYPE: PRT
<213> ORGANISM: Artificial sequence
<220> FEATURE:
<223> OTHER INFORMATION: Synthetic amino acid

<400> SEQUENCE: 25

Ala Arg Gly Phe Leu Glu Arg Leu Leu Leu Gly Arg Gln Gly Ala Tyr
1               5                   10                  15

Tyr Tyr Gly Met Asp Val
            20

<210> SEQ ID NO 26
<211> LENGTH: 10
<212> TYPE: PRT
<213> ORGANISM: Artificial sequence
<220> FEATURE:
<223> OTHER INFORMATION: Synthetic amino acid

<400> SEQUENCE: 26

Gly Gly Ser Ile Asn Ser Ser His Ser Phe
1               5                   10

<210> SEQ ID NO 27
<211> LENGTH: 7
<212> TYPE: PRT
<213> ORGANISM: Artificial sequence
<220> FEATURE:
<223> OTHER INFORMATION: Synthetic amino acid

<400> SEQUENCE: 27

Ile Tyr Ser Thr Gly Asn Ser
1               5

<210> SEQ ID NO 28
<211> LENGTH: 16
<212> TYPE: PRT
<213> ORGANISM: Artificial sequence
<220> FEATURE:
<223> OTHER INFORMATION: Synthetic amino acid

<400> SEQUENCE: 28

Ala Arg Glu Ser Leu Trp Asn Pro Asp Tyr Tyr Tyr Met Asp Val
1               5                   10                  15

<210> SEQ ID NO 29
<211> LENGTH: 6
<212> TYPE: PRT
<213> ORGANISM: Artificial sequence
<220> FEATURE:
<223> OTHER INFORMATION: Synthetic amino acid

<400> SEQUENCE: 29

Gln Asn Ile Arg Ser Phe
1               5

<210> SEQ ID NO 30
<211> LENGTH: 3
<212> TYPE: PRT
<213> ORGANISM: Artificial sequence
<220> FEATURE:
<223> OTHER INFORMATION: Synthetic amino acid

<400> SEQUENCE: 30

Ala Ala Ser
1
```

```
<210> SEQ ID NO 31
<211> LENGTH: 9
<212> TYPE: PRT
<213> ORGANISM: Artificial sequence
<220> FEATURE:
<223> OTHER INFORMATION: Synthetic amino acid

<400> SEQUENCE: 31

Gln Gln Ser Tyr Asn Thr Pro Pro Thr
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic amino acid

<400> SEQUENCE: 32

Gln Ile Ile Ser Ser Ser
1               5

<210> SEQ ID NO 33
<211> LENGTH: 3
<212> TYPE: PRT
<213> ORGANISM: Artificial sequence
<220> FEATURE:
<223> OTHER INFORMATION: Synthetic amino acid

<400> SEQUENCE: 33

Ala Ala Ser
1

<210> SEQ ID NO 34
<211> LENGTH: 11
<212> TYPE: PRT
<213> ORGANISM: Artificial sequence
<220> FEATURE:
<223> OTHER INFORMATION: Synthetic amino acid

<400> SEQUENCE: 34

Gln Gln Ser Tyr Ser Thr Pro Pro Glu Leu Thr
1               5                   10

<210> SEQ ID NO 35
<211> LENGTH: 6
<212> TYPE: PRT
<213> ORGANISM: Artificial sequence
<220> FEATURE:
<223> OTHER INFORMATION: Synthetic amino acid

<400> SEQUENCE: 35

Gln Ser Ile Ser Ser Ser
1               5

<210> SEQ ID NO 36
<211> LENGTH: 3
<212> TYPE: PRT
<213> ORGANISM: Artificial sequence
<220> FEATURE:
<223> OTHER INFORMATION: Synthetic amino acid

<400> SEQUENCE: 36

Ala Ala Ser
1
```

```
<210> SEQ ID NO 37
<211> LENGTH: 11
<212> TYPE: PRT
<213> ORGANISM: Artificial sequence
<220> FEATURE:
<223> OTHER INFORMATION: Synthetic amino acid

<400> SEQUENCE: 37

Gln Gln Ser Tyr Thr Met Pro Pro Glu Leu Thr
1               5                   10

<210> SEQ ID NO 38
<211> LENGTH: 6
<212> TYPE: PRT
<213> ORGANISM: Artificial sequence
<220> FEATURE:
<223> OTHER INFORMATION: Synthetic amino acid

<400> SEQUENCE: 38

Gln Ser Phe Ser Ser His
1               5

<210> SEQ ID NO 39
<211> LENGTH: 3
<212> TYPE: PRT
<213> ORGANISM: Artificial sequence
<220> FEATURE:
<223> OTHER INFORMATION: Synthetic amino acid

<400> SEQUENCE: 39

Ala Ala Ser
1

<210> SEQ ID NO 40
<211> LENGTH: 9
<212> TYPE: PRT
<213> ORGANISM: Artificial sequence
<220> FEATURE:
<223> OTHER INFORMATION: Synthetic amino acid

<400> SEQUENCE: 40

Gln Gln Ser Tyr Ser Val Pro Tyr Thr
1               5

<210> SEQ ID NO 41
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 41

Met Gly Val Lys Val Leu Phe Ala Leu Ile Cys Ile Ala Val Ala Glu
1               5                   10                  15

Ala Lys Pro Leu Ile Leu Arg Asp Cys Ser Val Ala Gly Trp Leu Leu
                20                  25                  30

Gly Asn Pro Met Cys Asp Glu Phe Ile Asn Val Pro Glu Trp Ser Tyr
            35                  40                  45

Ile Val Glu Lys Ala Asn Pro Val Asn Asp Leu Cys Tyr Pro Ser Asp
        50                  55                  60

Phe Asn Asp Tyr Glu Glu Leu Lys His Leu Leu Ser Arg Ile Asn His
65                  70                  75                  80

Phe Glu Lys Ile Gln Ile Ile Pro Lys Ser Ser Trp Ser Ser His Glu
                85                  90                  95
```

```
Ala Ser Leu Gly Val Ser Ser Ala Cys Pro Tyr Gln Gly Lys Ser Ser
            100                 105                 110

Phe Phe Arg Asn Val Val Trp Leu
            115                 120

<210> SEQ ID NO 42
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 42

Ile Lys Lys Asn Ser Thr Tyr Pro Thr Ile Lys Arg Ser Tyr Asn Asn
1               5                   10                  15

Thr Asn Gln Glu Asp Leu Leu Val Leu Trp Gly Ile His His Pro Asn
            20                  25                  30

Asp Ala Ala Glu Gln Thr Lys Leu Tyr Gln Asn Pro Thr Thr Tyr Ile
            35                  40                  45

Ser Val Gly Thr Ser Thr Leu Asn Gln Arg Leu Val Pro Arg Ile Ala
        50                  55                  60

Thr Arg Ser Lys Val Asn Gly Gln Ser Gly Arg Met Glu Phe Phe Trp
65                  70                  75                  80

Thr Ile Leu Lys Pro Asn Asp Ala Ile Asn Phe Glu Ser Asn Gly Asn
                85                  90                  95

Phe Ile Ala Pro Glu Tyr Ala Tyr Lys Ile Val Lys Lys Ala Ala His
            100                 105                 110

His His His His His
        115

<210> SEQ ID NO 43
<211> LENGTH: 231
<212> TYPE: PRT
<213> ORGANISM: Artificial sequence
<220> FEATURE:
<223> OTHER INFORMATION: Synthetic polypeptide

<400> SEQUENCE: 43

Gln Val Gln Leu Glu Glu Ser Gly Pro Gly Leu Val Lys Pro Ser Glu
1               5                   10                  15

Thr Leu Ser Leu Thr Cys Ser Val Ser Gly Val Ser Val Thr Ser Asp
            20                  25                  30

Ile Tyr Tyr Trp Thr Trp Ile Arg Gln Pro Pro Gly Lys Gly Leu Glu
            35                  40                  45

Trp Ile Gly Tyr Ile Phe Tyr Asn Gly Asp Thr Asn Tyr Asn Pro Ser
        50                  55                  60

Leu Lys Ser Arg Val Thr Met Ser Ile Asp Thr Ser Lys Asn Glu Phe
65                  70                  75                  80

Ser Leu Arg Leu Thr Ser Val Thr Ala Ala Asp Thr Ala Val Tyr Phe
                85                  90                  95

Cys Ala Arg Gly Thr Glu Asp Leu Gly Tyr Cys Ser Ser Gly Ser Cys
            100                 105                 110

Pro Asn His Trp Gly Gln Gly Thr Leu Val Thr Val Asp Ile Val Met
            115                 120                 125

Thr Gln Ser Pro Ser Ser Leu Ser Ala Ser Ile Gly Asp Arg Val Thr
        130                 135                 140

Ile Thr Cys Arg Pro Ser Gln Asn Ile Arg Ser Phe Leu Asn Trp Phe
```

```
145                 150                 155                 160

Gln His Lys Pro Gly Lys Ala Pro Lys Leu Leu Ile Tyr Ala Ala Ser
                165                 170                 175

Asn Leu Gln Ser Gly Val Pro Ser Arg Phe Ser Gly Ser Gly Ser Gly
                180                 185                 190

Thr Glu Phe Thr Leu Thr Ile Arg Ser Leu Gln Pro Glu Asp Phe Ala
            195                 200                 205

Thr Tyr Tyr Cys Gln Gln Ser Tyr Asn Thr Pro Pro Thr Phe Gly Gln
        210                 215                 220

Gly Thr Lys Val Glu Ile Lys
225                 230

<210> SEQ ID NO 44
<211> LENGTH: 231
<212> TYPE: PRT
<213> ORGANISM: Artificial sequence
<220> FEATURE:
<223> OTHER INFORMATION: Synthetic polypeptide

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Thr Glu Asp Leu Gly Tyr Cys Ser Gly Gly Ser Cys
            100                 105                 110

Pro Asn His Trp Gly Gln Gly Thr Leu Val Thr Val Asp Ile Gln Met
        115                 120                 125

Thr Gln Ser Pro Ser Ser Leu Ser Ala Ser Val Gly Asp Arg Val Thr
    130                 135                 140

Ile Thr Cys Arg Ala Ser Gln Ser Ile Ser Ser Tyr Leu Asn Trp Tyr
145                 150                 155                 160

Gln Gln Lys Pro Gly Lys Ala Pro Lys Leu Leu Ile Tyr Ala Ala Ser
                165                 170                 175

Ser Leu Gln Ser Gly Val Pro Ser Arg Phe Ser Gly Ser Gly Ser Gly
                180                 185                 190

Thr Asp Phe Thr Leu Thr Ile Ser Ser Leu Gln Pro Glu Asp Phe Ala
            195                 200                 205

Thr Tyr Tyr Cys Gln Gln Ser Tyr Ser Thr Pro Pro Thr Phe Gly Gln
        210                 215                 220

Gly Thr Lys Val Glu Ile Lys
225                 230

<210> SEQ ID NO 45
<211> LENGTH: 570
<212> TYPE: PRT
<213> ORGANISM: Artificial sequence
<220> FEATURE:
<223> OTHER INFORMATION: Synthetic polypeptide
```

<400> SEQUENCE: 45

Ser Lys Ser Arg Gly Tyr Lys Met Asn Thr Gln Ile Leu Val Phe Ala
1               5                   10                  15

Leu Val Ala Ser Ile Pro Thr Asn Ala Asp Lys Ile Cys Leu Gly His
            20                  25                  30

His Ala Val Ser Asn Gly Thr Lys Val Asn Thr Leu Thr Glu Arg Gly
        35                  40                  45

Val Glu Val Val Asn Ala Thr Glu Thr Val Glu Arg Thr Asn Val Pro
    50                  55                  60

Arg Ile Ser Lys Gly Lys Arg Thr Asp Leu Gly Gln Cys Gly Leu Leu
65                  70                  75                  80

Gly Thr Ile Thr Gly Pro Pro Gln Cys Asp Gln Phe Leu Glu Phe Ser
            85                  90                  95

Ala Asp Leu Ile Ile Glu Arg Arg Glu Gly Ser Asp Val Cys Tyr Pro
            100                 105                 110

Gly Lys Phe Val Asn Glu Glu Ala Leu Arg Gln Ile Leu Arg Glu Ser
        115                 120                 125

Gly Gly Ile Asp Lys Glu Thr Met Gly Phe Thr Tyr Ser Gly Ile Arg
    130                 135                 140

Thr Asn Gly Thr Thr Ser Ala Cys Arg Arg Ser Gly Ser Ser Phe Tyr
145                 150                 155                 160

Ala Glu Met Lys Trp Leu Leu Ser Asn Thr Asp Asn Ala Ala Phe Pro
            165                 170                 175

Gln Met Thr Lys Ser Tyr Lys Asn Thr Arg Lys Asp Pro Ala Leu Ile
            180                 185                 190

Ile Trp Gly Ile His His Ser Gly Ser Thr Thr Glu Gln Thr Lys Leu
    195                 200                 205

Tyr Gly Ser Gly Asn Lys Leu Ile Thr Val Gly Ser Ser Asn Tyr Gln
    210                 215                 220

Gln Ser Phe Val Pro Ser Pro Gly Ala Arg Pro Gln Val Asn Gly Gln
225                 230                 235                 240

Ser Gly Arg Ile Asp Phe His Trp Leu Ile Leu Asn Pro Asn Asp Thr
            245                 250                 255

Val Thr Phe Ser Phe Asn Gly Ala Phe Ile Ala Pro Asp Arg Ala Ser
            260                 265                 270

Phe Leu Arg Gly Lys Ser Met Gly Ile Gln Ser Glu Val Gln Val Asp
            275                 280                 285

Ala Asn Cys Glu Gly Asp Cys Tyr His Ser Gly Gly Thr Ile Ile Ser
    290                 295                 300

Asn Leu Pro Phe Gln Asn Ile Asn Ser Arg Ala Val Gly Lys Cys Pro
305                 310                 315                 320

Arg Tyr Val Lys Gln Glu Ser Leu Leu Leu Ala Thr Gly Met Lys Asn
            325                 330                 335

Val Pro Glu Ile Pro Lys Arg Arg Arg Gly Leu Phe Gly Ala Ile
            340                 345                 350

Ala Gly Phe Ile Glu Asn Gly Trp Glu Phe Leu Ile Asp Gly Trp Tyr
        355                 360                 365

Gly Phe Arg His Gln Asn Ala Gln Gly Glu Gly Thr Ala Ala Asp Tyr
    370                 375                 380

Lys Ser Thr Gln Ser Ala Ile Asp Gln Ile Thr Gly Lys Leu Asn Arg
385                 390                 395                 400

Leu Ile Glu Lys Thr Asn Gln Gln Phe Glu Leu Ile Asp Asn Glu Phe

```
                        405                 410                 415
Thr Glu Val Glu Arg Gln Ile Gly Asn Val Ile Asn Trp Thr Arg Asp
                420                 425                 430

Ser Met Thr Glu Val Trp Ser Tyr Asn Ala Glu Leu Leu Val Ala Met
            435                 440                 445

Glu Asn Gln His Thr Ile Asp Leu Ala Asp Ser Glu Met Asn Lys Leu
450                 455                 460

Tyr Glu Arg Val Lys Arg Gln Leu Arg Glu Asn Ala Glu Glu Asp Gly
465                 470                 475                 480

Thr Gly Cys Phe Glu Ile Phe His Lys Cys Asp Asp Cys Met Ala
                485                 490                 495

Ser Ile Arg Asn Asn Thr Tyr Asp His Ser Lys Tyr Arg Glu Glu Ala
                500                 505                 510

Ile Gln Asn Arg Ile Gln Ile Asp Pro Val Asp Lys Ile Glu Glu
                515                 520                 525

Ile Leu Ser Lys Ile Tyr His Ile Glu Asn Glu Ile Ala Arg Ile Lys
                530                 535                 540

Lys Leu Ile Gly Glu Ala Pro Gly Gly Ile Glu Gly Arg Glu Asn Leu
545                 550                 555                 560

Tyr Phe Gln Gly His His His His
                565                 570

<210> SEQ ID NO 46
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 47
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Thr Trp Val Arg Gln Ala Pro Gly Lys Gly Leu Glu Trp Val
```

```
                35                  40                  45
Ala Asn Ile Asn Gln Asp Gly Gly Glu Lys Tyr Phe Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Thr Leu Arg Ala Glu Asp Thr Ala Val Tyr Tyr Cys
                85                  90                  95

Ala Arg Gly Phe Leu Glu Arg Leu Leu Leu Gly Arg Gln Gly Ala Tyr
            100                 105                 110

Tyr Tyr Gly Met Asp Val
        115

<210> SEQ ID NO 48
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 48

Glu Val Gln Leu Val Gln Ser Gly Gly Gly Leu Val Gln Pro Gly Gly
1               5                   10                  15

Ser Leu Arg Leu Ser Cys Glu Ala Ser Arg Phe Thr Ser Ser Ser Tyr
            20                  25                  30

Trp Ile Thr Trp Val Arg Gln Ala Pro Gly Lys Gly Leu Glu Trp Val
        35                  40                  45

Ala Asn Ile Lys Gln Asp Gly Ser Glu Lys Tyr Phe Val Asp Ser Val
    50                  55                  60

Lys Gly Arg Phe Thr Ile Ser Arg Asp Asn Ala Ser Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Phe Leu Glu Arg Leu Leu Leu Gly Arg Gln Gly Ala Tyr
            100                 105                 110

Tyr Tyr Gly Met Asp Val
        115
```

HUMAN MONOCLONAL ANTIBODIES TO A NEW UNIVERSAL INFLUENZA A HEMAGGLUTININ HEAD DOMAIN EPITOPE

PRIORITY CLAIM

This application is a national phase application under 35 U.S.C. § 371 of International Application No. PCT/US2019/047606, filed Aug. 22, 2019, which claims benefit of priority to U.S. Provisional Application Ser. No. 62/721,675, filed Aug. 23, 2018, and U.S. Provisional Application Ser. No. 62/848,301, filed May 15, 2019, the entire contents of each of which are hereby incorporated by reference.

STATEMENT REGARDING FEDERALLY FUNDED RESEARCH

This invention was made with government support under grant number U19 AI117905 and contract HHSN272201400024C awarded by the National Institutes of Health. The government has certain rights in the invention.

FIELD OF THE DISCLOSURE

The present disclosure relates generally to the fields of medicine, infectious disease, and immunology. More particular, the disclosure relates to human antibodies binding to a previously unrecognized epitope in the head domain of influenza A hemagglutinin, the novel epitope recognized by such antibodies, and methods of use therefor.

BACKGROUND

The hypervariable influenza A virus (IAV) has been a primary cause of respiratory illnesses in the human population for centuries. Currently, IAV strains from subtypes H1N1 and H3N2, as well as influenza B viruses, are in human circulation and cause seasonal epidemics. Additionally, other zoonotic IAVs with H1, H3, H5, H6, H7, H9 and H10 HAs have caused sporadic outbreaks of human infections, some with exceedingly high morbidity and mortality rates (Freidl et al., 2014; Neumann and Kawaoka, 2015). Seasonal influenza vaccines are available, but due to the immense variability and continuous mutations in influenza viruses, current vaccines provide protection only against close isolates of the vaccine strains and, therefore, needs to be updated annually, according to predictions of which viruses will be next in circulation (Carrat and Flahault, 2007). Poor matches of the predicted vaccine strains with drifted seasonal viruses can lead to severe influenza seasons (Bridges et al., 2000; Carrat and Flahault, 2007; Nordin et al., 2001). More unpredictably, new influenza viruses emerging from genomic reassortment with drastically altered antigenicity can cause global pandemics. For instance, during the 2009 global pandemic influenza season, a new H1N1 lineage, from reassortment of a variety of avian, pig and human viruses, infected 10-21% of the world population and caused over half a million deaths (Dawood et al., 2012; Shrestha et al., 2011). Hence, investigation of how the immune response can counteract the ever-changing nature of influenza is of great importance for the development of new vaccines and therapeutics.

The hemagglutinin of influenza is one of the two main glycoproteins on the viral surface and a major target of neutralizing antibodies. Based on structure and antigenicity, there are eighteen defined subtypes (H1-H18) of IAV HAs belonging to two broad groups (Nobusawa et al., 1991; Russell et al., 2004; Tong et al., 2013). Influenza HA consists of an antigenically variable globular head domain containing the receptor-binding site (RBS) for viral attachment and a more conserved stem domain that mediates fusion of viral and cell membranes in the endosome (Carr and Kim, 1993; Weis et al., 1988; Wilson et al., 1981). The HA head domain is the immunodominant domain of the protein and is the target of most antibody responses induced by IAV vaccine or infection (Altman et al., 2015; Angeletti et al., 2017; Caton et al., 1982; Das et al., 2013; Gerhard et al., 1981). However, due to the high level of sequence and antigenic diversity occurring in the HA head domain and the incorporation of large number of glycans in this region to evade immune recognition, most head domain specific antibodies exhibit a very narrow breadth of protection.

Nonetheless, two classes of broadly neutralizing antibodies (bnAbs) against influenza HA have been discovered previously (Julien et al., 2012; Laursen and Wilson, 2013). The stem-targeted bnAbs, such as the murine monoclonal antibody (mAb) C179, human mAbs CR6261, F10 and A6, are the first class of antibodies found to have broad and heterosubtypic activities, some of which can target nearly all strains of HA across various subtypes and subgroups, e.g., CR9114, MEDI8852 (Corti et al., 2010; Corti et al., 2011; Dreyfus et al., 2013; Dreyfus et al., 2012; Ekiert et al., 2009; Ekiert et al., 2011; Friesen et al., 2014; Joyce et al., 2016; Kallewaard et al., 2016; Kashyap et al., 2008; Kashyap et al., 2010; Lang et al., 2017; Okuno et al., 1993; Smirnov et al., 1999). These bnAbs recognize the highly conserved stem region and block the viral fusion machinery. As a class, anti-stem antibodies tend to be less potent in virus neutralization assays in comparison to RBS-specific antibodies, but stem antibodies often also possess the ability to interact with FcγR on effector cells to mediate antibody-dependent cellular cytotoxicity (ADCC) and protection in vivo (Corti et al., 2011; DiLillo et al., 2016; DiLillo et al., 2014; He et al., 2015). These findings have led to the development of several stem-based immunogens for the purposes of "universal" influenza vaccination (Impagliazzo et al., 2015; Nachbagauer et al., 2016; Valkenburg et al., 2016; Yassine et al., 2015). However, inducing broad-spectrum stem antibodies through vaccination may be challenging due to reduced accessibility of this region on the viral surface and/or reduced immunogenicity.

A second class of bnAbs targeting the HA head domain also has been discovered (Ekiert et al., 2012; Hong et al., 2013; Joyce et al., 2016; Lee et al., 2014; Lee et al., 2012; Thornburg et al., 2016; Whittle et al., 2011; Xu et al., 2013; Yoshida et al., 2009; Zhu et al., 2013). Most of these head-targeted bnAbs recognize the relatively conserved RBS and block viral attachment and entry. Unlike stem-targeted bnAbs, which generally have heterosubtypic activities, the head-targeted bnAbs tend to have more restricted patterns of recognition within a subtype; for example, the H1-specific CH65, 5J8, and H2-specific 8M2 antibodies (Laursen and Wilson, 2013; Lee et al., 2014; Schmidt et al., 2015; Thornburg et al., 2016; Whittle et al., 2011; Xu et al., 2013). A few exceptions are C05, F045-92 and S139/1 that can react with the HA head domain from more than one HA subtype (Ekiert et al., 2012; Lee et al., 2014; Lee et al., 2012; Yoshida et al., 2009). However, their heterosubtypic activities are not extensive and they heavily rely on the avidity of bivalent IgG molecules to attain potent binding (~nM $K_D$).

SUMMARY

Treatment of influenza A virus (IAV) and the development of vaccines that broadly protect against highly diverse influenza virus serotypes are of clinical interest, but a significant challenge for vaccine development is defining conserved epitopes that are capable of eliciting cross-reactive protective antibodies in these diverse viruses. Isolation of naturally-occurring broad-spectrum human mAbs to IAV as described herein provides for identification of critical epitopes for rational design of structure-based broadly protective influenza vaccines.

Antibodies disclosed herein recognize an HA head domain epitope at the trimer interface, which site appears to be parallel but not overlapping with the receptor binding site. The epitope is a highly conserved site of vulnerability that is hidden in the HA trimer interface, which more pronounced in the HA0 form of the trimer. The antibodies show excellent binding affinity to diverse serotypes. A feature of this class of antibodies is mediation of ADCC activity and in vivo protection against major influenza subtypes that are pathogenic for humans, providing utility as a broad-spectrum antiviral therapeutic against various IAV infections. Embodiments of the invention include isolated antibodies and derivatives and fragments thereof, pharmaceutical formulations comprising one or more of the human anti-influenza virus monoclonal antibodies; and cell lines that produce these monoclonal antibodies. Also included are antigenic compositions comprising the HA trimer interface epitope presented in an immunogenic format.

In accordance with the present disclosure, a method of detecting an influenza A virus infection in a subject is provided, comprising (a) contacting a sample from said subject with one or a combination of antibodies or antibody fragments having clone-paired heavy and light chain CDR sequences from Tables 3 and 4, respectively; and (b) detecting influenza A virus in said sample by binding of said antibody or antibody fragment to an influenza A virus hemagglutinin in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or western blot. The method may further comprising performing steps (a) and (b) a second time and determining a change in influenza A virus hemagglutinin levels as compared to the first assay.

The one or a combination of antibodies or antibody fragments may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. An antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

In another embodiment, there is provided a method of treating a subject infected with influenza A virus or reducing the likelihood of infection of a subject at risk of contracting influenza A virus, comprising delivering to said subject one or a combination of antibodies or antibody fragments having clone-paired heavy and light chain CDR sequences from Tables 3 and 4, respectively. An antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. An antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. An antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody.

The one or a combination of antibodies or antibody fragments may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. The antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In a further embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. The antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In yet a further embodiment, there is provided a therapeutic formulation comprising one or a combination of antibodies or antibody fragments characterized by clone-paired heavy and light chain CDR sequences from Tables 3 and 4, respectively. The antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. The antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

Also provided is a therapeutic formulation comprising one or more expression vectors encoding a first antibody or antibody fragment as set forth above. The expression vector(s) may be Sindbis virus or VEE vector(s). The therapeutic formulation may be formulated for delivery by needle injection, jet injection, or electroporation. The formulation further comprising one or more expression vectors encoding for a second antibody or antibody fragment, such as a distinct antibody or antibody fragment of claims 26-34.

In an additional embodiment, there is provided a method of protecting the health of a placenta and/or fetus of a pregnant a subject infected with or at risk of infection with influenza A virus comprising delivering to said subject one or a combination of antibodies or antibody fragments having clone-paired heavy and light chain CDR sequences from Tables 3 and 4, respectively. The antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. The antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The one or a combination of antibodies or antibody fragments may be administered prior to infection, after exposure, or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

In one embodiment antigenic compositions are provided, which comprise all or a portion of an influenza epitope recognized by the FluA-20 antibody class. The epitope may comprise an interface region of the HA head domain, including the HA0 form. In some embodiments, an antigenic composition comprises a truncated HA head domain. In some embodiments, the antigenic composition is engineered to expose the interface region epitope. Epitope-focused vaccine design is a method in which immunogens are designed to elicit protective antibody responses against structural epitopes that are defined by protective antibodies isolated from vaccines or infected patients. In some embodiments, 'side-chain grafting' and 'backbone grafting' methods are used to transplant continuous or discontinuous epitopes to scaffold proteins of known structure, for epitope conformational stabilization and immune presentation. In other embodiments, a computational method to design scaffold proteins with full backbone flexibility, to allow greater precision in tailoring scaffold structures for particular epitope structures, is used. In some embodiments, the epitope is presented on a scaffold protein other than a naturally occurring IAV protein. In some embodiments, an antigenic composition comprises an influenza HA protein in which specific highly immunodominant residues are masked or deleted, so as to generate an immune response to the HA interface epitope. In some embodiments an HA protein is engineered to lack a trypsin cleavage site at around residue 329. Antigenic compositions providing HA interface epitopes can be formulated alone or in combination with conventional vaccines. Antigens may comprise, without limitation, HA head domain polypeptides, alone or in combination with an adjuvant. These antigenic compositions find use in screening assays, generation of monoclonal antibodies, and in vaccines. These vaccines/immunogens may be used in combination with current formulations, for example in a primer boost strategy to enhance immunity.

In yet an additional embodiment, there is provided a method of determining the antigenic integrity, correct conformation and/or correct sequence of an influenza A virus hemagglutinin antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced hemagglutinin antigen. The sample may comprise a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. The first antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the hemagglutinin antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said hemagglutinin antigen by detectable binding of said second antibody or antibody fragment to said hemagglutinin antigen. The second antibody or antibody fragment may be encoded by clone-paired variable sequences as set forth in Table 1; may be encoded by light and heavy chain variable sequences having 70%, 80%, or 90% identity to clone-paired variable sequences as set forth in Table 1; or may be encoded by light and heavy chain variable sequences having 95% identity to clone-paired sequences as set forth in Table 1. The second antibody or antibody fragment may comprise light and heavy chain variable sequences according to clone-paired sequences from Table 2; may comprise light and heavy chain variable sequences having 70%, 80% or 90% identity to clone-paired sequences from Table 2; or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the hemagglutinin antigen over time.

Also provided is a human monoclonal antibody or antibody fragment, or hybridoma or engineered cell producing the same, wherein said antibody binds to a transiently accessible epitope located at an interface of the influenza A hemagglutinin trimer, and/or provides in vivo protection against influenza A viruses, including without limitation activation of ADCC. The human monoclonal antibody or antibody fragment, or hybridoma or engineered cell producing the same may bind to (a) an influenza A subtype selected from the group consisting of H1, H2, H3, H4, H5, H6, H7, H8, H9, H10, H11. H12, H13, H14, H15, H16, H17 or H18; or (b) more than one influenza A subtype set forth in (a), such as H1 and H5, H1 and H3, H7 and H15; or (c) influenza A viruses from both Group 1 and 2, or (d) influenza A viruses from all medically relevant influenza A subtypes.

Further, applicant provides a therapeutic formulation comprising a human monoclonal antibody or antibody fragment described herein, and further comprising another antiviral molecule, which antiviral may be a second antibody described herein, a different antibody with specificity for IAV, or may be selected from the group consisting of a small molecule antiviral drug, an inhibitory RNA, a distinct antibody binding to a distinct epitope on the HA (such as the receptor binding domain, vestigial esterase domain, or the stem domain), or a distinct antibody binding to a non-HA influenza A protein (such as neuraminidase protein or M2 matrix protein).

Also disclosed is a method of treating a subject having an influenza A virus infection comprising administering to said subject the therapeutic formulation comprising (a) a human monoclonal antibody or antibody fragment as described herein, and (b) another antiviral molecule. The combination of agents may exert an additive effect or synergistic effect on virus inhibition, and/or may reduce the occurrence of viral escape from neutralization or drug inhibition.

Further disclosed is a heterosubtypic influenza HA antibody or fragment thereof that preferentially binds to uncleaved HA (HA0) on the surface of virus-infected cells. Such an antibody or fragment thereof may disrupt trimer integrity and/or prevent cell-to-cell transmission of virus infection, for example by activation of ADCC against infected cells conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Network analysis of sequences clonally related to FluA-20. (FIG. 1A) Timeline showing the vaccination history of FluA-20 donor and the time points from which FluA-20 (triangle) and its clonally related siblings (circles) were identified. (FIG. 1B) Nodes represent unique sequences observed in the inventor's database, with the size of the node correlating to the count of replicate sequences observed. The color of each node denotes the time point at which it was found; white for day (5), yellow for day (6), orange for day (11) and pink for day (14). The black node represents the $V_H4$-61/$J_H4$ germline sequence and the gray node represents an inferred common ancestor. The maroon, triangle-shaped node represents FluA-20. Edges drawn between nodes show that those sequences are more closely related to each other than to any other sequence. Edge distances are arbitrary and used only to visually clarify the graph. (FIG. 1C) Binding $EC_{50}$ (ng/ml) for FluA-20, rFluA-20 and FluA-20-UCA to HAs derived from different strains. The table is displayed in RYG color scale.

FIGS. 2A-D. FluA-20 antibodies prophylactically protect mice from sub-lethal challenge from pathogenic IAV for humans, likely through ADCC activity. Groups of mice (n=8) were treated with 10 mg/mL of either FluA-20 or a similarly prepared control antibody to an unrelated target (MRSA) and challenged 24 h later with either H1N1 A/Netherlands/602/2009 or H3N2 A/X-31 (6:2 PR8 backbone) or H5N1 A/barn swallow/Hong Kong/D10-1161/2010 (7:1 PR8 backbone) or H7N9 A/Shanghai/1/2013 (6:2 PR8 backbone). (FIG. 2A) The weight loss of mice (n=5) was measured daily for 14 days after inoculation (Day 0). The significance in weight loss between FluA-20 and the control group was calculated for each day using 2-way ANOVA and displayed on the graph as *(P<0.05), (P<0.01) and * (P<0.001). (FIG. 2B) Lung samples were collected from mice (n=3) per antibody group 6 days post-inoculation. The graph shows pulmonary virus titers in FluA-20 and control treated mice. (FIG. 2C) Cross-linking of FcγRIIIa. Binding curves were obtained by performing ELISA with serial dilutions of each antibody (FluA-20 and control mAbs FluA-45, FluA-55 and VRC01) onto HA-coated plates and assessing the ability of HA-bound mAbs to engage both Fc-binding sites on the soluble FcγRIIIa dimer. The dotted line indicates the limit of detection. (FIG. 2D) FluA-20 or control mAbs were each added independently on 96-well plates coated with purified A/California/07/2009 H1 HA. The percentage of NK cell activation was calculated from the number of NK cells incubated with HA-bound antibody that expressed CD107a and/or IFNγ. The mAbs are listed left-to-right in the figure corresponding to top-to-bottom of the listed antibodies.

FIGS. 3A-D. FluA-20 targets the 220-loop and the 90-loop at the trimer interface of the H1 head domain. (FIG. 3A) Structural overview of FluA-20 Fab in complex with the head domain of H1 HA (A/Solomon Islands/3/2006). FluA-20 Fab is shown as a backbone trace in blue heavy chain (H) and green light chain (L). The backbone of the HA head domain is shown as a yellow trace and residues contacted by FluA-20 are colored in red. (FIG. 3B) The H1 head domain is superimposed with one protomer colored in light grey surface from an HA trimer model (PDB 4M4Y). The adjacent HA protomers are shown with dark grey solid surface. The variable domain of FluA-20 would clash with a large volume of the head domain from an adjacent protomer in the HA trimer model. (FIG. 3C) FluA-20 interaction with H1. The salt bridge interaction between Asp98 (H) to Arg229 is shown as a red dashed line. A hydrogen bond between Asn55 (H) to Lys222 is presented with a grey line. Two additional hydrogen bonds are between the side chain of Thr96 (H) to main-chain carbonyl of Lys219 and Arg220 side chain to the main-chain carbonyl of Glu97 (H). Other hydrophobic residues that contribute to the interaction are shown with side chains. (FIG. 3D) The binding traces of HA head domain, or its mutants (at the concentration of 0.5 μM), to immobilized FluA-20 Fab in BLI assay are presented. The curves are listed top-to-bottom at the left hand side of the graph corresponding to top-to-bottom of the listed antibodies.

FIGS. 4A-B. FluA-20 interacts with H3 head domain. (FIG. 4A) The structure of FluA-20 in complex with the H3 head domain (A/Hong Kong/3/1968) is presented similarly as FIGS. 3A-D, with the H3 head domain is colored in wheat. The H3 residues interacting with FluA-20 are colored in red and the antibody footprint size on HA is analyzed. The H3 head domain is superimposed with one protomer in H3 trimer model (PDB 4FNK, shown as surface with different shade of grey for each protomer). (FIG. 4B) Interaction of FluA-20 to the H3 HA. A salt bridge interaction between R229 from HA and Asp98 (H) of FluA-20 is shown with a red line. Hydrogen bonds between Gln55 (L) to main chain amide of Trp222 and Asn53 (L) to Arg224 are presented with grey lines. Several hydrophobic residues that contribute to the interaction are shown with their side chains.

FIGS. 5A-C. Principal residues that FluA-20 recognizes in HA head domains are highly conserved across various subtypes. (FIGS. 5A-B) The binding core of FluA-20 in complex with H1 or H3 HA is highlighted by a salt bridge between Asp98 (H) and Arg229, which is enclosed by a circle of hydrophobic residues, including Pro96, Pro221, and Val223 of HA, Tyr49 (L) and Tyr100a of FluA-20. The conservation of the core residues in each HA subtypes is analyzed and displayed with identity percentages. (FIG. 5C) The HA residues in the epitope are analyzed for conservation across different subtypes. Despite variability in surrounding residues, the five core residues in the HA epitope (Pro98, Arg220, Pro221, Val223, and Arg229) remain extremely conserved, which accounts for the extraordinary breadth of the antibody.

FIGS. 6A-C. FluA-20 binding is inhibited by HA cleavage potentially via trimer dynamic changes. (FIG. 6A) The association and disassociation traces of HA0 or cleaved HAs from H1 (A/California/04/2009) and H7 (A/Shanghai/02/2003) to immobilized FluA-20. The HA concentrations were diluted at 1 μM. The lines in the graph are, from top-to-bottom, H7-FL, H1-FL, H7-Trypsin and H1-Trypsin. (FIG. 6B) Full-length HAs were expressed on the cellular surface of 293 cells. The cells were treated or untreated with trypsin before flow cytometry analysis. The mean fluorescence intensities (MFI) of cell staining with designated PE-labeled antibodies were plotted. The bars in the graph are UT, UT-Trypsin, H3 and H3-Trypsin left-to-right. (FIG. 6C) Deuterium exchange comparison of cleaved HA trimer to HA0 trimer from A/Netherlands/219/2003 (H7N7) by HDX-MS. One HA protomer in the model (PDB 4DJ6) is shown in colored backbone trace. Residues with slower deuterium exchange in cleaved HA are colored in blue and residue with faster deuterium exchange in cleaved HA are colored in red. Residues in grey represent no difference in deuterium exchange rate and residues in black indicate the peptides are not covered in the MS data.

FIGS. 7A-B. Conservation analysis on the trimer surface and interface of recent HA strains. A library of HA sequences that are recently isolated from human host since 2015 was used for surface conservation analysis, including 701 H1 sequences, 1,739 H3 sequences, and 17 other sequences of H5, H7 and H9 subtypes. The conservation score of each residue was presented with a blue-white-red color pattern on a H3 HA model (PDB 4O5n). Glycans observed in the x-ray crystal structure are shown with yellow spheres. (FIG. 7A) The conservation on HA trimer surface is mainly located in the stem region with highly overlapping epitopes targeted by many stem-specific antibodies (e.g., CR9114, FI6, and MEDI8852). Most surface in head domain on HA trimer surface is highly variable across different subtypes, with small conserved surface that is either segregated by variable patches or blocked by glycans. The exposed receptor-binding site is relatively conserved and thus is the major target of most bnAbs against HA domain. (FIG. 7B) The trimer interface possesses several patches of conserved surface, including the FluA-20 epitope. Similar as the trimer 'outer' surface, most of conserved patches are in the stem interface, the accessibility of which needs further investigation. The FluA-20 epitope in the head domain is uniquely conserved, with Pro96, Arg220, Pro221 and Arg229 of 95-98% identity across H1 and H3 subtypes and structurally conserved Val or Ile 221 in most HA sequences. The variability in 219, 222, and 225 residues is well accommodated by FluA-20 binding, since the antibody interactions are mainly to the HA main chains.

FIGS. 8A-D, related to FIGS. 1A-C, Table S1-2. Binding of FluA20 antibody to HA. (FIG. 8A) Phylogenetic tree of representative sibling antibodies of FluA-20 that were tested for binding in Table S1. (FIG. 8B) Binding curves used to calculate $K_D$ of FluA-20 Fab with different influenza HAs. Blue curves are the experimental data from biolayer interferometry (BLI) experiments, and red curves are the best global fits for a 1:1 binding model in the $K_D$ calculation. (FIG. 8C) Competition-binding assays were performed using bio-layer interferometry. The His-tagged A/California/07/2009 H1 HA was loaded onto Ni-NTA tips, and binding of two successively applied antibodies (IgG) was tested. MAb FluA-20 was competed against mAb 5J8, a receptor binding site mAb, or each of four stem-binding antibodies: CR9114, FI6v3, 39.29 or H3v-86. FluA-20 does not compete with either the RBS or the stem-antibodies indicated. (FIG. 8D) FluA-20 IgG is immobilized on the anti-human Fab CH1 biosensors. Strong binding to the head domains (0.5µ M concentration) of H1 (A/Solomon Islands/3/2006), H3 (A/Victoria/361/2011) and H7 (A/Shanghai/02/2013) is observed for immobilized FluA-20 in a BLI assay. The lines are, from top-to-bottom in the graph, H7 head, H1 head and H3 head.

FIGS. 9A-D, related to FIGS. 3A-D and FIGS. 4A-B. FluA-20 binds to the 220-Loop and 90-Loop of H1 and H3 HA. (FIGS. 9A-B) H1 HA trimer of A/California/04/2009 is shown in a secondary structure representation. Residues in H1 epitope (Pro96, Ile219, Arg220, Pro221, Lys222, Val223, and Arg229) that are contacted by FluA-20 are colored in red. These residues also interact with the adjacent protomer in the HA trimer. (FIGS. 9C-D) H3 HA trimer of A/Hong Kong/1/1968 is shown in a secondary structure representation. The key interacting residues in the H3 epitope (Pro96, Ser219, Arg220, Pro221, Trp222, Val223, and Arg229) that are contacted by FluA-20 are colored in red. Many of these residues also interact with the adjacent protomer in the HA trimer.

FIGS. 10A-C, related to FIGS. 5A-C. H5 epitope mapping with FluA-20 by HDX-MS and mutagenesis. (FIG. 10A) Difference map from deuterium exchange of the H5 head domain from A/Vietnam/1203/2004 (H5N1) with or without FluA-20 binding (SEQ ID NOs: 41 and 42). Residues with slower deuterium exchange in the presence of FluA-20 are colored in blue and residues with faster exchange are colored in red. (FIG. 10B) Regions of HA with slower deuterium exchange after binding FluA-20 are mapped in red onto the surface of H5 A/Vietnam/1203/2004 head domain (purple). (FIG. 10C) Mutations of the 220-loop residues substantially influence binding of FluA-20 IgG (as measured by BLI assays, IgG 25 µg). The R220A, V223A, and R229A mutants of H5 completely eliminate FluA-20 binding, whereas N224A, G225A, and Q226A mutants decrease FluA-20 binding. The mutations S221A, K222A, and G228A appear to slightly enhance FluA-20 binding.

FIGS. 11A-D, related to FIG. 5C. Simulation of FluA-20 binding to HAs from other subtypes. The head domains of H5 (FIG. 11A), H13 (FIG. 11B) and H7 HA (FIGS. 11C-D) are superimposed with H3 HA (colored in wheat) in complex with FluA-20. (FIG. 11A) H5 (A/Vietnam/1203/2004 (H5N1)) has serine at residue 221 (highlighted in red circle), instead of Pro221 in H1 and H3 subtypes. The $K_D$ values of FluA-20 Fab binding to either wild-type H5 or H5_S221P mutant were determined by BLI assay. (FIG. 11B) Instead of the salt bridge interaction between Asp98 (H) of FluA-20 and Arg229 in other HAs, H13 HA possesses two aromatic residues, Tyr223 and Trp229, that could contribute to the binding by aromatic stacking with Y100a (FIG. 11C) H7 HA of A/Shanghai/2/2013, which is colored in orange, aligns well to H3_FluA20 complex structure. (FIG. 11D) H7 HA of A/New York/107/2003 (grey) was aligned to the H3_FluA-20 complex structure. This H7 strain has a truncated 220-loop and is missing residues 221-228.

FIGS. 12A-B, related to FIG. 5C. FluA-20 accommodates variability in the HA 220-loop. Residues 219, 222, and 224 in the FluA-20 epitope exhibit considerable variation in various subtypes. However, the hydrogen bond interactions of FluA-20 to these variable residues are to their main chain (in grey lines), and the approach angle of FluA-20 successfully avoids contacts or collisions with bulky and variable side chains.

FIGS. 13A-B, related to FIG. 1C, Table S2. Sequence of unmutated common ancestor (Griffin et al., 2017) of FluA-20 and the intrinsic affinity of the UCA Fab to diverse influenza HAs. (FIG. 13A) Sequence of FluA-20 (SEQ ID NO: 43) and its UCA (SEQ ID NO: 44) are aligned. Mutated residues are colored as red and a unique disulfide bond in CDR H3 is highlighted in yellow. The key residues Asp98 (H), Tyr100a (H), Tyr48 (L), and Gln55 (L) that are critical for the interaction with HA originate from the UCA (in red circles). (FIG. 13B) Blue curves are the experimental data from biolayer interferometry (BLI) experiments, and red curves are the best global fits for a 1:1 binding model in the $K_D$ calculation.

FIGS. 14A-C, related to FIGS. 6A-C. Comparison of antibody binding to HA0 versus cleaved HA trimers. (FIG. 14A) Binding traces of HA0 trimer and cleaved HA trimer to receptor-binding site antibodies. The antibody used for H1 HA (A/California/04/2009) binding is antibody 5J8 and the antibody used for H7 HA binding (A/Shanghai/02/2013) is antibody H7.137. The graph shows H1 in the top two lines and H7 in the bottom two lines. (FIG. 14B) HA0 (A/Hong Kong/1/1968 (H3N2)) virus was incubated with serial dilutions of mAbs (FluA-20 or CR8020) either before or after treatment with 1 µg/mL of trypsin (Trp) at 37° C. for 45 minutes. The samples were trypsin-inactivated with 10% FBS before adding to MDCK monolayers. The dotted line indicates the baseline infection with HA0 virus (untreated). (FIG. 14C) Difference map from deuterium exchange of cleaved HA trimer compared to HA0 trimer from A/Netherlands/219/2003 (H7N7) by HDX-MS. (SEQ ID NO: 45)

FIG. 15. Cross-reactivity of binding of H5.28 or H5.31 to diverse HAs of influenza subtype A. Binding was tested using mammalian cell expressed recombinant HA proteins and biolayer interferometry (Octet) and ELISA.

FIG. 19. Glycan analysis of H5.28 and H5.31. Sequence analysis of the heavy chain variable regions showed that the two antibodies, which were isolated from one donor, were highly related somatic variants that are members of a single clonotype (sometimes called a lineage). The alignment revealed that H5.31 but not H5.28 has a potential glycosylation site. Protein expression followed by enzymatic treatment to remove glycans showed that indeed H5.31 was glycosylated. Binding assays comparing the H5.28, H5.31 and H5.31-deglycosylated antibodies did not show any differences in binding. (3-7=SEQ ID NO: 46; H5.28=SEQ ID NO: 47; H5.31=SEQ ID NO: 48)

FIG. 20. DXMS results for testing of binding of H7-200 to H7 HA antigen. The H7 HA trimer is shown. The receptor binding domain (shown in blue) is not affected by mAb binding. The fusion peptide in the stem domain is indicated in green. The peptide labeling reduced by mAb binding in DXMS analysis (indicating the epitope recognized) is indicated in orange.

FIGS. 21A-C. Network analysis of sequences clonally related to FluA-20 and FluA-20 reactivity to diverse HAs. (FIG. 21A) Timeline showing the vaccination history of FluA-20 donor and the time points from which FluA-20 (triangle) and its clonally related siblings (circles) were identified. (FIG. 21B) Nodes represent unique sequences observed in our database, with the size of the node correlating to the count of replicate sequences observed. The color of each node denotes the time point at which it was found; white for day 5, yellow for day 6, orange for day 11 and pink for day 14. The black node represents the $V_H4$-61/$J_H4$ germline sequence and the gray node represents an inferred common ancestor. The maroon, triangle-shaped node represents FluA-20. Edges drawn between nodes show that those sequences are more closely related to each other than to any other sequence. Edge distances are arbitrary and used only to visually clarify the graph. The somatic variants of FluA-20 that were expressed and tested are indicted. (FIG. 21C) ELISA binding $EC_{50}$ (ng/mL) values for FluA-20, recombinant FluA-20 (rFluA-20) and unmutated common ancestor of FluA-20 (FluA-20-UCA) to HAs derived from different strains representing group 1 (green) and group 2 (blue) IAVs. The table is displayed in purple-white color scale corresponding to strong-weak binding, respectively. The > symbol indicates that binding was not observed at concentrations <10 µg/mL.

FIGS. 22A-E. mAb FluA-20 exhibits protection in vivo against diverse IAV subtypes (FIG. 22A) Body weight change kinetics in mice that received FluA-20 prophylactically prior to sub-lethal challenge with IAV strains from H1N1, H3N2, H5N1 and H7N9. Mice were treated with 10 mg/kg of either FluA-20 or a similarly prepared control antibody to an unrelated target (MRSA) and challenged 24 h later with either H1N1 A/Netherlands/602/2009 or H3N2 A/X-31 (6:2 PR8 backbone) or H5N1 A/barn swallow/Hong Kong/D10-1161/2010 (7:1 PR8 backbone) or H7N9 A/Shanghai/1/2013 (6:2 PR8 backbone). The weight loss of mice (n=5) was measured daily for 14 days after inoculation (Day 0). The experiments were performed twice with similar results. (FIG. 22B) Survival and weight change kinetics in mice (n=10) prophylactically treated with different doses of FluA-20 (1 or 3 or 10 mg/kg) or 10 mg/kg of control IgG (DENV 2D22) or PBS prior to lethal challenge with mouse adapted H1N1 A/California/04/2009. One experimental group was treated with 30 mg/kg/day of oseltamivir for 5 days post-challenge as a positive control. ***P<0.001, compared to placebo-treated group; +++P<0.001, ++P<0.01, compared to DENV 2D22-treated group. (FIG. 22C) Percentage survival in mice prophylactically treated with 10 mg/kg of either FluA-20 or a recombinant form of CR6261 or control IgG (MRSA-147) prior to lethal challenge with H1N1 A/California/04/2009 virus. (FIG. 22D) Weight change in mice that were sub-lethally challenged with H1N1 A/California/04/2009 virus prior to therapeutic treatment with 10 mg/kg of either mAbs FluA-20 or a recombinant form of CR6261 or control IgG (MRSA-147) on day 1 post-inoculation. (FIG. 22E) Survival and weight change in mice lethally challenged with H3N2 and H5N1 viruses (same strains as FIG. 22A) prior to therapeutic treatment with 10 mg/kg of either mAbs FluA-20 or control IgG (MRSA-147) on days 1, 2 and 4 post-inoculation. Each group was compared to the mock-treated group in FIGS. 22A-E. Body weight change data in FIG. 22B and FIG. 22E are shown only for the animals that survived at each indicated time point. The weights in FIG. 22A. FIG. 22B, FIG. 22D) and FIG. 22E are shown as the group mean and the standard error of the mean.

FIGS. 23A-D. FluA-20 targets the 220-loop and the 90-loop at the trimer interface of the H1 head domain. (FIG. 23A) Structural overview of rFluA-20 Fab in complex with the head domain of H1 HA (A/Solomon Islands/3/2006). FluA-20 Fab is shown as a backbone trace in blue heavy chain (H) and green light chain (L). The backbone of the HA head domain is shown as a yellow trace and residues contacted by FluA-20 are colored in red. (FIG. 23B) The H1 head domain is superimposed with one protomer colored in light grey surface from an HA trimer structure (PDB 4M4Y). The adjacent HA protomers are shown with dark grey solid surface. The variable domain of FluA-20 would clash with a large area of the head domain from an adjacent protomer in the HA trimer model. (FIG. 23C) FluA-20 interaction with H1. The salt bridge interaction between Asp98 (H) to Arg229 is shown as a red dashed line. A hydrogen bond between Asn55 (H) to Lys222 is presented with a grey line. Two additional hydrogen bonds are between the side chain of Thr96 (H) to main-chain carbonyl of Lys219 and Arg220 side chain to the main-chain carbonyl of Glu97 (H). Other hydrophobic residues that contribute to the interaction are shown with side chains. (FIG. 23D) The binding traces of HA head domain, or its mutants (at the concentration of 0.5 µM), to immobilized rFluA-20 Fab in BLI assay are presented. The curves are listed top-to-bottom at the left hand side of the graph corresponding to top-to-bottom of the listed antibodies.

FIGS. 24A-B. FluA-20 interacts with H3 head domain. (FIG. 24A) The structure of rFluA-20 in complex with a H3 head domain (A/Hong Kong/3/1968) is presented similarly to FIG. 3, with the H3 head domain colored in wheat. The H3 residues interacting with FluA-20 are colored in red and the antibody footprint size on HA is analyzed. The H3 head domain is superimposed with one protomer of an H3 trimer structure (PDB 4FNK, shown as surface with different shade of grey for each protomer). (FIG. 24B) Interaction of FluA-20 to the H3 HA. A salt bridge between R229 from HA and Asp98 (H) of FluA-20 is shown with a red line. Hydrogen bonds between Gln55 (L) to main chain amide of Trp222 and Asn53 (L) to Arg224 are presented with grey lines. Several hydrophobic residues that contribute to the interaction are shown with their side chains.

FIGS. 25A-H. Critical residues involved in FluA-20 binding to different HAs. (FIGS. 25A-B) Principal residues that FluA-20 recognizes in HA head domains are highly conserved across various HA subtypes. The binding core of FluA-20 in complex with H1 (FIG. 25A) or H3 (FIG. 25B) HA is highlighted by a salt bridge between Asp98 (H) and Arg229, which is enclosed by a circle of hydrophobic residues, including Pro96, Pro221, and Val223 of HA, Tyr49 (L) and Tyr100a of FluA-20. The conservation of the core residues in each HA subtypes is analyzed and displayed with identity percentages. (FIGS. 25C-E and FIG. 25F) Simulation of FluA-20 binding to HAs from other subtypes. The head domains of H5 (FIG. 25C), H13 (FIG. 25D) or H7 HA (FIG. 25E and FIG. 25F) are superimposed with H3 HA (colored in wheat) in complex with FluA-20. (FIG. 25C) H5 (A/Vietnam/1203/2004 (H5N1)) has Ser221 (highlighted in red circle), instead of Pro221 in H1 and H3 subtypes. The $K_D$ values of FluA-20 Fab binding to either wild-type H5 or H5_S221P mutant were determined by BLI assay. (FIG. 25D) Instead of the salt bridge interaction between Asp98 (H) of FluA-20 and Arg229 in other HAs, H13 HA possesses two aromatic residues, Tyr223 and Trp229, that could contribute to the binding by aromatic stacking with Y100a. (FIG. 25E) H7 HA of A/Shanghai/2/2013, which is colored in orange, aligns well to H3_FluA20 complex structure. (FIG. 25F) H7 HA of A/New York/107/2003 (grey) was aligned to the H3_FluA-20 complex structure. This H7 strain has a truncated 220-loop and is missing residues 221-228. (FIGS. 25G-H) FluA-20 accommodates variability in the HA 220-loop of H1 (FIG. 25G) or H3 (FIG. 25H) HA. Residues 219, 222, and 224 in the FluA-20 epitope exhibit considerable variation in various subtypes. However, the hydrogen bond interactions of FluA-20 to these variable residues are to their main chain (in grey lines), and the approach angle of FluA-20 successfully avoids contacts or collisions with bulky and variable side chains.

FIGS. 26A-C. FluA-20 binding is inhibited by HA cleavage potentially via trimer dynamic changes. (FIG. 26A) The association and disassociation traces of HA0 or cleaved HAs from H1 (A/California/04/2009) or H7 (A/Shanghai/02/2003) to immobilized rFluA-20. The HA was tested at 1 µM concentration. The lines listed from top-to-bottom are H7-HA0, H1-HA0, H7+Trypsin and H1+Trypsin (FIG. 26B) HEK293F cells were either untransfected (UT) or transiently transfected with full-length H3 (A/Hong Kong/1/1968) HA cDNA for HA surface expression. The cells were either left untreated or treated with TPCK trypsin and then incubated with 10 µg/mL of mAb CR9114 or mAb FluA-20 followed by incubation with secondary goat anti-human IgG PE-labeled antibody. Antibody binding to cleaved and uncleaved HA on the cell surface was determined by flow cytometric analysis. The error bars represent mean±SD of technical replicates. Statistical significance was calculated using the unpaired two-tailed t-test with Graph-Pad software. The data are representative of two independent experiments. (FIG. 26C) Deuterium exchange comparison of cleaved HA trimer to HA0 trimer from A/Netherlands/219/2003 (H7N7) by HDX-MS. One HA protomer in the model (PDB 4DJ6) is shown in colored backbone trace. Peptides with slower deuterium exchange in cleaved HA are colored in blue, and peptides with faster deuterium exchange in cleaved HA are colored in red. Peptides in grey represent no difference in deuterium exchange rate and peptides in black indicate peptides that were not covered in the MS data.

FIGS. 27A-F. FluA-20 inhibits cell-cell spread, disrupts the uncleaved HA trimer protein, and does not require Fc-effector function for in vivo protection. (FIGS. 27A-C) demonstrate that FluA-20 diminishes cell-to-cell spread of influenza virus. (FIG. 27A) Representative images of 6-well plate wells with influenza virus A/Hong Kong/1/1968 foci developed on MDCK monolayers after 48 hours of incubation at presence of 10 µg/mL of irrelevant control mAb MRSA-147, FluA-20, CR9114, or equimolar concentration of zanamivir. Foci were immunostained with mouse anti-NP and anti-mouse HRP-conjugated detection antibodies and developed by TrueBlue substrate. Images were captured by CTL (Cellular Technology Ltd.). Images are representative of 3 replicates of 2 independent experiments (FIG. 27B) Quantitative determination of foci area reduction. Foci area calculated by ImageJ software and represented as percentage of total well area. Each value represents mean focus area±SD. (FIG. 27C) Concentration-dependent effect of focus area reduction. Each value represents the mean focus area±SD. The lines from top-to-bottom are MRSA-147, CR9114, FluA-20, and zanamivir. FIGS. 27D-E correspond to the in vivo protective efficacy of engineered Fc mutant variants of mAb FluA-20. Groups of BALB/c mice were inoculated i.p. with 10 mg/kg of indicated mAb on the day before respiratory challenge by the i.n. route with $1.24 \times 10^4$ focus forming units (FFU) of A/California/04/2009 virus and monitored for 14 days. The control group included mice treated with mAb MRSA-147 specific to an unrelated target. The protective efficacy of mAbs was assessed by weight change kinetics (FIG. 27D; cures at the right hand of the graph are, from top-to-bottom, rFluA-20 LALA, wt FluA-20, rFluA-20, rFluA-20 N297A and control), and clinical score (FIG. 27E; all but control have values of 1). The dotted line indicates the IACUC-stipulated endpoint for humane euthanasia. Data are cumulative of two independent experiments and represent the mean value±SEM, using 5-10 mice per group. Multiple group comparisons were performed using two-way ANOVA with Tukey's post-test for FIG. 27A. On the graph, the results of comparison between rFluA-20 IgG1-N297A-treated (grey) and rFluA-20 IgG1-treated (blue) groups are shown to demonstrate a significant difference in weight change between these two groups (denoted with * symbol), although the N297A Fc region mutation that abrogates FcR binding had a negligible impact of on overall protection by FluA-20. (FIG. 27F) Selected 2D class averages of H1 HA trimer (A/California/04/2009) after a 20-second incubation with FluA-20 Fab. All of the Fabs complexed HA were in monomeric form, while a few apo HA trimers were observed. All 2D class averages are shown in FIG. S7B. FluA-20 Fab is colored in blue and HA is in white. (FIG. 27G) Cartoon illustration showing that FluA-20 Fab (heavy chain in blue and light chain in green) results in dissociation of native HA trimer (grey), as assessed by negative-stain EM data shown in FIG. 27F and FIG. S7B.

FIGS. 28A-C, related to FIGS. 21A-C, Table S5. Binding of FluA-20 antibody to HA. (FIG. 28A) Binding curves for mAbs FluA-20, rFluA-20, FluA-20-UCA or an irrelevant control IgG (anti-MRSA) against HAs derived from indicated strain and subtype, as determined by Enzyme Linked Immunosorbent Assay (ELISA). (FIG. 28B) Phylogenetic tree of representative sibling antibodies of FluA-20 that were tested for binding. (FIG. 29C) Amino acid sequence of FluA-20 and the unmutated common ancestor (UCA) of FluA-20 are aligned. Mutated residues are colored as red and a unique disulfide bond in CDR H3 is highlighted in yellow. The key residues Asp98 (H), Tyr100a (H), Tyr48 (L), and Gln55 (L) that were later identified as critical for the interaction with HA are present in the UCA sequence (indicated by red dashed circles).

FIGS. 29A-B, related to FIGS. 22A-E. Lung titers of mice treated with FluA-20 in prophylactic or therapeutic settings. (FIG. 29A) Groups of mice (n=3) were treated prophylactically with 10 mg/mL of either FluA-20 or a similarly prepared control antibody to an unrelated target (MRSA) and challenged 24 h later with a sublethal dose of 0.1 $LD_{50}$ with either H1N1 A/Netherlands/602/2009 or H3N2 A/X-31 (6:2 PR8 backbone) or H5N1 A/barn swallow/Hong Kong/D10-1161/2010 (7:1 PR8 backbone) or H7N9 A/Shanghai/1/2013 (6:2 PR8 backbone). Lung samples were collected from mice for each antibody treated group at 6 days post-inoculation. The graph shows pulmonary virus titers in FluA-20 and control treated mice. (FIG. 29B) Groups of mice (n=3) were lethally challenged with 1.2 $LD_{50}$ of H3N2 A/X-31 or H5N1 A/barn swallow/Hong Kong/D10-1161/2010 or H7N9 A/Shanghai/1/2013 on PR8 backbone and were treated therapeutically with 10 mg/kg of FluA-20 or an irrelevant antibody (MRSA) via the intraperitoneal route on days 1, 2 and 4 post-challenge. Lungs were collected for virus titration at 5 days post-inoculation.

FIGS. 30A-B, related to FIGS. 23A-D. Binding of FluA-20 antibody to a unique site on the HA head domain. (FIG. 30A) Competition-binding assays were performed using bio-layer interferometry. The His-tagged A/California/07/2009 H1 HA was loaded onto Ni-NTA tips, and binding of two successively applied antibodies (IgG) was tested. MAb FluA-20 was competed against mAb 5J8, a receptor binding site mAb, or each of four stem-binding antibodies: CR9114, FI6v3, 39.29 or H3v-86. FluA-20 did not compete with either the RBS- or the stem-specific antibodies indicated. (FIG. 30B) FluA-20 IgG was immobilized on anti-human Fab CH1 biosensors. Strong binding to the head domains (0.5 μM concentration) of H1 (A/Solomon Islands/3/2006), H3 (A/Victoria/361/2011) and H7 (A/Shanghai/02/2013) HAs was observed for immobilized FluA-20 in a BLI assay.

FIGS. 31A-D, related to FIGS. 23A-D and 24A-B. FluA-20 binds to the 220-loop and 90-loop of H1 and H3 HA. (FIGS. 21A-B) H1 HA trimer of A/California/04/2009 is shown in a secondary structure representation. Residues identified to be in the H1 epitope (Pro96, Ile219, Arg220, Pro221, Lys222, Val223, and Arg229) that are contacted by FluA-20 are colored in red. These residues interact with the adjacent protomer in the unliganded HA trimer crystal structure. (FIGS. 31C-D) H3 HA trimer of A/Hong Kong/1/1968 is shown in a secondary structure representation. The key interacting residues in the H3 epitope (Pro96, Ser219, Arg220, Pro221, Trp222, Val223, and Arg229) that are contacted by FluA-20 are colored in red. Many of these residues interact with the adjacent protomer in the unliganded HA trimer crystal structure.

FIGS. 32A-C, FIGS. 25A-H. H5 epitope mapping with FluA-20 by HDX-MS and mutagenesis. (FIG. 32A) Difference map from deuterium exchange of the H5 head domain from A/Vietnam/1203/2004 (H5N1) with or without FluA-20 binding. Residues with slower deuterium exchange in the presence of FluA-20 are colored in blue and residues with faster exchange are colored in red; white regions indicate peptides for which there was no coverage. (FIG. 32B) Regions of HA with slower deuterium exchange after binding FluA-20 are mapped in red onto the surface of H5 A/Vietnam/1203/2004 head domain (purple). (FIG. 32C) Mutations of the 220-loop residues substantially influence binding of FluA-20 IgG (as measured by BLI assays, using 25 μg of IgG). The R220A, V223A, or R229A mutations in H5 HA completely eliminated FluA-20 binding, whereas N224A, G225A, or Q226A mutants decreased FluA-20 binding. Mutations S221A, K222A, and G228A each appeared to enhance FluA-20 binding slightly.

FIGS. 33A-C, related to FIGS. 26A-C. Comparison of antibody binding to HA0 versus cleaved HA trimers. (FIG. 33A) Binding traces of HA0 trimer or cleaved HA trimer (HAI/HA2) to receptor-binding site antibodies. The antibody used for binding to H1 HA (A/California/04/2009) was 5J8 and for H7 HA (A/Shanghai/02/2013) was H7.137. Top two lines are H1 and bottom two lines are H7. (FIG. 33B) HA0 [from A/Hong Kong/1/1968 (H3N2)] virus (V) produced in the absence of trypsin was incubated with serial dilutions of mAbs (FluA-20 or CR8020) either before or after treatment with 1 μg/mL of trypsin (Trp) at 37° C. for 45 minutes. The samples were trypsin-inactivated with 10% FBS before adding to MDCK cell monolayers. As a control, HA0 virus untreated with trypsin (and therefore inactive) was also added to MDCK cell monolayers. Following incubation, the cells were fixed and the presence of influenza nucleoprotein in the cells was determined by ELISA using a mouse anti-NP antibody. The dotted line indicates the baseline signal from the noninfectious HA0 virus (untreated). (FIG. 33C) Difference map from deuterium exchange of cleaved HA trimer compared to HA0 trimer from A/Netherlands/219/2003 (H7N7) by HDX-MS.

FIGS. 34A-F, related to FIGS. 27A-F. Functional characterization of FluA-20 IgG. FluA-20 was tested for (FIG. 34A) HA cleavage inhibition, (FIG. 34B) pH-induced HA conformational change inhibition, and (FIG. 34C) egress inhibition. (FIG. 34A) SDS-PAGE of 4 μg of recombinant HA0 protein (from A/Perth/16/2009 (H3N2) that was pre-mixed with either PBS or 40 μg of mAb FluA-20 or mAb CR8020 was either not treated (NT) or treated with TPCK-trypsin for 5, 20 or 40 minutes at 37° C. (FIG. 34B). Non-reducing SDS-PAGE of recombinant HA (H3 Perth) pre-incubated with either (1) PBS or (2) mAb FluA-20 or (3) mAb CR8020 for 1 h at pH 5.0 were neutralized to pH 8.4 and further treated with PBS or TPCK-trypsin for 12 hours. HA was also incubated with (4) PBS at pH 8.0 and treated with trypsin at pH 8.4 as a control. (FIG. 34C) Egress inhibition of FluA-20 was tested using H3 Texas virus.

Hemagglutination titer value was used to confirm virus egress from cell surface to supernatant. Data represent one of two independent experiments, each dot represents value per repeat, and lines represent the mean and standard deviation of assay triplicate. (FIG. 34D) Cross-linking of FcγRIIIa. Binding curves were obtained by performing ELISA with serial dilutions of each antibody (FluA-20 and control mAbs FluA-45, FluA-55 or HIV-specific mAb VRC01) onto HA-coated plates and assessing the ability of HA-bound mAbs to engage both Fc-binding sites on the soluble FcγRIIIa dimer. The dotted line indicates the limit of detection. (FIG. 34E) FluA-20 or control mAbs were each added independently on 96-well plates coated with purified A/California/07/2009 H1 HA. The percentage of NK cell activation was calculated from the number of NK cells incubated with HA-bound antibody that expressed CD107a and/or IFNγ. Antibodies are listed left-to-right as shown in listing top-to-bottom. (FIG. 34F) Sub-lethal respiratory challenge mouse model for influenza A H1N1 infection. Groups of BALB/c mice were inoculated i.n. with indicated dose of A/California/04/2009 virus and monitored for 14 days for weight change kinetics. Data represent the mean value±SEM, using five mice per group. The dotted line indicates the endpoint for humane euthanasia.

(FIG. 35A) Images of H1 HA0 trimer (A/California/04/2009) show intact trimer conformation without exposure of FluA-20 Fab. (FIG. 35B) 2D class average of H1 (A/California/04/2009) HA bound by FluA-20 Fab after 20-second incubation; only the monomeric form of the complex was observed. A few apo HA trimers also were observed, as denoted by the red box.

DESCRIPTION OF ILLUSTRATIVE EMBODIMENTS

Figure 8A:
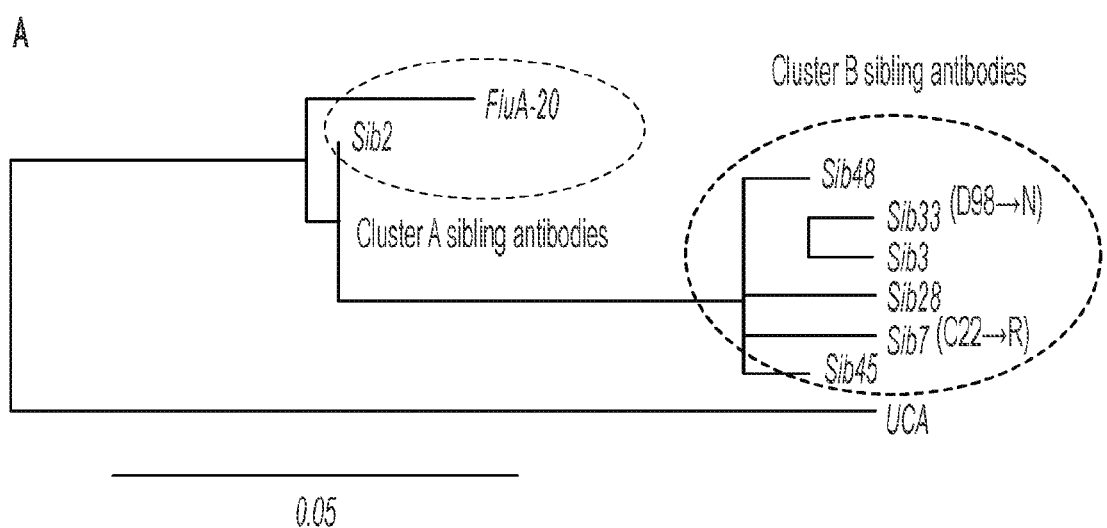

Here, the inventor reports an ultra-broad protective, naturally-occurring human antibody, designated FluA-20, which was isolated from a donor with an extensive previous influenza vaccination history. FluA-20 targets IAVs with exceptional breadth and affinity. The antibody recognizes the HA head from nearly all subtypes of influenza A viruses, with $K_D$ values of extending to low nanomolar, even in the monomeric Fab form. Instead of mediating classical neutralizing activity, FluA-20 exhibits antibody-dependent cell-mediated cytotoxicity (ADCC) activity and protects mice from sub-lethal challenges of major pathogenic influenza strains for humans (H1N1, H5N1, H3N2, and H7N9). Structural studies of FluA-20 with the HA head domain revealed a novel epitope on the non-RBS side of the 220-loop and the adjacent 90-loop. Despite the variability of the nearby sequences, the key residues recognized by FluA-20 remain exceedingly conserved across diverse subtypes, enabling FluA-20 to exhibit ultra-broad activity. Surprisingly, this epitope is largely buried in the peripheral interface of the native HA trimer. The discovery of FluA-20 epitope, and the ability of Flu-A20 to provide in vivo protection, suggests that the HA trimer interface (TI) can be exposed, perhaps transiently or partially. Targeting these 'hidden' surfaces provides anti-influenza treatments and vaccines.

These and other aspects of the disclosure are described in detail below.

I. Influenza A Virus

Influenza A virus causes influenza in birds and some mammals and is the only species of influenza virus A genus of the Orthomyxoviridae family of viruses. Strains of all subtypes of influenza A virus have been isolated from wild birds, although disease is uncommon. Some isolates of influenza A virus cause severe disease both in domestic poultry and, rarely, in humans. Occasionally, viruses are transmitted from wild aquatic birds to domestic poultry, and this may cause an outbreak or give rise to human influenza pandemics.

Influenza A viruses are negative-sense, single-stranded, segmented RNA viruses. The several subtypes are labeled according to an H number (for the type of hemagglutinin) and an N number (for the type of neuraminidase). There are 18 different known H antigens (H1 to H18) and 11 different known N antigens (N1 to N11). H17 was isolated from fruit bats in 2012. H18N11 was discovered in a Peruvian bat in 2013.

Each virus subtype has mutated into a variety of strains with differing pathogenic profiles; some are pathogenic to one species but not others, some are pathogenic to multiple species.

A filtered and purified influenza A vaccine for humans has been developed, and many countries have stockpiled it to allow a quick administration to the population in the event of an avian influenza pandemic. Avian influenza is sometimes called avian flu, and colloquially, bird flu. In 2011, researchers reported the discovery of an antibody effective against all types of the influenza A virus.

A. General

The influenza virus is an RNA virus of the family Orthomyxoviridae which comprises five genera: Influenzavirus A, Influenzavirus B, Influenzavirus C, Isavirus and Thogotovirus. The Influenzavirus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different subtypes based on the antibody response to these viruses. The subtypes that have been confirmed in humans, ordered by the number of known human pandemic deaths, are:

H1N1, which caused Spanish flu in 1918 and has been identified as the subtype of the 2009 outbreak of swine flu originating from Mexico H2N2, which caused Asian Flu in 1957

H3N2, which caused Hong Kong Flu in 1968

H5N1, a pandemic threat in the 2007-08 flu season

H7N7, which has unusual zoonotic potential

H1N2, endemic in humans and pigs

H9N2

H7N2

H7N3

H10N7

Influenza viruses A, B and C are very similar in structure. The virus particle is 80-120 nanometres in diameter and usually roughly spherical, although filamentous forms can occur. This particle is made of a viral envelope containing two main types of glycoproteins, wrapped around a central core. The central core contains the viral RNA genome and other viral proteins that package and protect this RNA. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2 (NEP), PA, PB1, PB1-F2 and PB2.

Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to HA and NA. These different types of HA and NA form the basis of the H and N distinctions in, for example, H5N1.

Influenza viruses bind through hemagglutinin onto sialic acid sugars on the surfaces of epithelial cells typically in the nose, throat and lungs of mammals and intestines of birds. The cell imports the virus by endocytosis. In the acidic endosome, part of the hemagglutinin protein fuses the viral envelope with the vacuole's membrane, releasing the viral RNA (vRNA) molecules, accessory proteins and RNA-dependent RNA polymerase into the cytoplasm. These proteins and vRNA form a complex that is transported into the cell nucleus, where the RNA-dependent RNA polymerase begins transcribing complementary positive-sense vRNA. The vRNA is either exported into the cytoplasm and translated or remains in the nucleus. Newly-synthesised viral proteins are either secreted through the Golgi apparatus onto the cell surface or transported back into the nucleus to bind vRNA and form new viral genome particles. Other viral proteins have multiple actions in the host cell, including degrading cellular mRNA and using the released nucleotides for vRNA synthesis and also inhibiting translation of host-cell mRNAs.

Negative-sense vRNAs that form the genomes of future viruses, RNA-dependent RNA polymerase, and other viral proteins are assembled into a virion. Hemagglutinin and neuraminidase molecules cluster into a bulge in the cell membrane. The vRNA and viral core proteins leave the nucleus and enter this membrane protrusion. The mature virus buds off from the cell in a sphere of host phospholipid membrane, acquiring hemagglutinin and neuraminidase with this membrane coat. As before, the viruses adhere to the cell through hemagglutinin; the mature viruses detach once their neuraminidase has cleaved sialic acid residues from the host cell. After the release of new influenza viruses, the host cell dies.

Because of the absence of RNA proofreading enzymes, the RNA-dependent RNA polymerase makes a single nucleotide insertion error roughly every 10 thousand nucleotides, which is the approximate length of the influenza vRNA. Hence, the majority of newly-manufactured influenza viruses are mutants, causing "antigenic drift." The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

B. Historical Pandemic Influenza A Outbreaks

The 1918 flu pandemic, commonly referred to as the Spanish Flu, was an influenza pandemic that spread to nearly every part of the world. It was caused by an unusually virulent and deadly Influenza A virus strain of subtype H1N1. Historical and epidemiological data are inadequate to identify the geographic origin of the virus. Most of its victims were healthy young adults, in contrast to most influenza outbreaks which predominantly affect juvenile, elderly, or otherwise weakened patients. The pandemic lasted from March 1918 to June 1920, spreading even to the Arctic and remote Pacific islands. It is estimated that anywhere from 20 to 100 million people were killed worldwide, or the approximate equivalent of one third of the population of Europe, more than double the number killed in World War I. This extraordinary toll resulted from the extremely high illness rate of up to 50% and the extreme severity of the symptoms, suspected to be caused by cytokine "storms." The pandemic is estimated to have affected up to one billion people-half the world's population at the time.

Scientists have used tissue samples from frozen victims to reproduce the virus for study. Among the conclusions of this research is that the virus kills via a cytokine storm, an overreaction of the body's immune system, which explains its unusually severe nature and the concentrated age profile of its victims. The strong immune systems of young adults ravaged the body, whereas the weaker immune systems of children and middle-aged adults caused fewer deaths.

The global mortality rate from the 1918/1919 pandemic is not known but is estimated at 2.5 to 5% of those who were infected died. Note this does not mean that 2.5-5% of the human population died; with 20% or more of the world population suffering from the disease to some extent, a case-fatality ratio this high would mean that about 0.5-1% (~50 million) of the whole population died. Influenza may have killed as many as 25 million in its first 25 weeks. Older estimates say it killed 40-50 million people while current estimates say 50 million to 100 million people worldwide were killed. This pandemic has been described as "the greatest medical holocaust in history" and may have killed more people than the Black Death.

An effort to recreate the 1918 flu strain (a subtype of avian strain H1N1) was a collaboration among the Armed Forces Institute of Pathology, Southeast Poultry Research Laboratory and Mount Sinai School of Medicine in New York; the effort resulted in the announcement (on Oct. 5, 2005) that the group had successfully determined the virus' genetic sequence, using historic tissue samples recovered by pathologist Johan Hultin from a female flu victim buried in the Alaskan permafrost and samples preserved from U.S. soldiers.

Kobasa et al. (2007) reported that monkeys (*Macaca fascicularis*) infected with the recreated strain exhibited classic symptoms of the 1918 pandemic and died from a cytokine storm—an overreaction of the immune system. This may explain why the 1918 flu had its surprising effect on younger, healthier people, as a person with a stronger immune system would potentially have a stronger overreaction. In December 2008 research by Yoshihiro Kawaoka of University of Wisconsin linked the presence of three specific genes (termed PA, PB1, and PB2) and a nucleoprotein derived from 1918 flu samples to the ability of the flu virus to invade the lungs and cause pneumonia. The combination triggered similar symptoms in animal testing.

The 2009 flu pandemic was a global outbreak of a new strain of H1N1 influenza virus, often referred to as "swine flu." The virus was first detected in April 2009 and contains a combination of genes from swine, avian (bird), and human influenza viruses. The outbreak began in the state of Veracruz, Mexico, with evidence that there had been an ongoing epidemic for months before it was officially recognized as such. The Mexican government closed most of Mexico City's public and private facilities in an attempt to contain the spread of the virus. However the virus continued to spread globally, clinics in some areas were overwhelmed by people infected, and the World Health Organization (WHO) and US Centers for Disease Control (CDC) stopped counting cases and in June declared the outbreak to be a pandemic.

While only mild symptoms are experienced by the majority of people, some have more severe symptoms. Mild symptoms may include fever, sore throat, cough, headache, muscle or joint pains, and nausea, vomiting, or diarrhea. Those at risk of a more severe infection include: asthmatics, diabetics, those with obesity, heart disease, the immunocompromised, children with neurodevelopmental conditions, and pregnant women. In addition, even for persons previously very healthy, a small percentage of patients will develop viral pneumonia or acute respiratory distress syndrome. This syndrome manifests itself as increased breathing difficulty and typically occurs 3-6 days after initial onset of flu symptoms.

Similar to other influenza viruses, pandemic H1N1 is typically contracted by person to person transmission through respiratory droplets. Symptoms usually last 4-6 days. Those with more severe symptoms or those in an at-risk group may benefit from antivirals (oseltamivir or zanamivir). The CDC estimates that, in the United States alone, as of Nov. 14, 2009, there had been 9,820 deaths (range 7,070-13,930) caused by swine flu. Currently, there are almost 15,000 confirmed deaths worldwide.

C. Diagnosis and Treatments

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include:
  Body aches, especially joints and throat
  Extreme coldness and fever
  Fatigue
  Headache
  Irritated watering eyes
  Reddened eyes, skin (especially face), mouth, throat and nose
  Abdominal pain (in children with influenza B)

It can be difficult to distinguish between the common cold and influenza in the early stages of these infections, but a flu can be identified by a high fever with a sudden onset and extreme fatigue. Diarrhea is not normally a symptom of influenza in adults, although it has been seen in some human cases of the H5N1 "bird flu" and can be a symptom in children.

Since antiviral drugs are effective in treating influenza if given early, it can be important to identify cases early. Of the symptoms listed above, the combinations of fever with cough, sore throat and/or nasal congestion can improve diagnostic accuracy. Two decision analysis studies suggest that during local outbreaks of influenza, the prevalence will be over 70%, and thus patients with any of these combinations of symptoms may be treated with neuraminidase inhibitors without testing. Even in the absence of a local outbreak, treatment may be justified in the elderly during the influenza season as long as the prevalence is over 15%.

The available laboratory tests for influenza continue to improve. The United States Centers for Disease Control and Prevention (CDC) maintains an up-to-date summary of available laboratory tests. According to the CDC, rapid diagnostic tests have a sensitivity of 70-75% and specificity of 90-95% when compared with viral culture. These tests may be especially useful during the influenza season (prevalence=25%) but in the absence of a local outbreak, or peri-influenza season (prevalence=10%).

Influenza's effects are generally much more severe and last longer than those of the common cold. Most people will recover in about one to two weeks, but others will develop life-threatening complications (such as pneumonia) . . . . Influenza, however, can be deadly, especially for the weak, old or chronically ill. The flu can worsen chronic health problems. People with emphysema, chronic bronchitis or asthma may experience shortness of breath while they have the flu, and influenza may cause worsening of coronary heart disease or congestive heart failure. Smoking is another risk factor associated with more serious disease and increased mortality from influenza.

According to the World Health Organization, "Every winter, tens of millions of people get the flu. Most are only ill and out of work for a week, yet the elderly are at a higher risk of death from the illness. It is known that the worldwide death toll exceeds a few hundred thousand people a year, but even in developed countries the numbers are uncertain, because medical authorities don't usually verify who actually died of influenza and who died of a flu-like illness." Even healthy people can be affected, and serious problems from influenza can happen at any age. People over 50 years old, very young children and people of any age with chronic medical conditions are more likely to get complications from influenza, such as pneumonia, bronchitis, sinus, and ear infections.

Common symptoms of the flu such as fever, headaches, and fatigue come from the huge amounts of proinflammatory cytokines and chemokines (such as interferon or tumor necrosis factor) produced from influenza-infected cells. In contrast to the rhinovirus that causes the common cold, influenza does cause tissue damage, so symptoms are not entirely due to the inflammatory response. This massive immune response can produce a life-threatening cytokine storm. This effect has been proposed to be the cause of the unusual lethality of both the H5N1 avian influenza, and the 1918 pandemic strain (see above).

In some cases, an autoimmune response to an influenza infection may contribute to the development of Guillain-Barré syndrome. However, as many other infections can increase the risk of this disease, influenza may only be an important cause during epidemics. This syndrome can also be a rare side-effect of influenza vaccines, with an incidence of about one case per million vaccinations.

People with the flu are advised to get plenty of rest, drink plenty of liquids, avoid using alcohol and tobacco and, if necessary, take medications such as paracetamol (acetaminophen) to relieve the fever and muscle aches associated with the flu. Children and teenagers with flu symptoms (particularly fever) should avoid taking aspirin during an influenza infection (especially influenza type B), because doing so can lead to Reye's syndrome, a rare but potentially fatal disease of the liver. Since influenza is caused by a virus, antibiotics have no effect on the infection; unless prescribed for secondary infections such as bacterial pneumonia, they may lead to resistant bacteria. Antiviral medication can be effective (see below), but some strains of influenza can show resistance to the standard antiviral drugs.

D. Influenza Virus Immunogens

Influenza hemagglutinin (HA) is an antigenic glycoprotein responsible for binding the virus to the cell that is being infected. There are 16 defined HA antigens. These subtypes are named H1 through H16. The last, H16, was discovered only recently on influenza A viruses isolated from black-headed gulls from Sweden and Norway. The first three hemagglutinins, H1, H2, and H3, are found in human influenza viruses.

HA has two functions. Firstly, it allows the recognition of target vertebrate cells, accomplished through the binding of these cells' sialic acid-containing receptors. Secondly, once bound it facilitates the entry of the viral genome into the target cells by causing the fusion of host endosomal membrane with the viral membrane. HA binds to the monosaccharide sialic acid which is present on the surface of its target cells, which causes the viral particles to stick to the cell's surface. The cell membrane then engulfs the virus and the portion of the membrane that encloses it pinches off to form a new membrane-bound compartment within the cell called an endosome, which contains the engulfed virus. The cell then attempts to begin digesting the contents of the endosome by acidifying its interior and transforming it into a lysosome. However, as soon as the pH within the endosome drops to about 6.0, the original folded structure of the HA molecule becomes unstable, causing it to partially unfold, and releasing a very hydrophobic portion of its peptide chain that was previously hidden within the protein. This so-called "fusion peptide" inserts itself into the endosomal membrane. Then, when the rest of the HA molecule refolds into a new structure (which is more stable at the lower pH), it pulls the endosomal membrane next to the virus particle's own membrane, causing the two to fuse together. Once this has happened, the contents of the virus, including its RNA genome, are free to pour out into the cell's cytoplasm.

HA is a homotrimeric integral membrane glycoprotein. It is shaped like a cylinder and is approximately 13.5 nanometers long. The three identical monomers that constitute HA are constructed into a central a helix coil; three spherical heads contain the sialic acid binding sites. HA monomers are synthesized as precursors that are then glycosylated and cleaved into two smaller polypeptides: the HA1 and HA2 subunits. Each HA monomer consists of a long, helical chain anchored in the membrane by HA2 and topped by a large HA1 globule.

II. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to influenza A virus will have several applications. These include the production of diagnostic kits for use in detecting and diagnosing influenza A virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce influenza A-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1 \times 10^{-6}$ to $1 \times 10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such h as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope). The non-contiguous epitope formed at the interface of the HA head domain is an epitope of interest for the antibodies described herein.

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267:252-259; Engen and Smith (2001) Anal. Chem. 73: 256A-265A. When the antibody neutralizes influenza A virus, antibody escape mutant variant organisms can be isolated by propagating influenza A virus in vitro or in animal models in the presence of high concentrations of the antibody. Sequence analysis of the influenza A virus gene encoding the antigen targeted by the antibody can reveal the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-influenza A virus antibody, the above-described binding methodology is performed in two orientations: In a first orientation, the reference antibody is allowed to bind to the influenza A virus antigen under saturating conditions followed by assessment of binding of the test antibody to the influenza A virus molecule. In a second orientation, the test antibody is allowed to bind to the influenza A virus antigen molecule under saturating conditions followed by assessment of binding of the reference antibody to the influenza A virus molecule. If, in both orientations, only the first (saturating) antibody is capable of binding to the influenza A virus, then it is concluded that the test antibody and the reference antibody compete for binding to the influenza A virus. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "s," J. Biol. Chem. 277 (30): 26733-26740; Davies J. et al. (2001) "s," Biotechnology & Bioengineering 74 (4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1-6) Dextran Increases Its Affinity For Antigen*," J. Exp. Med. 168 (3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143 (8): 2595-2601; Routledge, E. G. et al. (1995) "*The Effect Of Aglycosylation On The Immunogenicity Of A Humanized Therapeutic CD3 Monoclonal Antibody*," Transplantation 60 (8): 847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277 (30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as $E.$ $coli$, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within +2 is preferred, those that are within +1 are particularly preferred, and those within +0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG1 can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Certain of the antibodies described herein engage both binding sites of dimeric low affinity ectodomains of FcγRIIIa, which may provide utility in activation of ADCC.

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAbs but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., Nature Biotech., 22 (10), 1302-1306, 2004; Chennamsetty et al., PNAS, 106 (29), 11937-11942, 2009; Voynov et al., Biocon. Chem., 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366:449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab').sub.2 bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175:217-225 (1992) describe the production of a humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998). doi:10.1038/nbt0798-677pmid: 9661204). For example, bispecific antibodies have been produced using leucine zippers (Kostelny et al., J. Immunol., 148 (5): 1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579:3264; Wong and Scott, Nat. Rev. Mol. Cell Biol. 2004; 5:959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147:60, 1991; Xu et al., Science, 358 (6359): 85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2) n-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
(a) a first Fab molecule which specifically binds to a first antigen
(b) a second Fab molecule which specifically binds to a second antigen, and wherein the variable domains VL and VH of the Fab light chain and the Fab heavy chain are replaced by each other,
wherein the first antigen is an activating T cell antigen and the second antigen is a target cell antigen, or the first antigen is a target cell antigen and the second antigen is an activating T cell antigen; and
wherein
i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index). In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/anti-viral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/anti-viral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Influenza A Virus Infection

A. Formulation and Administration

The present disclosure provides pharmaceutical compositions comprising anti-influenza A virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of influenza A virus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939, 350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl) propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting influenza A virus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of influenza A virus in a subject. A wide variety of assay formats are contemplated, but specifically those that would be used to detect influenza A virus in a fluid obtained from a subject, such as saliva, blood, plasma, sputum, semen or urine. The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of influenza A virus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing influenza A virus and contacting the sample with a first antibody in accordance with the present disclosure, as the case may be, under conditions effective to allow the formation of immunocomplexes.

These methods include methods for purifying influenza A virus or related antigens from a sample. The antibody will preferably be linked to a solid support, such as in the form of a column matrix, and the sample suspected of containing the influenza A virus or antigenic component will be applied to the immobilized antibody. The unwanted components will be washed from the column, leaving the influenza A virus antigen immunocomplexed to the immobilized antibody, which is then collected by removing the organism or antigen from the column.

The immunobinding methods also include methods for detecting and quantifying the amount of influenza A virus or related components in a sample and the detection and quantification of any immune complexes formed during the binding process. Here, one would obtain a sample suspected of containing influenza A virus or its antigens and contact the sample with an antibody that binds influenza A virus or components thereof, followed by detecting and quantifying the amount of immune complexes formed under the specific conditions. In terms of antigen detection, the biological sample analyzed may be any sample that is suspected of containing influenza A virus or influenza A virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to influenza A virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the influenza A virus or influenza A virus antigen is added to the wells. After binding and washing to remove non-specifically bound immune complexes, the bound antigen may be detected. Detection may be achieved by the addition of another anti-influenza A virus antibody that is linked to a detectable label. This type of ELISA is a simple "sandwich ELISA." Detection may also be achieved by the addition of a second anti-influenza A virus antibody, followed by the addition of a third antibody that has binding affinity for the second antibody, with the third antibody being linked to a detectable label.

In another exemplary ELISA, the samples suspected of containing the influenza A virus or influenza A virus antigen are immobilized onto the well surface and then contacted with the anti-influenza A virus antibodies of the disclosure. After binding and washing to remove non-specifically bound immune complexes, the bound anti-influenza A virus antibodies are detected. Where the initial anti-influenza A virus antibodies are linked to a detectable label, the immune complexes may be detected directly. Again, the immune complexes may be detected using a second antibody that has binding affinity for the first anti-influenza A virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of influenza A virus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled influenza A virus monoclonal antibodies to determine the amount of influenza A virus antibodies in a sample. The basic format would include contacting a known amount of influenza A virus monoclonal antibody (linked to a detectable label) with influenza A virus antigen or particle. The influenza A virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in $-70°$ C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect influenza A virus or influenza A virus antigens, the antibodies may be included in the kit. The immunodetection kits will thus comprise, in suitable container means, a first antibody that binds to influenza A virus or influenza A virus antigen, and optionally an immunodetection reagent.

In certain embodiments, the influenza A virus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the influenza A virus or influenza A virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones-malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective influenza A virus antibodies. Antibodies, antibody fragment, or variants and derivatives thereof, as described in the present disclosure may also be used in a kit for monitoring vaccine manufacture with the desired immunogenicity.

VI. Examples

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Influenza viruses. The virus stocks were made from the supernatant of virus-infected MDCK cell culture monolayers in plain Dulbecco's Modified Eagle Medium (Gibco DMEM, Invitrogen, 11965) with 2 μg/mL of TPCK-trypsin.

To obtain virus with uncleaved HA0 on the surface, the stocks were made by inoculating MDCK cells with virus for 1 hr. The cells were washed thoroughly and replenished with plain DMEM without TPCK-trypsin. The supernatant containing the virus was harvested at 48 hours post inoculation.

Expression of soluble HA proteins. Sequences encoding the HA genes of interest were optimized for mammalian cell expression, and cDNAs were synthesized (Genscript) as soluble trimeric constructs as described previously (Bangaru et al., 2016). HA protein was expressed by transient transfection of 293F cells with polyethylenimine (PEI) transfection reagent and grown in expression medium (Freestyle 293 Expression Medium; Invitrogen, 12338). Cell supernatants were harvested after 7 days, filtered sterilized with a 0.4 μm filter and recombinant protein purified with HisTrap TALON FF crude columns (GE Healthcare Life Sciences).

PBMC isolation and hybridoma generation. The study was approved by the Vanderbilt University Medical Center Institutional Review Board. Peripheral blood was collected with heparin anticoagulation from a healthy donor with prior history of many seasonal influenza vaccinations and participation in clinical trials of experimental H5N1 subunit vaccinations. PBMCs from the donor were isolated by density gradient separation on Ficoll, cryopreserved and stored in the vapor phase of liquid nitrogen until use. Generation of human hybridoma cell lines secreting human monoclonal antibodies was performed as described previously (Smith et al., 2012). Briefly, human B cells in the PBMC suspension were immortalized by transformation with EBV in the presence of CpG10103, cyclosporin A and a Chk2 inhibitor and plated in 384-well culture plates. On day 8, the supernatants from transformed B cells were used to screen for the presence of heterosubtypic antibodies that bound broadly to HA antigens from H1, H3, H7 or H9 subtypes using a capture ELISA. The recombinant HA antigens used for screening were based on the sequence of HAs from the following influenza strains: H1 A/California/04/2009, H1 A/Texas/36/1991, H3 A/Hong Kong/1/1968, H3 A/Victoria/3/1975, H7 A/Shanghai/2/2013, H7 A/Netherlands/219/2003 or H9 A/Hong Kong/1073/99. Cells from the wells containing B cells secreting heterosubtypic HA-reactive antibodies were fused with HMMA2.5 myeloma cells using a BTX ECM 2001 electro cell manipulator. After fusion, human hybridomas were selected in medium with HAT solution containing ouabain. The hybridomas were cloned by flow cytometric sorting of single cells into 384 well plates and then expanded in culture. Particular clones for downstream studies were selected by choosing the clone for each independently derived hybridoma line that exhibited the highest level of IgG secretion.

Production of IgG for mAb FluA-20 from hybridoma cells. The selected cloned cell line secreting mAb FluA-20 was grown initially in hybridoma growth medium (ClonaCell-HY medium E from STEMCELL Technologies, 03805) and then switched to serum-free medium (GIBCO Hybridoma-SFM, Invitrogen, 12045084) for antibody expression and purification. IgG from the hybridoma cell line supernatants was purified by affinity chromatography using protein G columns (GE Life Sciences, Protein G HP Columns). Purified FluA-20 IgG generated from hybridomas was used for all $EC_{50}$ and $IC_{50}$ studies, competition-binding studies, HDX-MS, and ADCC assays and mouse studies.

Determination of half maximal effective concentration ($EC_{50}$) for binding. To determine $EC_{50}$ concentrations for binding, the inventors performed ELISA using 384-well plates that were coated overnight at 2 μg/mL with the recombinant HA protein of interest. The plates then were blocked with 50 μL of 5% non-fat dry milk, 2% goat serum and 0.1% Tween-20 in PBS for 1 hr at RT. The plates were washed and three-fold dilutions of the mAb starting from 10 μg/mL were added to the wells and incubated for an hour. The plates were washed and 25 μL of 1:4,000 dilution of anti-human IgG alkaline phosphatase conjugate (Meridian Life Science, W99008A) was added. After a final wash, 25 μL of phosphatase substrate solution (1 mg/mL p-nitrophenol phosphate in 1 M Tris aminomethane) was added to the plates, incubated for 20 minutes and the optical density values were measured at 405 nm wavelength on a BioTek plate reader. The plates were washed 3 times between each step with PBS containing 0.1% Tween-20. Each dilution was performed in quadruplicate, and the $EC_{50}$ values were calculated in Prism software (GraphPad) using non-linear regression analysis. The experiment was conducted twice independently. The bound antibodies were assessed by the secondary antibody, anti-human IgG alkaline phosphatase conjugate (Meridian Life Science, W99008A) as previously described (Bangaru et al., 2016).

Hemagglutinin inhibition (HAI) and microneutralization assays. Neutralization potential of FluA-20 was determined by microneutralization assay and HAI assay, as previously described (Bangaru et al., 2016).

Dimeric recombinant soluble FcγRIIIa (CD16a) binding ELISA. A dimeric recombinant soluble FcγRIIIa (rsFcγRIIIa) ELISA was used to model the need for ADCC-inducing Abs to cross link FcγRIIIa (Wines et al., 2016). A 96-well ELISA plate was coated with 50 ng of purified influenza HA protein from H1N1 A/California/07/2009 (Sino Biological Inc., 11085-V08B) protein overnight at 4° C. in PBS. The plates were treated as described (Wines et al., 2016). Briefly, the plates were blocked for 1 h and 50 μL of antibodies (FluA-20, FluA-45, FluA-55 or an unrelated negative control mAb [HIV-specific VRC01]) at various concentrations (40 μg/mL to 2.4 ng/mL) were added to the plates. The plates were washed with PBST and 50 μL of 0.1 μg/mL rsFcγRIIIa (V176) dimer was added to the wells and incubated for 1 h at 37° C. Pierce High Sensitivity Streptavidin-HRP (ThermoFisher Scientific, 21130) was diluted 1:10,000 in PBSE/BSA and added to wells. The plates were developed with TMB substrate solution and the reaction was stopped with 1 M HCl. The plates were read at an absorbance of 450 nm.

NK cell activation assay. 96-well ELISA plates were coated with 600 ng of purified influenza HA protein from H1N1 A/California/07/2009 (Sino Biological Inc., 11085-V08B) overnight at 4° C. in PBS. The plates were washed and incubated with 10 μg/mL, 1 μg/mL or 0.1 μg/mL of antibodies (FluA-20, FluA-45, FluA-55 or VRC01) diluted in PBS for 2 h at 37° C. Plates were washed and $5\times10^5$ purified NK cells were added to each well. NK cells were purified from freshly isolated PBMCs using the EasySep human NK cell enrichment kit (STEMCELL Technologies, 19055). Mouse anti-human CD107a allophycocyanin-H7 antibody (clone H4A3; BD Biosciences, 561343), 5 μg/mL brefeldin A (Sigma-Aldrich, B6542) and 5 μg/mL monensin (BD GolgiStop; BD Biosciences, 554724) were added to the cells and incubated for 5 h. Purified NK cells then were incubated with anti-human CD3 PerCP (clone SP34-2; BD Biosciences, 552851) and anti-human CD56 allophycocyanin (clone B159; BD Biosciences, 555518) for 30 min at RT. Cells were fixed and permeabilized for 10 min and then incubated with anti-human IFNγ AF700 (clone B27; BD Biosciences, 561024) in the dark. Finally, cells again were fixed with 1% formaldehyde, and data were acquired for 20,000-50,000 events using an LSRFortessa flow cytometer (BD Biosciences).

Competition-binding groups. Biolayer interferometry on an Octet Red instrument (ForteBio) was used to perform competition-binding assays as described (Bangaru et al., 2016). Briefly, the inventors loaded the HA from H1 A/California/04/2009 onto Ni-NTA tips at a concentration of 20 µg/mL, and then tested binding of two successively applied mAbs at 50 µg/mL. All antigen and antibody dilutions were made in 1× kinetic buffer (ForteBio, 18-5032). The antibodies were defined as competing antibodies if the first antibody reduced binding of the second antibody by more than 70 percent. The antibodies were defined as non-competing antibodies if the first antibody reduced binding of the second antibody by less than 30 percent.

Next-generation DNA sequence analysis of expressed antibody variable genes. Total RNA was extracted from 10 million PBMCs. A one-step RT-PCR was performed for 25 cycles using heavy-chain BIOMED-2 variable antibody gene-specific primers (Van Dongen et al., 2003) and the OneStep SuperScript III with Platinum® Taq High Fidelity kit (Invitrogen, 11304011). The Illumina-specific adapters were added using the Illumina TruSeq Library Preparation Kit (Illumina, FC-121-3001) according to the manufacturer's recommendations. The final amplicon libraries were sequenced on an Illumina MiSeq instrument using the MiSeq PE-300 v3 reagent kit (Illumina, MS-102-3001). Sequence analysis was performed using IG-BLAST v1.4, and results were parsed to MongoDB for further study.

Identifying clonally related sequences. From a database of annotated antibody sequences obtained from this donor, HCDR3s with $V_H4-61/J_H4$ lineage were queried. These HCDR3 sequences were pairwise aligned to the HCDR3 of FluA-20 using a PAM30 matrix, with penalties for gap opening and gap extension of −14 and −3, respectively. HCDR3 sequences with a Hamming distance of ≤3 to FluA-20 were selected as siblings and the 'full length' nucleotide and amino acid sequence was queried from the inventors' database for further analysis.

Visualizing clonally related sequences. A network graph was built from the aligned, full length sequences queried as described previously. Identical sequences were clustered into single nodes, and edges were drawn between two nodes if their Hamming distance was the lowest compared to all other nodes. Nodes denoting the inferred common ancestor and the germline $V_H4-61/J_H2$ sequence were manually added. This network was visualized using Cytoscape and manually adjusted for visual clarity (to prevent nodes from overlapping edges to which they are not connected, and to shorten distances between nodes that are closely related).

In vivo efficacy of FluA-20 Ig.G Female C57/bl 6 mice aged 6-8 weeks were obtained from Charles River Laboratories, Wilmington, MA, and housed under specified pathogen-free conditions with food and water ad libitum. Experimental groups of 8 mice were given i.p. with 10 mg/kg of either FluA-20 or a similarly prepared control human antibody to an unrelated target (a mAb to methicillin-resistant *Staphylococcus aureus*; MRSA). They were challenged 24 hours later with a sublethal dose (0.1 $LD_{50}$) of either H1N1 A/Netherlands/602/2009 or H3N2 A/X-31 (6:2 PR8 backbone) or H5N1 A/barn swallow/Hong Kong/D10-1161/2010 (7:1 PR8 backbone) or H7N9 A/Shanghai/1/2013 (6:2 PR8 backbone). Challenge under mild ketamine/xylazine anesthesia was by intranasal administration of 50 µl virus preparation diluted in PBS. Decrease in body weight was used as a measure of morbidity after infection. Mice (n=5) were weighed every day for 14 days post-challenge. Mice that had lost >25% of their initial body weight were killed. All infections were conducted under BSL-2+ containment and were authorized by the Institutional Ethics Committee on Experimental Animals.

For pulmonary titers, mice from each group (n=3) were killed at 6 days post-inoculation and lungs were removed aseptically, snap frozen on dry ice and stored at −80° C. until titration. Lungs were homogenized in 1 ml PBS using a Fastprep 24 homogenizer (MP Biomedicals). The homogenates were centrifuged (5 min, 16100×g, 4° C.) to remove cellular debris and used for virus titration by plaque assay. Hereto, 200 µl of tenfold dilutions of homogenized lungs in PBS were used for infecting confluent monolayers of MDCK cells. Virus was allowed to attach to MDCK cells for 1 h at 37° C. Cells were washed once with warm PBS and overlayed with oxoid agar (Oxoid Ltd., Basingstoke, Hampshire) prepared using $NaHCO_3$-buffered serum-free 2×MEM/BA containing DEAE Dextran and supplemented with TPCK-treated trypsin (1 µg/ml). Endpoint virus titers were determined by visualizing virus plaques 2 days after infection by staining with H1N1 post challenge serum (1/1000 dilution), horseradish peroxidase-conjugated sheep-derived anti-mouse serum (GE Healthcare UK, NA-931) and TrueBlue substrate (KPL-Seracare, 5510-0031).

Evaluation on the ADCC activity of FluA-20 IgG. A dimeric recombinant soluble form of FcγRIIIa (rsFcγRIIIa) was used in ELISA to model the ability of ADCC-inducing Abs to cross link FcγRIIIa (Wines et al., 2016). NK cell activation assay was performed 96-well ELISA plates were coated with 600 ng of purified influenza HA protein from H1N1 A/California/07/2009 (Sino Biological Inc., 11085-V08B). The plates were incubated with different antibodies and $5×10^5$ purified NK cells were added to each well. The activation of NK cells was evaluated by the expression of CD107a and IFNγ.

Fab and IgG cloning, expression and purification for binding kinetic assay and X-ray crystal structure determination. FluA-20 Fab and IgG were expressed in 293F mammalian cells for determination of the binding kinetics and structures as previously described (Garces et al., 2015; Irimia et al., 2016).

$K_D$ determination by bio-layer interferometry. An Octet RED instrument (ForteBio, Inc.) was used to determine $K_D$ of the antibody-antigen interactions by bio-layer interferometry. To examine the binding of FluA20 or the UCA Fab to different HAs, biotinylated HA molecules were immobilized onto streptavidin-coated biosensors (ForteBio, Inc.) and incubated with FluA20 or the UCA Fabs at highest concentration of 1 µM and with 2-fold dilution. The signals for each binding events were measured in real-time and $K_D$ values determined by fitting to a 1:1 binding model.

Preparation of HA head domains. In brief, DNA fragments for the head domains (residues 52-263 of H1 HA (A/Solomon Islands/3/2006) and residue 43-306 of H3 HA (A/Hong Kong/1/1968)) were amplified separately with PCR reaction. The head domain DNA fragments were individually cloned into the pFastBac vector with an N-terminal gp67 secretion signal peptide and a C-terminal $His_6$ tag. Recombinant bacmid DNA was generated via the Bac-to-Bac system (Invitrogen) and Baculovirus was generated by transfecting purified bacmid DNA in to Sf9 cells. HA head domains were expressed by infecting the High Five cells with the recombinant virus, shaking at 110 r.p.m. for 72 h at 28° C. The secreted head domain protein was purified from the supernatant via Ni-NTA Superflow (Qiagen) and gel filtration on a Superdex75 column (GE Healthcare) in 20 mM Tris-HCl pH 8.0, 150 mM NaCl.

Peptide fragmentation and deuterium exchange mass spectrometry. To maximize peptide probe coverage, the optimized quench condition was determined prior to deuteration studies (Hsu et al., 2009; Li et al., 2011). In short, the HA head domain was diluted with buffer of 8.3 mM Tris, 150 mM NaCl, in $H_2O$, pH 7.15) at 0° C. and then quenched with 0.8% formic acid (v/v) containing various concentration of GuHCl (0.8-6.4 M) and Tris(2-carboxyethyl) phosphine (TCEP) (0.1 or 1.0 M). After incubating on ice for 5 min, the quenched samples were diluted 4-fold with 0.8% formic acid (v/v) containing 16.6% (v/v) glycerol and then were frozen at −80° C. until they were transferred to the cryogenic autosampler. Using the quench buffer of 6.4 M GuHCl, 1.0 M TCEP in 0.8% formic acid gave an optimal peptide coverage map.

The samples later were thawed automatically on ice and then immediately passed over an AL-20-pepsin column (16 µL bed volume, 30 mg/mL porcine pepsin (Sigma)). The resulting peptides were collected on a C18 trap and separated using a C18 reversed phase column (Vydac) running a linear gradient of n0.046% (v/v) trifluoroacetic acid, 6.4% (v/v) acetonitrile to 0.03% (v/v) trifluoroacetic acid, 38.4% (v/v) acetonitrile over 30 min with column effluent directed into an Orbitrap Elite mass spectrometer (Thermo-Fisher Scientific). Data were acquired in both data-dependent MS: MS mode and MS1 profile mode. Proteome Discoverer software (Thermo Finnigan Inc.) was used to identify the sequence of the peptide ions. DXMS Explorer (Sierra Analytics Inc., Modesto, CA) was used for the analysis of the mass spectra as described previously (Hamuro et al., 2004). FluA-20 mAb bound HAs were prepared by mixing FluA-20 mAb with monomeric H5 A/Vietnam/03/2204 HA head domain at a 1:1.1 stoichiometric ratio. The mixtures were incubated at 25° C. for 30 min. All functionally deuterated samples, with the exception of the equilibrium-deuterated control, and buffers were pre-chilled on ice and prepared in the cold room.

Functional deuterium-hydrogen exchange reaction was initiated by diluting free HA or antibody-bound HA stock solution with $D_2O$ buffer (8.3 mM Tris, 150 mM NaCl, in D20, pDREAD 7.15) at a 1:2 vol/vol ratio. At 10 sec, 100 sec and 1,000 sec, the quench solution was added to the respective samples, and then samples were frozen at −80° C. In addition, nondeuterated samples, equilibrium-deuterated back-exchange control samples were prepared as previously described (Hsu et al., 2009; Li et al., 2011; Lu et al., 2012). The centroids of the isotopic envelopes of nondeuterated, functionally deuterated, and fully deuterated peptides were measured using DXMS Explorer, and then converted to corresponding deuteration levels with corrections for back-exchange (Zhang and Smith, 1993).

Structure determination of FluA-20 Fab and complexes of FluA-20 with HA head domains. Purified FluA-20 and complexes of FluA-20 and H1 head domain or_H3 head domain were concentrated to 8-10 mg/ml for crystallization. The conditions of crystals for x-ray data collection are listed:
Apo FluA20 Fab: 20° C.
0.2 M tri-sodium citrate, 20% (w/v) PEG3350 cryo-protected by addition of 15% glycerol)
FluA-20_H1 head domain: 20° C.
0.1 M phosphate-citrate, pH 4.2, 40% (v/v) PEG300
No additional cryo-protection FluA-20_H3 head domain: 4° C.
0.1 M Tris-HCl pH 8.5, 0.2 M lithium sulfate, 40% (v/v) PEG400
No additional cryo-protection X-ray diffraction data were collected at multiple beamline (Tables S3-4). The diffraction data were processed with HKL2000 and the structure was determined by molecular replacement in Phaser (McCoy et al., 2007). The initial models for FluA-20 were adapted from PDB 4KMT for the light chain and PDB 5BV7 for the heavy chain. The structures for H1 and H3 head domains were adapted from PDB models 4YJZ and 4FP8. Refinement was carried out in Refmac (Skubak et al., 2004), Phenix (Adams et al., 2010), and model rebuilding was performed manually in Coot (Emsley and Cowtan, 2004) and the model was validated by MolProbity (Chen et al., 2010).

Structural analysis. Interaction and interface analysis is carried out on online server PDBePISA on the world-wide-web at ebi.ac.uk/pdbe/pisa/. Structure figures were generated by MacPyMol (DeLano Scientific LLC).

Site-directed mutagenesis of genes encoding HA or antibody proteins. Primers for site-directed mutagenesis were designed using the Agilent QuikChange Primer Design program (Agilent Technologies). The Quickchange Lightning Multi-Site Mutagenesis kit (Agilent, 210515-5) was used to introduce mutations into cDNAs encoding the antibody heavy chain genes or HA genes. The plasmids encoding mutants of FluA-20 heavy or light chains were transfected with the corresponding unmutated FluA-20 light or heavy chains, respectively. Antibodies encoded by cDNA with engineered mutations were purified and tested for binding to HA in ELISA, and the $EC_{50}$ values for binding were determined using Prism software (GraphPad).

Conservation analysis of the FluA-20 binding epitope. Libraries for full-length and non-redundant human influenza H1 and H3 sequences were downloaded in January 2017 from the Influenza Virus Resource at the NCBI database (Bao et al., 2008). The H1 library includes 11,267 sequences and the H3 library includes 12,584 sequences. The HA sequence alignment was performed by MUSCLE (Edgar, 2004) and analyzed using EMBOSS program (Rice et al., 2000) and custom shell scripts based on SEQCONV+ (the Roth Lab, UC Davis).

Conservation analysis of the overall HA surface. A library of HA sequences that were recently isolated from humans since 2015 was used for surface conservation analysis, including 701 H1 sequences, 1739 H3 sequences, and 17 other sequences of H5, H7 and H9 subtypes. The sequences were aligned with MUSCLE (Edgar, 2004) software and the conservation scores for each residue were analysis with ConSurf server and presented on an H3 HA model (PDB 4O5n) (Lee et al., 2014).

Comparison of FluA-20 binding to HA0 and cleaved HA trimer by Biolayer interferometry (BLI). Baculovirus-expressed HA0 was prepared for the binding studies by cloning the HA ectodomain genes into the pFastBac vector with an N-terminal gp67 secretion signal peptide and a C-terminal BirA biotinylation site, thrombin cleavage site, foldon trimerization domain, and His6 tag. HA0 was expressed in High five cells and the secreted HA0 purified from the supernatant via Ni-NTA Superflow (Qiagen) and gel filtration. The HA0 trimer fractions were concentrated for BLI assays. To prepare cleaved HA trimer, the HA0 trimer was incubated with trypsin at 4° C. overnight (mass ratio of trypsin: HA0≈1:1000). The HA cleavage was determined by SDS-PAGE electrophoresis with reducing agent.

The cleaved HA was purified by gel filtration and the trimer HA concentrated for BLI assay.

To evaluate antibody binding, Fabs of FluA-20 and RBS-antibodies (5J8 for H1 binding (Hong, 2013 #170) and H7.137 for H7 binding (Thornburg et al., 2016)) were firstly immobilized onto anti-human CH1 biosensors (ForteBio, Inc.) in the BLI buffer of PBS pH 7.4, 0.01% BSA and 0.002% Tween 20. The Fab-coated sensors were then incubated with corresponding HA0 and cleaved HA at 1 µM concentration for 120s to evaluate the association, and then incubated with BLI buffer for 120s to evaluate the dissociation.

Flow cytometric analysis of antibody binding to cell-surface expressed HA. HEK293F cells grown in expression medium (Freestyle 293 Expression Medium; Invitrogen, protein and incubated at 37° C. for 36 hours. Untransfected (UT) or transfected cells were washed and treated with either DMEM containing TPCK trypsin (2 µg/mL) or plain DMEM for 15 minutes at 37° C. Cells were washed with PBS containing 2% of heat inactivated FBS and 2 mM EDTA (FACS buffer) and incubated with either mAb CR9114 or mAb FluA-20 (10 µg/mL) for 30 min at RT and for 5 min at 37° C. The cells were washed with FACS buffer and incubated with secondary goat anti-human IgG PE antibody (Southern Biotech, 2040-09) for 1 hour at 4° C., fixed with 4% formaldehyde in PBS, and analyzed by flow cytometry using an LSR-2 cytometer (BD Biosciences). Data for a total of up to 20,000 of cell events were acquired and analyzed with FlowJo software (Tree Star).

HDX-MS to comparison the dynamic change of H7 HA0 trimer and cleaved HA trimer. H7 HA (A/Netherlands/219/2003) was expressed in HEK293F cells (Bangaru et al., 2016). In brief, sequences encoding the HA genes were optimized for expression, and cDNAs were synthesized (Genscript) as soluble trimeric constructs by replacing the transmembrane and cytoplasmic domain sequences with cDNAs encoding the GCN4 trimerization domain and a His-tag at the C-terminus. Synthesized genes were subcloned into the pcDNA3.1 (+) mammalian expression vector (Invitrogen). HA protein was expressed by transient transfection of 293F cells with polyethylenimine transfection reagent and grown in expression medium (Freestyle 293 Expression Medium; Invitrogen, 12338). The HA0 protein was harvested after 7 days with HisTrap TALON FF crude columns and the HA0 trimer purified via gel filtration. To obtained cleaved HA trimer, the HA0 protein was treated with trypsin at 37° C. for 30 mins and the cleaved HA trimer further purified by gel filtration.

Prior to conducting comparative hydrogen-deuterium exchange experiments with H7 HA0 or with cleaved H7HA, the quench condition for best sequence coverage of HA was 6.4M GuHCl, 1 M TCEP and 0.8% formic acid, as previously described (Aiyegbo et al., 2014; Li et al., 2011; Marsh et al., 2013).

To initiate hydrogen-deuterium exchange reactions, 2 µl of pre-chilled protein stock solution (free un-cleaved H7 HA0, 1.8 mg/ml; cleaved H7 HA, 1.6 mg/ml) was diluted into 4 µl D20 buffer (8.3 mM Tris, 150 mM NaCl, in D20, pDREAD 7.2) at 0° C. At indicated time of 10 sec, 100 sec, 1000 sec, 10000 sec and 100000 sec, the exchange reaction was quenched by the addition of 9 µl of optimized quench solution at 0° C. After incubating on ice for 5 min, the quenched sample was diluted 5-fold with 0.8% formic acid containing 16.6% glycerol, immediately frozen on dry ice and stored at −80° C. In addition, un-deuterated samples and equilibrium-deuterated control samples were also prepared. All samples were then loaded onto the inventors' in-house LC instrument for online digestion and separation (Aiyegbo et al., 2014). The resulting peptides were directed into an OrbiTrap Elite Mass Spectrometer (Thermo Fisher Scientific, San Jose, CA) for DXMS analysis. Instrument settings have been optimized for HDX analysis. The data acquisition was carried out in a data-dependent mode and the five or ten most abundant ions were selected for MS/MS analysis. Proteome Discoverer software was used for peptide identification. The centroids of each peptide was calculated with HDExaminer, and then converted to corresponding deuteration levels with corrections for back-exchange (Zhang and Smith, 1993).

Isolation of additional antibodies to the interface region of the HA trimer from subjects boosted with an experimental influenza A H5N1 vaccine. Additional human hybridomas secreting human mAbs to the interface epitope recognized by FluA-20 were generated from PBMCs collected as above, but from subjects who received a H5N1 vaccine. PBMCs were isolated from blood from healthy adult donors who had participated previously in a Phase I clinical trial of an experimental H5N1 vaccine candidate in healthy adult subjects (NIH study DMID 04-062). The vaccine was a monovalent inactivated subvirion vaccine prepared by Chiron Vaccines (now part of Novartis). The virus used to prepare the working seed and the vaccine was produced by reverse genetics using the modified hemagglutinin- and unaltered neuraminidase-encoding genes from the influenza A/Vietnam/1203/2004 (H5N1) strain and all other genes from A/Puerto Rico/8/34 (H1N1). Hybridomas were generated using the methods described above, using recombinant H5N1 Vietnam 2005 strain antigens as the primary screen in ELISA, to isolate the H5.28 and H5.31 clones. The mAbs were tested for breadth of binding to HAs from diverse subtypes of influenza A, as above.

Isolation of additional antibodies to the interface region of the HA trimer from a subject boosted with an experimental influenza A H5N1 vaccine. Additional human hybridomas secreting human mAbs to the interface epitope recognized by FluA-20 were generated from PBMCs collected as above, but from a subject who received a H5N1 vaccine. PBMCs were isolated from the blood of a healthy adult donor who had participated previously in a Phase I clinical trial of an experimental H5N1 vaccine candidate in healthy adult subjects (NIH study DMID 04-062). The vaccine was a monovalent inactivated subvirion vaccine prepared by Chiron Vaccines (now part of Novartis). The virus used to prepare the working seed and the vaccine was produced by reverse genetics using the modified hemagglutinin- and unaltered neuraminidase-encoding genes from the influenza A/Vietnam/1203/2004 (H5N1) strain and all other genes from A/Puerto Rico/8/34 (H1N1). Hybridomas were generated using the methods described above, using recombinant H5N1 Vietnam 2005 strain antigens as the primary screen in ELISA, to isolate the H5.28 and H5.31 clones. The mAbs were tested for breadth of binding to HAs from diverse subtypes of influenza A, as above.

Isolation of an antibody to the interface region of the HA trimer from a subject infected with influenza A H7N9 virus. An additional human hybridomas secreting a human mAb to the interface epitope recognized by FluA-20 was generated from PBMCs collected as above, but from a subject who was naturally infected with influenza A H7N9 virus was traveling in China. PBMCs were isolated from the blood of this otherwise healthy adult donor after recovery from H7N9 infection. The inventors used recombinant H7 HA protein from the H7 strain A/Shanghai/02/2013 H7N9 as the antigen in a primary screen in ELISA, to isolate the H7-200 clone.

The mAb was tested for breadth of binding to HAs from diverse subtypes of influenza A, as above.

Example 2—Results

Figure 1A:
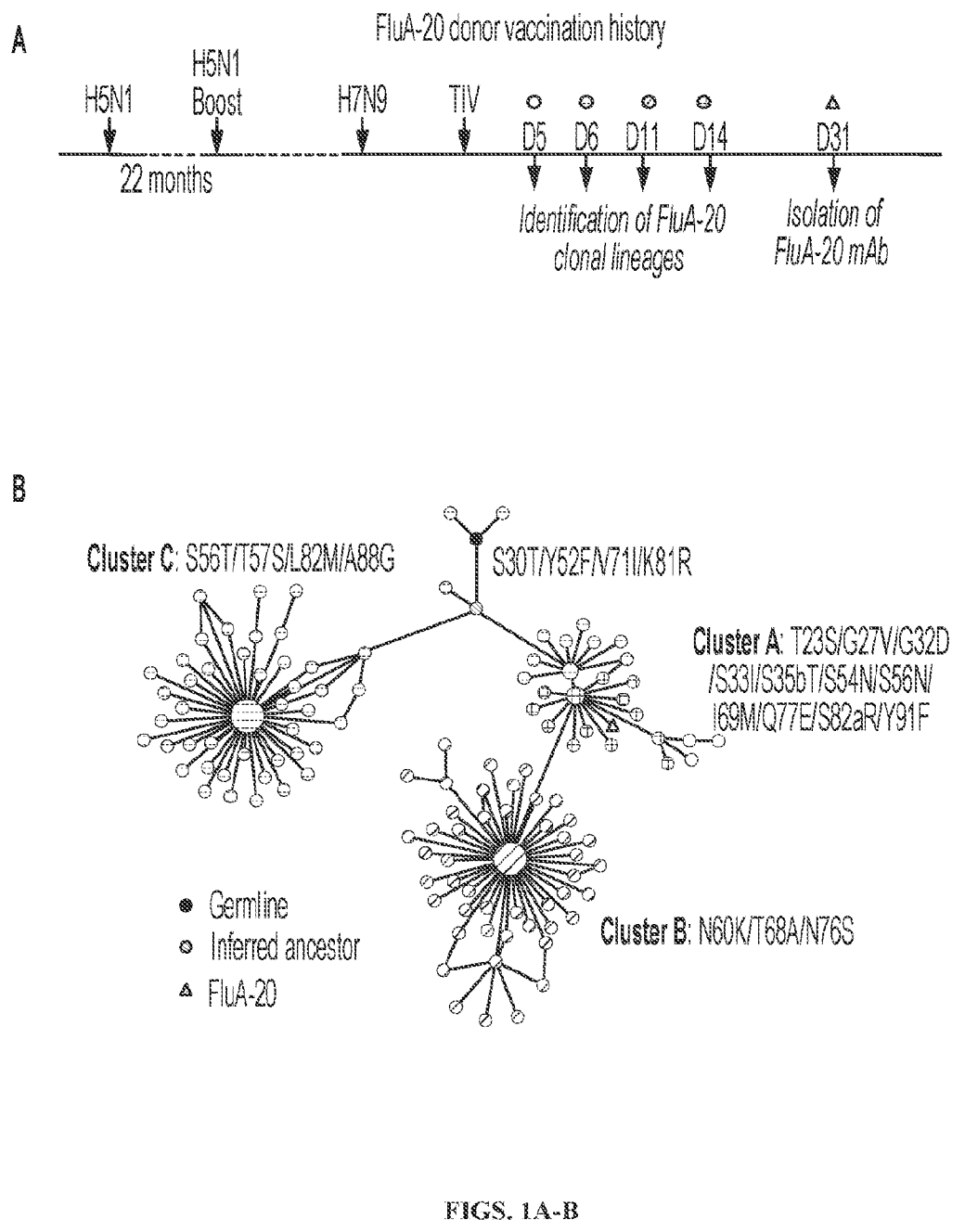

Isolation of human monoclonal antibody (mAb) FluA-20 and its sibling antibodies. The inventor identified a donor who had received annual licensed inactivated seasonal vaccines for over two decades. The donor also had participated previously in clinical trials of experimental H5N1 and H7N9 subunit vaccines in the NIH Vaccine Treatment and Evaluation Unit (FIG. 1A). The first H5 vaccine was a monovalent inactivated subvirion vaccine that incorporate the HA from A/Vietnam/1203/2004 (VN/1203) H5N1 clade 1 influenza virus (batch 04-067), and each dose consisted of 90 μg of hemagglutinin (DMID study 04-062). After 22 months, the individual was boosted with a monovalent inactivated surface antigen influenza A (H5N1) vaccine made from the modified HA and NA of A/Anhui/01/2005 (H5N1) (DMID study 07-0022). The volunteer subsequently received an H7 subunit vaccine [in DMID 13-0033; a phase II human clinical trial with monovalent inactivated influenza A/Shanghai/02/2013 H7N9]). For the current study, the donor was vaccinated with a 2014-15 seasonal trivalent inactivated influenza vaccine (TIV) on day 0. Peripheral blood samples were obtained using heparin anticoagulation on days 0, 3, 4, 5, 6, 7, 10, 11, 14 and 31 following immunization.

Cryopreserved PBMC samples from day 31 after seasonal vaccination were immortalized by EBV transformation and the supernatants were screened for the presence of antibodies that displayed heterosubtypic binding breath to recombinant HA proteins derived from H1 (A/California/04/2009, A/Texas/36/1991), H3 (A/Hong Kong/1/1968, A/Victoria/3/1975), H7 (A/Shanghai/2/2013, A/Netherlands/219/2003) and H9 (A/Hong Kong/1073/99) subtypes by capture ELISA. The hybridoma cell line secreting the FluA-20 mAb was isolated from a B cell line that exhibited heterosubtypic breadth during the initial screen. Two additional broadly reactive non-neutralizing heterosubtypic mAbs also were isolated and used in these studies for comparative purposes, designated FluA-45 and FluA-55. These mAbs are antibodies that were isolated from individuals previously vaccinated with an experimental H7 vaccine (in the NIH Vaccine Treatment and Evaluation Unit [DMID 13-0033; a phase II human clinical trial with monovalent inactivated influenza A/Shanghai/02/2013 H7N9]).

The inventor also discovered sequences that may have been related clonally to FluA-20 (i.e., "siblings"), defining two sequences as clonally related if they share use of the same $V_H$ and $J_H$ gene and have three or fewer amino acid differences in their HCDR3 region. He identified siblings to FluA-20 in blood samples from four time points: days 5, 6, 11 and 14 post-vaccination with TIV. He inferred that the majority of these siblings arose from one common ancestor, and cluster into three major families (Cluster A, B and C) that differ by mutations across the $V_H$ gene region (FIG. 1B). Network analysis of these sequences reveals that FluA-20 arose from blasting cells present at day 6 that also were observed at day 14 (FIG. 1B). The inventor also tested several sibling antibodies related to FluA-20 from cluster A and cluster B (FIG. 8A and Table S1). Several sibling antibodies, such as Sib 2, Sib 3, and Sib 45, appear to have very similar activity and breadth as FluA-20 (Table S1), suggesting that multiple variations of this FluA-20 clonotype were sustained in the repertoire that did not acquire functional differences. Also, the inventor found that two sibling antibodies, Sib 28 and Sib 48 in a phylogenetic cluster that was more mutated than FluA-20, lost binding to some H3 and H5 HAs, and Sib 7 and Sib 33 completely lost activity to any HA tested, likely due to the introduction of additional somatic mutations.

Activity profiling of FluA-20 for interaction with various subtypes of influenza HA. To investigate the breadth of the cloned mAb FluA-20, the inventor tested purified IgG for binding activity to HA from various subtypes. FluA-20 exhibited extraordinary binding breadth and affinity to recombinant HA belonging to group 1 (H1, H2, H5, H6, H8, H9, H12 and H13) and group 2 (H3, H4, H7, H10, H14 and H15) viruses, with $EC_{50}$ values for binding ranging from 4 to 800 ng/ml (FIG. 1C).

Figure 8B:
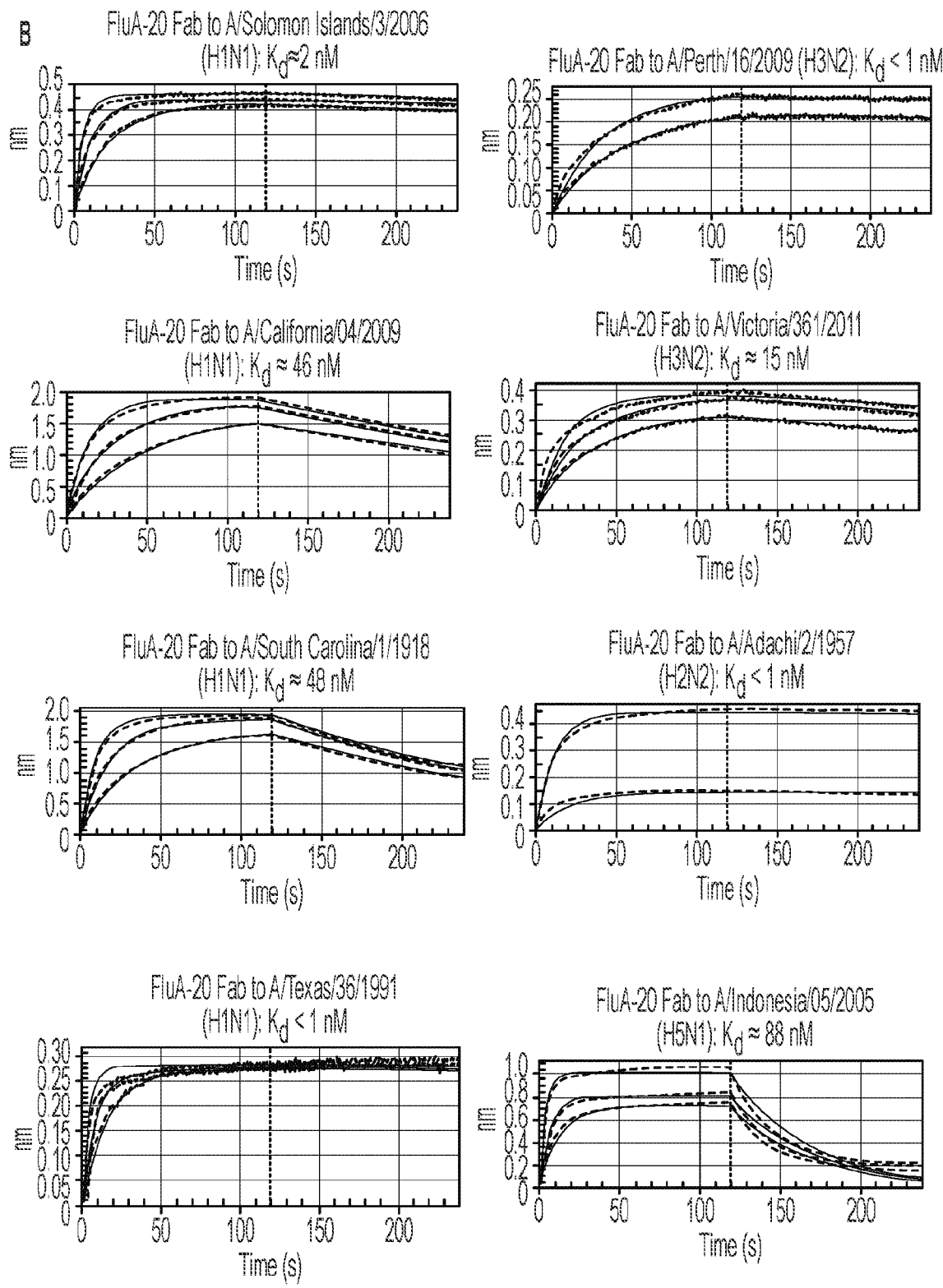
Figure 8B:
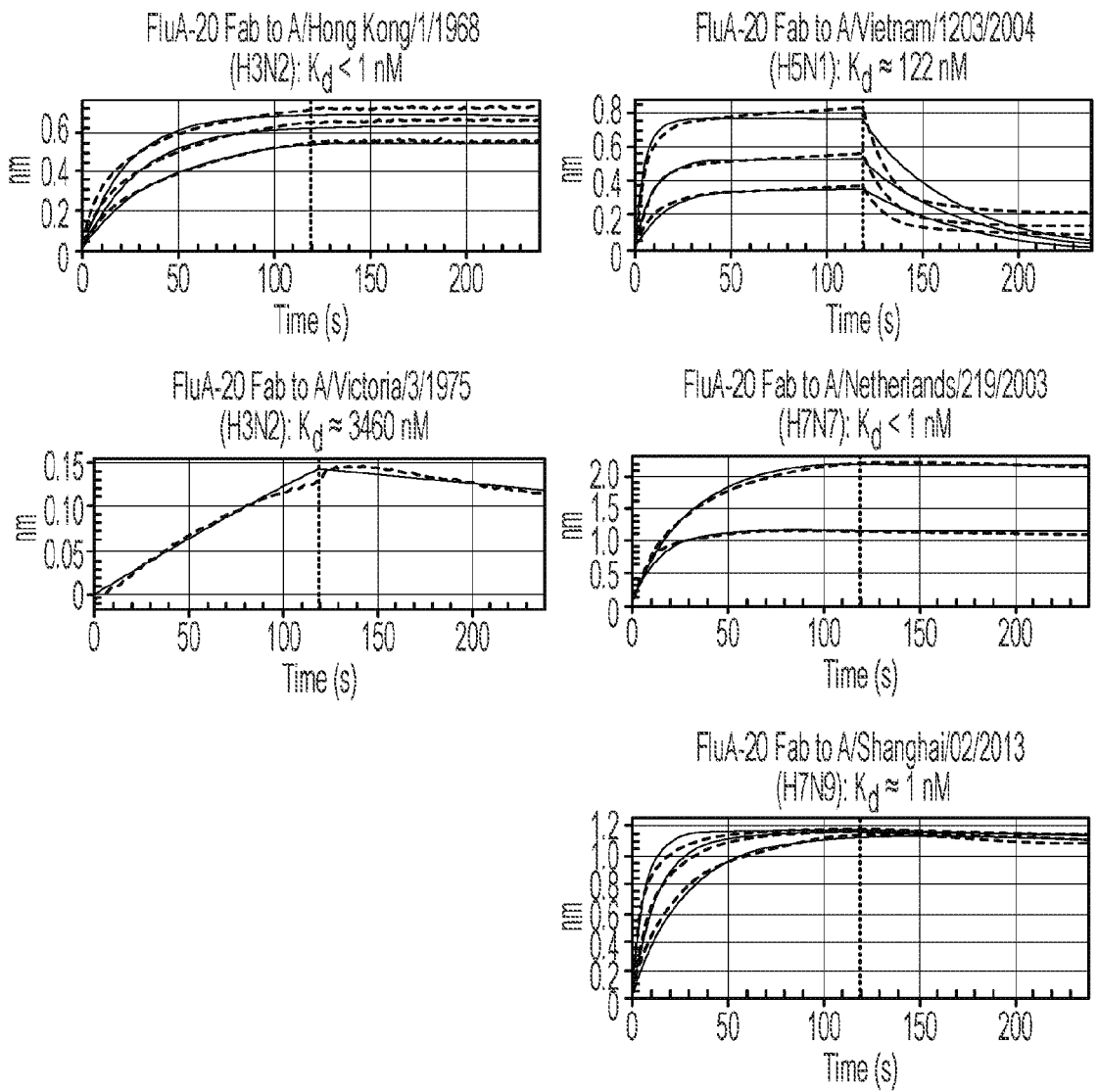

Genes of the wild-type FluA-20 variable domain were synthesized and a recombinant form of FluA-20 (rFluA-20) IgG protein was expressed. Generally, rFluA-20 IgG showed the same binding spectrum, but slightly lower affinities to the panel of HAs in comparison to the hybridoma-produced FluA-20 IgG protein. Additionally, the inventor recombinantly expressed the FluA-20 Fab and assessed its binding kinetics to representative HA subtypes that are pathogenic for humans using a bio-layer interferometry assay. Remarkably, even in its monovalent Fab form, FluA-20 interacted with most HA molecules from H1, H2, H3, H5, and H7 subtypes with $K_D$ values less than 100 nM (with several less than 1 nM, Table S2, FIG. 8B).

FluA-20 exhibits prophylactic efficacy in vivo against viruses of influenza type A H1N1, H3N2, H5N1 or H7N9 subtypes. To examine the in vivo protection of mAb FluA-20, the inventor chose A/Netherlands/602/2009 (H1N1), A/X-31 (H3N2), A/barn swallow/Hong Kong/D10-1161/2010 (H5N1) and A/Shanghai/1/2013 virus strains (H7N9), representative of group 1 and group 2 IAVs, for prophylactic studies. C57BL/6 mice (n=8 per group) were administered 10 mg/kg of FluA-20 or a similarly prepared control antibody by the intraperitoneal route, and then challenged 24 hours later intranasally with a sub-lethal dose of virus. Mice treated with FluA-20 (n=5) showed complete protection from weight loss after H1N1 challenge (FIG. 2A), whereas mice challenged with H3N2, H5N1 or H7N9 strains showed significantly faster recovery from weight loss compared to control animals (FIG. 2A). Additionally, FluA-20 treatment reduced pulmonary lung titers (day 6) following H1N1 and H7N9 challenge (FIG. 2B).

FluA-20 lacks neutralizing function but possesses antibody dependent cellular cytotoxicity (ADCC) activity. The inventor found that the in vivo protection delivered by FluA-20 was not mediated by direct neutralization of virus. The FluA-20 antibody was tested in micro-neutralization assays against H1N1 A/California/04/2009, H3N2 A/Texas/50/2012 or H7N9 A/Shanghai/2/2013 (6:2 PR8 backbone) viruses. FluA-20 did not exhibit any neutralizing activity at concentrations up to 20 μg/mL. Additionally, neutralizing activity was not detected against pseudoviruses displaying the HA from H1N1, H3N2 or H5N1 subtype viruses (data not shown).

ADCC has emerged as a major mechanism by which broadly reactive influenza stem antibodies may confer protection, and interactions between antibody Fc and FcγR have been shown to be critical for in vivo protection (DiLillo et al., 2016; DiLillo et al., 2014). To examine if FluA-20 could mediate ADCC activity, the inventor performed an ELISA-based screen using recombinant soluble (rs), dimeric, low-affinity ectodomains (rsFcγR) of FcγRIIIa (Wines et al., 2016). These rsFcγR low-affinity dimers require simultaneous engagement of both receptors by HA-bound IgGs to achieve stable binding in ELISA. Four similarly prepared antibodies, FluA-20, FluA-45, FluA-55 or VRC01 (an HIV-reactive negative control mAb) were added to plates coated with H1 A/California/04/2009 HA to test for their ability to engage both binding sites on rsFcγR simultaneously. The FluA-20 IgG strongly engaged the rsFcγR dimers, demonstrating its potential to mediate ADCC activity, while neither the HA-reactive mAbs FluA-45 and FluA-55 nor the HIV-specific control mAb VRC-01 engaged these FcγR molecules (FIG. 2C).

To test whether this FcγR binding activity corresponded with functional ADCC activity, the inventor examined the ability of these antibodies to activate primary CD3" CD56+ NK cells following incubation with HA from A/California/04/2009. NK cell activation was measured as the percentage of NK cells expressing intracellular IFN-γ and/or CD107a (markers for degranulation) (Al-Hubeshy et al., 2011; Alter et al., 2004). A robust concentration-dependent increase of NK cell activation was observed for FluA-20 (1.3, 9.2% or 14.6% NK cell activation at 0.1, 1 or 10 µg/mL FluA-20 respectively), while FluA-45, FluA-55 and VRC01 did not exhibit any NK cell activation (FIG. 2D). Taken together, these results indicated that the in vivo prophylactic efficacy against IAVs of the non-neutralizing FluA-20 mAb is likely mediated by engaging FcγR and inducing potent ADCC activity.

FluA-20 IgG does not compete with other RBS or stem-specific antibodies. To determine whether FluA-20 binds to previously known vulnerability sites of HA, the inventor used bio-layer interferometry to measure if FluA-20 competes for HA binding against other known bnAbs. FluA-20 does not appear to compete for binding to HA with RBS-mAbs (5J8) or stem-specific mAbs (CR9114, FI6v3, 39.29 and H3v-86) (FIG. 8C). Additionally, he observed that FluA-20 potently interacted with the truncated HA head domains from multiple HA subtypes (FIG. 8D). These data indicate that FluA-20 recognizes a novel epitope on the HA head domain that is conserved across most influenza A viruses.

Structural characterization of FluA-20 in complex with the HA head from H1 A/Solomon Islands/3/2006 reveals a novel epitope at the trimer interface. To decipher this novel site of vulnerability on the HA head, crystal structures of apo FluA-20 Fab and its complex with the HA head domain from A/Solomon Islands/3/2006 (H1N1) were determined at 1.73 Å and 2.85 Å resolutions, respectively (Tables S3-4). Two HA head domains, each bound by one Fab, were present in the crystal asymmetric unit.

The complex structure revealed that FluA-20 recognizes an epitope that is parallel to, but does not overlap with, the receptor-binding site (RBS) (FIG. 3A). The antibody interacts primarily with the 220-loop and has some contacts to the 90-loop, creating buried surface areas of 617 Å2 and 98 Å2 on each loop. After superimposing the HA head domain in the Fab complex with an H1 HA trimer model (PDB 4M4Y), this epitope was found to be hidden in the HA trimer interface and not accessible for antibody binding (FIG. 3B). In fact, the non-RBS side of 220-loop is an important surface for interaction of the HA with its adjacent protomer in the native trimer (FIGS. 9A-B). The variable domain of FluA-20 would overlap with the head domain from an adjacent protomer in the HA trimer (FIG. 3B). These results suggest that FluA-20 recognizes HA in a form different from the canonical trimer.

The interaction of FluA-20 with the HA head domain is mediated mainly by a groove between CDR H3 and L2, with some contacts from CDR H1 to the edge of its epitope (FIG. 3A). Many contacts of FluA-20 to HA are centered on Arg229 (FIG. 3C). Firstly, Asp98 (H) of FluA-20 makes a salt bridge with Arg229 (FIG. 3C). Surrounding this salt bridge is an enclosed hydrophobic pocket formed by both HA and FluA-20 residues, including Pro221, Val223, and Pro96 of HA and Tyr49 (L) and Tyr100a (H) of FluA-20 (FIG. 3C). The aromatic side chains of Tyr100a (H) of FluA-20 are positioned approximately 4 Å away from the positive amine of Arg229 in HA and likely form cation-π interactions that would strengthen the binding. Alanine mutation of Arg229 completely abolished binding of FluA-20 to the HA (FIG. 3D). Glycine mutation of Val223 or Pro96 in the HA epitope also substantially decreased HA binding by FluA-20, indicating that these hydrophobic contacts between the non-polar residues in HA to Tyr49 (L) and Tyr100a (H) of FluA-20 are important for its activity (FIG. 3D). Reciprocally, D98A (H) or Y49A (L) mutants of FluA-20 disrupted binding to all targeted HAs, and alanine mutation of Tyr100a (H) in FluA-20 also eliminated binding to most HA subtypes (Table S5).

Other than the intricate binding core, several hydrogen bonds are involved in the binding of FluA-20 to HA. The side-chain amine of HA Arg220 hydrogen bonds to the main-chain carbonyl of Glu97 (H) from the antibody (FIG. 3C). Additionally, Gln55 (L) side-chain carbonyl contacts the main-chain amide of Lys222 on the HA (FIG. 3C, FIG. 12A). As a result, mutation of either HA Arg220 or Gln55 (L) of FluA-20 decreases the binding interaction (FIG. 3D, Table S5).

Structural characterization of FluA-20 in complex with HA head of H3 A/Hong Kong/1/1968. The inventor also determined the crystal structure of FluA-20 Fab with the HA head domain of A/Hong Kong/1/1968 (H3N2), at 2.10 Å resolution (Table S4). Each asymmetric unit includes one FluA-20 in complex with one H3 head domain. FluA-20 also interacts with a similar epitope on the H3 head domain as with H1 with similar interactions (FIG. 4A, FIGS. 9C-D). The structural alignment of H3 head domain bound by FluA-20 with the H3 trimer model (PDB 4FNK) again indicates that the antibody interacts with HA in a form other than the canonical trimer (FIG. 4A).

Additional hydrogen bonds are made between the side-chain amine of Gln55 (L) of FluA-20 to the main-chain carbonyl of Trp222 in HA and Asn53 (L) side-chain carbonyl to the Arg224 main-chain amine (FIG. 4B, FIG. 12B). Gln55 (L) appears to be important for FluA-20 binding to many other HA strains, although it is not for H3 (A/Hong Kong/1/1968) and a few other strains (FIG. 4B, Table S5). The interaction by Asn53 (L) is not required for the antibody binding to most HAs (Table S5).

Hydrogen deuterium exchange mass spectrometry (HDX-MS) experiments confirms interaction FluA-20 with H5 HA. To confirm that FluA-20 interacts with the equivalent epitope on H5 HA, the inventor conducted HDX-MS experiments with a monomeric head domain of H5 (A/Vietnam/1203/2004) to identify peptides on the surface of HA that are occluded following binding of FluA-20. H5 HA head domain protein was labeled with deuterated water in the presence or absence of the FluA-20 IgG. The head domain protein was digested with pepsin, and deuterium labeling of resulting peptides was measured by mass spectrometry. He found that FluA-20 blocked labeling of peptides comprising of residues 210-223 (FIGS. 10A-B), consistent with the identification of the epitope on the H1 and H3 HA subtypes. Mutations of the 220-loop in H5 (A/Vietnam/1203/2004) show substantial influences on FluA-20 binding. Single mutants of R220A, V223A, or R229A in H5 completely abolished the FluA-20 activity, illustrating that the antibody engages similar binding mechanism for H5 as those observed for H1 and H3 (FIG. 10C).

The FluA-20 epitope is highly conserved across different subtypes of IAV HA. FluA-20 engages a highly conserved binding core in its recognition of H1 and H3 HAs. The five HA residues with which FluA-20 primarily interacts, namely Pro96, Arg220, Pro221, Val223, and Arg229, are extremely conserved among all human H1N1 viruses (95% conservation for Pro96, and over 98% conservation for the other four residues) (FIG. 5A). In human H3N2 viruses, conservation of key residues in the epitope is generally above 97%, except for residue 223. Approximately 22% of H3 strains encode a Val223 residue, including A/Hong Kong/1/1968 (H3N2) (FIG. 5B), but 70% of H3 HAs possess an Ile223. Two strains of H3 with the Ile223 variant were tested in the activity profiling, (A/Texas/50/2012) and (A/Switzerland/9715293/2013), and they both bind to FluA-20 with high affinity. Thus, FluA-20 can effectively accommodate either Val or Ile at position 223.

The sequences of the major epitope residues recognized by FluA-20 in other HA subtypes are summarized in FIG. 5C. Remarkably, the five residues that directly interact with FluA-20 (highlighted) remain extremely conserved across different strains and subtypes, which explains the extraordinary breadth of FluA-20. Some mutations and deletions in these five key residues in the epitope of a few HAs may inhibit binding to FluA-20. For instance, Arg229 is essential for electrostatic interactions with FluA-20 (FIGS. 5A-B). The Ile229 substitution of H3 (A/Minnesota/11/10) likely renders it the only H3 strain that FluA-20 fails to recognize among those tested, whereas a Trp229 residue in H13 (A/gull/Maryland/704/1977) can be tolerated. Comparison of the H13 structure (PDB 4KPQ) with the H1 or H3 complexes with FluA-20 shows that H13 possesses a unique pair of mutations, Tyr223 and Trp229 (FIG. 11B). Possible aromatic stacking of these two residues with Tyr100a (H) of FluA-20 may compensate for the loss of the Arg229 contacts.

Compared to H1 and H3, two H5 strains with Ser221 (the common substitution in the H5 subtype) exhibit weaker binding of FluA-20 (FIG. 1C and FIG. 11A). Ser221 does not appear to change the 220-loop conformation (FIG. 11A); however, the decrease of side-chain hydrophobicity or difference in the rigidity of 220-loop may have affected FluA-20 binding. In fact, a Pro221 mutation in H5 (A/Vietnam/1203/2004) substantially rescues the affinity to FluA-20 to a similar level as H1 and H3 (FIG. 11A). Of the two H7 strains tested, H7 of A/New York/107/2003 has a truncated 220-loop (missing residues), but still retains the critical Arg229. As a result, this H7 shows decreased binding by FluA-20, compared to H7 from A/Shanghai/2/2013 (FIGS. 11C-D). Considerable variation nevertheless exists at some residues in the FluA-20 epitope, particularly for 219, 222, and 224 that are located very close to the binding core. However, the interactions of FluA-20 with these variable residues are only to their main chain, and the approach angle of FluA-20 enables the antibody to successfully accommodate these variable side chains (FIGS. 12A-B).

Mutation experiments confirm the critical contact residues in the FluA-20 IgG paratope. To determine the paratope residues that are critical to FluA-20 binding, the inventor mutated Tyr34, Thr96, Glu97, Aps98, Tyr100a and Cys101 on the heavy chain (H) and Tyr49, Asn53 and Gln55 on the light chain (L) to alanine and determined binding of each mutant to HAs from different subtypes. Two mutants D98A (H) and Y49A (L) showed complete loss of binding to all tested HAs, validating the importance of the electrostatic interaction between Asp98 (H) of FluA-20 and Arg229 on HA and the hydrophobic interaction between Tyr49 (L) to HA residues (Table S5, FIGS. 5A-B). Furthermore, Q55A (L) mutant showed >10-fold or complete loss of binding $EC_{50}$ to all HAs except H1 A/Texas/36/1991, H3 A/Hong Kong/1/1968 and H7 A/Netherlands/219/2003, while the Y100aA (H) mutant also showed >10-fold loss of binding $EC_{50}$ to all HAs except H3 A/Hong Kong/1/1968 (Table S5). Additionally, C101A (H) or N53A (L) also disrupted binding to H5 A/Indonesia/5/2005 H A. Collectively, these findings indicate that, while the binding core of the FluA-20 interaction with different HAs is highly conserved, some variations can occur with different HAs.

Figure 13B:
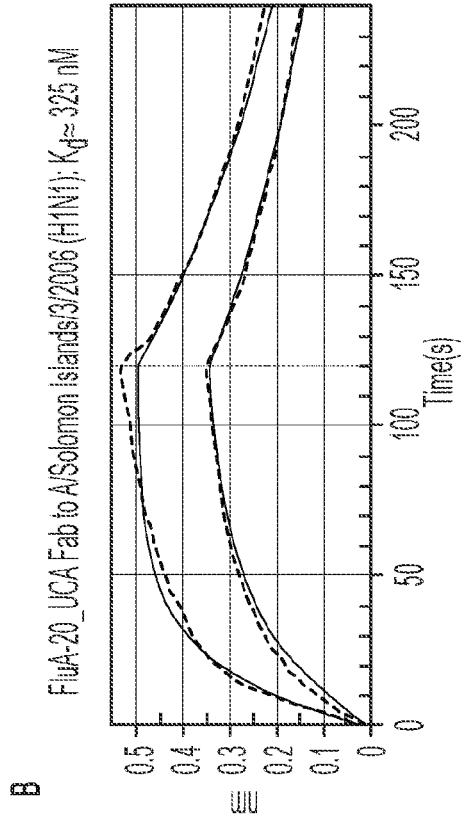

Unmutated common ancestor-origin interactions drive the activity and specificity of the FluA-20 lineage. The inventor also investigated the unmutated common ancestor (UCA) of FluA-20, which is encoded by the $V_H4$-61/D2-15/$J_H4$ and $V_K1$-39/$J_K1$ antibody variable gene segments. Compared to the UCA sequence, FluA-20 contains 17 somatic mutations in the heavy chain variable gene amino-acid sequence and 12 in the light chain variable gene sequence (FIG. 13A). Nonetheless, the UCA antibodies (IgG or Fab) of FluA-20 appear to retain substantial binding breadth when compared to affinity-matured FluA-20 (FIG. 1C, FIG. 13B, Table S2). This finding is consistent with the observation that most of the FluA-20 residues that directly interact with HA are conserved from the UCA antibody, especially the key HA-contacting Asp98 (H), Y100a (H), Y49 (L), and Gln55 (L) (FIG. 13A). Compared to the UCA antibody, FluA-20 displays not only an increase in binding potency, but also greater breadth with additional recognition of many H3 and H5 HAs (FIG. 1C, Table S2).

Binding of FluA-20 to HA is inhibited by HA cleavage likely through trimer dynamic changes. During viral replication, HA is synthesized initially as a single polypeptide precursor protein, HA0. As the protein folds, HA assembles into a trimer in the endoplasmic reticulum (ER), before its transportation to the cellular surface (Copeland et al., 1986; Gething et al., 1986). HA0 can be cleaved post-translationally at an arginine (or rarely a lysine) around residue 329 into two subunits, HA1 and HA2, the mature form of HA. HA cleavage is a prerequisite for viral infectivity (Chen et al., 1998; Steinhauer, 1999). Previous studies indicated that the HA cleavage process is promiscuous as to when and where the HA is cleaved in vivo (Klenk and Garten, 1994; Klenk and Rott, 1988; Webster and Rott, 1987), while cleavage is generally achieved by trypsin treatment in vitro.

Figure 14C:
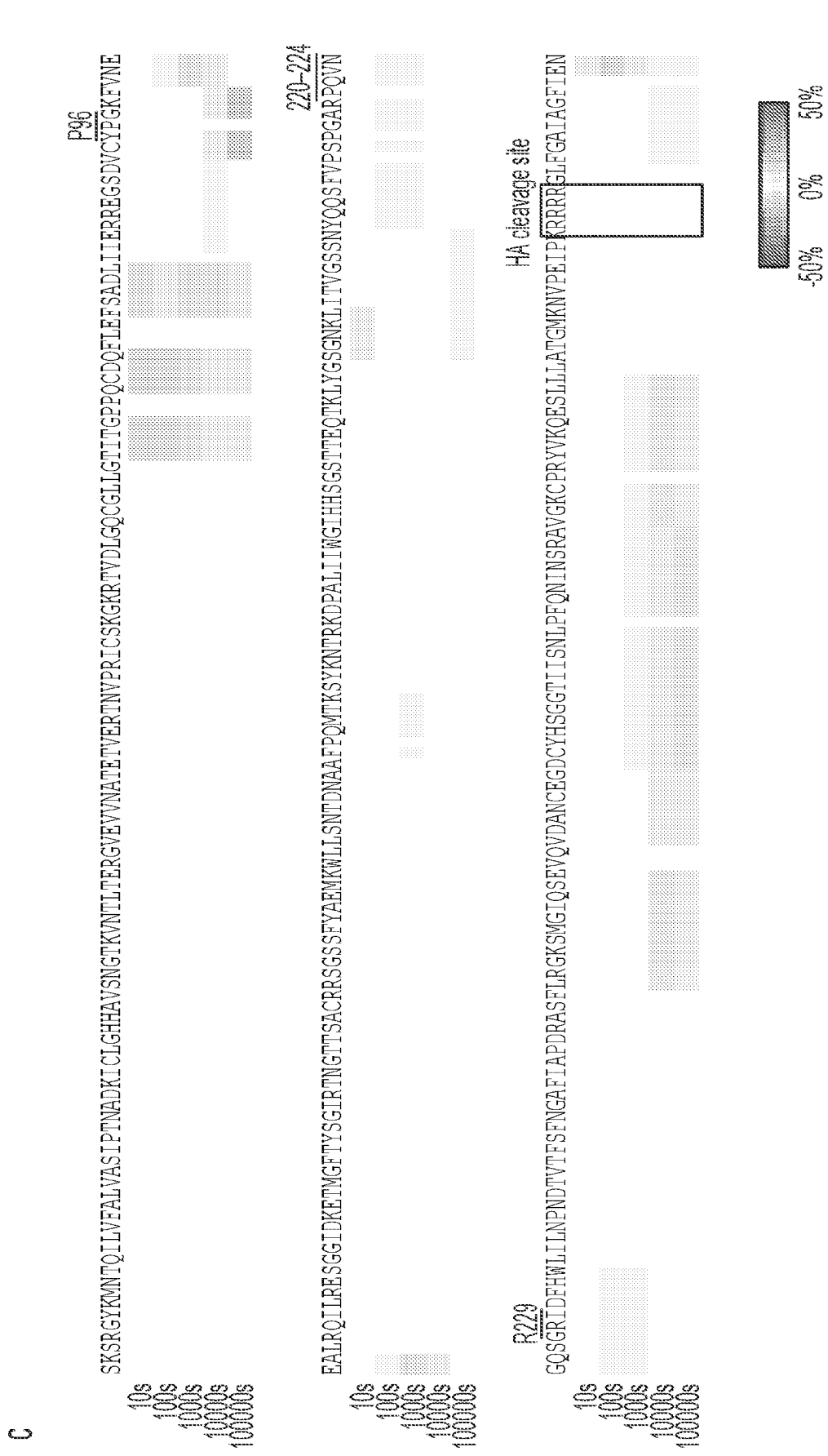
Figure 14C:
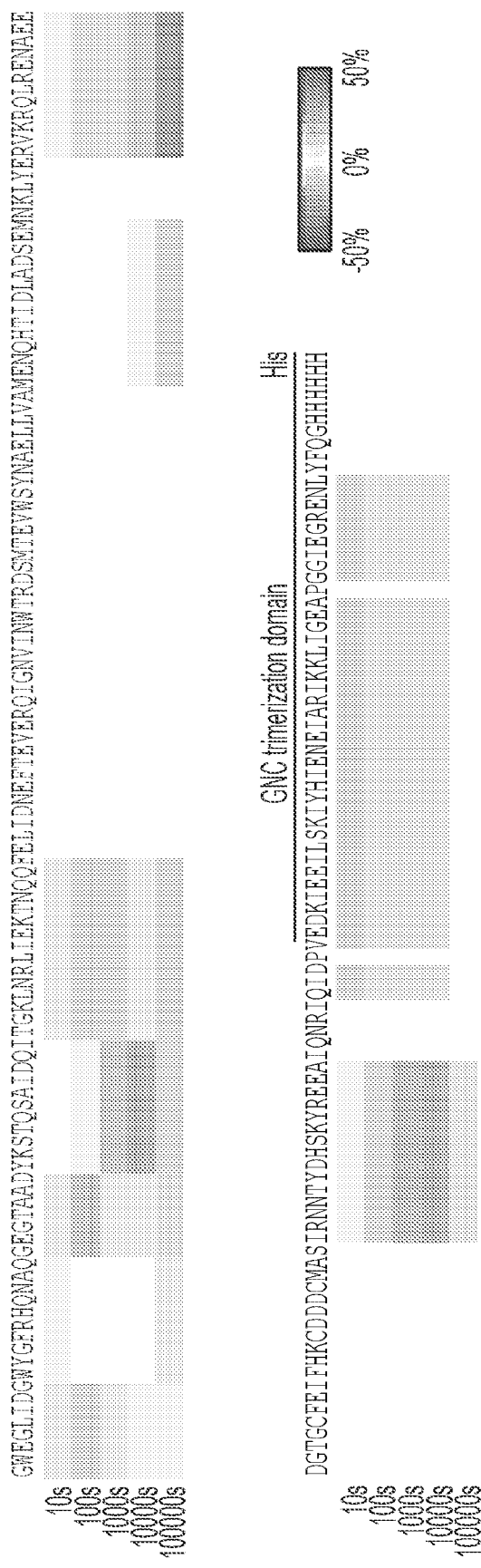

The inventor observed that trypsin cleavage of HA substantially decreased binding of FluA-20 to soluble H1 and H7 HA (FIG. 6A), while differences in binding of the RBS-binding antibodies were not observed after cleavage (FIG. 14A). Since the FluA20 binding epitope is buried in the HA trimer interface, the biased inhibition of FluA-20 binding, but not the 'outer' surface binding antibodies, suggests a potential decrease of dynamics in HA trimer after trypsin treatment, so that the FluA-20 epitope in the trimer interface may be less frequently or less proportionally exposed after the HA cleavage. The inventor also assessed FluA-20 binding to cellular surface HA and whether the surface HA recognition is affected by trypsin treatment. He performed flow cytometric analysis to measure binding of two antibodies, CR9114 or FluA-20, to H3 A/Hong Kong/1/1968 HA expressed on HEK293F cells, either untreated or treated with trypsin. Consistent with the inventor's observations with soluble, recombinant HA protein, FluA-20 displayed significantly lower binding to HA on trypsin-treated cells compared to untreated cells (2.6-fold), while a decrease of CR9114 binding was not observed after trypsin treatment (FIG. 6B). The inventor also performed an HDX-MS experiment with either HA0 or trypsin-treated HA trimers and observed an overall reduction of deuterium exchange in the cleaved HA molecules compared to HA0 proteins at the three time points tested, except for some loops near the vestigial esterase subdomain of HA head (FIG. 6C and FIG. 14C). The inventor also tested the effect of HA cleavage on susceptibility to neutralization by FluA-20. Even though Flu-20 did bind uncleaved HA to a higher degree than to cleaved, it still did not neutralize virus with uncleaved HA (virus produced in the absence of trypsin). (FIG. 14B). In summary, these data suggest that HA cleavage into its functional form reduces HA trimer dynamics, which may inhibit exposure of the FluA-20 epitope in the matured, functional form of HA on virions. This model would explain why the antibody could facilitate ADCC through recognition of uncleaved HA on infected cells, but not neutralize budding infectious virion particles that have cleaved HA on the surface.

Binding of H5.28 and H5.31 to HA antigens and neutralization testing. The inventor tested purified mAb for the H5.28 and H5.31 mAbs for binding to HA molecules from diverse influenza A subtypes as above using Octet biosensor or ELISA (FIG. 15). The inventors found that both mAbs bound to a very diverse array of influenza A antigens, including to A/California/04/2009 H1N1, A/Fort Monthouth/1947 (H1N1) A/South Carolina/1/1918 (H1N1), A/Japan/305/1957 (H2N2), A/Hong Kong/1/1968 (H3N2), A/Indonesia/5/2005 (H5N1), A/Vietnam/03/2204 (H5N1), A/Netherlands/219/2003 (H7N9), A/turkey/Wisconsin/1/1966 (H9N2), A/chicken/Germany/N/1948 (H10N7), A/duck/Alberta/60/1976 (H12N5), A/mallard duck/Astrakhan/263/1982 (H14N5). Thus, these antibodies, like FluA-20, exhibit an ultra-broad pattern of recognition of influenza A strains and subtypes. Competition-binding studies demonstrated H5.28 and H5.31 compete for binding on the HA head domain, thus they recognize a similar antigenic site. The inventor performed neutralization assays using a reassortant virus made from modified hemagglutinin- and unaltered neuraminidase-encoding genes from the influenza A/Vietnam/03/2204 (H5N1), strain and all other genes from A/Puerto Rico/8/34 (H1N1). The mAbs did not mediate neutralization or HAI activity for that HA when tested at concentrations up to 10 µg/mL.

Figure 16:
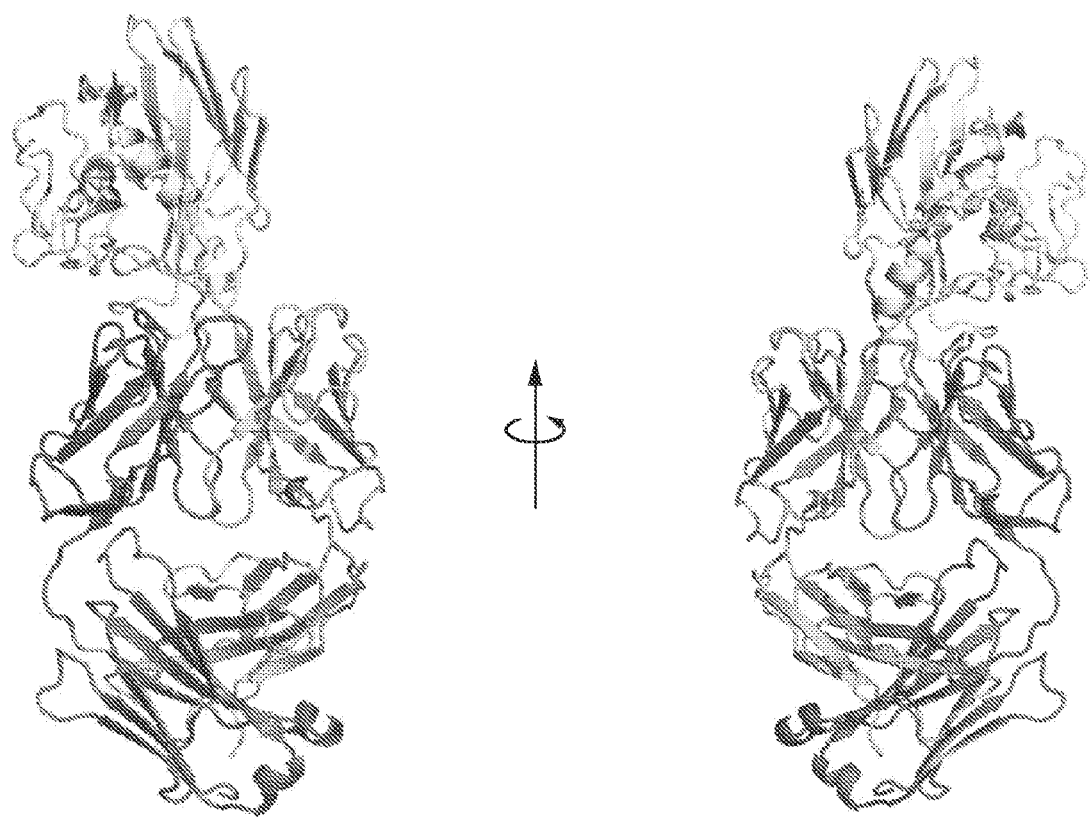
FIG. 16. Crystal structure of the complex of H5.28 Fab with the H5 HA head domain monomer from A/VietNam/1203/2004. The antibody binds to the same trimer interface site as FluA-20.
Figure 17:
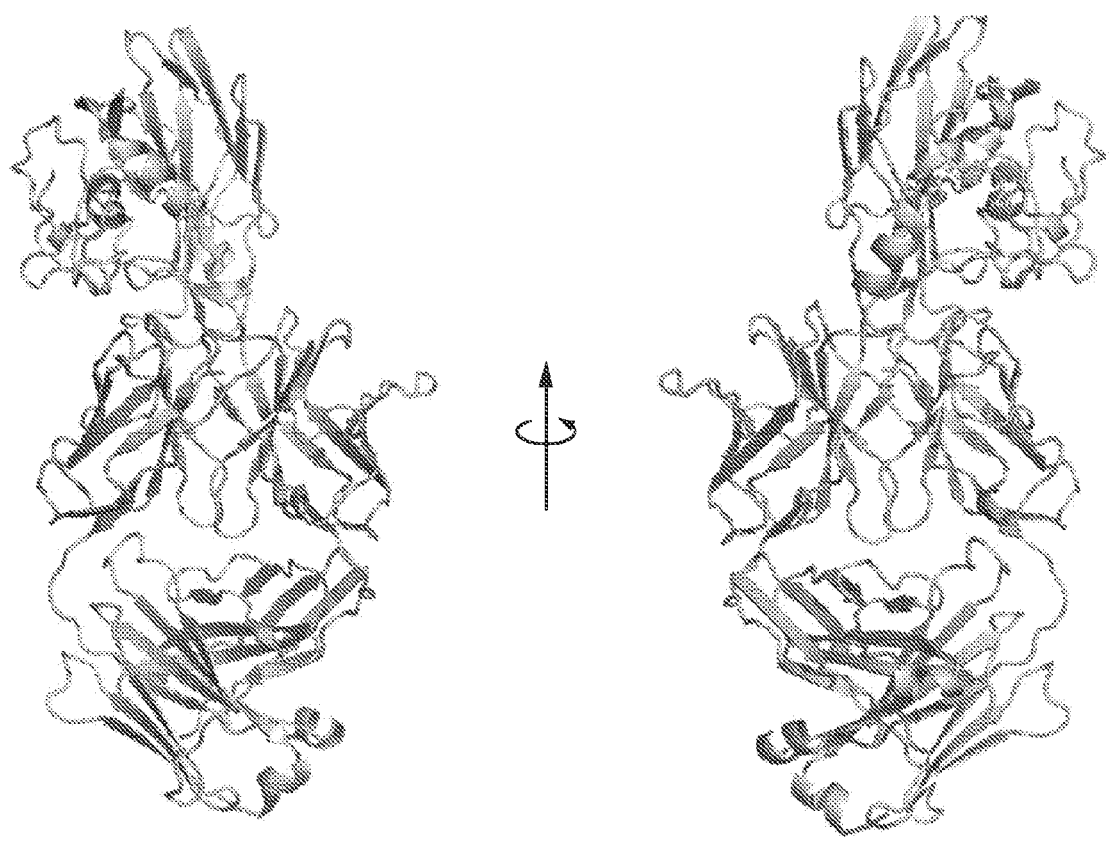
FIG. 17. Crystal structure of the complex of H5.31 Fab with the H5 HA head domain monomer from A/VietNam/1203/2004. The antibody binds to the same trimer interface site as FluA-20 and H5.28.
Figure 18:
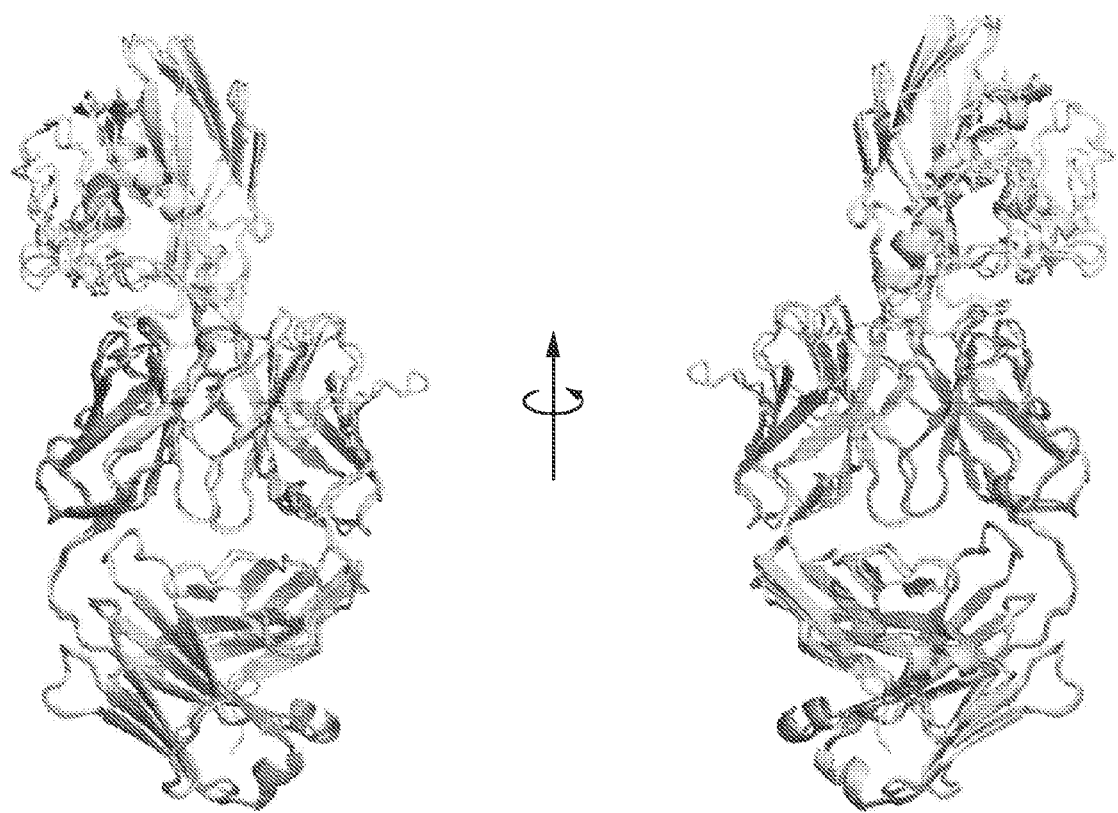
FIG. 18. Overlay of the crystal structures of the complexes of H5.28 or H5.31 Fab with the H5 HA head domain monomer from A/VietNam/1203/2004. The H5.28 and H5.31 antibodies interact with the trimer interface epitope in a very similar method.

Crystal structures of the complexes of H5.28 and H5.31 with the HA head domain from A/Vietnam/03/2204 (H5N1). Like the structure of the FluA20 to HA described above, both H5.28 and H5.31 bind to the HA trimer interface antigenic site (FIG. 16 [H5.28], FIG. 17 [H5.31], FIG. 18 [overlay of complexes of H5.28 and H5.31 on VN HA]. Like FluA-20, H5.28 and H5.31 binding to HA does not block the HA receptor binding site but rather the antibodies bind to the interface region within the HA trimer head. Many features of the interaction of the HCDR3 loops of the three antibodies is very similar to each other, showing that all three of these antibodies are members of a structural class with similar interactions, and thus also members of a functional class of antibodies that inhibits virus by a non-neutralizing mechanism through binding to the HA interface.

The inventor noted glycosylation of the Fab for H5.31, but this did not seem to affect binding or function of the antibody (FIG. 19). Sequence analysis of the heavy chain variable regions showed that the two antibodies, which were isolated from one donor, were highly related somatic variants that are members of a single clonotype (sometimes called a lineage) (FIG. 19). The alignment revealed that H5.31 but not H5.28 has a potential glycosylation site (FIG. 19). Protein expression followed by enzymatic treatment to remove glycans showed that indeed H5.31 was glycosylated (FIG. 19). Binding assays comparing the H5.28, H5.31 and H5.31-deglycosylated antibodies did not show any differences in binding (FIG. 19).

Figure 20:
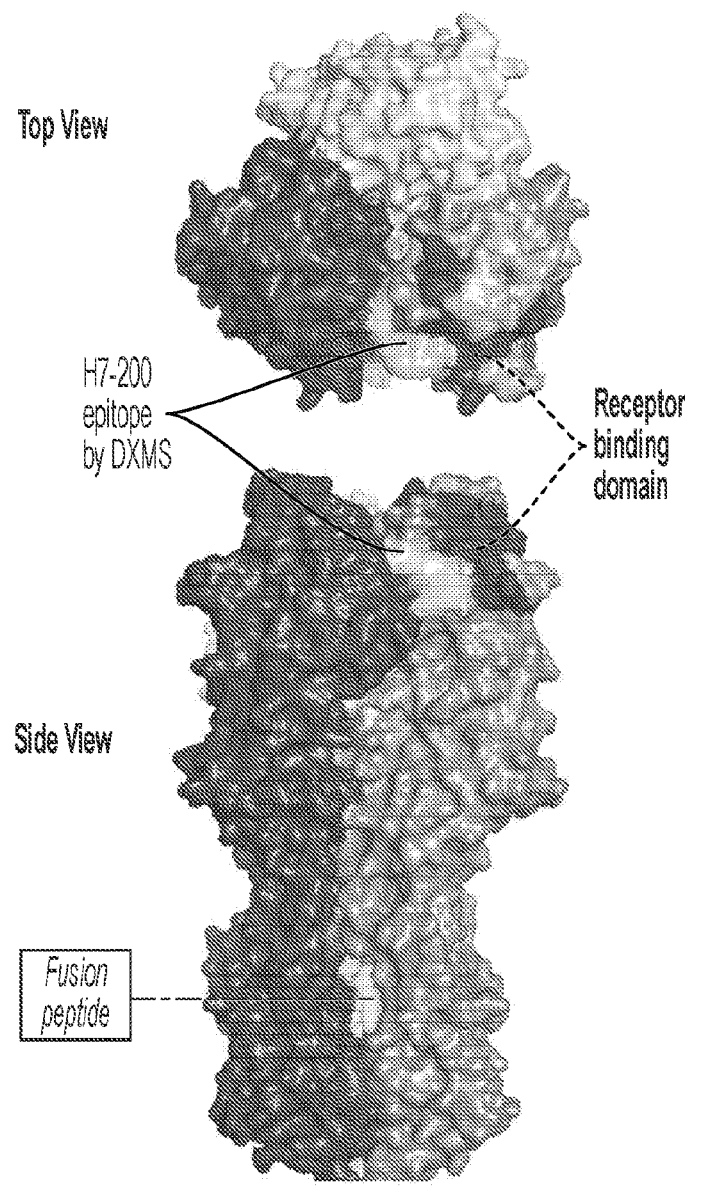

Binding of H7-200 to HA antigens and neutralization testing. The inventor tested purified mAb for the H7-200 mAb for binding to HA molecules from diverse influenza A subtypes as above, and diverse strains from the H7 subtype. The inventors found that mAb H7-200 bound to influenza A Group 2 antigens from the H7 and H15 subtypes, including to HA from A/New York/107/2003 (H7N2), A/Shanghai/1/2013 (H7N9), A/NL/219/03 (H7N7) and A/wedge-tailed shearwater/Western Australia/2576/1979 (H15N9). It did not bind to HAs from H1, H2, H3, or H5 subtype. Competition-binding studies demonstrated H7-200 binds on the HA head domain near the antigenic site B. The inventor performed neutralization assays using a reassortant virus made from modified hemagglutinin- and unaltered neuraminidase-encoding genes from the influenza A/Shanghai/1/2013 (H7N9) strain and all other genes from A/Puerto Rico/8/34 (H1N1). The minimal effective concentration for neutralization of H7-200 determined for this reassortant virus incorporating the A/Shanghai/1/2013 (H7N9) HA protein was 10 µg/mL. The mAb did not mediate HAI activity for that HA when tested at concentrations up to 10 µg/mL. DXMS testing showed however that the antibody bound to the interface epitope also recognized by F1A-20, H5.28 and H5.31 (FIG. 20). Thus, the data show that H7-200 is a fourth representative of the new structural class of antibody that recognizes the interface of HA protomers, and also is a member of the functional class of heterosubtypic antibodies that inhibit virus by a non-neutralizing mechanism.

Example 3—Discussion

Isolation of naturally-occurring broad-spectrum human mAbs to IAV holds great promise for discovery of new candidate therapeutics, as well as identifying critical epitopes for rational design of structure-based broadly protective influenza vaccines. Nearly all of the broadly neutralizing antibodies with extensive heterosubtypic activities discovered to date recognize the conserved HA stem region (FIG. 7A), while most broadly neutralizing antibodies to the head domain have more restricted activity often within a given subtype, due to the extensive hypervariability in the head region (FIG. 7A) (Hong et al., 2013; Joyce et al., 2016; Julien et al., 2012b; Lee et al., 2014; Thornburg et al., 2016; Whittle et al., 2011; Wu and Wilson, 2017; Xu et al., 2013; Zhu et al., 2013).

In this work, the inventor reports the isolation and characterization of the ultra-broad protective antibody FluA-20 that recognizes the HA head domain from nearly all IAV HA subtypes with excellent binding affinity. The discovery of the FluA-20 epitope unexpectedly revealed a highly conserved site of vulnerability that is hidden in the HA trimer interface (FIG. 7B). Although FluA-20 does not neutralize representative viruses from H1N1 and H3N2 subtypes in microneutralization assays, this antibody mediates ADCC activity and confers in vivo protection against major influenza subtypes that are pathogenic for humans (FIGS. 2A-D). When administered prophylactically, FluA-20 protected mice against H1N1, H3N2, H5N1 or H7N9 challenge (FIGS. 2A-D). Therefore, FluA-20 could potentially serve as a broad-spectrum antiviral therapeutic against various IAV infections.

It is a striking observation that FluA-20, which recognizes an epitope obscured in the HA trimer interface, is able to deliver in vivo protection against the viruses. Previous studies have demonstrated that the assembly of HA trimer occurs in the endoplasmic reticulum (ER), prior to its transport to the cellular surface. Unoligomerized HA monomers are not transported to the Golgi complex (Copeland et al., 1986; Copeland et al., 1988; Gething et al., 1986). Therefore, the HA molecules on the cellular or viral surface generally have been considered to be stable trimers, with the trimer interface regarded as inaccessible and thus not targetable by the immune response or therapeutics. The ability of FluA-20 to confer in vivo protection strongly suggests that HA molecules, to some extent, could be dynamic and more heterogeneous in their conformations than the inventor has observed previously, and that the trimer interface can be partially or transiently accessible. Similar phenomenon, previously described as 'breathing', has been observed for the envelope glycoproteins from other viruses, such as HIV (Munro et al., 2014; Munro and Mothes, 2015). The study here provides the first high-resolution characterization of an interface epitope, demonstrating that the hemagglutinin trimer could indeed feature similar 'breathing' motions. The inventor found that the dynamics of the HA trimer is more pronounced in the uncleaved HA0 than in the cleaved HA, as assessed by HDX-MS studies (FIG. 6C). An early study from Yewdell et al. reported the characterization of murine mAb Y8-10C2, the epitope of which was indicated to be present between adjacent protomers in the globular head domain by mutagenesis study. The study also implied that changes made near the fusion loop could indirectly affect the flexibility of the globular head domain and lead to resistance against Y8-10C2 (Yewdell et al., 1993). Nevertheless, the effect of trypsin-mediated cleavage on the conformational dynamics of the globular head domain in HA trimer conformation is poorly understood. HA dynamic changes also were found in the pH-activated fusion step, with the HA head interface region becoming more stabilized and the fusion peptide and surrounding HA stem residues becoming more dynamic at an intermediate pH prior to the pH of fusion (Garcia et al., 2015).

Furthermore, it appears that the generation of the FluA-20 mAb that recognizes the trimer interface represents the invention of not only a single antibody, but rather a class of antibodies that bind to the trimer interface and inhibit virus by a non-neutralizing mechanism. The inventors e present here three additional representative monoclonal antibodies in this class, H5.28, H5.31 and H7-200. With crystallography of the complexes of H5.28 and H5.31 on HA, or DXMS studies of the epitope of H7.200, the inventors show each of these antibodies binds to the interface between the head domains of the three protomers in the HA trimer. This new method for interrupting the function of the HA protein (which much mediate attach and fusion to cells) by recognizing the interface represents an entirely new class of antibody, indeed an entirely new class of antiviral drug. Further, the epitope the inventors discovered by mapping the antigenic site recognized by these four representative antibodies could be used as a new universal influenza vaccine, or a component of a new universal influenza vaccine.

Example 4—Materials and Methods

Expression of soluble HA proteins. Sequences encoding the HA genes of interest were optimized for mammalian cell expression, and cDNAs were synthesized (Genscript) as soluble trimeric constructs as described previously (Bangaru et al., 2016). HA protein was expressed by transient transfection of 293F cells with polyethylenimine (PEI) transfection reagent and grown in expression medium (Freestyle 293 Expression Medium; Invitrogen, 12338). Cell supernatants were harvested after 7 days, filtered sterilized with a 0.4 μm filter and recombinant protein purified with HisTrap TALON FF crude columns (GE Healthcare Life Sciences).

PBMC isolation and hybridoma generation. The study was approved by the Vanderbilt University Medical Center Institutional Review Board. Peripheral blood was collected from a healthy donor with prior history of many seasonal influenza vaccinations experimental H5N1 subunit vaccinations after written informed consent. PBMCs from the donor were isolated by density gradient separation on Ficoll, cryopreserved and stored in the vapor phase of liquid nitrogen until use. Generation of human hybridoma cell lines secreting human mAbs was performed as described previously (Smith et al., 2012). Briefly, human B cells in the PBMC suspension were immortalized by transformation with EBV in the presence of CpG10103, cyclosporin A, and a Chk2 inhibitor and plated in 384-well culture plates. On day 8, the supernatants from transformed B cells were used to screen for the presence of heterosubtypic antibodies that bound broadly to HA antigens from H1, H3, H7 or H9 subtypes using a capture ELISA. The recombinant HA antigens used for screening were based on the sequence of HAs from the following influenza strains: H1 A/California/04/2009, H1 A/Texas/36/1991, H3 A/Hong Kong/1/1968, H3 A/Victoria/3/1975, H7 A/Shanghai/2/2013, H7 A/Netherlands/219/2003 or H9 A/Hong Kong/1073/99. Cells from the wells containing B cells secreting heterosubtypic HA-reactive antibodies were fused with HMMA2.5 myeloma cells using a BTX ECM 2001 electro cell manipulator. After fusion, human hybridomas were selected in medium with HAT solution containing ouabain. The hybridomas were cloned by flow cytometric sorting of single cells into 384-well plates and then expanded in culture. Particular clones for downstream studies were selected by choosing the clone for each independently derived hybridoma line that exhibited the highest level of IgG secretion.

Production of IgG for mAb FluA-20 from hybridoma cells. The selected cloned cell line secreting mAb FluA-20 was grown initially in hybridoma growth medium (Clona-Cell-HY medium E from STEMCELL Technologies, 03805) and then switched to serum-free medium (GIBCO Hybridoma-SFM, Invitrogen, 12045084) for antibody expression and purification. IgG from the hybridoma cell line supernatants was purified by affinity chromatography using protein G columns (GE Life Sciences, Protein G HP Columns). Purified FluA-20 IgG generated from hybridomas was used for all $EC_{50}$ and $IC_{50}$ studies, competition-binding studies, HDX-MS studies, and ADCC assays and mouse studies.

Next-generation DNA sequence analysis of expressed antibody variable genes. Total RNA was extracted from 10 million PBMCs. A one-step RT-PCR was performed for 25 cycles using heavy-chain BIOMED-2 variable antibody gene-specific primers as previously described (Bangaru et al., 2016; Thornburg et al., 2016) (Van Dongen et al., 2003) and the OneStep SuperScript III with Platinum® Taq High Fidelity kit (Invitrogen, 11304011). The Illumina-specific adapters were added using the Illumina TruSeq Library Preparation Kit (Illumina, FC-121-3001) according to the manufacturer's recommendations. The final amplicon libraries were sequenced on an Illumina MiSeq instrument using the MiSeq PE-300 v3 reagent kit (Illumina, MS-102-3001). Sequence analysis was performed using IG-BLAST v1.4, and results were parsed to MongoDB for further study.

Identifying clonally related sequences. From a database of annotated antibody sequences obtained from this donor, the inventors queried HCDR3s in sequences encoded by both of the inferred germline genes for FluA-20 ($V_H$4-61 and $J_H$4). These HCDR3 sequences were pairwise aligned to the HCDR3 of FluA-20 using a PAM30 matrix, with penalties for gap opening and gap extension of −14 and −3, respectively. HCDR3 sequences with a Hamming distance of ≤3 to FluA-20 were selected as siblings and the 'full length' nucleotide and amino acid sequence was queried from the inventors' database for further analysis.

Visualizing clonally related sequences. A network graph was built from the aligned, full-length sequences queried as described above. Identical sequences were clustered into single nodes, and edges were drawn between two nodes if their Hamming distance was the lowest compared to all other nodes. Nodes denoting the inferred common ancestor and the germline $V_H$4-61/$J_H$4 sequence were added manually. This network was visualized using Cytoscape and manually adjusted for visual clarity (to prevent nodes from overlapping edges to which they are not connected, and to shorten distances between nodes that are closely related).

Characterization of antibody isotype, subclass, and variable genes. The isotype and subclass of secreted antibodies were determined by ELISA. Antibody heavy and light chain variable region genes were sequenced from antigen-specific hybridoma lines that had been cloned biologically using flow cytometric single cell sorting. Briefly, total RNA was extracted using the RNeasy Mini kit (Qiagen, 74106) and reverse-transcriptase PCR (RT-PCR) amplification of the antibody gene cDNAs was performed using the PrimeScript One Step RT-PCR kit (Clontech, RR055A) according to the manufacturer's protocols with gene-specific primers as previously described (Thornburg et al., 2016). PCR products were purified using Agencourt AMPure XP magnetic beads (Beckman Coulter) and sequenced directly using an ABI3700 automated DNA sequencer without cloning. The identities of gene segments and mutations from germlines were determined by alignment using ImMunoGeneTics database (Brochet et al., 2008; Giudicelli and Lefranc, 2011).

Determination of half-maximal effective concentration ($EC_{50}$) for binding. To determine $EC_{50}$ concentrations for binding, the inventors performed ELISA using 384-well plates that were coated overnight at 2 µg/mL with the recombinant HA protein of interest. The plates then were blocked with 50 µL of 5% non-fat dry milk, 2% goat serum and 0.1% Tween-20 in PBS for 1 h at RT. The plates were washed and three-fold dilutions of the mAb starting from 10 µg/mL were added to the wells and incubated for an hour. The plates were washed and 25 µL of 1:4,000 dilution of anti-human IgG alkaline phosphatase conjugate (Meridian Life Science, W99008A) was added. After a final wash, 25 µL of phosphatase substrate solution (1 mg/mL p-nitrophenol phosphate in 1 M Tris aminomethane) was added to the plates, incubated for 20 minutes and the optical density values were measured at 405 nm wavelength on a BioTek plate reader. The plates were washed 3 times between each step with PBS containing 0.1% Tween-20. Each dilution was performed in quadruplicate, and the $EC_{50}$ values were calculated in Prism software (GraphPad) using non-linear regression analysis. The experiment was conducted twice independently.

Prophylaxis studies with sub-lethal challenge and therapeutic studies with lethal challenge in mice. Female BALB/c mice aged 6-8 weeks were obtained from Charles River Laboratories, Wilmington, MA, and housed under specified pathogen-free conditions with food and water ad libitum. For the prophylaxis studies, experimental groups of 8 mice were given i.p. with 10 mg/kg of either FluA-20 or a similarly prepared control human antibody to an unrelated target (a mAb to methicillin-resistant *Staphylococcus aureus*; MRSA). They were challenged 24 hours later with a sublethal dose (0.1 $LD_{50}$) of either H1N1 A/Netherlands/602/2009 or H3N2 A/X-31 (6:2 PR8 backbone) or H5N1 A/barn swallow/Hong Kong/D10-1161/2010 (7:1 PR8 backbone) or H7N9 A/Shanghai/1/2013 (6:2 PR8 backbone). Challenge under mild ketamine/xylazine anesthesia was by intranasal administration of 50 µl virus preparation diluted in PBS. Body weight change after virus challenge was used to assess protection. Mice (n=5) were weighed every day for 14 days post-challenge. The significance in weight loss between FluA-20 and the control group was calculated for each day using 2-way ANOVA with Tukey's multiple comparisons test and displayed on the graph as *($P<0.05$), ($P<0.01$) and *($P<0.001$)

For the treatment studies, experimental groups of five mice were challenged with 1.2 $LD_{50}$ of H3N2, H5N1 or H7N9 viruses on PR8 backbone—a dose that resulted in 40 to 100% lethality in mock-treated animals. Mice were given 10 mg/kg of FluA20 or irrelevant antibody (MRSA) via the intraperitoneal route on days 1, 2 and 4 post-inoculation. Mice were monitored daily for body weight change and survival for 14 days after challenge. Mice that had lost >25% of their initial body weight were humanely euthanized. Survival curves were estimated using the Kaplan Meier method and curves compared using the two-sided log rank test with subjects right censored, if they survived until the end of the study. *=$p<0.05$; $p<0.01$; *−=$p<0.001$; ns—non-significant. Statistical analyses were performed using Prism v7.2 (GraphPad).

All infections were conducted under BSL-2$^+$ containment and were authorized by the Institutional Ethics Committee on Experimental Animals at Icahn School of Medicine at Mount Sinai. For pulmonary titers, mice from each group (n=3) were killed at 6 days (prophylaxis) or 5 days (therapy) post-inoculation and lungs were removed aseptically, snap frozen on dry ice and stored at −80° C. until titration. Lungs were homogenized in 1 ml PBS using a Fastprep 24 homogenizer (MP Biomedicals). The homogenates were centrifuged (5 min, 16,100×g, 4° C.) to remove cellular debris and used for virus titration by plaque assay. Then, 200 µL of ten-fold dilutions of homogenized lungs in PBS were used for infecting confluent monolayers of MDCK cells. Virus was allowed to attach to MDCK cells for 1 h at 37° C. Cells were washed once with warm PBS and overlaid with oxoid agar (Oxoid Ltd., Basingstoke, Hampshire) prepared using $NaHCO_3$-buffered serum-free 2×MEM/BA containing DEAE Dextran and supplemented with TPCK-treated trypsin (1 µg/mL). Endpoint virus titers were determined by visualizing virus plaques 2 days after infection by staining with H1N1 post challenge serum (1/1,000 dilution), horseradish peroxidase-conjugated sheep-derived anti-mouse serum (GE Healthcare UK, NA-931) and TrueBlue substrate (KPL-Seracare, 5510-0031).

Prophylaxis studies with lethal challenge and therapeutic with sublethal challenge mouse model for influenza A H1N1 infection. For prophylaxis studies against lethal H1N1 challenge, groups of ten 6-8 months old DBA/2J mice (The Jackson Laboratory) were treated with 10 mg/kg of either rFluA-20 IgG or positive control (CR6261) IgG or unrelated target control (MRSA-147) IgG 24-hours prior to being intra-nasally challenged with a lethal dose of 1,076 focus forming units (FFU) of H1N1 A/California/07/2009. Mice were monitored for survival for 20 days after challenge. Moribund mice (little mobility), or mice that had lost >30% of their initial body weight (IACUC stipulated humane endpoint) were euthanized. Survival curves were estimated using the Kaplan Meier method and curves compared using the two-sided log rank test with subjects right censored, if they survived until the end of the study.

For therapeutic studies against sub-lethal H1N1 challenge, groups of ten BALB/c mice were challenged with a sublethal dose of $6.4 \times 10^4$ FFU and were given 10 mg/kg of FluA20 IgG or CR6261 IgG or MRSA-147 IgG via the intraperitoneal route on day 1 post-inoculation. Mice were monitored for 14 days for weight change kinetics. Weight change curves were compared using 2-way Anova with Tukey's multiple comparisons test.

FluA-20 prophylaxis dose-optimization against mouse-adapted influenza A H1N1 lethal challenge. Experimental groups of 10 female BALB/c mice obtained from Charles River Laboratories (Wilmington, MA) were administered either 1, 3 or 10 mg/kg of FluA-20 IgG or 10 mg/kg of unrelated target control (mAb 2D22 specific for dengue virus envelope protein) IgG or 0.1 mL PBS by IP injection. At 24 h after mAb treatment, the mice were anesthetized by IP injection of ketamine/xylazine (50/5 mg/kg) followed by intranasal exposure to a 90 µL suspension of approximately 2,200 50% cell culture infectious dose ($CCID_{50}$/mL) of mouse-adapted influenza H1N1 A/California/04/2009 virus that was kindly provided by Dr. Elena Govorkova (St. Jude Children's Research Hospital, Memphis, TN). Mice in a control group of 10 animals were treated with osteltamivir that was given by IP twice daily (bid) for 5 days, starting at 1 h post-infection. The animals were observed for 21 days and survival was based on body weight-loss cutoffs of <30% of initial weight. Survival curves were compared by the Mantel-Cox log-rank test. Mean day of death (MDD) comparisons were made by one-way ANOVA with Dunnett's multiple comparisons test. Differences in the number of survivors between mAb-treated and placebo groups were analyzed by the Fisher's exact (two-tailed) test. Calculations were made using Prism 8.0 (GraphPad Software, San Diego, CA). This study was conducted in the AAALAC-accredited laboratory animal research center of Utah State University in accordance with the approval of the institutional animal care and use committee of Utah State University.

Competition-binding groups. Biolayer interferometry on an Octet Red instrument (FortéBio) was used to perform competition-binding assays as described. Briefly, the inventors loaded the HA from H1 A/California/04/2009 onto Ni-NTA tips at a concentration of 20 µg/mL, and then tested binding of two successively applied mAbs at 50 µg/mL. All antigen and antibody dilutions were made in 1× kinetic buffer (FortéBio, 18-5032). The antibodies were defined as competing antibodies if the first antibody reduced binding of the second antibody by more than 70 percent. The antibodies were defined as non-competing antibodies if the first antibody reduced binding of the second antibody by less than 30 percent.

Fab and IgG cloning, expression and purification for binding kinetic assay and X-ray crystal structure determination. FluA-20 Fab and IgG were expressed in 293F mammalian cells for determination of the binding kinetics and structures as previously described (Garces et al., 2015; Irimia et al., 2016). The heavy and light chains of the Fab were cloned independently into the phCMV3 vector and fused with the N-terminal IgK secretion signal peptide. A His6 tag was added to the C-terminus of the Fab heavy chain. Recombinant DNAs for both heavy and light chains were purified separately and co-transfected into 293F cells. The cells were cultured for 6-7 days at 37° C., while shaking at 125 r.p.m. Secreted Fabs were purified Ni-NTA Superflow (Qiagen), monoS chromatography (GE Healthcare).

To generate IgG for a given antibody, the DNA fragment of the $V_H$ domain was fused with the DNA fragment of heavy chain Fc domain of human IgG1 via PCR. The full-length gene was cloned into the phCMV3 vector with the N-terminal IgK secretion signal peptide. IgG was expressed in 293F cells, as above, and purified by Protein G and monoS chromatography (GE Healthcare) and gel filtration.

Preparation of HA head domains. In brief, DNA fragments for the head domains (residues 52-263 of H1 HA (A/Solomon Islands/3/2006) and residue 43-306 of H3 HA (A/Hong Kong/1/1968)) were amplified separately with PCR reaction. The head domain DNA fragments were individually cloned into the pFastBac vector with an N-terminal gp67 secretion signal peptide and a C-terminal His6 tag. Recombinant bacmid DNA was generated via the Bac-to-Bac system (Invitrogen) and baculoviruses were generated by transfecting purified bacmid DNA in to Sf9 cells. HA head domains were expressed by infecting the High Five cells with the recombinant virus, shaking at 110 r.p.m. for 72 h at 28° C. The secreted head domain protein was purified from the supernatant via Ni-NTA Superflow (Qiagen) and gel filtration on a Superdex75 column (GE Healthcare) in 20 mM Tris-HCl pH 8.0, 150 mM NaCl.

$K_D$ determination by bio-layer interferometry. An Octet RED instrument (FortéBio, Inc.) was used to determine $K_D$ of the antibody-antigen interactions by bio-layer interferometry. The association and dissociation curves were processed using the Prism GraphPad. To examine the binding of FluA-20 or the UCA Fab to different HAs, biotinylated HA molecules were diluted to 10-50 µg/mL in PBS pH 7.4, 0.01% BSA and 0.002% Tween 20. HAs were immobilized onto streptavidin-coated biosensors (FortéBio, Inc.) and incubated with FluA-20 or the UCA Fabs at highest concentration of 1 µM and with 2-fold dilution. The signals for each binding events were measured in real-time and $K_d$ values determined by fitting to a 1:1 binding model.

Structure determination of FluA-20 Fab and complexes of FluA-20 with HA head domains. All complex samples were concentrated to 8-10 mg/mL for crystallization screening on the inventors' high-throughput robotic Rigaku CrystalMation system at TSRI using sitting-drop vapor diffusion. The conditions of crystals for x-ray data collection are as follows: Apo FluA-20 Fab (20° C.; 0.2 M tri-sodium citrate, 20% (w/v) PEG3350, cryo-protected by addition of 15% glycerol); FluA-20_H1 head domain (20° C.; 0.1 M phosphate-citrate, pH 4.2, 40% (v/v) PEG300; No additional cryo-protection); FluA-20_H3 head domain (4° C.; 0.1 M Tris-HCl pH 8.5, 0.2 M lithium sulfate, 40% (v/v) PEG400; no additional cryo-protection). X-ray diffraction data were collected at multiple beamlines (Tables S3-4). The diffraction data were processed with HKL2000 and the structure was determined by molecular replacement in Phaser (McCoy et al., 2007). The initial models for FluA-20 were adapted from PDB 4KMT for the light chain and PDB 5BV7 for the heavy chain. The structures for H1 and H3 head domains were adapted from PDB models 4YJZ and 4FP8. Refinement was carried out in Refmac (Skubak et al., 2004), Phenix (Adams et al., 2010), model rebuilding was performed manually in Coot (Emsley and Cowtan, 2004), and the model was validated by MolProbity (Chen et al., 2010).

Structural analysis. Interaction and interface analysis is carried out on online server PDBePISA at world-wide-web at ebi.ac.uk/pdbe/pisa/. Structure figures were generated by MacPyMol (DeLano Scientific LLC).

Peptide fragmentation and deuterium exchange mass spectrometry. To maximize peptide probe coverage, the optimized quench condition was determined prior to deuteration studies (Hsu et al., 2009; Li et al., 2011). In short, the HA head domain was diluted with buffer of 8.3 mM Tris, 150 mM NaCl, in $H_2O$, pH 7.15) at 0° C. and then quenched with 0.8% formic acid (v/v) containing various concentration of GuHCl (0.8-6.4 M) and Tris(2-carboxyethyl) phosphine (TCEP) (0.1 or 1.0 M). After incubating on ice for 5 min, the quenched samples were diluted 4-fold with 0.8% formic acid (v/v) containing 16.6% (v/v) glycerol and then were frozen at −80° C. until they were transferred to the cryogenic autosampler. Using the quench buffer of 6.4 M GuHCl, 1.0 M TCEP in 0.8% formic acid gave an optimal peptide coverage map.

The samples later were thawed automatically on ice and then immediately passed over an AL-20-pepsin column (16 µL bed volume, 30 mg/mL porcine pepsin (Sigma)). The resulting peptides were collected on a C18 trap and separated using a C18 reversed phase column (Vydac) running a linear gradient of 0.046% (v/v) trifluoroacetic acid, 6.4% (v/v) acetonitrile to 0.03% (v/v) trifluoroacetic acid, 38.4% (v/v) acetonitrile over 30 min with column effluent directed into an Orbitrap Elite mass spectrometer (Thermo-Fisher Scientific). Data were acquired in both data-dependent MS: MS mode and MS1 profile mode. Proteome Discoverer software (Thermo Finnigan Inc.) was used to identify the sequence of the peptide ions. DXMS Explorer (Sierra Analytics Inc., Modesto, CA) was used for the analysis of the mass spectra as described previously (Hamuro et al., 2004). FluA-20 mAb bound HAs were prepared by mixing FluA-20 mAb with monomeric H5 A/Vietnam/03/2204 HA head domain at a 1:1.1 stoichiometric ratio. The mixtures were incubated at 25° C. for 30 min. All functionally deuterated samples, with the exception of the equilibrium-deuterated control, and buffers were pre-chilled on ice and prepared in the cold room.

Functional deuterium-hydrogen exchange reaction was initiated by diluting free HA or antibody-bound HA stock solution with $D_2O$ buffer (8.3 mM Tris, 150 mM NaCl, in D20, pDREAD 7.15) at a 1:2 vol/vol ratio. At 10 sec, 100 sec and 1,000 sec, the quench solution was added to the respective samples, and then samples were frozen at −80° C. In addition, nondeuterated samples, equilibrium-deuterated back-exchange control samples were prepared as previously described (Hsu et al., 2009; Li et al., 2011; Lu et al., 2012). The centroids of the isotopic envelopes of nondeuterated, functionally deuterated, and fully deuterated peptides were measured using DXMS Explorer, and then converted to corresponding deuteration levels with corrections for back-exchange (Zhang and Smith, 1993).

Conservation analysis of the FluA-20 binding epitope. Libraries for full-length and non-redundant human influenza H1 and H3 sequences were downloaded in January 2017 from the Influenza Virus Resource at the NCBI database (Bao et al., 2008). The H1 library includes 11,267 sequences and the H3 library includes 12,584 sequences. The HA sequence alignment was performed by MUSCLE (Edgar, 2004) and analyzed using EMBOSS program (Rice et al., 2000) and custom shell scripts based on SEQCONV+ (Roth Lab, UC Davis).

Conservation analysis of the overall HA surface. A library of HA sequences that were recently isolated from human hosts since 2015 was used for surface conservation analysis, including 701 H1 sequences, 1,739 H3 sequences, and 17 other sequences of H5, H7 and H9 subtypes. The sequences were aligned with MUSCLE (Edgar, 2004) software and the conservation scores for each residue were analysis with ConSurf server (Ashkenazy et al., 2016; Celniker et al., 2013) and displayed on an H3 HA model (PDB 4O5N).

Comparison of FluA-20 binding to HA0 and cleaved HA trimer by Biolayer interferometry (BLI). Baculovirus-expressed HA0 was prepared for the binding studies by cloning the HA ectodomain genes into the pFastBac vector with an N-terminal gp67 secretion signal peptide and a C-terminal BirA biotinylation site, thrombin cleavage site, foldon trimerization domain, and His6 tag. HA0 was expressed in High five cells and the secreted HA0 purified from the supernatant via Ni-NTA Superflow (Qiagen) and gel filtration. The HA0 trimer fractions were concentrated for BLI assays. To prepare cleaved HA trimer, the HA0 trimer was incubated with trypsin at 4° C. overnight (mass ratio of trypsin: HA0≈1:1,000). The HA cleavage was determined by SDS-PAGE electrophoresis with reducing agent. The cleaved HA was purified by gel filtration and the HA trimer concentrated for BLI assay. To evaluate antibody binding, Fabs of FluA-20 and RBS-antibodies 5J8 for H1 binding (Hong et al., 2013) and H7.137 for H7 binding (Thornburg et al., 2016) were firstly immobilized onto anti-human CH1 biosensors (ForteBio, Inc.) in the BLI buffer of PBS pH 7.4, 0.01% BSA and 0.002% Tween 20. The Fab-coated sensors were then incubated with corresponding HA0 and cleaved HA at 1 µM concentration for 120 s to evaluate the association, and then incubated with BLI buffer for 120 s to evaluate the dissociation.

Site-directed mutagenesis of genes encoding HA or antibody proteins. Primers for site-directed mutagenesis were designed using the Agilent QuikChange Primer Design program (Agilent Technologies). The Quickchange Lightning Multi-Site Mutagenesis kit (Agilent, 210515-5) was used to introduce mutations into cDNAs encoding the antibody heavy chain genes or HA genes. The plasmids encoding mutants of FluA-20 heavy or light chains were transfected with the corresponding unmutated FluA-20 light or heavy chains, respectively. Antibodies encoded by cDNA with engineered mutations were purified and tested for binding to HA in ELISA, and the $EC_{50}$ values for binding were determined using Prism software (GraphPad).

Influenza viruses. The virus stocks were made from the supernatant of virus-infected MDCK cell culture monolayers in plain Dulbecco's Modified Eagle Medium (Gibco DMEM, Invitrogen, 11965) with 2 µg/mL of TPCK-trypsin. To obtain virus with uncleaved HA0 on the surface, the stocks were made by inoculating MDCK cells with virus for 1 hr. The cells were washed thoroughly and replenished with plain DMEM without TPCK-trypsin. The supernatant containing the virus was harvested at 48 hours post inoculation.

Hemagglutinin inhibition (HAI) and microneutralization assays. Neutralization potential of FluA-20 was determined by microneutralization and HAI assays, as previously described (Bangaru et al., 2016).

HA cleavage inhibition assay. To assess the ability of FluA-20 to block HA cleavage, 4 µg of recombinant HA0 protein from H3 A/Perth/16/2009 was incubated with either PBS or 40 µg of mAb FluA-20 or mAb CR8020 for 1 h at 37° C. Following incubation, the antibody-HA mixture was either untreated or treated with 2.5 µg/mL of TPCK-treated trypsin and further incubated for 5, 20 and 40 minutes at 37° C. Samples were analyzed by SDS-PAGE.

pH-dependent conformational change assay. To determine the ability of FluA-20 to inhibit the low pH dependent conformational change in HA, 2.5 µg of pre-cleaved HA protein from H3 A/Perth/16/2009 was incubated with 5 µg of mAb FluA-20 or mAb CR8020. Reaction mixtures were incubated at 37° C. for 1 h at pH 5.0. Separate reactions containing no antibody were incubated at pH 5.0 or pH 8.0 to be used as controls. Following incubation, all the mixtures were neutralized with pH 8.4 Tris buffer and were then either untreated or treated with TPCK-trypsin at 20:1 (wt: wt) ratio of HA to trypsin. Samples were incubated for 12 h at 37° C. and then analyzed by non-reducing SDS-PAGE Egress assay. Cell culture monolayers of MDCK cells in 96-well plates were washed three times with PBS and inoculated with an MOI 1 of A/Texas/50/2012 H3N2 in Virus Growth Media with TPCK-treated trypsin (VGM) for 3 hour at 37° C., 5% $CO_2$. The inoculum was removed from cells, and cells were washed three times with PBS. 10 µg/mL of mAbs in VGM: FluA-20, irrelevant control mAb MRSA-147 or known egress inhibitor IgG mAb H3v-47, or an equimolar concentration (66.7 nM) of the neuraminidase inhibitor drug zanamivir (GlaxoSmithKline) were added to cells in triplicate. Cells were incubated for 21 hours at 37° C., 5% $CO_2$. Supernatants were collected, clarified at 300×g for 15 min to remove cell debris. Serial two-fold dilutions of supernatants in PBS were added to an equal volume of 0.5% turkey red blood cells in v-bottom plates to determine the virus titer by hemagglutination assay. Hemagglutination titers were determined as endpoint titer values.

Molecular engineering of antibody variable gene domains and generation of Fc mutants. For the expression of recombinant forms of antibody clones, nucleotide sequences of antibody variable domains were optimized for mammalian expression and synthesized on the BioXP 3200 System (SGI-DNA). These inserts were then joined with a 6.8-kb EcoR1/HindIII digested backbone of pML-huCG1 for expression of γ1 or BgIII/NotI digested backbone of pML-huCk or pML-huCL vectors for κ or λ chains, respectively, using the NEBuilder HiFi DNA Assembly master mix (NEB, E2621). For the generation of Fc mutants, 4 nucleotide sequences of antibody constant domains with single mutations (K332A, D265A, and N297A) and a double mutant (L234A, L235A) in the constant heavy chain region (CH2) were optimized for mammalian expression and synthesized on the BioXP 3200 (SGI-DNA). These inserts were then joined with a 6.0-kb HindIII/XbaI digested backbone of pML-huCG1 (McLean et al., 2000) for construction of 4 separate γ1 mutant chains using the NEBuilder HiFi DNA Assembly master mix (NEB).

Dimeric recombinant soluble FcγRIIIa (CD16a) binding ELISA. A dimeric recombinant soluble FcγRIIIa (rsFcγRIIIa) ELISA was used to model the need for ADCC-inducing Abs to cross link FcγRIIIa (Wines et al., 2016). A 96-well ELISA plate was coated with 50 ng of purified influenza HA protein from H1N1 A/California/07/2009 (Sino Biological Inc., 11085-V08B) protein overnight at 4° C. in PBS. The plates were treated as described (Wines et al., 2016). Briefly, the plates were blocked with PBS 1 mM EDTA, 1% BSA (PBSE/BSA) for 1 h and 50 µL of antibodies (FluA-20, FluA-45, FluA-55 or an unrelated negative control antibody, i.e., a recombinant form of HIV-specific mAb VRC01) at various concentrations (40 µg/mL to 2.4 ng/ml) were added to the plates. The plates were washed with PBST (PBS with 0.1% Tween-20) and 50 µL of 0.1 µg/mL rsFcγRIIIa (V176) dimer was added to the wells and incubated for 1 h at 37° C. Pierce High Sensitivity Streptavidin-HRP (ThermoFisher Scientific, 21130) was diluted 1:10,000 in PBSE/BSA and added to wells. The plates were developed with TMB substrate solution and the reaction was stopped with 1 M HCl. The plates were read at an absorbance of 450 nm.

NK cell activation assay. 96-well ELISA plates were coated with 600 ng of purified influenza HA protein from H1N1 A/California/07/2009 (Sino Biological Inc., 11085-V08B) overnight at 4° C. in PBS. The plates were washed and incubated with 10 µg/mL, 1 µg/mL or 0.1 µg/mL of antibodies (FluA-20, FluA-45, FluA-55 or VRC01) diluted in PBS for 2 h at 37° C. Plates were washed and 5×10$^5$ purified NK cells were added to each well. NK cells were purified from freshly isolated PBMCs using the EasySep human NK cell enrichment kit (STEMCELL Technologies, 19055). Mouse anti-human CD107a allophycocyanin-H7 antibody (clone H4A3; BD Biosciences, 561343), 5 g/mL brefeldin A (Sigma-Aldrich, B6542) and 5 µg/mL monensin (BD GolgiStop; BD Biosciences, 554724) were added to the cells and incubated for 5 h. Purified NK cells then were incubated with anti-human CD3 PerCP (clone SP34-2; BD Biosciences, 552851) and anti-human CD56 allophycocyanin (clone B159; BD Biosciences, 555518) for 30 min at RT. Cells were fixed and permeabilized for 10 min and then incubated with anti-human IFNγ AF700 (clone B27; BD Biosciences, 561024) in the dark. Finally, cells again were fixed with 1% formaldehyde, and data were acquired for 20,000-50,000 events using an LSRFortessa flow cytometer (BD Biosciences).

In vivo efficacy of FluA-20 Fc mutants. To determine the contribution of FluA-20 Fc-mediated activity to overall protection observed in vivo, groups of BALB/cJ mice were prophylactically treated with 10 mg/kg of either FluA-20 IgG1 or rFluA-20 IgG1 or rFluA-20-N297A IgG1 or rFluA-20-LALA IgG1 or MRSA-147 IgG 24-hours prior to being intra-nasally challenged with 1.2×10$^4$ focus forming units (FFU) of H1N1 A/California/07/2009. Mice were monitored for 14 days for weight change and disease (clinical score).

Sub-lethal respiratory challenge mouse model for influenza A H1N1 infection. Groups of BALB/c mice were inoculated intranasally with different doses (538, 2,690, 13,400 or 67,000 FFU) of A/California/04/2009 virus and were monitored for 14 days for weight change kinetics and the disease. Weight loss of more than 20% total weight was the IACUC stipulated endpoint for humane euthanasia. Based on the results obtained from this study, a dose of 1.2×10$^4$ FFU was deemed appropriate for the challenge studies with FluA-20 Fc mutants.

Focus size reduction assay. To examine the ability of mAb FluA-20 to reduce focus size, a predetermined amount of H3N2 A/Hong Kong/1/1968 virus was incubated with dilutions (10, 5 or 1 µg/mL) of mAb FluA-20 or irrelevant control mAb MRSA-147 or mAb CR9114 or molar equivalents of zanamivir in the presence of TPCK-treated trypsin for 1 h at 37° C. The mixture then was used to inoculate a monolayer of MDCK cells in 6-well plates, followed by incubation at 37° C. for 1 h with intermittent rocking. The Avicel overlay (1.2% Avicel in DMEM) supplemented with the corresponding mAb dilutions and 1 µg/mL of TPCK-treated trypsin then was added to each well. The plates were incubated for 48 h at 37° C. Following incubation, the plates were washed and fixed with 1 mL of 80% methanol/20% PBS. The presence of influenza nucleoprotein in the fixed cells was determined using a 1:6,000 dilution of mouse anti-NP antibody (BEI Resources, NR 4282) as the primary antibody and 1:500 of peroxidase-labeled goat anti-mouse antibodies (SeraCare) as the secondary antibody. The foci were visualized subsequently using TrueBlue peroxidase substrate (KPL, Inc.). Images were captured by an CTL Immunospot S5 Analyzer. Foci area as percentage of total area was calculated by ImageJ software (NIH).

Flow cytometric analysis of antibody binding to cell-surface expressed HA. HEK293F cells grown in expression medium (Freestyle 293 Expression Medium; Invitrogen, protein and incubated at 37° C. for 36 h. Untransfected (UT) or transfected cells were washed and treated with either DMEM containing TPCK trypsin (2 µg/mL) or plain DMEM for 15 min at 37° C. Cells were washed with PBS containing 2% of heat inactivated FBS and 2 mM EDTA (FACS buffer) and incubated with either mAb CR9114 or mAb FluA-20 (10 µg/mL) for 30 min at RT and for 5 min at 37° C. The cells were washed with FACS buffer and incubated with secondary goat anti-human IgG PE antibody (Southern Biotech, 2040-09) for 1 hour at 4° C., fixed with 4% formaldehyde in PBS, and analyzed by flow cytometry using an LSR-2 cytometer (BD Biosciences). Data for a total of up to 20,000 of cell events were acquired and analyzed with FlowJo software (Tree Star).

HDX-MS to comparison the dynamic change of H7 HA0 trimer and cleaved HA trimer. H7 HA (A/Netherlands/219/2003) was expressed in HEK293F cells (Bangaru et al., 2016). In brief, sequences encoding the HA genes were optimized for expression, and cDNAs were synthesized (Genscript) as soluble trimeric constructs by replacing the transmembrane and cytoplasmic domain sequences with cDNAs encoding the GCN4 trimerization domain and a His-tag at the C-terminus. Synthesized genes were subcloned into the pcDNA3.1 (+) mammalian expression vector (Invitrogen). HA protein was expressed by transient transfection of 293F cells with polyethylenimine transfection reagent and grown in expression medium (Freestyle 293 Expression Medium; Invitrogen, 12338). The HA0 protein was harvested after 7 days with HisTrap TALON FF crude columns and the HA0 trimer purified via gel filtration. To obtained cleaved HA trimer, the HA0 protein was treated with trypsin at 37° C. for 30 mins and the cleaved HA trimer further purified by gel filtration.

Prior to conducting comparative hydrogen-deuterium exchange experiments with H7 HA0 or with cleaved H7HA, the quench condition for best sequence coverage of HA was 6.4 M GuHCl, 1 M TCEP and 0.8% formic acid, as previously described (Aiyegbo et al., 2014; Li et al., 2011; Marsh et al., 2013). To initiate hydrogen-deuterium exchange reactions, 2 µL of pre-chilled protein stock solution (free uncleaved H7 HA0, 1.8 mg/mL; cleaved H7 HA, 1.6 mg/mL) was diluted into 4 µL $D_2O$ buffer (8.3 mM Tris, 150 mM NaCl, in D20, pDREAD 7.2) at 0° C. At indicated times of 10 sec, 100 sec, 1,000 sec, 10,000 sec and 100,000 sec, the exchange reaction was quenched by the addition of 9 µL of optimized quench solution at 0° C. After incubating on ice for 5 min, the quenched sample was diluted 5-fold with 0.8% formic acid containing 16.6% glycerol, immediately frozen on dry ice and stored at −80° C. In addition, un-deuterated samples and equilibrium-deuterated control samples were also prepared. All samples were then loaded onto the inventors' in-house LC instrument for online digestion and separation (Aiyegbo et al., 2014). The resulting peptides were directed into an OrbiTrap Elite Mass Spectrometer (Thermo Fisher Scientific, San Jose, CA) for DXMS analysis. Instrument settings have been optimized for HDX analysis. The data acquisition was carried out in a data-dependent mode and the five or ten most abundant ions were selected for MS/MS analysis. Proteome Discoverer software was used for peptide identification. The centroids of each peptide was calculated with HDExaminer, and then converted to corresponding deuteration levels with corrections for back-exchange (Zhang and Smith, 1993).

Negative stain electron microscopy. FluA-20 Fab was incubated with uncleaved H1 HA trimer for 20 seconds at 5 times molar excess of Fab. The complex was added to carbon-coated 400 mesh cooper grids and stained with 2% uranyl formate. Micrographs were collected on a 120 kv Tecnai Spirit microscope with a 4k×4k TemCam F416 camera using Leginon (Potter et al., 1999). Images then were processed with Appion (Lander et al., 2009). Particles were selected with DoGpicker (Voss et al., 2009), and 2D classes were generated with MSA/MRA (Ogura et al., 2003). Particles were false colored in Photoshop.

Example 5—Results

Isolation of broadly reactive human mAb FluA-20. The inventors identified a donor who had received annual licensed inactivated seasonal vaccines for over two decades. The donor also had participated previously in clinical trials of experimental H5N1 and H7N9 subunit vaccines in the Vanderbilt NIH Vaccine Treatment and Evaluation Unit (FIG. 21A). The first H5 vaccine was a monovalent inactivated subvirion vaccine that incorporate the HA from A/Vietnam/1203/2004 (VN/1203) H5N1 clade 1 influenza virus (batch 04-067), and each dose consisted of 90 µg of hemagglutinin (NIH Division of Microbiology and Infectious Diseases [DMID] study 04-062). After 22 months, the individual was boosted with a monovalent inactivated surface antigen influenza A (H5N1) vaccine made from the modified HA and NA of A/Anhui/01/2005 (H5N1) (DMID study 07-0022). The volunteer subsequently received an H7 subunit vaccine (in DMID 13-0033; a phase II human clinical trial with monovalent inactivated influenza A/Shanghai/02/2013 H7N9). For the current study, the donor was vaccinated with a 2014-15 seasonal trivalent inactivated influenza vaccine (TIV) on day 0. Peripheral blood samples were obtained on days 0, 3, 4, 5, 6, 7, 10, 11, 14 and 31 following immunization.

Cryopreserved PBMC samples from day 31 after seasonal vaccination were immortalized by EBV transformation and the supernatants were screened for the presence of antibodies that displayed heterosubtypic binding breath to recombinant HA proteins derived from H1 (A/California/04/2009, A/Texas/36/1991), H3 (A/Hong Kong/1/1968, A/Victoria/3/1975), H7 (A/Shanghai/2/2013, A/Netherlands/219/2003) and H9 (A/Hong Kong/1073/99) subtypes by ELISA. The hybridoma cell line secreting the FluA-20 mAb was isolated from a B cell line that exhibited heterosubtypic breadth during the initial screen. Two additional broadly reactive non-neutralizing heterosubtypic mAbs also were isolated and used in these studies for comparative purposes, designated FluA-45 and FluA-55. These mAbs were isolated from individuals previously vaccinated with an experimental H7 vaccine (in the NIH Vaccine Treatment and Evaluation Unit (DMID 13-0033; a phase II human clinical trial with monovalent inactivated influenza A/Shanghai/02/2013 H7N9).

The inventors performed deep sequence analysis of antibody variable gene sequences in circulating PBMCs in the donor and discovered sequences that appeared clonally related to FluA-20 (i.e., "siblings"), defining two sequences as clonally related if they shared use of the same $V_H$ and $J_H$ gene and differed by three or fewer amino acids in the HCDR3 region. The inventors identified siblings to FluA-20 in blood samples from four time points: days 5, 6, 11 and 14 post-vaccination with TIV. The inventors inferred that the majority of these siblings arose from one common ancestor, and clustered into three major groups (designated Cluster A, B and C) that differ by point mutations across the $V_H$ gene region (FIG. 21B). Network analysis of these sequences suggested that FluA-20 arose from cells present at day 6 that also were observed at day 14 (FIG. 21B).

Figure 21C:
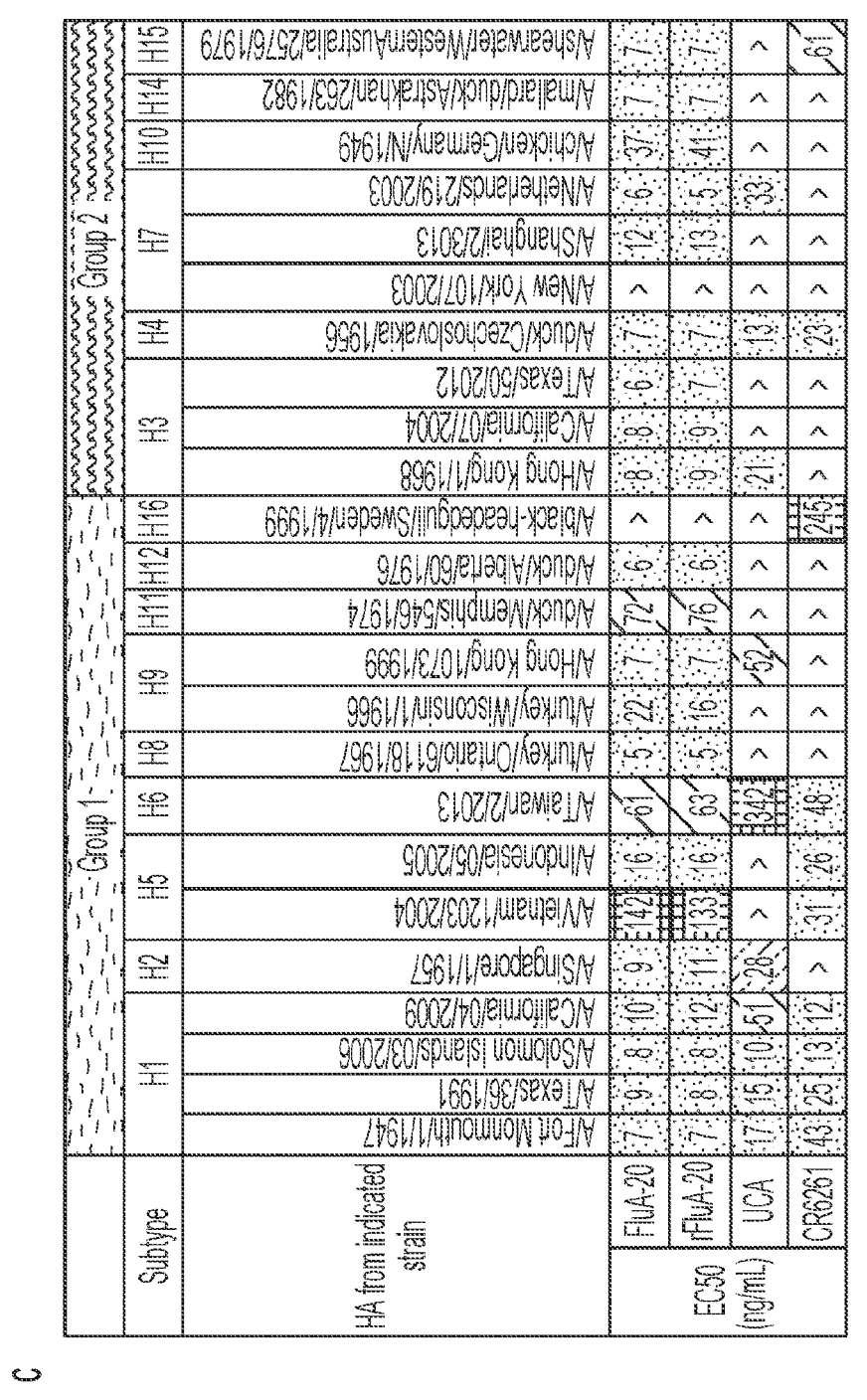
Figure 28A:
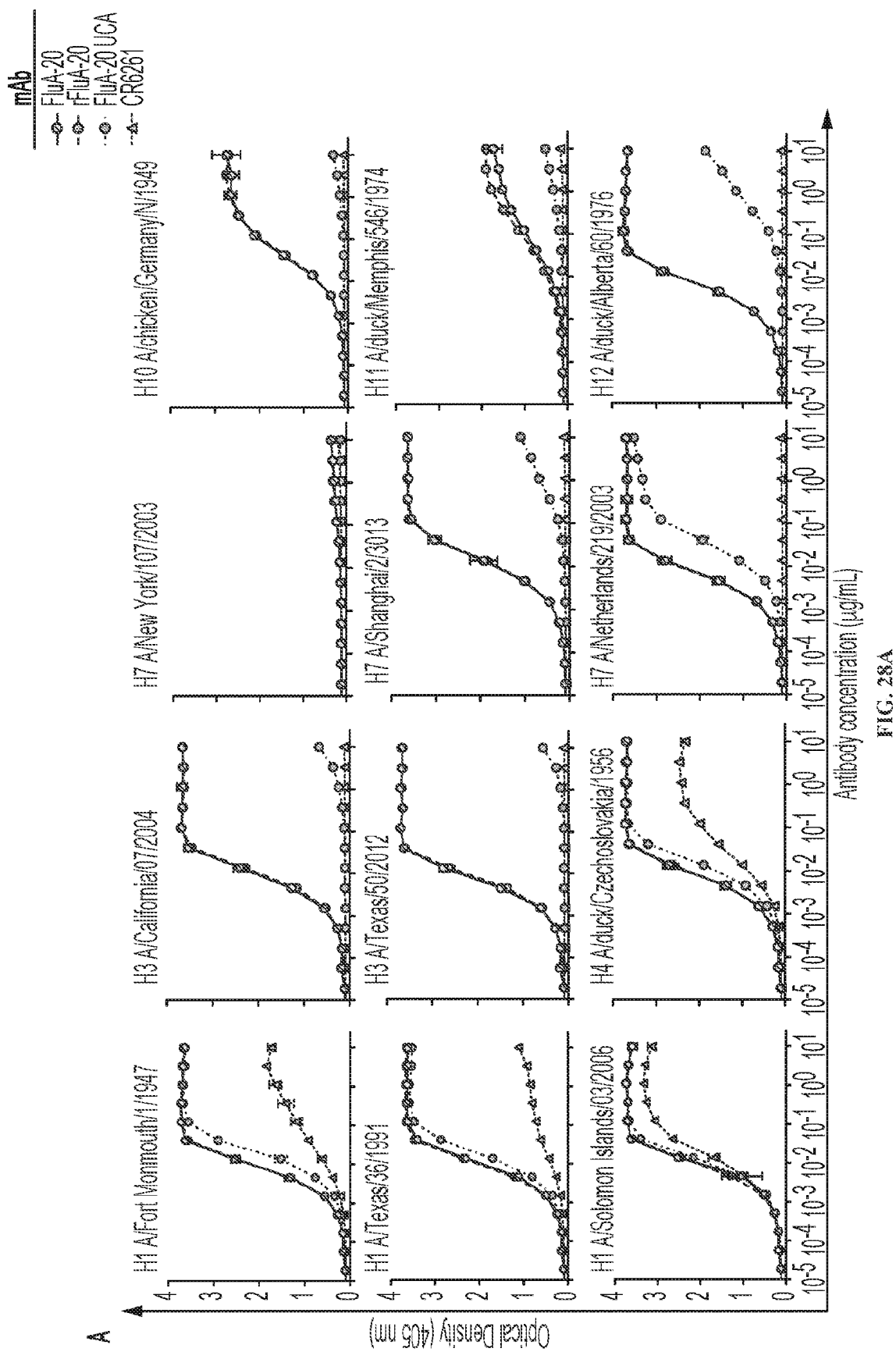
Figure 28A:
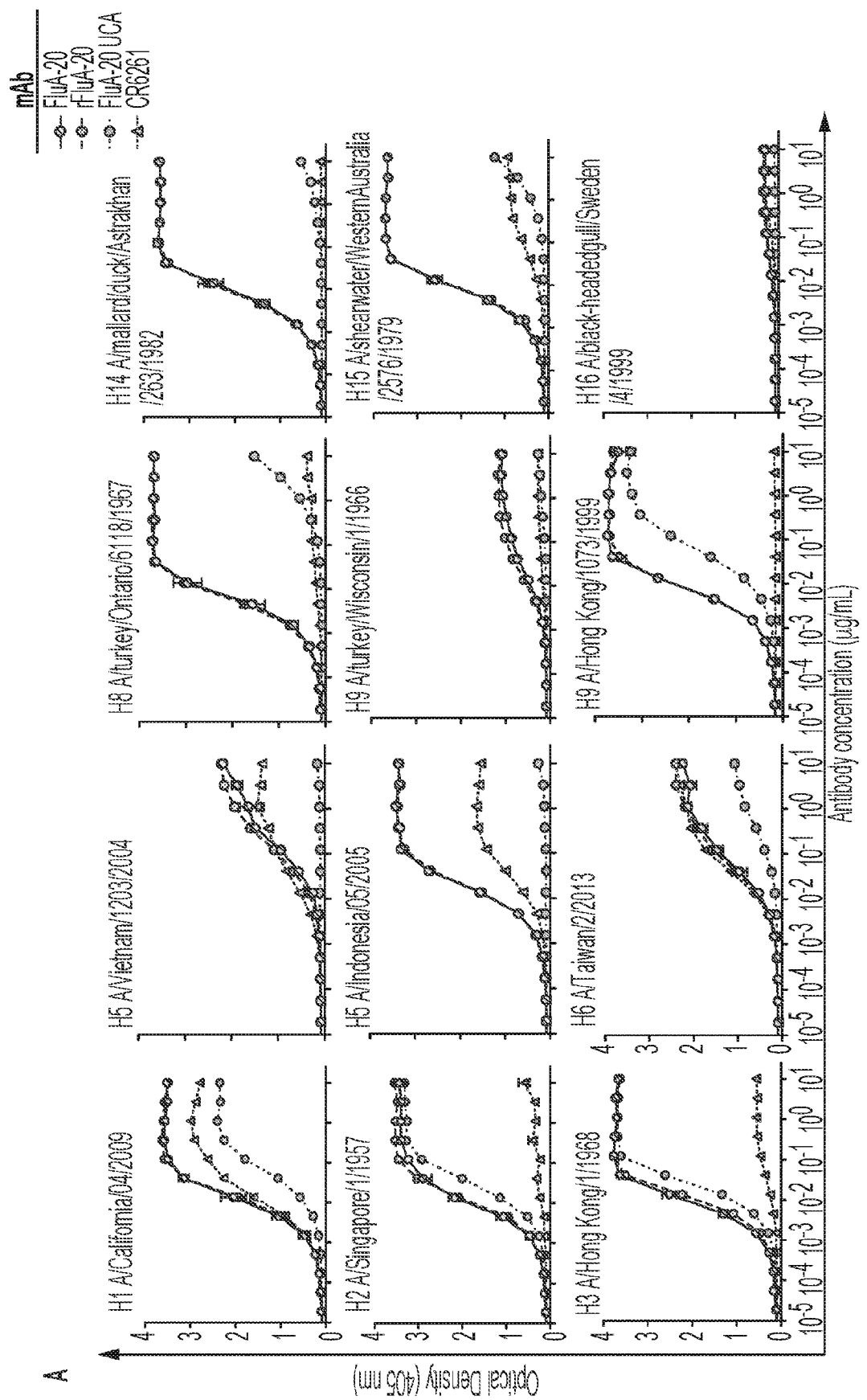

Binding profile of FluA-20 and sibling antibodies with various subtypes of influenza type A HA molecules. To investigate the breadth of the isolated mAb FluA-20, the inventors tested purified IgG for binding activity to HA from different IAV subtypes; all HA proteins used were recombinant trimers. FluA-20 exhibited extraordinary binding breadth and affinity to recombinant HAs belonging to group 1 (H1, H2, H5, H6, H8, H9, H11 and H12) and group 2 (H3, H4, H7, H10, H14 and H15) viruses, with $EC_{50}$ values for binding ranging from 5 ng/ml to 142 ng/ml (FIGS. 21C and 28A). Genes of the wild-type FluA-20 variable domain were synthesized and a recombinant form of FluA-20 IgG protein was expressed; hybridoma-generated antibody (designated FluA-20) was used for the assays unless the recombinant form is specified (designated as rFluA-20). As expected, rFluA-20 IgG showed a similar binding spectrum to the hybridoma-produced FluA-20 IgG protein (FIGS. 21C and 28A). Additionally, the inventors recombinantly expressed FluA-20 as an Fab fragment and assessed its kinetics of binding to representative HA subtypes that are pathogenic for humans using a bio-layer interferometry assay (Table S5). Remarkably, even in this monovalent form, rFluA-20 Fab interacted with most HA molecules from H1, H2, H3, H5, and H7 subtypes with $K_D$ values less than 100 nM (with several less than 1 nM, Table S5).

The inventors also recombinantly expressed and tested several somatic variant ("sibling") antibodies related to FluA-20 from cluster A and cluster B (FIG. 28B). Three sibling antibodies, Sib 2, Sib 3, and Sib 45, appeared to have very similar activity and breadth as rFluA-20 (Table S6). Also, the inventors found that two sibling antibodies, Sib 28 and Sib 48 in a phylogenetic cluster that was more mutated than FluA-20, lost binding to some H3, H5 and H14 HAs, and Sib 7 and Sib 33 completely lost activity to any HA tested, likely due to the introduction of additional somatic mutations (Table S6). These findings suggested that FluA-20 clonotype is represented by multiple variations with diverse reactivity breadth in the immune repertoire.

Unmutated common ancestor-origin interactions drive the activity of the FluA-20 lineage. FluA-20 belongs to the IgG1 subclass and is encoded by the $V_H4$-61/D2-15/$J_H4$ and $V_K1$-39/$J_K1$ antibody variable gene segments, which represents a genetic configuration not previously reported for broadly reactive human influenza antibodies. The analysis of the FluA-20 cDNA sequence revealed that FluA-20 shares 93% identity with both the $V_H4$-61*01 and $V_K1$-39*01 germline genes. Compared to the inferred unmutated common ancestor sequence (FluA-20-UCA), FluA-20 harbored 16 somatic mutations in the heavy chain variable gene amino-acid sequence and 11 in the light chain variable gene sequence (FIG. 28C). Remarkably, recombinantly expressed UCA antibodies (expressed as either IgG or Fab forms) of FluA-20 appeared to retain the substantial binding breadth of rFluA-20 (FIGS. 21C and 28A; Table S5). Nonetheless, compared to the UCA antibody, rFluA-20 displayed not only an increase in binding potency, but also greater breadth with additional recognition of many H3 and H5 HAs.

Figure 22E:
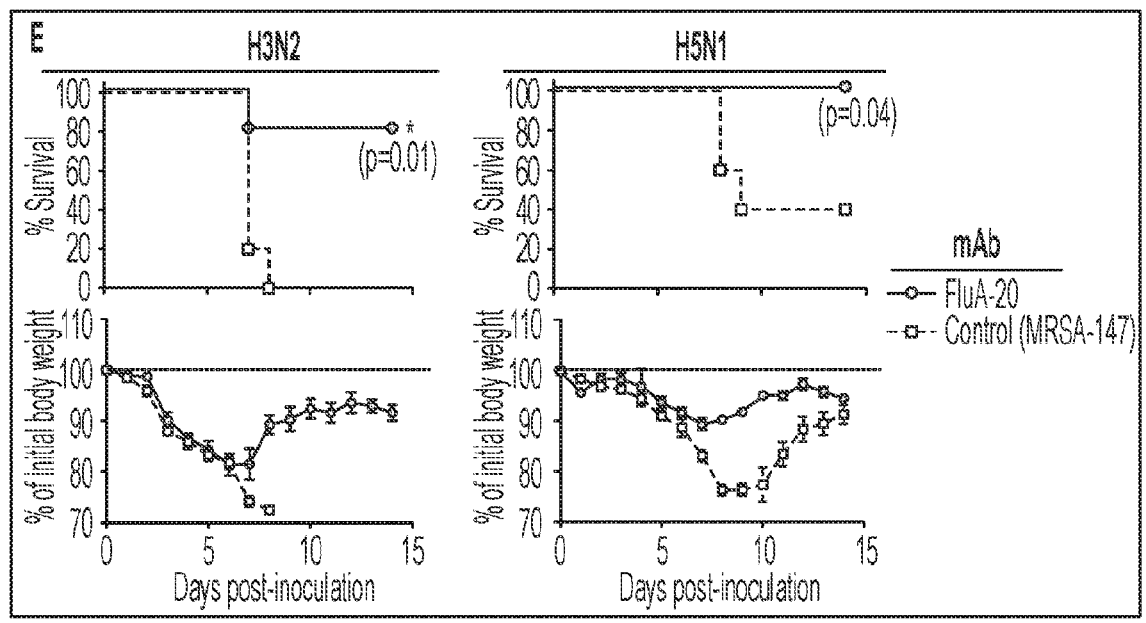

FluA-20 exhibits prophylactic and therapeutic efficacy in vivo against viruses of diverse IAV subtypes. 1) Sublethal influenza mouse model of antibody prophylaxis. To examine if mAb FluA-20 could mediate protective activity in vivo, the inventors chose A/Netherlands/602/2009 (H1N1), A/X-31 (H3N2), A/barn swallow/Hong Kong/D10-1161/2010 (H5N1) and A/Shanghai/1/2013 virus strains (H7N9), representative of group 1 and group 2 IAVs, for prophylactic studies. BALB/c mice (n=8 per group) were administered 10 mg/kg of FluA-20 IgG or a similarly prepared control antibody by the intraperitoneal route, and then challenged 24 hours later intranasally with a sub-lethal dose of virus. Mice treated with FluA-20 (n=5) showed complete protection from weight loss after H1N1 challenge (FIG. 22A), whereas mice challenged with H3N2, H5N1 or H7N9 strains showed significantly faster recovery from weight loss compared to control animals (FIG. 22A). Additionally, FluA-20 treatment reduced pulmonary lung titers (day 6 post-inoculation) following H1N1 and H7N9 challenge (FIG. 29A). 2) Lethal influenza BALB/c mouse model of antibody prophylaxis using mouse-adapted H1N1 virus. To further evaluate the optimal dose of FluA-20 for prophylactic efficacy, the inventors chose to test 3 different doses of FluA-20 against lethal challenge with mouse-adapted H1N1 A/California/04/2009 virus. BALB/c (n=10 per group) mice were IP injected with either 1 or 3 or 10 mg/kg of FluA-20 or mg/kg of a control antibody or PBS 14 hours prior to intranasal challenge with H1N1 virus. As a control, one experimental group was treated with the commercially available IAV drug oseltamivir twice daily for 5 days, starting at 1 h post-inoculation. Remarkably, FluA-20 provided significant protection against mortality and protection against severe weight loss at all three tested doses, with groups that received 3 or 10 mg/kg showing better efficacy than groups with oseltamivir (FIG. 22B). 3) Lethal influenza DBA/2J mouse model of antibody prophylaxis using human H1N1 virus. The inventors also evaluated mAb FluA-20 for prophylactic efficacy against lethal challenge with non-mouse adapted H1N1 A/California/04/2009 virus in DBA/2J mice and observed significant protection in FluA-20-treated mice (10 mg/kg) compared to mice that were given mock control IgG (FIG. 22C). 4) Sublethal influenza BALB/c mouse model of antibody therapy using human H1N1 virus. To determine the therapeutic potential of FluA-20, the inventors measured protection against weight loss after sublethal challenge of mice with human H1N1 virus. Mice treated with mAb FluA-20, similarly to mice that treated with a positive control mAb CR6261, showed significant protection against severe weight loss and faster recovery (day 6-10 post-challenge) when compared to mock-treated mice (FIG. 22D). 4) Lethal influenza BALB/c mouse model of antibody therapy using H3 and H5 viruses. The inventors also tested efficacy of mAb FluA-20 treatment in a lethal model by measuring survival, weight loss and lung virus titers in BALB/c mice (n=5 per group) that were lethally challenged with H3N2 or H5N1 viruses on PR8 backbone and treated IP next day with mAb FluA-20 or control mAb MRSA-147 (FIGS. 22E and 29B). Treatment with mAb FluA-20 showed a significant protection from mortality (FIG. 22E). Collectively, these results indicate the ability of mAb FluA-20 to protect prophylactically and therapeutically in vivo against sublethal or lethal virus challenge against influenza A virus strains of diverse subtypes.

FluA-20 IgG does not compete for binding to HA with other RBS- or stem-specific antibodies. To determine whether FluA-20 binds to previously known sites of vulnerability on HA, the inventors used bio-layer interferometry to measure if FluA-20 competed for HA binding against other known bnAbs. Surprisingly, FluA-20 did not compete for binding to HA with RBS-mAbs (mAb 5J8) or stem-specific mAbs (mAbs CR9114, F16v3, 39.29 or H3v-86) (FIG. 30A). Additionally, the inventors observed that FluA-20 interacted well with truncated HA head domains lacking the stem region, derived from multiple HA subtypes (FIG. 30B). These data indicated that FluA-20 recognizes a distinct protective epitope on the HA head domain that is conserved across most influenza A viruses.

Structural characterization of FluA-20 in complex with the HA head from H1 A/Solomon Islands/3/2006 revealed a novel epitope at the trimer interface. To identify this novel site of vulnerability on the HA head, crystal structures of the apo form of rFluA-20 Fab and its complex with the HA head domain from A/Solomon Islands/3/2006 (H1N1) were determined at 1.73 Å and 2.85 Å resolution, respectively (Tables S7-8). Two HA head domains, each bound by one Fab, were present in the crystal asymmetric unit.

The complex structure revealed that FluA-20 recognizes an epitope that is parallel to, but does not overlap with, the receptor-binding site (RBS) (FIG. 23A). The antibody interacts primarily with the 220-loop and has some contact with the 90-loop, creating buried surface areas of 617 Å2 and 98 Å2 on each loop. After superimposing the HA head domain in the Fab complex with an H1 HA trimer structure (PDB 4M4Y), the FluA-20 epitope was found to be hidden in the HA trimer interface and not accessible for antibody binding (FIG. 23B). In fact, the non-RBS side of 220-loop is an important surface for interaction of the HA with its adjacent protomer in the native trimer (FIGS. 31A-B). The variable domain of FluA-20 on the monomeric head domain overlaps with the head domain from an adjacent protomer in the HA trimer structure (FIG. 23B). These results suggested that FluA-20 recognizes HA in a form different from the canonical closed trimer structure.

The interaction of FluA-20 with the HA head domain is mediated mainly by a groove between CDR H3 and L2, with some contacts from CDR H1 to the edge of its epitope (FIG. 23A). Many contacts of FluA-20 with HA are centered on Arg229 (FIG. 23C). First, Asp98 (H) of FluA-20 makes a salt bridge with Arg229 (FIG. 23C). Surrounding this salt bridge is an enclosed hydrophobic pocket formed by both HA and FluA-20 residues, including Pro221, Val223, and Pro96 of HA and Tyr49 (L) and Tyr100a (H) of FluA-20 (FIG. 23C). The aromatic ring of Tyr100a (H) of FluA-20 is positioned approximately 4 Å away from the basic amine of Arg229 in HA and likely forms cation-π interactions that would strengthen the binding. Alanine mutation of Arg229 completely abolished binding of FluA-20 to the HA (FIG. 23D). Glycine mutation of Val223 or Pro96 in the HA epitope also substantially decreased HA binding by FluA-20, indicating that these hydrophobic contacts between the non-polar residues in HA to Tyr49 (L) and Tyr100a (H) of FluA-20 are important for its activity (FIG. 23D). Reciprocally, D98A (H) or Y49A (L) mutants of FluA-20 disrupted binding to all targeted HAs, and an alanine mutation of Tyr100a (H) in FluA-20 also eliminated binding to most HA subtypes (Table S9).

Other than the intricate binding core, several hydrogen bonds are involved in the binding of FluA-20 to HA. The side-chain amine of HA Arg220 hydrogen bonds to the main-chain carbonyl of Glu97 (H) from the antibody (FIG. 23C). Additionally, the Gln55 (L) side-chain carbonyl interacts with the main-chain amide of Lys222 on the HA (FIG. 23C). As a result, mutation of either HA Arg220 or Gln55 (L) of FluA-20 decreases the binding interaction (FIG. 23D, Table S9).

Structural characterization of FluA-20 in complex with HA head of H3 A/Hong Kong/1/1968. The inventors also determined the crystal structure of rFluA-20 Fab in complex with the HA head domain of A/Hong Kong/1/1968 (H3N2), at 2.10 Å resolution (Table S8). Each asymmetric unit includes one FluA-20 in complex with one H3 head domain. FluA-20 interacts with a similar epitope on the H3 head domain as with H1, with similar interactions (FIGS. 24A, 31C-D). The structural alignment of H3 head domain bound by FluA-20 with the H3 trimer model (PDB 4FNK) again indicated that the antibody interacts with HA in a form other than the canonical trimer (FIG. 24A).

Additional hydrogen bonds are made between the side-chain amine of Gln55 (L) of FluA-20 to the main-chain carbonyl of Trp222 in HA and the Asn53 (L) side-chain carbonyl to the Arg224 main-chain amide (FIGS. 24B, 31B). Gln55 (L) appears to be important for FluA-20 binding to many other HA strains, although not for H3 (A/Hong Kong/1/1968) and a few other strains (FIG. 24B, Table S9). The interaction by Asn53 (L) is not required for antibody binding to most HAs (Table S9).

Hydrogen deuterium exchange mass spectrometry (HDX-MS) experiments confirms interaction of the FluA-20 with the H5 HA trimer interface. To confirm that FluA-20 interacts with the equivalent epitope on H5 HA, the inventors conducted HDX-MS experiments with a monomeric head domain of H5 (A/Vietnam/1203/2004) to identify peptides on the surface of HA that are occluded following binding of FluA-20. H5 HA head domain protein was labeled with deuterated water in the presence or absence of the FluA-20 IgG. The head domain protein was digested with pepsin, and deuterium labeling of resulting peptides was measured by mass spectrometry. The inventors found that FluA-20 blocked labeling of peptides comprising of residues 210-223 (FIGS. 32A-B), consistent with the location of the epitope in the co-crystal structures with the subtype H1 or H3 HAs. Mutations of the 220-loop in H5 (A/Vietnam/1203/2004) showed substantial influence on FluA-20 binding. Single mutants of R220A, V223A, or R229A in H5 HA completely abolished FluA-20 binding, confirming that the antibody uses a similar binding mechanism for H5 as those observed for H1 and H3 (FIG. 32C).

The FluA-20 epitope is highly conserved across different subtypes of IAV HA. FluA-20 engages a highly conserved binding core in its recognition of H1 and H3 HAs. The five HA residues with which FluA-20 primarily interacts, namely Pro96, Arg220, Pro221, Val223, and Arg229, are highly conserved among all human H1N1 viruses (95% conservation for Pro96, and over 98% conservation for the other four residues) (FIG. 25A). In human H3N2 viruses, conservation of key residues in the epitope is generally above 97%, except for residue 223. Approximately 22% of H3 strains encode Val223, including A/Hong Kong/1/1968 (H3N2) (FIG. 25B), but 70% of H3 HAs possess Ile223. Two strains of H3 with the Ile223 variant were tested in the activity profiling, (A/Texas/50/2012) and (A/Switzerland/9715293/2013), and both bind to FluA-20 with high affinity. Thus, FluA-20 can effectively accommodate either Val or Ile at HAI position 223.

The sequences of the major epitope residues recognized by FluA-20 in other HA subtypes are summarized in Table 5. Remarkably, the five major epitope residues (P96, R220, P221, V/I223 and R229) that directly interact with FluA-20 remain highly conserved across different strains and subtypes, which explains the extraordinary breadth of FluA-20. Some mutations or deletions in these five key residues in the epitope of a few HAs may inhibit binding to FluA-20. For instance, Arg229 is essential for electrostatic interactions with FluA-20 (Table 5, FIGS. 25A-B). An Ile229 substitution in H3 A/Minnesota/11/10 likely renders it the only H3 strain that FluA-20 fails to recognize among those tested, whereas a Trp229 residue in H13 (A/gull/Maryland/704/1977) can be tolerated. Comparison of the H13 structure (PDB 4KPQ) with the H1 or H3 complexes with FluA-20 shows that H13 possesses a unique pair of mutations, Tyr223 and Trp229 (FIG. 25D). Possible aromatic stacking of these two residues with Tyr100a (H) of FluA-20 may compensate for the loss of the Arg229 contacts.

Compared to H1 and H3, two H5 strains with Ser221 (a common substitution in the H5 subtype) exhibited weaker binding of FluA-20 (FIG. 25C). Ser221 does not appear to change the 220-loop conformation (FIG. 25C); however, the decrease of side-chain hydrophobicity or difference in the rigidity of 220-loop may have affected FluA-20 binding. In fact, a Pro221 mutation in H5 (A/Vietnam/1203/2004) substantially rescued the affinity to FluA-20 to a level similar to that of H1 or H3 (FIG. 25C). Of the two H7 strains tested, the H7 HA of A/New York/107/2003 has a truncated 220-loop (missing residues), but still retains the critical Arg229. As a result, this H7 HA shows decreased binding by FluA-20, compared to H7 from A/Shanghai/2/2013 (FIGS. 21C, 25E-F). Considerable variation nevertheless exists at some residues in the FluA-20 epitope, particularly for 219, 222, and 224 that are located very close to the epitope binding core. However, the interactions of FluA-20 with these variable residues are only to their main chain, and the approach angle of FluA-20 enables the antibody to successfully accommodate these variable side chains (FIGS. 25G-H).

Mutation experiments confirm the critical contact residues in the FluA-20 IgG paratope. To determine the paratope residues that are critical for FluA-20 binding, the inventors mutated Tyr34, Thr96, Glu97, Aps98, Tyr100a or Cys101 on the heavy chain (H) and Tyr49, Asn53 or Gln55 on the light chain (L) to alanine and recombinantly expressed each variant to determined relative binding to HAs from different subtypes compared to rFluA-20. Two mutants D98A (H) and Y49A (L) showed complete loss of binding to all tested HAs, validating the importance of the electrostatic interaction between Asp98 (H) of FluA-20 and Arg229 on HA and the hydrophobic interaction between Tyr49 (L) to HA residues (Table S9, FIGS. 25A-B). Furthermore, Q55A (L) mutant showed >10-fold or complete loss of binding $EC_{50}$ to all HAs except H1 A/Texas/36/1991, H3 A/Hong Kong/1/1968 and H7 A/Netherlands/219/2003, while the Y100aA (H) mutant also showed >10-fold loss of binding $EC_{50}$ to all HAs except H3 A/Hong Kong/1/1968 (Table S9). Additionally, C101A (H) or N53A (L) also disrupted binding to H5 A/Indonesia/5/2005 H A. Collectively, these findings indicate that, while the binding core of the FluA-20 interaction with different HAs is highly conserved, some variations can occur with different HAs. These findings are also consistent with the inventors' observation that the FluA-20-UCA, which carries the key HA-contacting residues Asp98 (H), Y100a (H), Y49 (L), and Gln55 (L), retains much of the binding breadth compared to FluA-20 (FIGS. 21C and 28C).

Binding of FluA-20 to HA is inhibited by HA cleavage, likely through dynamic changes in the HA trimer. During viral replication, HA is synthesized initially as a single polypeptide precursor protein, HA0. As the protein folds, HA assembles into a trimer in the endoplasmic reticulum (ER), before its transportation to the cellular surface (Copeland et al., 1986; Gething et al., 1986). HA0 can be cleaved post-translationally at an arginine (or rarely a lysine) around residue 329 into two subunits, HAI and HA2, the mature form of HA. HA cleavage is a prerequisite for viral infectivity (Chen et al., 1998; Steinhauer, 1999). Previous studies indicated that the HA cleavage process is promiscuous as to when and where the HA is cleaved in vivo (Klenk and Garten, 1994; Klenk and Rott, 1988; Webster and Rott, 1987), while cleavage can generally be achieved by trypsin treatment in vitro.

Figure 35A:
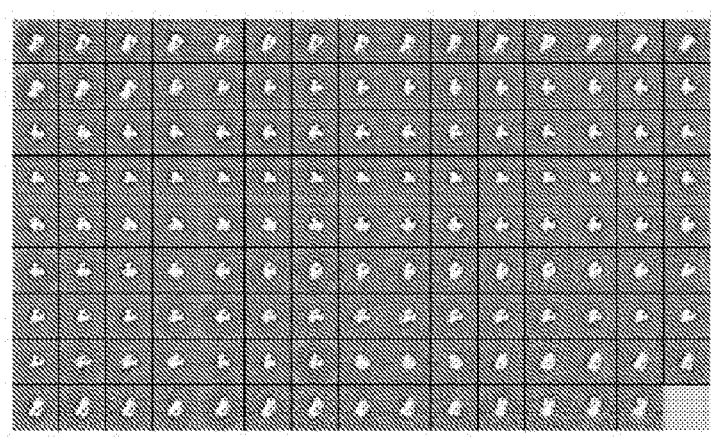
FIGS. 35A-B, related to FIGS. 27A-F. Exposure of HA trimer to FluA-20 Fab results in immediate disruption of native HA trimer, as assessed by negative-stain EM (nsEM).

The inventors observed that trypsin cleavage of HA substantially decreased binding of FluA-20 to soluble H1 or H7 HA (FIG. 26A), while differences in binding of the RBS-binding antibodies were not observed after cleavage (FIG. 35A). Since the FluA-20 binding epitope is buried in the HA trimer interface, the biased inhibition of FluA-20 binding, but not the 'outer' surface binding antibodies, suggests a potential decrease of dynamics in HA trimer after trypsin treatment, so that the FluA-20 epitope in the trimer interface may be less frequently or less proportionally exposed after the HA cleavage. The inventors also assessed FluA-20 binding to cellular surface HA and tested whether the surface HA recognition is affected by trypsin treatment. The inventors performed flow cytometric analysis to measure binding of two antibodies, CR9114 or FluA-20, to H3 A/Hong Kong/1/1968 HA expressed on HEK293F cells, either untreated or treated with trypsin. Consistent with the inventors' observations with soluble, recombinant HA protein, FluA-20 displayed substantially lower binding to HA on trypsin-treated cells compared to untreated cells (2.6-fold), while a decrease of the stem antibody CR9114 binding was not observed after trypsin treatment (FIG. 26B).

Figure 33C:
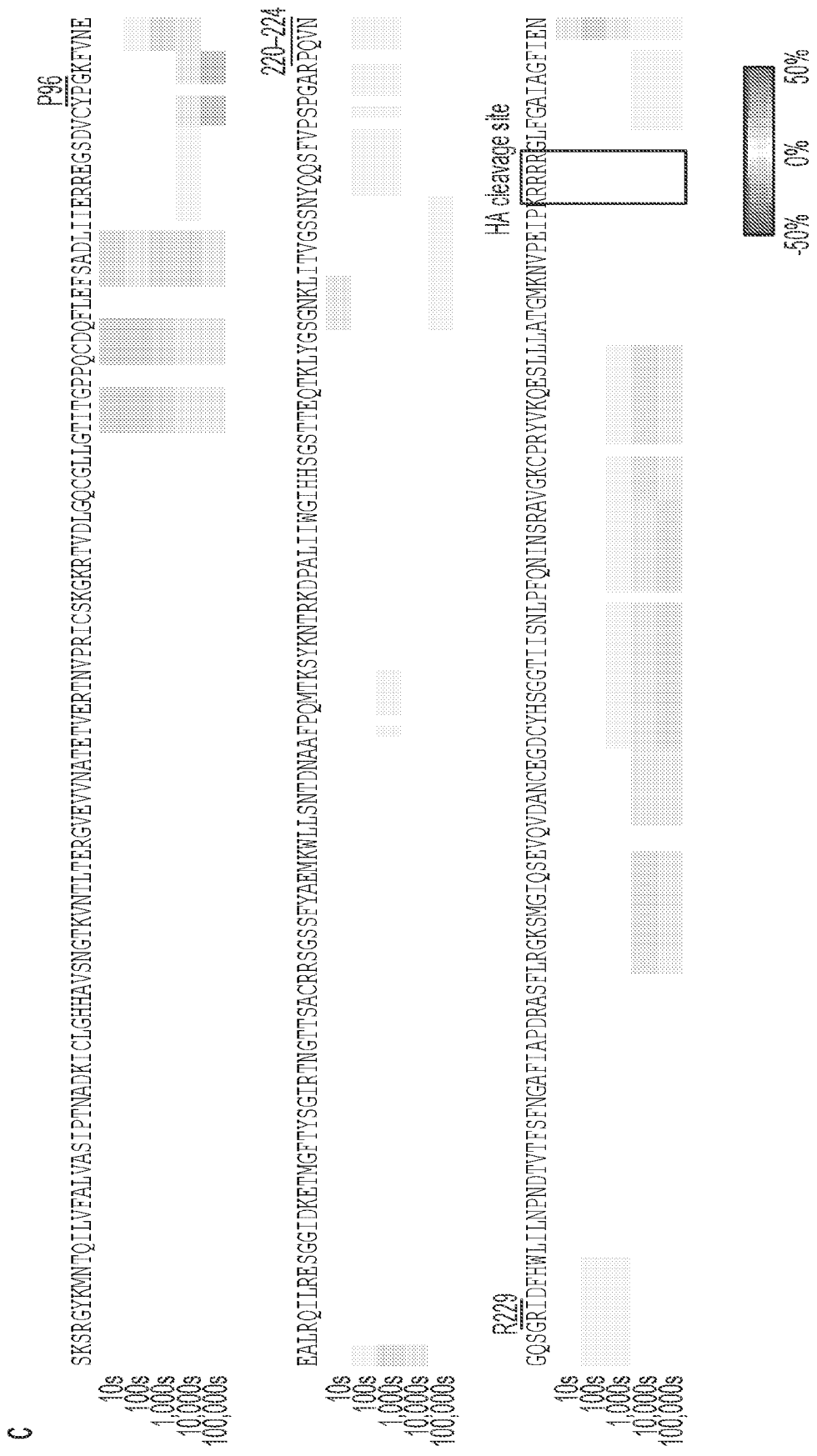
Figure 33C:
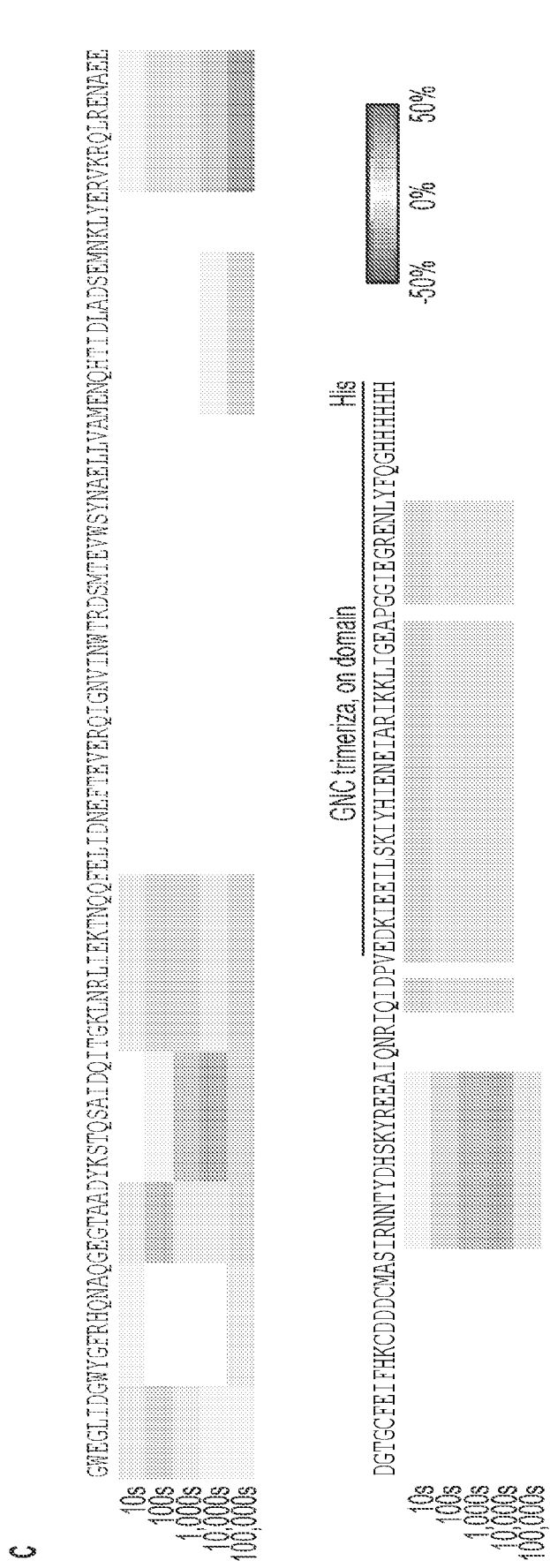

To examine if this specificity of FluA-20 for uncleaved HA is due to better epitope accessibility in the uncleaved form, the inventors performed an HDX-MS experiment with either HA0 or trypsin-treated HA trimers to compare their trimer dynamics. Indeed, they observed an overall reduction of deuterium exchange in the cleaved HA molecules compared to HA0 proteins at the three time points tested, except for some loops near the vestigial esterase subdomain of HA head (FIGS. 26C, 33C). In summary, these data suggest that HA cleavage into its functional form reduces HA trimer dynamics, which may inhibit exposure of the FluA-20 epitope in the matured, functional form of HA on virions.

FluA-20 inhibits cell-to-cell spread, potentially by disrupting native HA trimers. The inventors next examined the molecular basis for in vivo protection mediated by mAb FluA-20. They observed that FluA-20 did not exhibit neutralizing activity when tested by hemagglutinin inhibition assay (HAI) or microneutralization assays against H1N1 A/California/04/2009, H3N2 A/Texas/50/2012 or H7N9 A/Shanghai/2/2013 (6:2 PR8 backbone) viruses. They also performed microneutralization assays with uncleaved HA0 virus (H3N2 A/Hong Kong/1/1968) to test the effect of HA cleavage on susceptibility to neutralization by FluA-20. Although FluA-20 binds HA0 to a higher extent than its cleaved form, it did not neutralize HA0 virus (virus produced in the absence of trypsin) (FIG. 33B). Consistent with the absence of neutralizing activity, FluA-20 did not block trypsin-mediated cleavage of HA (FIG. 34A) or inhibit the pH-dependent conformational change of HA (FIG. 34B). However, when tested for neutralization activity in plaque assay with H3N2 A/Hong Kong/1/1968 virus, FluA-20 showed a 3.8-fold reduction in the plaque size compared to the control antibody (MRSA-147), as measured by the % foci area per well (FIGS. 27A-B). FluA-20 showed a dose-dependent inhibition of cell-to-cell spread of the virus with inhibitory activity comparable to that of broadly neutralizing antibody CR9114 (FIGS. 27A-C). Zanamivir, a neuraminidase inhibitor that functions by blocking viral egress, displayed efficient inhibition of cell-to-cell virus spread and was used as a positive control. To examine if FluA-20 reduced spread by inhibiting viral egress, the inventors performed an egress inhibition assay with H3N2 A/Texas/50/2012 H3N2. They observed that FluA-20 did not inhibit egress, while mAb H3v-47 (which has been previously shown to have egress inhibition activity comparable to that of zanamivir (Bangaru et al., 2018)) showed potent egress inhibition (FIG. 34C). Collectively, these results indicate that FluA-20 inhibits IAV in a novel mechanism by binding of mAb FluA-20 to the HA trimer interface and blocking cell-to-cell spread.

In addition to neutralizing activity, Fc-mediated ADCC activity has emerged as a major mechanism by which broadly reactive influenza antibodies confer in vivo protection (DiLillo et al., 2016; DiLillo et al., 2014). To examine if FluA-20 also could mediate ADCC activity, the inventors performed an ELISA-based screen using recombinant soluble (rs), dimeric, low-affinity ectodomains (rsFcγR) of FcγRIIIa (Wines et al., 2016). These rsFcγR low-affinity dimers require simultaneous engagement of both receptors by HA-bound IgGs to achieve stable binding in ELISA. Four similarly prepared antibodies, FluA-20, FluA-45, FluA-55 or VRC01 (an HIV-reactive negative control mAb) were added to plates coated with H1 A/California/04/2009 HA to test for their ability to engage both binding sites on rsFcγR simultaneously (Kristensen et al., 2016). The FluA-20 IgG strongly engaged the rsFcγR dimers, while neither the HA-reactive mAbs FluA-45 and FluA-55 nor the HIV-specific control mAb VRC-01 engaged these FcγR molecules (FIG. 34D). To test whether this FcγR binding activity was associated with functional ADCC activity, the inventors examined the ability of these antibodies to activate primary CD3" CD56+NK cells following incubation with HA from A/California/04/2009 in vitro (Jegaskanda et al., 2013). NK cell activation was measured as the percentage of NK cells expressing intracellular IFN-γ and/or CD107a (markers for degranulation) (Al-Hubeshy et al., 2011; Alter et al., 2004). A robust concentration-dependent increase of NK cell activation was observed for FluA-20 (1.3, 9.2% or 14.6% NK cell activation at 0.1, 1 or 10 μg/mL FluA-20 respectively), while FluA-45, FluA-55 and VRC01 did not exhibit any NK cell activation (FIG. 34E). To further investigate if this activity contributes to protection in vivo, the inventors engineered two separate Fc mutant variants, N297A and L234A/L235A (LALA), in the FluA-20 IgG1 sequence. Introduction of these mutations in IgG Fc have been shown to reduce or abrogate binding of Fc to both human and mouse FcγRs (Arduin et al., 2015; Chao et al., 2009; Hezareh et al., 2001; Morgan et al., 1995). The inventors compared the protective efficacy of FluA-20 Fc variants with recombinant and hybridoma-derived FluA-20 by measuring weight loss and clinical score in BALB/c mice that were injected prophylactically with 10 mg/kg of mAb 24 hours prior to challenge with $1.2 \times 10^4$ FFU of H1N1 A/California/04/2009 virus. The virus titer optimal for challenge studies was determined initially by challenging animals with different titers of virus (FIG. 34F). Surprisingly, both Fc variants exhibited significant protection against the H1N1 challenge compared to the control antibody (FIG. 7D). Although mice treated with the N297A Fc variant antibody demonstrated significant differences in weight loss compared to rFluA-20, the inventors did not observe a significant impact on the overall protection (FIGS. 27D-E). Taken together, these results indicate that although FluA-20 has the ability to robustly activate NK cells in vitro, the Fc-mediated ADCC activity is dispensable for its protective role in vivo.

Figure 35B:
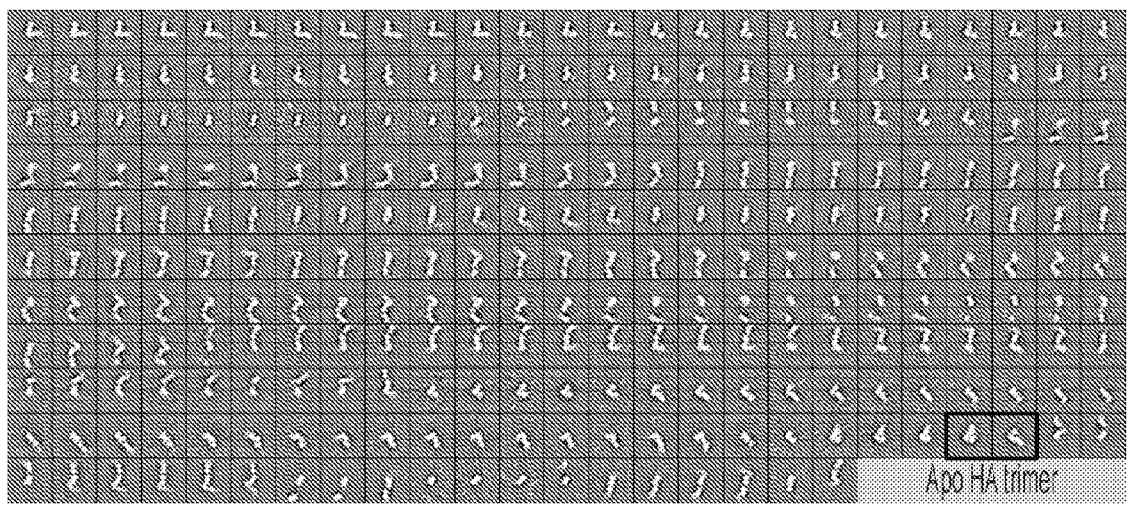

From the structural studies, it is apparent that FluA-20 binding to the HA trimer should destabilize the trimeric interface of native HA. To directly examine the effect of FluA-20 binding to trimer, the inventors performed negative-stain electron microscopy (nsEM) of FluA-20 Fab-HA (uncleaved H1 A/California/04/2009) complexes incubated at various time points. Native H1 HA0 trimer remained in its trimeric conformation during nsEM sample preparation (FIG. 35A). In contrast, the inventors observed that upon exposure to FluA-20 even for 20 seconds (the shortest time point that could be tested), the HA0 trimers quickly transformed to Fab-bound monomeric HA, with only a small fraction of Fab-free HA remaining in a trimeric conformation (FIGS. 27G and 35B). Despite extensive trials, the intermediate stage of this structural change could not be obtained, apparently due to the rapid transformation of the HA0 from trimeric to monomeric states induced by antibody binding. These results strongly suggest that FluA-20 is indeed capable of binding the uncleaved HA0 trimer, exaggerating the trimer dynamics to almost fully dissociate the trimer in vitro (FIGS. 27F-G). The ability to selectively disrupt HA0 trimers on the surface of infected cells and the ability to inhibit cell-cell spread suggested that FluA-20 represents a distinct class of potent bnAbs.

Example 6—Discussion

Isolation of naturally occurring broad-spectrum human mAbs to IAV holds great promise for discovery of new candidate therapeutics, as well as identifying critical epitopes for rational design of structure-based broadly protective influenza vaccines. Nearly all of the broadly neutralizing antibodies with extensive heterosubtypic activities discovered to date recognize the conserved HA stem region, while most broadly neutralizing antibodies (bnAbs) to the head domain have more restricted activity often within a given subtype, due to the extensive hypervariability in the head region (Hong et al., 2013; Joyce et al., 2016; Julien et al., 2012; Lee et al., 2014; Thornburg et al., 2016; Whittle et al., 2011; Wu and Wilson, 2017; Xu et al., 2013; Zhu et al., 2013). Although some bnAbs that target the head domain have been isolated in the recent years (Ekiert et al., 2012; Lee et al., 2012), none of them display extensive heterosubtypic breadth comparable to that of the best HA stem antibodies.

In this work, the inventors report the isolation and characterization of the broadly protective antibody FluA-20 that recognizes the HA head domain from nearly all IAV HA subtypes with excellent binding affinity. The discovery of the FluA-20 epitope unexpectedly revealed a highly conserved site of vulnerability that is hidden in the HA trimer interface. Although FluA-20 does not neutralize representative viruses from H1N1 and H3N2 subtypes in microneutralization assays, this antibody exhibits some unique properties in that it rapidly disrupts HA trimers and inhibits the cell-to-cell spread of virus. The antibody also mediates ADCC activity in vitro, although this activity was not essential to the in vivo protective effects. FluA-20 conferred in vivo protection in mice against strains representing several major influenza A subtypes that are pathogenic for humans. When administered prophylactically or therapeutically, FluA-20 protected mice against challenge with diverse IAV strains. Therefore, FluA-20 is a candidate for a broad-spectrum antiviral therapeutic against various IAV infections.

It is a striking observation that FluA-20, which recognizes an epitope obscured in the HA trimer interface, is able to mediate in vivo protection against the viruses. Previous studies have demonstrated that the assembly of HA trimer occurs in the endoplasmic reticulum (ER), prior to its transport to the cellular surface. Non-oligomerized HA monomers are not transported to the Golgi complex (Copeland et al., 1986; Copeland et al., 1988; Gething et al., 1986). Therefore, the HA molecules on the cellular or viral surface generally have been considered to be stable trimers, with the trimer interface regarded as inaccessible and thus not targetable by the immune response or therapeutics. The ability of FluA-20 to confer in vivo protection strongly suggests that HA molecules are dynamic and more heterogeneous in their conformations than the inventors have observed previously, and that the trimer interface is partially or transiently accessible. Similar phenomenon, previously described as 'breathing', has been observed for the envelope glycoproteins from other viruses, such as West Nile virus (Dowd et al., 2011), dengue virus (Dowd and Pierson, 2018; Rey and Lok, 2018; Rey et al., 2018), and HIV (Munro et al., 2014; Munro and Mothes, 2015). Previous computational predictions also have led to speculations that mutations distant to the RBS could affect HA trimer dynamics and allosterically modify functional properties, such as receptor binding, of the HA trimer (Yoon et al., 2015). The studies here provide the first high-resolution characterization of an interface epitope, demonstrating that the HA trimer could indeed feature similar 'breathing' motions. The inventors found that the dynamics of the HA trimer is more pronounced in the uncleaved HA0 form than in the cleaved HA, as assessed by HDX-MS studies. A study from Yewdell et al. reported the characterization of murine mAb Y8-10C2, the epitope of which was indicated to be present between adjacent protomers in the globular head domain by mutagenesis study (Yewdell et al., 1993). The study also implied that changes made near the fusion loop could indirectly affect the flexibility of the globular head domain and lead to resistance against Y8-10C2. The effect of trypsin-mediated cleavage on the conformational dynamics of the globular head domain in HA trimer conformation is poorly understood. HA dynamic changes also were found in the pH-activated fusion step, with the HA head interface region becoming more stabilized and the fusion peptide and surrounding HA stem residues becoming more dynamic at an intermediate pH prior to the pH of fusion (Garcia et al., 2015).

A recent study by Lee et al. reported the identification of three non-neutralizing but protective human antibodies to H1 and H3 that bound to monomeric but not trimeric forms of HA (Lee et al., 2016). The 22 Å negative-stain EM models of the Fab complexes with the HA protomer indicated that these antibodies bind to a region on the HA head (entirely different from the FluA-20 epitope) that is not fully accessible in the intact HA trimer. The discovery of these HA trimer interface (TI)-targeted antibodies is particularly interesting in that, similar to the receptor-binding site and the stem region of HA, the trimer interface also possesses patches of highly conserved surfaces (Yusuf et al., 2013); however, these potentially vulnerable sites have not been investigated for therapeutic or vaccine development. The findings presented here could lead to more comprehensive and detailed assessment on the accessibility of the HA trimer interface and potential therapeutics or vaccines that target this hidden and conserved surface.

TABLE S1

Binding of FluA-20 sibling antibodies to HAs from the indicated strains

| | | Binding $EC_{50}$ (µg/ml) for mutant for indicated chain | | | | | | | |
|---|---|---|---|---|---|---|---|---|---|
| Subtype | Strain | FluA-20 | Sib 2 | Sib 3 | Sib 7 | Sib 28 | Sib 33 | Sib 45 | Sib 48 |
| H1 | A/Solomom Islands/03/2006 | 0.05 | 0.07 | 0.04 | NB | 0.09 | NB | 0.04 | 0.08 |
| | A/Texas/36/1991 | 0.05 | 0.09 | 0.05 | NB | 0.08 | NB | 0.04 | 0.06 |
| H2 | A/Singapore/1/1957 | 0.18 | 0.14 | 0.07 | NB | 0.29 | NB | 0.08 | 0.42 |
| H3 | A/Hong Kong/1/1968 | 0.04 | 0.08 | 0.06 | NB | 0.07 | NB | 0.04 | 0.07 |
| | A/Texas/50/2012 | 0.09 | 0.09 | 0.05 | NB | > | NB | 0.07 | NB |
| | A/Switzerland/9715293/2013 | 0.55 | 0.32 | 0.16 | NB | NB | NB | 0.34 | NB |
| H5 | A/Indonesia/5/2005 | 6.05 | 0.43 | 1.21 | NB | NB | NB | 0.46 | NB |
| H7 | A/Netherlands/219/2003 | 0.05 | 0.11 | 0.07 | NB | 0.09 | NB | 0.05 | 0.11 |
| | A/Shanghai/2/2013 | 0.12 | 0.10 | 0.10 | NB | 0.49 | NB | 0.12 | 0.57 |
| H9 | A/HongKong/1073/99 | 0.41 | 0.22 | 0.09 | NB | 0.33 | NB | 0.12 | 0.82 |
| H12 | A/duck/Alberta/60/1976 | 0.05 | 0.07 | 0.04 | NB | 0.08 | NB | 0.04 | 0.12 |
| H14 | A/mallard duck/Astrakhan/263/1982 | 0.95 | 0.35 | 0.19 | NB | 1.72 | NB | 0.26 | NB |
| H15 | Australia/2576/1979 | 0.08 | 0.16 | 0.10 | NB | 0.38 | NB | 0.10 | 1.20 |

TABLE S2

Affinity of FluA-20 Fab and its UCA Fab to diverse HAs as determined by bio-layer interferometry.

| | | $K_D$ (nM) | |
|---|---|---|---|
| | HA strain | FluA-20 Fab | FluA-20 UCA Fab |
| Group 1 | A/Solomon Islands/03/2006 (H1N1) | 2 | 325 |
| | A/South Carolina/1/1918 (H1N1) | 46 | 937 |
| | A/California/04/2009 (H1N1) | 48 | 1430 |
| | A/Texas/36/1991 (H1N1) | <1 | 348 |
| | A/Adachi/2/1957 (H2N2) | <1 | 201 |
| | A/Indonesia/05/2005 (H5N1) | 88 | — |
| | A/Vietnam/1203/2004 (H5N1) | 122 | — |
| Group 2 | A/Hong Kong/1/1968 (H3N2) | <1 | 486 |
| | A/Victoria/3/1975 (H3N2) | 3460 | — |
| | A/Victoria/361/2011 (H3N2) | 15 | — |
| | A/Perth/16/2009 (H3N2) | <1 | — |
| | A/Netherlands/219/2003 (H7N7) | <1 | 1020 |
| | A/Shanghai/02/2013 (H7N9) | <1 | 745 |

'—': No binding was observed of the Fab at 2 µM concentration.

TABLE S3

X-ray data collection and refinement statistics for FluA-20 Fab

| Data collection | FluA-20 Fab |
|---|---|
| Beamline | APS 23 ID-D |
| Wavelength (Å) | 1.03319 |
| Space group | $P2_1$ |
| Unit cell parameters (Å, °) | a = 83.6 |
| | b = 52.6, |
| | c = 104.8; |
| | β = 93.8 |
| Resolution (Å) | 50.00 – 1.73 (1.76-1.73) |
| Observations | 318,735 |
| Unique reflections | 92,959 (4,414) |
| Redundancy | 3.5 (3.2) |
| Completeness (%) | 97.8 (93.6) |
| $<I/\sigma_I>$ | 11.8 (2.4) |
| $R_{sym}{}^a$ | 0.10 (0.39) |
| $R_{pim}{}^b$ | 0.05 (0.21) |
| $CC_{1/2}{}^c$ | 1.00 (0.84) |
| Refinement statistics | |
| Resolution (Å) | 45.68 – 1.73 (1.74-1.73) |
| Refs used in refinement | 92,945 (1,671) |
| $R_{work}$ (%)$^d$ | 20.2 |
| $R_{free}$ (%)$^e$ | 23.8 |
| Protein atoms | 6,612 |
| Waters | 1,044 |
| Other | 0 |
| B-value (Å$^2$) | |
| Average B-value | 20 |
| Protein | 18 |
| Water | 30 |
| Wilson B-value | 16 |
| RMSD | |
| Bond length (Å) | 0.007 |
| Bond angles (°) | 0.93 |
| Ramachandran plots (%)$^f$ | |
| Favored | 98.1 |
| Outliers | 0.0 |
| PDB | 5WN7 |

Values in parentheses are for the highest-resolution shell.

$^a R_{sym} = \Sigma_{hkl} \Sigma_i | I_{hkl,i} - <I_{hkl}> | / \Sigma_{hkl} \Sigma_i I_{hkl,I}$ and $^b R_{pim} = \Sigma_{hkl} (1/(n-1))^{1/2} \Sigma_i | I_{hkl,i} - <I_{hkl}> | / \Sigma_{hkl} \Sigma_i I_{hkl,i}$, where $I_{hkl,i}$ is the scaled intensity of the $i^{th}$ measurement of reflection h, k, l, $<I_{hkl}>$ is the average intensity for that reflection, and n is the redundancy (Weiss and Hilgenfeld, 1997).

$^c CC_{1/2}$ = Pearson Correlation Coefficient between two random half datasets.

$^d R_{work} = \Sigma_{hkl} | F_o - F_c | \Sigma_{hkl} | F_o | \times 100$.

$^e R_{free}$ was calculated as for $R_{work}$ but on a test set comprising 5% of the data excluded from refinement.

$^f$Calculated using MolProbity (Chen et al., 2010).

TABLE S4

X-ray data collection and refinement statistics for FluA-20 in complex with the head domain of H1 (A/Solomon Islands/3/2006) or H3 (A/Hong Kong/1/1968)

| Data collection | FluA-20_H1 head | FluA-20_H3 head |
|---|---|---|
| Beamline | APS 23 ID-D | SSRL12-2 |
| Wavelength (Å) | 1.03315 | 0.97946 |
| Space group | $P2_12_12_1$ | $P4_12_12$ |
| Unit cell parameters (Å) | a = 100.5 | a= |
| | b = 109.8, | b = 84.6, |
| | c = 146.4; | c = 271.7 |
| Resolution (Å) | 50.00 – 2.85 (2.90-2.85) | 50.00 – 2.10 (2.14-2.10) |
| Observations | 248,941 | 391,682 |
| Unique reflections | 36,921 (1,436) | 59,236 (2,895) |
| Redundancy | 6.8 (5.2) | 6.6 (5.6) |
| Completeness (%) | 95.7 (74.6) | 99.6 (99.6) |
| $<I/\sigma_I>$ | 20.6 (2.0) | 18.4 (1.8) |
| $R_{sym}{}^a$ | 0.13 (0.78) | 0.11 (0.83) |
| $R_{pim}{}^b$ | 0.05 (0.31) | 0.04 (0.33) |

TABLE S4-continued

X-ray data collection and refinement statistics for FluA-20
in complex with the head domain of H1 (A/Solomon
Islands/3/2006) or H3 (A/Hong Kong/1/1968)

| Data collection | FluA-20_H1 head | FluA-20_H3 head |
|---|---|---|
| $CC_{1/2}{}^c$ | 1.00 (0.91) | 1.00 (0.70) |
| Refinement statistics | | |
| Resolution (Å) | 48.17 – 2.85 (2.93-2.85) | 37.82 – 2.10 (2.12-2.10) |
| Refs used in refinement | 36,821 (2,125) | 59,094 (2,525) |
| $R_{work}$ (%)$^d$ | 23.7 | 20.2 |
| $R_{free}$ (%)$^e$ | 25.7 | 23.9 |
| Protein atoms | 10,008 | 5,387 |
| Waters | — | 346 |
| Glycan atoms | 84 | 14 |
| B-value (Å$^2$) | | |
| Average B-value | 74 | 47 |
| Protein | 74 | 47 |
| Glycan | 108 | 66 |
| Water | — | 47 |
| Wilson B-value | 65 | 33 |
| RMSD | | |
| Bond length (Å) | 0.011 | 0.014 |
| Bond angles (°) | 1.60 | 1.62 |
| Ramachandran plots (%)$^f$ | | |
| Favored | 96.6 | 98.1 |
| Outliers | 0.3 | 0.1 |
| PDB | 5WNC | 5WND |

Values in parentheses are for the highest-resolution shell.

$^a R_{sym} = \Sigma_{hkl} \Sigma_i | I_{hkl,i} - <I_{hkl}> | / \Sigma_{hkl} \Sigma_i I_{hkl,i}$ and $^b R_{pim} = \Sigma_{hkl} (1/(n-1))^{1/2} \Sigma_i | I_{hkl,i} - <I_{hkl}> | /$
$\Sigma_{hkl} \Sigma_i | I_{hkl,i}$, where $I_{hkl,i}$ is the scaled intensity of the i$^{th}$ measurement of reflection h, k, l, $< I_{hkl} >$ is the average intensity for that reflection, and n is the redundancy (Weiss and Hilgenfeld, 1997).
$^c CC_{1/2}$ = Pearson Correlation Coefficient between two random half datasets.
$^d R_{work} = \Sigma_{hkl} | F_o - F_c | E_{hkl} | F_o | \times 100$.
$^e R_{free}$ was calculated as for $R_{work}$, but on a test set comprising 5% of the data excluded from refinement.
$^f$ Calculated using MolProbity (Chen et al., 2010).

TABLE S5

Affinity of FluA-20 Fab and its UCA Fab to diverse HA
molecules, as determined by bio-layer interferometry

| | | $K_D$ (nM) | |
|---|---|---|---|
| | HA strain | FluA-20 Fab | FluA-20 UCA Fab |
| Group 1 | A/Solomon Islands/03/2006 (H1N1) | 2 | 325 |
| | A/South Carolina/1/1918 (H1N1) | 46 | 937 |
| | A/California/04/2009 (H1N1) | 48 | 1,430 |
| | A/Texas/36/1991 (H1N1) | <1 | 348 |
| | A/Adachi/2/1957 (H2N2) | <1 | 201 |
| | A/Indonesia/05/2005 (H5N1) | 88 | — |
| | A/Vietnam/1203/2004 (H5N1) | 122 | — |
| Group 2 | A/Hong Kong/1/1968(H3N2) | <1 | 486 |
| | A/Victoria/361/2011 (H3N2) | 15 | — |
| | A/Perth/16/2009 (H3N2) | <1 | — |
| | A/Netherlands/219/2003 (H7N7) | <1 | 1,020 |
| | A/Shanghai/02/2013 (H7N9) | <1 | 745 |

—indicates binding was not observed for the Fab at 2 μM.

TABLE S6

Binding of FluA-20 somatic variants ("siblings") to diverse HA molecules from indicated strains

| | | Binding EC$_{50}$ (μg/mL) for mutant for indicated chain | | | | | | | |
|---|---|---|---|---|---|---|---|---|---|
| Subtype | Strain | rFluA-20 | Sib 2 | Sib 3 | Sib 7 | Sib 28 | Sib 33 | Sib 45 | Sib 48 |
| H1 | A/Solomon Islands/03/2006 | 0.008 | 0.07 | 0.04 | NB | 0.09 | NB | 0.04 | 0.08 |
| | A/Texas/36/1991 | 0.008 | 0.09 | 0.05 | NB | 0.08 | NB | 0.04 | 0.06 |
| H2 | A/Singapore/1/1957 | 0.011 | 0.14 | 0.07 | NB | 0.29 | NB | 0.08 | 0.42 |
| H3 | A/Hong Kong/1/1968 | 0.009 | 0.08 | 0.06 | NB | 0.07 | NB | 0.04 | 0.07 |
| | A/Texas/50/2012 | 0.007 | 0.09 | 0.05 | NB | > | NB | 0.07 | NB |
| H5 | A/Indonesia/5/2005 | 0.016 | 0.43 | 1.21 | NB | NB | NB | 0.46 | NB |
| H7 | A/Netherlands/219/2003 | 0.005 | 0.11 | 0.07 | NB | 0.09 | NB | 0.05 | 0.11 |
| | A/Shanghai/2/2013 | 0.013 | 0.10 | 0.10 | NB | 0.49 | NB | 0.12 | 0.57 |
| H9 | A/Hong Kong/1073/99 | 0.007 | 0.22 | 0.09 | NB | 0.33 | NB | 0.12 | > |
| H12 | A/duck/Alberta/60/1976 | 0.006 | 0.07 | 0.04 | NB | 0.08 | NB | 0.04 | 0.12 |

TABLE S6-continued

Binding of FluA-20 somatic variants ("siblings") to diverse HA molecules from indicated strains

| | | Binding EC$_{50}$ (µg/mL) for mutant for indicated chain | | | | | | | |
|---|---|---|---|---|---|---|---|---|---|
| Subtype | Strain | rFluA-20 | Sib 2 | Sib 3 | Sib 7 | Sib 28 | Sib 33 | Sib 45 | Sib 48 |
| H14 | A/mallard duck/Astrakhan/263/1982 | 0.007 | 0.35 | 0.19 | NB | > | NB | 0.26 | NB |
| H15 | A/shearwater/Western Australia/2576/1979 | 0.007 | 0.16 | 0.10 | NB | 0.38 | NB | 0.10 | > |

> indicates EC$_{50}$ values 100 fold higher than FluA-20
NB indicates no binding was observed at antibody concentrations below 10 µg/mL

TABLE S7

X-ray data collection and refinement statistics for FluA-20 Fab

| Data collection | FluA-20 Fab |
|---|---|
| Beamline | APS 23 ID-D |
| Wavelength (Å) | 1.03319 |
| Space group | P2$_1$ |
| Unit cell parameters (Å; °) | a = 83.6 |
| | b = 52.6, |
| | c = 104.8; |
| | β = 93.8 |
| Resolution (Å) | 50.00 – 1.73 (1.76-1.73) |
| Observations | 318,735 |
| Unique reflections | 92,959 (4,414) |
| Redundancy | 3.5 (3.2) |
| Completeness (%) | 97.8 (93.6) |
| <I/σ$_I$> | 11.8 (2.4) |
| R$_{sym}$$^a$ | 0.10 (0.39) |
| R$_{pim}$$^b$ | 0.05 (0.21) |
| CC$_{1/2}$$^c$ | 1.00 (0.84) |
| Refinement statistics | |
| Resolution (Å) | 45.68 – 1.73 (1.74-1.73) |
| Refs used in refinement | 92,945 (1,671) |
| R$_{work}$ (%)$^d$ | 20.2 |
| R$_{free}$ (%)$^e$ | 23.8 |
| Protein atoms | 6,612 |
| Waters | 1,044 |
| Other | 0 |
| B-value (Å$^2$) | |
| Average B-value | 20 |
| Protein | 18 |
| Water | 30 |
| Wilson B-value | 16 |
| RMSD | |
| Bond length (Å) | 0.007 |
| Bond angles (°) | 0.93 |
| Ramachandran plots (%)$^f$ | |
| Favored | 98.1 |
| Outliers | 0.0 |
| PDB | 5WN7 |

Values in parentheses are for the highest-resolution shell.

$^a$R$_{sym}$ = Σ$_{hkl}$ Σ$_i$ | I$_{hkl,i}$ – <I$_{hkl}$> | / Σ$_{hkl}$ Σ$_i$ I$_{hkl,i}$ and $^b$R$_{pim}$ = Σ$_{hkl}$ (1/(n – 1))$^{1/2}$ Σ$_i$ | I$_{hkl,i}$ – <I$_{hkl}$> | / Σ$_{hkl}$ Σ$_i$ I$_{hkl,i}$, where I$_{hkl,i}$ is the scaled intensity of the i$^{th}$ measurement of reflection h, k, l, <I$_{hkl}$> is the average intensity for that reflection, and n is the redundancy (Weiss and Hilgenfeld, 1997).

$^c$CC$_{1/2}$ = Pearson Correlation Coefficient between two random half datasets.

$^d$R$_{work}$ = Σ$_{hkl}$ | F$_o$ – F$_c$ | E$_{hkl}$ | F$_o$ | × 100.

$^e$R$_{free}$ was calculated as for R$_{work}$, but on a test set comprising 5% of the data excluded from refinement.

$^f$Calculated using MolProbity (Chen et al., 2010).

TABLE S8

X-ray data collection and refinement statistics for FluA-20 in complex with the head domain of H1 (A/Solomon Islands/3/2006) or H3 (A/Hong Kong/1/1968) HA

| Data collection | FluA-20_H1 head | FluA-20_H3 head |
|---|---|---|
| Beamline | APS 23 ID-D | SSRL12-2 |
| Wavelength (Å) | 1.03315 | 0.97946 |
| Space group | P2$_1$2$_1$2$_1$ | P4$_1$2$_1$2 |
| Unit cell parameters (Å) | a = 100.5 | a= |
| | b = 109.8, | b = 84.6, |
| | c = 146.4; | c = 271.7 |
| Resolution (Å) | 50.00 – 2.85 (2.90-2.85) | 50.00 – 2.10 (2.14-2.10) |
| Observations | 248,941 | 391,682 |
| Unique reflections | 36,921 (1,436) | 59,236 (2,895) |
| Redundancy | 6.8 (5.2) | 6.6 (5.6) |
| Completeness (%) | 95.7 (74.6) | 99.6 (99.6) |
| <I/σ$_I$> | 20.6 (2.0) | 18.4 (1.8) |
| R$_{sym}$$^a$ | 0.13 (0.78) | 0.11 (0.83) |
| R$_{pim}$$^b$ | 0.05 (0.31) | 0.04 (0.33) |
| CC$_{1/2}$$^c$ | 1.00 (0.91) | 1.00 (0.70) |
| Refinement statistics | | |
| Resolution (Å) | 48.17 – 2.85 (2.93-2.85) | 37.82-2.10 (2.12-2.10) |
| Refs used in refinement | 36,821 (2,125) | 59,094 (2,525) |
| R$_{work}$ (%)$^d$ | 23.7 | 20.2 |
| R$_{free}$ (%)$^e$ | 25.7 | 23.9 |
| Protein atoms | 10,008 | 5,387 |
| Waters | — | 346 |
| Glycan atoms | 84 | 14 |
| B-value (Å2) | | |
| Average B-value | 74 | 47 |
| Protein | 74 | 47 |
| Glycan | 108 | 66 |
| Water | — | 47 |
| Wilson B-value | 65 | 33 |
| RMSD | | |
| Bond length (Å) | 0.011 | 0.014 |
| Bond angles (°) | 1.60 | 1.62 |
| Ramachandran plots (%)$^f$ | | |
| Favored | 96.6 | 98.1 |
| Outliers | 0.3 | 0.1 |
| PDB | 5WNC | 5WND |

Values in parentheses are for the highest-resolution shell.

$^a$R$_{sym}$ = Σ$_{hkl}$ Σ$_i$ | I$_{hkl,i}$ – <I$_{hkl}$> | / Σ$_{hkl}$ Σ$_i$ I$_{hkl,i}$ and $^b$R$_{pim}$ = Σ$_{hkl}$ (1/(n – 1))$^{1/2}$ Σ$_i$ | I$_{hkl,i}$ – <I$_{hkl}$> | / Σ$_{hkl}$ Σ$_i$ I$_{hkl,i}$, where I$_{hkl,i}$ is the scaled intensity of the i$^{th}$ measurement of reflection h, k, l, <I$_{hkl}$> is the average intensity for that reflection, and n is the redundancy (Weiss and Hilgenfeld, 1997).

$^c$CC$_{1/2}$ = Pearson Correlation Coefficient between two random half datasets.

$^d$R$_{work}$ = Σ$_{hkl}$ | F$_o$ – F$_c$ | E$_{hkl}$ | F$_o$ | × 100.

$^e$R$_{free}$ was calculated as for R$_{work}$, but on a test set comprising 5% of the data excluded from refinement.

$^f$Calculated using MolProbity (Chen et al., 2010).

TABLE S5

Binding of FluA-20 paratope mutants to diverse HA molecules from indicated strains

| | | Binding EC50 (µg/mL) for mutant for indicated chain | | | | | | | | | |
|---|---|---|---|---|---|---|---|---|---|---|---|
| | | Wild-type | Heavy chain | | | | | | Light chain | | |
| Subtype | Strain | rFluA-20 | Y34A | T96A | E97A | D98A | Y100aA | C101A | Y49A | N53A | Q55A |
| H1 | A/Solomon Islands/03/2006 | 0.008 | 0.04 | 0.03 | 0.07 | NB | > | 0.20 | NB | 0.05 | > |
| | A/Texas/36/1991 | 0.008 | 0.05 | 0.04 | 0.05 | NB | > | 0.15 | NB | 0.04 | 0.23 |
| H2 | A/Singapore/1/1957 | 0.011 | 0.11 | 0.07 | 0.13 | NB | > | 0.44 | NB | 0.16 | NB |
| H3 | A/Hong Kong/1/1968 | 0.009 | 0.07 | 0.10 | 0.07 | NB | 0.07 | 0.13 | NB | 0.06 | 0.08 |
| | A/Texas/50/2012 | 0.007 | 0.16 | 0.07 | 0.18 | NB | > | 0.39 | NB | 0.09 | NB |
| H5 | A/Indonesia/5/2005 | 0.016 | > | 0.11 | > | NB | > | > | NB | > | NB |
| H7 | A/Netherlands/219/2003 | 0.005 | 0.07 | 0.04 | 0.08 | > | > | 0.17 | > | 0.05 | 0.17 |
| | A/Shanghai/2/2013 | 0.013 | 0.44 | 0.37 | 1.00 | NB | > | > | NB | 0.87 | NB |
| H9 | A/Hong Kong/1073/99 | 0.007 | 0.21 | 0.10 | 0.36 | NB | > | > | NB | 0.17 | NB |
| H12 | A/duck/Alberta/60/1976 | 0.006 | 0.05 | 0.04 | 0.06 | NB | > | 0.09 | NB | 0.03 | > |
| H14 | A/mallard duck/Astrakhan/263/1982 | 0.007 | 0.54 | 0.23 | 0.64 | NB | > | > | NB | > | NB |
| H15 | A/shearwater/Western Australia/2576/1979 | 0.007 | 0.10 | 0.07 | 0.12 | NB | > | 0.11 | NB | 0.06 | > |

> indicates EC50 values 100 fold higher than wild-type rFluA-20
NB indicates no binding was observed at antibody concentrations below 10 µg/mL

TABLE 1

NUCLEOTIDE SEQUENCES FOR ANTIBODY VARIABLE REGIONS

| Clone | Variable Sequence Region | SEQ ID NO: |
|---|---|---|
| heavy FluA-20 | CAGGTGCAGCTGCAGGAGTCGGGCCCAGGACTGGTGAAGCCTTCGGAGACCC TGTCCCTCACCTGCTCTGTCTCTGGTGTCTCCGTCACCAGTGATATTTACTACTG GACCTGGATCCGGCAGCCCCCAGGGAAGGGACTGGAGTGGATTGGGTATATC TTTTATAATGGGGACACCAACTACAACCCCTCCCTCAAGAGTCGAGTCACCATG TCAATCGACACGTCCAAGAACGAGTTCTCCCTGAGGCTGACGTCTGTGACCGC TGCGGACACGGCCGTGTATTTCTGTGCCAGAGGGACAGAAGATCTAGGATATT GTAGTAGTGGTAGCTGCCCGAATCACTGGGGCCAGGGAACCCTGGTCACCGT CTCCTCA | 1 |
| FluA-20 light | GACATCCAGATGACCCAGTCTCCATCCTCCCTGTCTGCATCTATAGGAGACAGA GTCACCATCACTTGCCGGCCAAGTCAGAACATTCGGAGTTTTTTGAATTGGTTT CAGCACAAACCAGGGAAAGCCCCAAAACTCCTGATCTATGCTGCATCCAATTT GCAGAGTGGGGTCCCATCAAGGTTCAGTGGCAGTGGATCTGGGACAGAATTC ACTCTCACCATCAGGAGTCTGCAACCTGAAGATTTTGCAACTTACTACTGTCAA CAGAGTTACAATACCCCTCCGACGTTCGGCCAAGGGACCAAGGTGGAAATCAA A | 2 |
| H5.28 heavy | GAGGTGCAGCTGGTGGAGTCTGGGGGAGGCTTGGTCCAGCCTGGGGGGTCC CTGAGACTCTCCTGTGCAGCCTCTGGATTCACCTTCAGTACCTATTGGATGACC TGGGTCCGCCAGGCTCCAGGGAAGGGGCTGGAGTGGGTGGCCAACATAAACC AAGATGGAGGTGAGAAATACTTTGTGGACTCTGTGAAGGGCCGATTCACCATC TCCAGAGACAACGCCAAAAATTCACTGTTTCTGCAAATGAACACCCTGAGAGC CGAGGACACGGCTGTGTATTACTGTGCGAGAGGATTTTTGGAGAGGTTATTAT TGGGCCGACAAGGGGCCTACTACTACGGGATGGACGTCTGGGGCCAAGGGAC CACGGTCACCGTCTCCTCA | 3 |
| H5.28 light | GACATCCAGATGACCCAGTCTCCATCCTCCCTGTCTGCATCTGTCGGAGACAGA GTCAGCATGACTTGCCGGGCAAGTCAGATCATTAGTAGTTCCTTAAATTGGTAT CAGCAGAAACCAGGGAAAGCCCCTAAACTCCTGATCTATGCTGCATCCAATTT ACAAAGTGGGGTCCCATCAAGGTTCAGTGGCAGTGGATCTGGGACAGATTTC ACTCTCACCATCAGCAGTCTGCAACCTGAAGATTTTGCAACTTACTACTGTCAA CAGAGTTACAGTACCCCTCCGGAGCTCACTTTCGGCGGAGGGACCAAGGTGG AAATCAAA | 4 |
| H5.31 heavy | GAGGTGCAGCTGGTGCAGTCTGGGGGAGGCTTGGTCCAACCTGGGGGGTCCC TGAGACTCTCCTGTGAAGCCTCTAGATTCACCTCCAGTTCCTATTGGATAACCT GGGTCCGCCAGGCTCCAGGGAAGGGGCTGGAGTGGGTGGCCAATATAAAGC AAGATGGAAGTGAGAAATACTTTGTGGACTCTGTGAAGGGCCGATTCACCATC TCCAGAGACAACGCCAGTAATTCACTGTATCTGCAAATGAGCAGCCTGAGAGC CGAGGACACGGCTGTGTATTACTGTGCGAGAGGATTTTTGGAGAGGTTATTAT TGGGCCGACAAGGGGCCTACTACTACGGGATGGACGTCTGGGGCCAAGGGAC CACGGTCACCGTCTCCTCA | 5 |
| H5.31 light | GACATCCAGATGACCCAGTCTCCATCCTCCCTGTCTGCATCTGTCGGAGACAGA GTCACCATGACTTGCCGGGCAAGTCAGAGCATTAGTAGTTCCTTAAATTGGTAT CAACAGAAACCAGGGAAAGCCCCTAAACTCCTGATCTATGCTGCATCCAATTTA CAAAGTGGGGTCCCATCAAGGTTCAGTGGCAGTGGATCTGGGACAGATTTCAC | 6 |

TABLE 1-continued

NUCLEOTIDE SEQUENCES FOR ANTIBODY VARIABLE REGIONS

| Clone | Variable Sequence Region | SEQ ID NO: |
|---|---|---|
| | TCTCACCATCAGCAGTCTGCAACCTGAAGATTTTGCAACTTACTACTGTCAACA<br>GAGTTACACTATGCCTCCGGAGCTCACTTTCGGCGGAGGGACCAAGGTACAGA<br>TCAAA | |
| H7-200 heavy | CAGGTGCAGCTGGTGGAGTCGGGCCCAGGACTGGTGAAGCCTTCACAGACCC<br>TGTCCCTCACCTGCACTGTCTCTGGTGGCTCCATCAACAGTAGTCATTCCTTCTG<br>GAGTTGGATCCGCCAGCCCGCCGGGAAGGGACTGGAGTGGATTGGGCGTATC<br>TATTCCACTGGGAACTCCAACTACAACCCCTCCCTCAAGAGTCGAGTCACCATA<br>TCATTAGACACGTCCAAGAACCAATTCTCCCTGAAGTTGAGCTCTGTGACCGCC<br>GCAGACACGGCCGTGTATTACTGTGCGAGAGAATCCCTATGGAATCCGGATTA<br>CTACTACTACATGGACGTCTGGGGCAAAGGGACCCTGGTCACCGTCTCCTCA | 7 |
| H7-200 light | GACATTGTGATGACCCAGTCTCCATCCTCCCTGTCTGCATCTGTAGGAGACAGA<br>GTCACCATCACTTGCCGGGCAAGTCAGAGCTTTAGCAGCCATTTGAATTGGTAT<br>CAGCAGAAACCAGGCAGAGCCCCTGACCTCCTGATCTATGCTGCATCCAGTTT<br>GCACAGTGGGGTCCCATCAAGGTTCAGTGGCAGTGGATCTGGGACAGATTTC<br>ACTCTCACCATCAGCAGTCTTCAACCTGAAGACTTTGCAGTTTACTACTGTCAAC<br>AGAGTTACAGTGTCCCGTACACTTTTGGCCAGGGGACCAAGCTGAGATCAAA | 8 |

TABLE 2

PROTEIN SEQUENCES FOR ANTIBODY VARIABLE REGIONS

| Clone | Variable Sequence | SEQ ID NO. |
|---|---|---|
| FluA-20 heavy | QVQLQESGPGLVKPSETLSLTCSVSGVSVTSDIYYWTWIRQPPGKGLEWIGYIFYN<br>GDTNYNPSLKSRVTMSIDTSKNEFSLRLTSVTAADTAVYFCARGTEDLGYCSSGSC<br>PNHWGQGTLVTVSS | 9 |
| FluA-20 light | DIQMTQSPSSLSASIGDRVTITCRPSQNIRSFLNWFQHKPGKAPKLLIYAASNLQS<br>GVPSRFSGSGSGTEFTLTIRSLQPEDFATYYCQQSYNTPPTFGQGTKVEIK | 10 |
| H5.28 heavy | EVQLVESGGGLVQPGGSLRLSCAASGFTFSTYWMTWVRQAPGKGLEWVANINQDGGE<br>KYFVDSVKGRFTISRDNAKNSLFLQMNTLRAEDTAVYYCARGFLERLLLGRQGAYYYGMD<br>VWGQGTTVTVSS | 11 |
| H5.28 light | DIQMTQSPSSLSASVGDRVSMTCRASQIISSSLNWYQQKPGKAPKLLIYAASNLQSGVPS<br>RFSGSGSGTDFTLTISSLQPEDFATYYCQQSYSTPPELTFGGGTKVEIK | 12 |
| H5.31 heavy | EVQLVQSGGGLVQPGGSLRLSCEASRFTSSSYWITWVRQAPGKGLEWVANIKQ<br>DGSEKYFVDSVKGRFTISRDNASNSLYLQMSSLRAEDTAVYYCARGFLERLLLGRQ<br>GAYYYGMDVWGQGTTVTVSS | 13 |
| H5.31 light | DIQMTQSPSSLSASVGDRVTMTCRASQSISSSLNWYQQKPGKAPKLLIYAASNLQ<br>SGVPSRFSGSGSGTDFTLTISSLQPEDFATYYCQQSYTMPPELTFGGGTKVQIK | 14 |
| H7-200 heavy | QVQLVESGPGLVKPSQTLSLTCTVSGGSINSSHSFWSWIRQPAGKGLEWIGRIYS<br>TGNSNYNPSLKSRVTISLDTSKNQFSLKLSSVTAADTAVYYCARESLWNPDYYYM<br>DVWGKGTLVTVSS | 15 |
| H7-200 light | DIVMTQSPSSLSASVGDRVTITCRASQSFSSHLNWYQQKPGRAPDLLIYAASSLHS<br>GVPSRFSGSGSGTDFTLTISSLQPEDFAVYYCQQSYSVPYTFGQGTKLQIK | 16 |

TABLE 3

CDR HEAVY CHAIN SEQUENCES

| Antibody | CDRH1 (SEQ ID NO) | CDRH2 (SEQID NO) | CDRH3 (SEQ ID NO) |
|---|---|---|---|
| FluA-20 | GVSVTSDIYY (17) | IFYNGDT (18) | ARGTEDLGYCSSGSCPNH (19) |
| H5.28 | GFTESTYW (20) | INQDGGEK (21) | ARGFLERLLLGRQGAYYYGMDV (22) |

TABLE 3-continued

CDR HEAVY CHAIN SEQUENCES

| Antibody | CDRH1 (SEQ ID NO) | CDRH2 (SEQID NO) | CDRH3 (SEQ ID NO) |
|---|---|---|---|
| H5.31 | RFTSSSYW (23) | IKQDGSEK (24) | ARGFLERLLLGRQGAYYYGMDV (25) |
| H7-200 | GGSINSSHSF (26) | IYSTGNS (27) | ARESLWNPDYYYMDV (28) |

TABLE 4

CDR LIGHT CHAIN SEQUENCES

| Antibody | CDRH1 (SEQ ID NO) | CDRH2 (SEQ ID NO) | CDRH3 (SEQ ID NO) |
|---|---|---|---|
| FluA-20 | QNIRSF (29) | AAS (30) | QQSYNTPPT (31) |
| H5.28 | QUSSS (32) | AAS (33) | QQSYSTPPELT (34) |
| H5.31 | QSISSS (35) | AAS (36) | QQSYTMPPELT (37) |
| H7-200 | QSFSSH (38) | AAS (39) | QQSYSVPYT (40) |

TABLE 5

Conservation analysis of FluA-20 epitope residues on HA across different IAV strains

| | | Affinity $EC_{50}$ | 90-Loop | | | 220-Loop | | | | | | |
|---|---|---|---|---|---|---|---|---|---|---|---|---|
| Subtype | Strain | (ng/mL) | 86 | 96 | 98 | 216 | 219 | 220 | 221 | 222 | 223 | 224 | 229 |
| H1 | A/Solomon Islands/03/2006 | 5 | N | P | H | E | K | R | P | K | V | R | R |
| | A/California/04/2009 | 8 | S | P | D | E | I | R | P | K | V | R | R |
| | A/Texas/36/1991 | 4 | N | P | Y | E | K | R | P | K | V | R | R |
| H2 | A/Singapore/1/1957 | 7 | N | P | S | D | T | R | P | K | V | N | R |
| H3 | A/Hong Kong/1/1968 | 6 | S | P | D | N | S | R | P | W | V | R | R |
| | A/Texas/50/2012 | 4 | S | P | D | N | S | R | P | R | I | R | R |
| | A/Switzerland/9715293/2013 | 19 | S | P | D | N | S | R | P | R | I | R | R |
| | A/Minnesota/11/10 | > | S | P | D | N | S | R | P | W | V | R | I |
| H5 | A/Vietnam/1203/2004 | 283 | N | P | D | R | T | R | S | K | V | N | R |
| | A/Indonesia/05/2005 | 85 | N | P | N | K | T | R | S | K | V | N | R |
| H7 | A/New York/107/2003$^a$ | 808 | R | P | R | N | A | R | — | — | — | — | R |
| | A/Shanghai/2/2013 | 66 | R | P | K | S | A | R | P | Q | V | N | R |
| H9 | A/Hong Kong/1073/99 | 9 | S | P | N | V | P | R | P | L | V | N | R |
| H13 | A/gull/Maryland/704/1977 | 70 | A | P | E | E | V | R | P | G | Y | N | W |
| H14 | A/mallard duck/Astrakhan/263/1982 | 13 | P | P | D | N | S | R | P | R | V | R | R |
| H16 | A/black-headed gull/Sweden/4/1999 | > | N | P | E | E | T | R | I | G | — | D | W |

> indicates no FluA-20 binding to corresponding HAs at concentrations tested, up to 10 μg/mL
The major epitope contact residues are in bold All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., s., 12 (4), 480-489, 1990.
Allred et al., Arch. Surg., 125 (1), 107-113, 1990.
Atherton et al., Biol. of Reproduction, 32, 155-171, 1985.
Barzon et al., Euro Surveill. 2016 Aug. 11; 21 (32).
Beltramello et al., Cell Host Microbe 8, 271-283, 2010.
Brown et al., J. Immunol. Meth., 12; 130 (1): 111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74 (2): 425-433, 1977.
De Jager et al., Semin. Nucl. Med. 23 (2), 165-179, 1993.
Dholakia et al., J. Biol. Chem., 264, 20638-20642, 1989.
Diamond et al., J Virol 77, 2578-2586, 2003.
Doolittle and Ben-Zeev, Methods Mol. Biol., 109: 215-237, 1999.

Duffy et al., *N. Engl. J. Med.* 360, 2536-2543, 2009.

Elder et al. Infections, infertility and assisted reproduction. Part II: Infections in reproductive medicine & Part III: Infections and the assisted reproductive laboratory. Cambridge UK: Cambridge University Press; 2005.

Gefter et al., *Somatic Cell Genet.,* 3:231-236, 1977.

Gornet et al., *Semin Reprod Med.* 2016 September; 34 (5): 285-292. Epub 2016 Sep. 14.

Gulbis and Galand, *Hum. Pathol.* 24 (12), 1271-1285, 1993.

Halfon et al., *PLOS ONE* 2010; 5 (5) e10569

Hessell et al., *Nature* 449, 101-4, 2007.

Khatoon et al., *Ann. of Neurology,* 26, 210-219, 1989.

King et al., *J. Biol. Chem.,* 269, 10210-10218, 1989.

Kohler and Milstein, *Eur. J. Immunol.,* 6, 511-519, 1976.

Kohler and Milstein, *Nature,* 256, 495-497, 1975.

Kyte and Doolittle, *J. Mol. Biol.,* 157 (1): 105-132, 1982.

Mansuy et al., *Lancet Infect Dis.* 2016 October; 16 (10): 1106-7.

Nakamura et al., In: *Enzyme Immunoassays: Heterogeneous and Homogeneous Systems,* Chapter 27, 1987.

O'Shannessy et al., *J. Immun. Meth.,* 99, 153-161, 1987.

Persic et al., *Gene* 187:1, 1997

Potter and Haley, *Meth. Enzymol.,* 91, 613-633, 1983.

Purpura et al., *Lancet Infect Dis.* 2016 October; 16 (10): 1107-8. Epub 2016 Sep. 19.

Remington's Pharmaceutical Sciences, 15th Ed., 3:624-652, 1990.

Tang et al., *J. Biol. Chem.,* 271:28324-28330, 1996.

Wawrzynczak & Thorpe, In: *Immunoconjugates, Antibody Conjugates In Radioimaging And Therapy Of Cancer,* Vogel (Ed.), NY, Oxford University Press, 28, 1987.

Yu et al., *J Immunol Methods* 336, 142-151, doi: 10.1016/j.jim.2008.04.008, 2008.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr. D Biol. Crystallogr. 66, 213-221.

Aiyegbo, M. S., Eli, I. M., Spiller, B. W., Williams, D. R., Kim, R., Lee, D. E., Liu, T., Li, S., Stewart, P. L., and Crowe, J. E., Jr. (2014). Differential accessibility of a rotavirus VP6 epitope in trimers comprising type I, II, or III channels as revealed by binding of a human rotavirus VP6-specific antibody. J. Virol. 88, 469-476.

Al-Hubeshy, Z. B., Coleman, A., Nelson, M., and Goodier, M. R. (2011). A rapid method for assessment of natural killer cell function after multiple receptor crosslinking. J. Immunol. Methods 366, 52-59.

Alter, G., Malenfant, J. M., and Altfeld, M. (2004). CD107a as a functional marker for the identification of natural killer cell activity. J. Immunol. Methods 294, 15-22.

Altman, M. O., Bennink, J. R., Yewdell, J. W., and Herrin, B. R. (2015). Lamprey VLRB response to influenza virus supports universal rules of immunogenicity and antigenicity. eLife 4, 07467.

Angeletti, D., Gibbs, J. S., Angel, M., Kosik, I., Hickman, H. D., Frank, G. M., Das, S. R., Wheatley, A. K., Prabhakaran, M., Leggat, D. J., et al. (2017). Defining B cell immunodominance to viruses. Nat. Immunol. 18, 456-463.

Ashkenazy, H., Abadi, S., Martz, E., Chay, O., Mayrose, I., Pupko, T., and Ben-Tal, N. (2016). ConSurf 2016: an improved methodology to estimate and visualize evolutionary conservation in macromolecules. Nucleic Acids Res. 44, W344-350.

Bangaru, S., Nieusma, T., Kose, N., Thornburg, N. J., Finn, J. A., Kaplan, B. S., King, H. G., Singh, V., Lampley, R. M., Sapparapu, G., et al. (2016). Recognition of influenza H3N2 variant virus by human neutralizing antibodies. JCI Insight 1, e86673.

Bangaru, S., Zhang, H., Gilchuk, I. M., Voss, T. G., Irving, R. P., Gilchuk, P., Matta, P., Zhu, X., Lang, S., Nieusma, T., et al. (2018). A multifunctional human monoclonal neutralizing antibody that targets a unique conserved epitope on influenza HA. Nat. Commun. 9, 2669.

Bao, Y. M., Bolotov, P., Dernovoy, D., Kiryutin, B., Zaslavsky, L., Tatusova, T., Ostell, J., and Lipman, D. (2008). The influenza virus resource at the national center for biotechnology information. J. Virol. 82, 596-601.

Bridges, C. B., Thompson, W. W., Meltzer, M. I., Reeve, G. R., Talamonti, W. J., Cox, N. J., Lilac, H. A., Hall, H., Klimov, A., and Fukuda, K. (2000). Effectiveness and cost-benefit of influenza vaccination of healthy working adults-A randomized controlled trial. JAMA 284, 1655-1663.

Brochet, X., Lefranc, M. P., and Giudicelli, V. (2008). IMGT/V-QUEST: the highly customized and integrated system for IG and TR standardized V-J and V-D-J sequence analysis. Nucleic Acids Res. 36, W503-508.

Carr, C. M., and Kim, P. S. (1993). A spring-loaded mechanism for the conformational change of influenza hemagglutinin. Cell 73, 823-832.

Carrat, F., and Flahault, A. (2007). Influenza vaccine: the challenge of antigenic drift. Vaccine 25, 6852-6862.

Caton, A. J., Brownlee, G. G., Yewdell, J. W., and Gerhard, W. (1982). The antigenic structure of the influenza virus A/PR/8/34 hemagglutinin (H1 subtype). Cell 31, 417-427.

Celniker, G., Nimrod, G., Ashkenazy, H., Glaser, F., Martz, E., Mayrose, I., Pupko, T., and Ben-Tal, N. (2013). ConSurf: using evolutionary data to raise testable hypotheses about protein function. Isr. J. Chem. 53, 199-206.

Chao, D. T., Ma, X., Li, O., Park, H., and Law, D. (2009). Functional characterization of N297A, a murine surrogate for low-Fc binding anti-human CD3 antibodies. Immunol. Invest. 38, 76-92.

Chen, J., Lee, K. H., Steinhauer, D. A., Stevens, D. J., Skehel, J. J., and Wiley, D. C. (1998). Structure of the hemagglutinin precursor cleavage site, a determinant of influenza pathogenicity and the origin of the labile conformation. Cell 95, 409-417.

Chen, V. B., Arendall, W. B., 3rd, Headd, J. J., Keedy, D. A., Immormino, R. M., Kapral, G. J., Murray, L. W., Richardson, J. S., and Richardson, D. C. (2010). MolProbity: all-atom structure validation for macromolecular crystallography. Acta Crystallogr. D Biol. Crystallogr. 66, 12-21.

Copeland, C. S., Doms, R. W., Bolzau, E. M., Webster, R. G., and Helenius, A. (1986). Assembly of influenza hemagglutinin trimers and its role in intracellular transport. J. Cell Biol. 103, 1179-1191.

Copeland, C. S., Zimmer, K. P., Wagner, K. R., Healey, G. A., Mellman, I., and Helenius, A. (1988). Folding, trimerization, and transport are sequential events in the biogenesis of influenza virus hemagglutinin. Cell 53, 197-209.

Corti, D., Suguitan, A. L., Jr., Pinna, D., Silacci, C., Fernandez-Rodriguez, B. M., Vanzetta, F., Santos, C., Luke, C. J., Torres-Velez, F. J., Temperton, N. J., et al. (2010). Heterosubtypic neutralizing antibodies are produced by individuals immunized with a seasonal influenza vaccine. J. Clin. Invest. 120, 1663-1673.

Corti, D., Voss, J., Gamblin, S. J., Codoni, G., Macagno, A., Jarrossay, D., Vachieri, S. G., Pinna, D., Minola, A., Vanzetta, F., et al. (2011). A neutralizing antibody selected from plasma cells that binds to group 1 and group 2 influenza A hemagglutinins. Science 333, 850-856.

Das, S. R., Hensley, S. E., Ince, W. L., Brooke, C. B., Subba, A., Delboy, M. G., Russ, G., Gibbs, J. S., Bennink, J. R., and Yewdell, J. W. (2013). Defining influenza A virus hemagglutinin antigenic drift by sequential monoclonal antibody selection. Cell Host Microbe 13, 314-323.

Dawood, F. S., Iuliano, A. D., Reed, C., Meltzer, M. I., Shay, D. K., Cheng, P. Y., Bandaranayake, D., Breiman, R. F., Brooks, W. A., Buchy, P., et al. (2012). Estimated global mortality associated with the first 12 months of 2009 pandemic influenza A H1N1 virus circulation: a modelling study. Lancet Infect. Dis. 12, 687-695.

DiLillo, D. J., Palese, P., Wilson, P. C., and Ravetch, J. V. (2016). Broadly neutralizing anti-influenza antibodies require Fc receptor engagement for in vivo protection. J. Clin. Invest. 126, 605-610.

DiLillo, D. J., Tan, G. S., Palese, P., and Ravetch, J. V. (2014). Broadly neutralizing hemagglutinin stalk-specific antibodies require FcγR interactions for protection against influenza virus in vivo. Nat. Med. 20, 143-151.

Dowd, K. A., Jost, C. A., Durbin, A. P., Whitehead, S. S., and Pierson, T. C. (2011). A dynamic landscape for antibody binding modulates antibody-mediated neutralization of West Nile virus. PLOS Pathog. 7, e1002111.

Dowd, K. A., and Pierson, T. C. (2018). The many faces of a dynamic virion: Implications of viral breathing on flavivirus biology and immunogenicity. Annu. Rev. Virol. 5, 185-207.

Dreyfus, C., Ekiert, D. C., and Wilson, I. A. (2013). Structure of a classical broadly neutralizing stem antibody in complex with a pandemic H2 influenza virus hemagglutinin. J. Virol. 87, 7149-7154.

Dreyfus, C., Laursen, N. S., Kwaks, T., Zuijdgeest, D., Khayat, R., Ekiert, D. C., Lee, J. H., Metlagel, Z., Bujny, M. V., Jongeneelen, M., et al. (2012). Highly conserved protective epitopes on influenza B viruses. Science 337, 1343-1348.

Edgar, R. C. (2004). MUSCLE: multiple sequence alignment with high accuracy and high throughput. Nucleic Acids Res. 32, 1792-1797.

Ekiert, D. C., Bhabha, G., Elsliger, M. A., Friesen, R. H., Jongeneelen, M., Throsby, M., Goudsmit, J., and Wilson, I. A. (2009). Antibody recognition of a highly conserved influenza virus epitope. Science 324, 246-251.

Ekiert, D. C., Friesen, R. H., Bhabha, G., Kwaks, T., Jongeneelen, M., Yu, W., Ophorst, C., Cox, F., Korse, H. J., Brandenburg, B., et al. (2011). A highly conserved neutralizing epitope on group 2 influenza A viruses. Science 333, 843-850.

Ekiert, D. C., Kashyap, A. K., Steel, J., Rubrum, A., Bhabha, G., Khayat, R., Lee, J. H., Dillon, M. A., O'Neil, R. E., Faynboym, A. M., et al. (2012). Cross-neutralization of influenza A viruses mediated by a single antibody loop. Nature 489, 526-532.

Freidl, G. S., Meijer, A., de Bruin, E., de Nardi, M., Munoz, O., Capua, I., Breed, A. C., Harris, K., Hill, A., Kosmider, R., et al. (2014). Influenza at the animal-human interface: a review of the literature for virological evidence of human infection with swine or avian influenza viruses other than A (H5N1). Euro Surveill. 19 (18). pii: 20793.

Friesen, R. H., Lee, P. S., Stoop, E. J., Hoffman, R. M., Ekiert, D. C., Bhabha, G., Yu, W., Juraszek, J., Koudstaal, W., Jongeneelen, M., et al. (2014). A common solution to group 2 influenza virus neutralization. Proc. Natl. Acad. Sci. U.S.A. 111, 445-450.

Garces, F., Lee, J. H., de Val, N., de la Pena, A. T., Kong, L., Puchades, C., Hua, Y., Stanfield, R. L., Burton, D. R., Moore, J. P., et al. (2015). Affinity maturation of a potent family of HIV antibodies is primarily focused on accommodating or avoiding glycans. Immunity 43, 1053-1063.

Garcia, N. K., Guttman, M., Ebner, J. L., and Lee, K. K. (2015). Dynamic changes during acid-induced activation of influenza hemagglutinin. Structure 23, 665-676.

Gerhard, W., Yewdell, J., Frankel, M. E., and Webster, R. (1981). Antigenic structure of influenza virus haemagglutinin defined by hybridoma antibodies. Nature 290, 713-717.

Gething, M. J., McCammon, K., and Sambrook, J. (1986). Expression of wild-type and mutant forms of influenza hemagglutinin: the role of folding in intracellular transport. Cell 46, 939-950.

Giudicelli, V., and Lefranc, M. P. (2011). IMGT/junctionanalysis: IMGT standardized analysis of the V-J and V-D-J junctions of the rearranged immunoglobulins (IG) and T cell receptors (TR). Cold Spring Harb. Protoc. 2011, 716-725.

Hamuro, Y., Anand, G. S., Kim, J. S., Juliano, C., Stranz, D. D., Taylor, S. S., and Woods, V. L., Jr. (2004). Mapping intersubunit interactions of the regulatory subunit (RIalpha) in the type I holoenzyme of protein kinase A by amide hydrogen/deuterium exchange mass spectrometry (DXMS). J. Mol. Biol. 340, 1185-1196.

He, W., Mullarkey, C. E., Duty, J. A., Moran, T. M., Palese, P., and Miller, M. S. (2015). Broadly neutralizing antiinfluenza virus antibodies: enhancement of neutralizing potency in polyclonal mixtures and IgA backbones. J. Virol. 89, 3610-3618.

Hezareh, M., Hessell, A. J., Jensen, R. C., van de Winkel, J. G., and Parren, P. W. (2001). Effector function activities of a panel of mutants of a broadly neutralizing antibody against human immunodeficiency virus type 1. J. Virol. 75, 12161-12168.

Hong, M., Lee, P. S., Hoffman, R. M., Zhu, X., Krause, J. C., Laursen, N. S., Yoon, S. I., Song, L., Tussey, L., Crowe, J. E., Jr., et al. (2013). Antibody recognition of the pandemic H1N1 influenza virus hemagglutinin receptor binding site. J. Virol. 87, 12471-12480.

Hsu, S., Kim, Y., Li, S., Durrant, E. S., Pace, R. M., Woods, V. L., Jr., and Gentry, M. S. (2009). Structural insights into glucan phosphatase dynamics using amide hydrogendeuterium exchange mass spectrometry. Biochemistry 48, 9891-9902.

Impagliazzo, A., Milder, F., Kuipers, H., Wagner, M. V., Zhu, X., Hoffman, R. M., van Meersbergen, R., Huizingh, J., Wanningen, P., Verspuij, J., et al. (2015). A stable trimeric influenza hemagglutinin stem as a broadly protective immunogen. Science 349, 1301-1306.

Irimia, A., Sarkar, A., Stanfield, R. L., and Wilson, I. A. (2016). Crystallographic identification of lipid as an integral component of the epitope of HIV broadly neutralizing antibody 4E10. Immunity 44, 21-31.

Jegaskanda, S., Job, E. R., Kramski, M., Laurie, K., Isitman, G., de Rose, R., Winnall, W. R., Stratov, I., Brooks, A. G., Reading, P. C., and Kent, S. J. (2013). Cross-reactive influenza-specific antibody-dependent cellular cytotoxicity antibodies in the absence of neutralizing antibodies. J. Immunol. 190, 1837-1848

Joyce, M. G., Wheatley, A. K., Thomas, P. V., Chuang, G. Y., Soto, C., Bailer, R. T., Druz, A., Georgiev, I. S., Gillespie, R. A., Kanekiyo, M., et al. (2016). Vaccine-induced antibodies that neutralize group 1 and group 2 influenza A viruses. Cell 166, 609-623.

Julien, J. P., Lee, P. S., and Wilson, I. A. (2012). Structural insights into key sites of vulnerability on HIV-1 Env and influenza HA. Immunol. Rev. 250, 180-198.

Kallewaard, N. L., Corti, D., Collins, P. J., Neu, U., McAuliffe, J. M., Benjamin, E., Wachter-Rosati, L., Palmer-Hill, F. J., Yuan, A. Q., Walker, P. A., et al. (2016). Structure and function analysis of an antibody recognizing all influenza A subtypes. Cell 166, 596-608.

Kashyap, A. K., Steel, J., Rubrum, A., Estelles, A., Briante, R., Ilyushina, N. A., Xu, L., Swale, R. E., Faynboym, A. M., Foreman, P. K., et al. (2010). Protection from the 2009 H1N1 pandemic influenza by an antibody from combinatorial survivor-based libraries. PLOS Pathog. 6, e1000990.

Klenk, H. D., and Garten, W. (1994). Host cell proteases controlling virus pathogenicity. Trends Microbiol. 2, 39-43.

Klenk, H. D., and Rott, R. (1988). The molecular biology of influenza virus pathogenicity. Adv. Virus Res. 34, 247-281.

Kristensen, A. B., Lay, W. N., Ana-Sosa-Batiz, F., Vanderven, H. A., Madhavi, V., Laurie, K. L., Carolan, L., Wines, B. D., Hogarth, M., Wheatley, A. K., and Kent, S. J. (2016). Antibody responses with Fc-mediated functions after vaccination of HIV-infected subjects with trivalent influenza vaccine. J. Virol. 90, 5724-5734.

Lander, G. C., Stagg, S. M., Voss, N. R., Cheng, A., Fellmann, D., Pulokas, J., Yoshioka, C., Irving, C., Mulder, A., Lau, P. W., et al. (2009). Appion: an integrated, database-driven pipeline to facilitate EM image processing. J. Struct. Biol. 166, 95-102.

Lang, S., Xie, J., Zhu, X., Wu, N. C., Lerner, R. A., and Wilson, I. A. (2017). Antibody 27F3 broadly targets influenza A group 1 and 2 hemagglutinins through a further variation in VH1-69 antibody orientation on the HA stem. Cell Rep 20, 2935-2943.

Laursen, N. S., and Wilson, I. A. (2013). Broadly neutralizing antibodies against influenza viruses. Antiviral Res. 98, 476-483.

Lee, J., Boutz, D. R., Chromikova, V., Joyce, M. G., Vollmers, C., Leung, K., Horton, A. P., DeKosky, B. J., Lee, C. H., Lavinder, J. J., et al. (2016). Molecular-level analysis of the serum antibody repertoire in young adults before and after seasonal influenza vaccination. Nat. Med. 22, 1456-1464.

Lee, P. S., Ohshima, N., Stanfield, R. L., Yu, W., Iba, Y., Okuno, Y., Kurosawa, Y., and Wilson, I. A. (2014). Receptor mimicry by antibody F045-092 facilitates universal binding to the H3 subtype of influenza virus. Nat. Commun. 5, 3614.

Lee, P. S., Yoshida, R., Ekiert, D. C., Sakai, N., Suzuki, Y., Takada, A., and Wilson, I. A. (2012). Heterosubtypic antibody recognition of the influenza virus hemagglutinin receptor binding site enhanced by avidity. Proc. Natl. Acad. Sci. USA 109, 17040-17045.

Li, S., Tsalkova, T., White, M. A., Mei, F. C., Liu, T., Wang, D., Woods, V. L., Jr., and Cheng, X. (2011). Mechanism of intracellular cAMP sensor Epac2 activation: cAMP-induced conformational changes identified by amide hydrogen/deuterium exchange mass spectrometry (DXMS). J. Biol. Chem. 286, 17889-17897.

Lu, W. D., Liu, T., Li, S., Woods, V. L., Jr., and Hook, V. (2012). The prohormone proenkephalin possesses differential conformational features of subdomains revealed by rapid H-D exchange mass spectrometry. Protein Sci. 21, 178-187.

Marsh, J. J., Guan, H. S., Li, S., Chiles, P. G., Tran, D., and Morris, T. A. (2013). Structural insights into fibrinogen dynamics using amide hydrogen/deuterium exchange mass spectrometry. Biochemistry 52, 5491-5502.

McCoy, A. J., Grosse-Kunstleve, R. W., Adams, P. D., Winn, M. D., Storoni, L. C., and Read, R. J. (2007). Phaser crystallographic software. J. Appl. Crystallogr. 40, 658-674.

Morgan, A., Jones, N. D., Nesbitt, A. M., Chaplin, L., Bodmer, M. W., and Emtage, J. S. (1995). The N-terminal end of the CH2 domain of chimeric human IgG1 anti-HLA-DR is necessary for C1q, Fc gamma RI and Fc gamma RIII binding. Immunology 86, 319-324.

Munro, J. B., Gorman, J., Ma, X., Zhou, Z., Arthos, J., Burton, D. R., Koff, W. C., Courter, J. R., Smith, A. B., 3rd, Kwong, P. D., et al. (2014). Conformational dynamics of single HIV-1 envelope trimers on the surface of native virions. Science 346, 759-763.

Munro, J. B., and Mothes, W. (2015). Structure and dynamics of the native HIV-1 env trimer. J. Virol. 89, 5752-5755.

Neumann, G., and Kawaoka, Y. (2015). Transmission of influenza A viruses. Virology 479-480, 234-246.

Nobusawa, E., Aoyama, T., Kato, H., Suzuki, Y., Tateno, Y., and Nakajima, K. (1991). Comparison of complete amino acid sequences and receptor-binding properties among 13 serotypes of hemagglutinins of influenza A viruses. Virology 182, 475-485.

Nordin, J., Mullooly, J., Poblete, S., Strikas, R., Petrucci, R., Wei, F., Rush, B., Safirstein, B., Wheeler, D., and Nichol, K. L. (2001). Influenza vaccine effectiveness in preventing hospitalizations and deaths in persons 65 years or older in Minnesota, New York, and Oregon: data from 3 health plans. J. Infect. Dis. 184, 665-670.

Ogura, T., Iwasaki, K., and Sato, C. (2003). Topology representing network enables highly accurate classification of protein images taken by cryo electron-microscope without masking. J. Struct. Biol. 143, 185-200.

Okuno, Y., Isegawa, Y., Sasao, F., and Ueda, S. (1993). A common neutralizing epitope conserved between the hemagglutinins of influenza-A virus H1 and H2 strains. J. Virol. 67, 2552-2558.

Potter, C. S., Chu, H., Frey, B., Green, C., Kisseberth, N., Madden, T. J., Miller, K. L., Nahrstedt, K., Pulokas, J., Reilein, A., et al. (1999). Leginon: a system for fully automated acquisition of 1000 electron micrographs a day. Ultramicroscopy 77, 153-161.

Rey, F. A., and Lok, S. M. (2018). Common features of enveloped viruses and implications for immunogen design for next-generation vaccines. Cell 172, 1319-1334.

Rey, F. A., Stiasny, K., Vaney, M. C., Dellarole, M., and Heinz, F. X. (2018). The bright and the dark side of human antibody responses to flaviviruses: lessons for vaccine design. EMBO Rep. 19, 206-224.

Rice, P., Longden, I., and Bleasby, A. (2000). EMBOSS: the european molecular biology open software suite. Trends Genet. 16, 276-277.

Russell, R. J., Gamblin, S. J., Haire, L. F., Stevens, D. J., Xiao, B., Ha, Y., and Skehel, J. J. (2004). H1 and H7 influenza haemagglutinin structures extend a structural classification of haemagglutinin subtypes. Virology 325, 287-296.

Schmidt, A. G., Therkelsen, M. D., Stewart, S., Kepler, T. B., Liao, H. X., Moody, M. A., Haynes, B. F., and Harrison, S. C. (2015). Viral receptor-binding site antibodies with diverse germline origins. Cell 161, 1026-1034.

Shrestha, S. S., Swerdlow, D. L., Borse, R. H., Prabhu, V. S., Finelli, L., Atkins, C. Y., Owusu-Edusei, K., Bell, B., Mead, P. S., Biggerstaff, M., et al. (2011). Estimating the burden of 2009 pandemic influenza A (H1N1) in the United States (April 2009-April 2010). Clin. Infect. Dis. 52 Suppl 1, S75-82.

Skubak, P., Murshudov, G. N., and Pannu, N. S. (2004). Direct incorporation of experimental phase information in model refinement. Acta Crystallogr. D Biol. Crystallogr. 60, 2196-2201.

Smirnov, Y. A., Lipatov, A. S., Gitelman, A. K., Okuno, Y., Van Beek, R., Osterhaus, A. D., and Claas, E. C. (1999). An epitope shared by the hemagglutinins of H1, H2, H5, and H6 subtypes of influenza A virus. Acta Virol. 43, 237-244.

Smith, S. A., Zhou, Y., Olivarez, N. P., Broadwater, A. H., de Silva, A. M., and Crowe, J. E., Jr. (2012). Persistence of circulating memory B cell clones with potential for dengue virus disease enhancement for decades following infection. J. Virol. 86, 2665-2675.

Steinhauer, D. A. (1999). Role of hemagglutinin cleavage for the pathogenicity of influenza virus. Virology 258, 1-20.

Thornburg, N. J., Zhang, H., Bangaru, S., Sapparapu, G., Kose, N., Lampley, R. M., Bombardi, R. G., Yu, Y. C., Graham, S., Branchizio, A., et al. (2016). H7N9 influenza virus neutralizing antibodies that possess few somatic mutations. J. Clin. Invest. 126, 1482-1494.

Tong, S., Zhu, X., Li, Y., Shi, M., Zhang, J., Bourgeois, M., Yang, H., Chen, X., Recuenco, S., Gomez, J., et al. (2013). New world bats harbor diverse influenza A viruses. PLOS Pathog. 9, e1003657.

Valkenburg, S. A., Mallajosyula, V. V., Li, O. T., Chin, A. W., Carnell, G., Temperton, N., Varadarajan, R., and Poon, L. L. (2016). Stalking influenza by vaccination with pre-fusion headless HA mini-stem. Sci. Rep. 6, 22666.

Van Dongen, J. J., Langerak, A. W., Bruggemann, M., Evans, P. A., Hummel, M., Lavender, F. L., Delabesse, E., Davi, F., Schuuring, E., Garcia-Sanz, R., et al. (2003). Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia 17, 2257-2317.

Voss, N. R., Yoshioka, C. K., Radermacher, M., Potter, C. S., and Carragher, B. (2009). DoG Picker and TiltPicker: software tools to facilitate particle selection in single particle electron microscopy. J. Struct. Biol. 166, 205-213.

Webster, R. G., and Rott, R. (1987). Influenza virus A pathogenicity: the pivotal role of hemagglutinin. Cell 50, 665-666.

Weis, W., Brown, J. H., Cusack, S., Paulson, J. C., Skehel, J. J., and Wiley, D. C. (1988). Structure of the influenza virus haemagglutinin complexed with its receptor, sialic acid. Nature 333, 426-431.

Weiss, M. S., and Hilgenfeld, R. (1997). On the use of the merging R factor as a quality indicator for X-ray data. J. Appl. Crystallogr. 30, 203-205.

Whittle, J. R. R., Zhang, R. J., Khurana, S., King, L. R., Manischewitz, J., Golding, H., Dormitzer, P. R., Haynes, B. F., Walter, E. B., Moody, M. A., et al. (2011). Broadly neutralizing human antibody that recognizes the receptor-binding pocket of influenza virus hemagglutinin. Proc. Natl. Acad. Sci. USA 108, 14216-14221.

Wilson, I. A., Skehel, J. J., and Wiley, D. C. (1981). Structure of the haemagglutinin membrane glycoprotein of influenza virus at 3 A resolution. Nature 289, 366-373.

Wines, B. D., Vanderven, H. A., Esparon, S. E., Kristensen, A. B., Kent, S. J., and Hogarth, P. M. (2016). Dimeric FcgammaR ectodomains as probes of the Fc receptor function of anti-influenza virus IgG. J. Immunol. 197, 1507-1516.

Wu, N. C., and Wilson, I. A. (2017). A perspective on the structural and functional constraints for immune evasion: insights from influenza virus. J. Mol. Biol. 429, 2694-2709.

Xu, R., Krause, J. C., McBride, R., Paulson, J. C., Crowe, J. E., Jr., and Wilson, I. A. (2013). A recurring motif for antibody recognition of the receptor-binding site of influenza hemagglutinin. Nat. Struct. Mol. Biol. 20, 363-370.

Yassine, H. M., Boyington, J. C., McTamney, P. M., Wei, C. J., Kanekiyo, M., Kong, W. P., Gallagher, J. R., Wang, L., Zhang, Y., Joyce, M. G., et al. (2015). Hemagglutinin-stem nanoparticles generate heterosubtypic influenza protection. Nat. Med. 21, 1065-1070.

Yewdell, J. W., Taylor, A., Yellen, A., Caton, A., Gerhard, W., and Bachi, T. (1993). Mutations in or near the fusion peptide of the influenza virus hemagglutinin affect an antigenic site in the globular region. J. Virol. 67, 933-942.

Yoon, S. W., Chen, N., Ducatez, M. F., McBride, R., Barman, S., Fabrizio, T. P., Webster, R. G., Haliloglu, T., Paulson, J. C., Russell, C. J., et al. (2015). Changes to the dynamic nature of hemagglutinin and the emergence of the 2009 pandemic H1N1 influenza virus. Sci. Rep. 5, 12828.

Yoshida, R., Igarashi, M., Ozaki, H., Kishida, N., Tomabechi, D., Kida, H., Ito, K., and Takada, A. (2009). Cross-protective potential of a novel monoclonal antibody directed against antigenic site B of the hemagglutinin of influenza A viruses. PLOS Pathog. 5, e1000350.

Yusuf, M., Konc, J., Sy Bing, C., Trykowska Konc, J., Ahmad Khairudin, N. B., Janezic, D., and Wahab, H. A. (2013). Structurally conserved binding sites of hemagglutinin as targets for influenza drug and vaccine development. J. Chem. Inf. Model. 53, 2423-2436.

Zhang, Z., and Smith, D. L. (1993). Determination of amide hydrogen exchange by mass spectrometry: a new tool for protein structure elucidation. Protein Sci. 2, 522-531.

Zhu, X., Guo, Y. H., Jiang, T., Wang, Y. D., Chan, K. H., Li, X. F., Yu, W., McBride, R., Paulson, J. C., Yuen, K. Y., et al. (2013). A unique and conserved neutralization epitope in H5N1 influenza viruses identified by an antibody against the A/Goose/Guangdong/1/96 hemagglutinin. J. Virol. 87, 12619-12635.

What is claimed is:

1. A method of treating a subject infected with influenza A virus or reducing the likelihood of infection of a subject at risk of contracting influenza A virus, comprising administering to said subject an antibody or antibody fragment having heavy chain CDR1-3 sequences and light chain CDR1-3 sequences of SEQ ID NOS: 17-19 and SEQ ID NOS: 29-31, respectively, or administering an RNA or DNA sequence or vector encoding the antibody or antibody fragment.

2. The method of claim 1, the antibody or antibody fragment is encoded by light and heavy chain variable sequences of SEQ ID NOS: 2 and 1, respectively.

3. The method of claim 1, the antibody or antibody fragment is encoded by light and heavy chain variable sequences having 95% identity to SEQ ID NOS: 2 and 1, respectively.

4. The method of claim 1, wherein said antibody or antibody fragment is encoded by light and heavy chain variable sequences having 70%, 80%, or 90% identity to SEQ ID NOS: 2 and 1, respectively.

5. The method of claim 1, wherein said antibody or antibody fragment comprises light and heavy chain variable sequences according to sequences of SEQ ID NOS: 10 and 9, respectively.

6. The method of claim 1, wherein said antibody or antibody fragment comprises light and heavy chain variable sequences having 70%, 80% or 90% identity to SEQ ID NOS: 10 and 9, respectively.

7. The method of claim 1, wherein said antibody or antibody fragment comprises light and heavy chain variable sequences having 95% identity to SEQ ID NOS: 10 and 9, respectively.

8. The method of claim 1, wherein the antibody fragment is a recombinant scFv (single chain fragment variable) antibody, Fab fragment, F(ab')$_2$ fragment, or Fv fragment.

9. The method of claim 1, wherein said antibody is an IgG, or a recombinant IgG antibody or antibody fragment that comprises an Fc portion mutated to eliminate or enhance FcR interactions, to increase half-life and/or increase therapeutic efficacy, or comprises a glycan modification to eliminate or enhance FcR interactions.

10. The method of claim 1, wherein said antibody is a chimeric antibody or a bispecific antibody.

11. The method of claim 1, wherein said antibody or antibody fragment is administered prior to infection or after infection.

12. The method of claim 1, wherein said subject is a pregnant female, a sexually active female, or a female undergoing fertility treatments.

13. The method of claim 1, wherein delivering comprises antibody or antibody fragment administration, or genetic delivery with an RNA or DNA sequence or vector encoding the antibody or antibody fragment.

14. The method of claim 1, wherein said antibody or antibody fragment has an antiviral molecule attached thereto.

15. The method of claim 9, wherein the mutation to eliminate or enhance FcR interactions, to increase half-life and/or increase therapeutic efficacy is a LALA, N297, GASD/ALIE, YTE or LS mutation.

16. The method of claim 9, wherein said glycan modification is a result of enzymatic or chemical addition or removal of glycans, or expression in a cell line engineered with a defined glycosylating pattern.

* * * * *